(12) United States Patent
Leroux-Roels et al.

(10) Patent No.: US 6,555,114 B1
(45) Date of Patent: Apr. 29, 2003

(54) IMMUNODOMINANT HUMAN T-CELL EPITOPES OF HEPATITIS C VIRUS

(75) Inventors: Geert Leroux-Roels, Ghent (BE); Robert Deleys, Grimbergen (BE); Goort Maertens, Bruges (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 08/635,886

(22) PCT Filed: Oct. 28, 1994

(86) PCT No.: PCT/EP94/03555

§ 371 (c)(1), (2), (4) Date: Apr. 25, 1996

(87) PCT Pub. No.: WO95/12677

PCT Pub. Date: May 11, 1995

(30) Foreign Application Priority Data

Nov. 4, 1993 (EP) .............................. 93402718

(51) Int. Cl.⁷ .......................... A61K 39/29; C12Q 1/70; C07K 14/00
(52) U.S. Cl. .......................... 424/228.1; 435/5; 530/324
(58) Field of Search .......................... 424/228.1; 435/5; 530/324

(56) References Cited

U.S. PATENT DOCUMENTS

| 5,350,671 A | * | 9/1994 | Houghton et al. ............. 435/5 |
| 5,428,145 A | | 6/1995 | Okamoto et al. |
| 5,709,995 A | | 1/1998 | Chisari et al. |
| 5,847,101 A | | 12/1998 | Okayama et al. |
| 6,027,729 A | | 2/2000 | Houghton et al. |

FOREIGN PATENT DOCUMENTS

| EP | 0 468 527 A2 | 1/1992 | |
| EP | 0 468 657 A2 | 1/1992 | |
| EP | 0 485 209 A1 | 5/1992 | |
| EP | 0 759 937 | 3/1997 | |
| WO | WO 92/22571 | 12/1992 | |
| WO | 9300365 | * 1/1993 | .......... A61K/39/29 |
| WO | WO 93/06126 | 4/1993 | |
| WO | WO 93/15207 | 8/1993 | |
| WO | WO 93/18054 | 9/1993 | |

OTHER PUBLICATIONS

Falk et al., "Consensus Motifs and Peptides Ligands of MHC Class I Molecules," Som. Immunology 5: 81–94 (1993).*

Roitt et al, "Immunology", pp. 8.3, 8.4 (copyright 1985), Gower Medical Publishing, London, England.

Roitt et al, "Immunology", pp. 7.6, 7.7 (copyright 1989), Gower Medical Publishing, London, England.

Farci et al 1992 Science 258 pp. 135–140.

Falk et al 1991 Nature 351 pp. 290–296.

Janeway et al, "Immunology", pp. 8.2, 8.3 (copyright 1994), Current Biology Ltd./Garland Publishing Inc.

Koziel et al, Journal of Immunology, 149, 3339–3344 (1992).

Lin et al. "The Hepatitis C Virus Genome: a Guide to its Conserved Sequences and Candidate Epitopes", Virus Research, 30 (1993) 27–41.

Stuyver et al., "Analysis of the Putative $E^1$ Envelope and NS4a Epitope Regions of HCV Type $3^1$", Biochemical and Biophysical Research Communications, vol. 192, No. 2, 1993, pp. 635–641.

Virus Research, vol. 30, No. 1, Oct. 1993, Amsterdam, NL, pp 27–41, Lin, H.J. et al 'The Hepatitis C Virus Genome: a guide to its Conserved Sequences and Candidate Epitops' see p. 22, line 25—line 26; table 3.

Gastroenterology, vol. 104, No. 4PT2, Apr. 1993, p A660, Journal of Virology, vol. 67, No. 12, Dec. 1993, pp. 7522–7532; Kozie et al; 'Hepatitis C Virus 9HCV)–specific cytotoxic T lymphocytes recognize et al'.

Journal of Medical Virology, vol. 40, No. 2, Jue 1993, New York, NY, pp. 150–156, Lesniewski et al, Hypervariable 5'–Terminus of Hepatitis C Virus E2/NS1 Encodes Antigenically Distinct Variants.

Proceedings of the National Academy of Sciences of USA, vol. 89, Apr. 1992, Washington US, pp. 3468–3472, Weiner et al 'Evidence For Immune Selection of Hepatitis C Virus (HCV) Putative et al'.

* cited by examiner

Primary Examiner—Mary K. Zeman
Assistant Examiner—Lori A. Clow
(74) Attorney, Agent, or Firm—Nixon & Vanderhye PC

(57) ABSTRACT

The present invention relates to a polypeptide of about 8 to about 100 amino acids containing at least about 8 contiguous amino acids selected from the core, and/or the E1, and/or E2, and/or the NS3 regions of the HCV polyprotein, with the contiguous amino acids containing a T-cell stimulating epitope.

15 Claims, 31 Drawing Sheets

FIGURE 1. Evolution of lymphoproliferative responses and transaminase activities in HCV patient #632

FIGURE 3

BE8309 NS3 SEQUENCE

GVAKAVDFVPVESMETTMRSPVFTDNSSPPAVPQTFQVAHLHAPTGSGKSTKVPAAYAA
QGYKVLVLNPSVAATLGFGAYMSKAHGVDPNIRTGVRTITTGAPITYSTYGKFLADGGC
SGGAYDIICDECHSIDSTSILGIGTVLDQAETAGARLVVLATATPPGSVTVPHPNIEE
VALSSTGEIPFYGKAIPIEVIKGGRHLIFCHSKKKCDELAAKLSGFGINAVAYYRGLDV
SVIPTSGDVVVATDALMTGFTGDFDSVIDCNTCVTQTVDFS

FIGURE 4A

```
                            1                                                50
                            MSTNPKPQRKTKRNTNRRPQDVKFPGGGQIVGGVYLLPRRGPRLGVRATR
SEQ ID NO:
179  HCV-H      1a          --------------------------------------------------
180  HCV-1      1a          ---I----------------------------------------------
181  HC-J1      1a          --------------------------------------------------
182  HCVEC1     1a          --------------------------------------------------
183  HCVHCT18   1a          --------------------------------------------------
184  HCVHCT23   1a          --------------------------------------------------
185  HCVHCT27   1a          --------------------------------------------------
186  HCVTH      1a          --------------------------------------------------
187  HCV-J      1b          --------------------------------------------------
188  HC-J4.83   1b          ---------------------------------Y------------T---
189  HC-J4.91   1b          ---------------------------------Y-----V------T---
190  HCV-China  1b          --------------------------------------------------
191  HCV-JTA    1b          --------------------------------------------------
192  HCV-JTB    1b          --------------------------------------------------
193  HCV-BK     1b          ---------------G----------------------------------
194  HCV-JK1    1b          --------------------------------------------------
195  HCV-T      1b          ----------------------------------------------P---
196  BNL1       1d          --------------------------------------------------
197  BNL2       1d          --------------------------------------------------
198  CAM1078    1e          ---------------------------------------V------A---
199  FR2        1f          --------------------------------------------------
200  HC-J6      2a          --------------------------------------------------
201  HC-J8      2b          --------------------------------------------------
```

| SEQ ID NO: | | | 1 | | | | | 50 |
|---|---|---|---|---|---|---|---|---|
| 202 | CH610 | 2c | ------------------------------------------------- | | | | | |
| 203 | CH114 | 2c | ------------------------------------------------- | | | | | |
| 204 | NE92 | 2d | ------------------------------------------------- | | | | | |
| 205 | BNL3 | 2e | ------------------------------------------------- | | | | | |
| 206 | FR4 | 2f | ----------------------------------------------P-- | | | | | |
| 207 | HD10 | 3a | ------------------------------------------------- | | | | | |
| 208 | BR33 | 3a | ------------------------------------------------- | | | | | |
| 209 | BR36 | 3a | ------------------------------------------------- | | | | | |
| 210 | NZL1 | 3a | ------------------------------------------------- | | | | | |
| 211 | HCVTR | 3b | ---L---Q---L---N---------------------V-------V--- | | | | | |
| 212 | GB809-4 | 4a | ------------------------------------------------- | | | | | |
| 213 | GB116 | 4c | ------------------------------------------------- | | | | | |
| 214 | GB215 | 4c | ------------------------------------------------- | | | | | |
| 215 | GB358 | 4c | ------------------------------------------------- | | | | | |
| 216 | GB809 | 4c | ------------------------------------------------- | | | | | |
| 217 | DK13 | 4d | ------------------------------------------------- | | | | | |
| 218 | CAM600 | 4e | --------------------M---------------------------- | | | | | |
| 219 | GB809 | 4e | --------------------M---------------------------- | | | | | |
| 220 | CAMG22 | 4f | --------------------M---------------------------- | | | | | |
| 221 | GB549 | 4g | ------------------------------------------------- | | | | | |
| 222 | GB438 | 4h | ----L-------------------------------------------- | | | | | |
| 223 | CAR4/1205 | 4i | ------------------------------------------------- | | | | | |
| 224 | CAR4/901 | 4? | ------------------------------------------------- | | | | | |

| SEQ ID NO: | | | 1 | | | | | | | | 50 |
|---|---|---|---|---|---|---|---|---|---|---|---|
| 225 | BNL7 | 4k | ------- | --- | --- | -M- | --- | --- | --- | --- | --- |
| 226 | BE95 | 5a | ---L--- | --- | --- | --- | --- | --- | --- | --- | --- |
| 227 | BE100 | 5a | ---L--- | --- | --- | --T- | --- | --- | -M- | --- | --- |
| 228 | HK2 | 6a | ---L--- | --- | --- | -M- | --- | --- | --- | --- | --- |
| 229 | FR1 | 7a | ---L--- | -I- | --- | --- | --- | --- | --- | --- | --- |
| 230 | VN4 | 8a | ---L--- | --- | --- | -M- | --- | --- | --- | --- | --- |
| 231 | VN12 | 8b | ---L--- | --- | --- | --- | --- | --- | --- | --- | --- |
| 232 | VN13 | 9a | ---L--- | -X- | --- | --- | --- | --V- | --- | -Q- | --- |
| 233 | NE98 | 10a | ---L--- | --- | --- | --- | --- | --- | --- | --- | -V- |

FIGURE 4C

| SEQ ID NO: (continued) | | | 51 KTSERSQPRGRRQPIPKARRPEGRTWAQPGYPWPLYGNEGCGWAGWLLSP 100 |
|---|---|---|---|
| 179 | HCV-H | 1a | ------------------------------------------------- |
| 180 | HCV-1 | 1a | ---------------------V--------------------------- |
| 181 | HC-J1 | 1a | ------------------------------------------------- |
| 182 | HCVEC1 | 1a | ------------------------------------------------- |
| 183 | HCVHCT18 | 1a | ------------------------------------------------- |
| 184 | HCVHCT23 | 1a | ------------------------------------------------- |
| 185 | HCVHCT27 | 1a | ------------------------------------------------- |
| 186 | HCVTH | 1a | ------------------------------------------------- |
| 187 | HCV-J | 1b | ------------W-------------------------------M---- |
| 188 | HC-J4.83 | 1b | --------------------Q-----A-----------------L---- |
| 189 | HC-J4.91 | 1b | --------------------Q-----A-----------------L---- |
| 190 | HCV-China | 1b | ---------------------------------------------F---- |
| 191 | HCV-JTA | 1b | --------------------------A-----------------L---- |
| 192 | HCV-JTB | 1b | --------------------Q-----A-----------------L---- |
| 193 | HCV-BK | 1b | --------------------Q-----A-----------------L---- |
| 194 | HCV-JK1 | 1b | --------------------Q-----A-----------------L---- |
| 195 | HCV-T | 1b | -----M--------------------S-----------------L--V- |
| 196 | BNL1 | 1d | --------------------X-----S------------------L---- |
| 197 | BNL2 | 1d | ---------------D----QSD---X---H------------------- |
| 198 | CAM1078 | 1e | --------------------E------------------------------ |
| 199 | FR2 | 1f | --------------------------S-------------A--------- |
| 200 | HC-J6 | 2a | ---------------D----ST-KS-GK--------------L------ |
| 201 | HC-J8 | 2b | ---------------D----ST-KS-GK--------------L------ |

FIGURE 4D

```
SEQ ID NO:
(continued)                51                                                              100
202 CH61D         2c      ----------------------------D--TT-KS-GR-------------L-----------
203 CH114         2c      ----------------------------D--TT-KS-GR-----------------------
204 NE92          2d      ----------------------------D--T-KS-GK----------L-------------
205 BNL3          2e      ----------------------------D-XAT--S-GR-----------L-------------
206 FR4           2f      ----------------------------D--XAT-KS-GR----------L-------------
207 HD10          3a      ----------------------------D--AT-KS-GR-------------------------
208 BR33          3a      ----------------------------------------------------------------
209 BR36          3a      ----------------------------------------------------------------
210 NZL1          3a      ----------------------------------------------------------------
211 HCVTR         3b      ----------KQ-HL-----SR----S-------------------------------------
212 GB809_1       4a      ----------------------------------------------------------------
213 GB116         4c      ----------------------------------------------------------------
214 GB215         4c      ----------------------------------------------------------------
215 GB35e         4c      ----------------------------------------------------------------
216 GB809         4c      ----------------------------------------------------------------
217 DK13          4d      ------------QL----S---------------------------K---L-------------
218 CAM600        4e      ------------T-----S---------------------------------------------
219 GB809         4e      ------------------S---------------------------------------------
220 CAMG22        4f      ------------------S---------------------------------------------
221 GB549         4g      ----------------------------------------------------------------
222 GB438         4h      ----------------------------------------------------------------
223 CAR4/1205     4i      ----------------------------------------------------------------
224 CAR4/901      4?      ----------------------------------------------------------------
```

```
SEQ ID NO:                    51                                                  100
(continued)
225 BNL7    4k   --------------------------------------------------
226 BE95    5a   ------------------S-----------S-------------------
227 BE100   5a   ---------------Q-T--S-G-----------A----L-----X----
228 HK2     6a   ---------------Q-Q---H----------------------------
229 FR1     7a   -------------V-Q-T--S-G---------------------------
230 VN4     8a   ----A--------V-HQT--------------------------------
231 VN12    8b   -------------V-QNQ--------------------------------
232 VN13    9a   -------------V-HQT--------------------------------
233 NE98   10a   ------S------R-T----S-----------------------------
```

FIGURE 4G

```
                         101                                      150
                         RGSRPSWGPTDPRRRSRNLGKVIDTLTCGFADLMGYIPLVGAPLGGAARA
SEQ ID NO:
(continued)
 179  HCV-H      1a      -------------------------------------------------
 180  HCV-1      1a      -------------------------------------------------
 181  HC-J1      1a      -------------------------------------------------
 182  HCVEC1     1a      -------------------------------------------------
 183  HCVHCT18   1a      -------------------------------------------------
 184  HCVHCT23   1a      -------------------------------------------------
 185  HCVHCT27   1a      ----------------------------------R--------------
 186  HCVTH      1a      -------------------------------------------------
 187  HCV-J      1b      -------------------------------------------------
 188  HC-J4.83   1b      -------------------------------------------------
 189  HC-J4.91   1b      -------------------------------------------------
 190  HCV-China  1b      -------------------------------------------------
 191  HCV-JTA    1b      -------------------------------------------------
 192  HCV-JTB    1b      -------------------------------------------------
 193  HCV-BK     1b      Y----R-------------------------------------------
 194  HCV-JK1    1b      ---N---------------------------------------------
 195  HCV-T      1b      ---N---------------------------------------------
 196  BNL1       1d      -------------------------------------------------
 197  BNL2       1d      ----T--------------------------------------------
 198  CAM1078    1e      -------------------------------------------------
 199  FR2        1f      ----N-------H---V--------------------------V-----
 200  HC-J6      2a      ----N-------H-------R----I------------------V--S-T
 201  HC-J8      2b      -------------------------------------------V--V-V-
```

FIGURE 4H

| SEQ ID NO: (continued) | | 101 | | | | | | | | | | | | | | | | | | | | | | | | | | | | | | | | | | | | | | | | | | | | | | | | 150 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 225 BNL7 | 4k | - | - | - | - | - | N | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| 226 BE95 | 5a | - | - | - | N | - | - | N | - | - | K | - | - | - | - | - | - | - | - | - | - | - | - | - | - | - | - | - | - | - | - | - | - | - | - | - | G | - | I | - | - | V | - | - | - | - | - | - | - | - | - |
| 227 BE100 | 5a | - | - | - | N | - | - | N | - | - | - | - | - | - | - | - | - | - | - | - | - | - | V | - | - | - | - | - | - | - | - | - | - | - | - | - | G | - | V | - | - | V | - | - | - | - | - | - | - | - | - |
| 228 HK2 | 6a | - | - | - | H | - | - | N | - | - | - | - | - | - | - | - | - | - | - | - | - | - | - | - | - | - | - | - | - | - | - | - | - | V | - | - | - | - | - | - | - | V | - | A | - | - | - | - | - | - | - |
| 229 FR1 | 7a | - | - | - | N | - | - | N | - | - | - | - | - | - | - | - | - | - | - | - | - | - | - | - | - | - | X | X | L | - | - | - | - | V | L | - | G | - | - | - | - | V | - | A | - | - | - | - | - | - | - |
| 230 VN4 | 8a | - | - | - | N | - | - | N | - | - | - | - | - | - | - | - | - | - | - | - | - | - | - | - | - | - | - | - | - | - | - | - | - | V | - | - | - | - | - | - | - | V | - | A | - | - | - | - | - | - | - |
| 231 VN12 | 8b | - | - | - | D | - | X | - | N | - | X | - | - | - | - | - | - | - | - | - | - | - | - | - | - | - | - | - | - | - | - | - | - | - | - | - | - | - | X | - | - | V | - | X | - | - | - | - | - | - | - |
| 281 VN13 | 9a | - | - | - | - | - | - | - | - | - | - | - | - | - | - | - | - | - | N | - | - | - | - | X | - | - | - | - | - | - | - | - | - | E | - | - | - | - | - | - | - | V | - | AE | - | - | - | - | - | - | - |
| 282 NE98 | 10a | X | - | - | - | - | - | - | - | - | - | - | - | - | - | - | - | N | - | - | N | - | - | X | - | - | - | - | - | - | - | - | - | - | - | - | - | X | X | - | - | I | E | - | - | - | - | - | - | - | - |

FIGURE 4I

| SEQ ID NO: (continued) | | | 151                                            200<br>LAHGVRVLEDGVNYATGNLPGCSFSIFLLALLSCLTVPASAYQVRNSTGL |
|---|---|---|---|
| 180 | HCV-1 | 1a | -------------------------------------------------- |
| 179 | HCV-H | 1a | ---------------------------------------------S---I |
| 181 | HC-J1 | 1a | -------------------------------------------------- |
| 182 | HCVEC1 | 1a | ---------------------------------------------S---- |
| 183 | HCVHCT18 | 1a | -----------------------------H-------------------- |
| 184 | HCVHCT23 | 1a | -------------------------------------------------- |
| 185 | HCVHCT27 | 1a | ---------------------------------------------S---I |
| 186 | HCVTH | 1a | ----------------L--------------------------------- |
| 187 | HCV-J | 1b | ---------------------------I---------------E---VS-I |
| 188 | HC-J4.83 | 1b | ---------------------------I---------------E---VS-I |
| 189 | HC-J4.91 | 1b | ---------------------------I---------------E---VS-I |
| 190 | HCV-China1b | 1b | ---------------------------T---------------E---VS-I |
| 191 | HCV-JTA | 1b | ---------------------------I---------------------AS- |
| 192 | HCV-JTB | 1b | ---------------------------I---------------------RS- |
| 193 | HCV-BK | 1b | ---------------------------T-------V-T-E---E-H-VS-I |
| 194 | HCV-JK1 | 1b | ---------------------------T-------V-T-E---E---VS-V |
| 195 | HCV-T | 1b | ---------------------------I-------V---E-H-VS-I |
| 279 | BNL1 | 1d | --------------------------------------XT-HE---AS-V |
| 280 | BNL2 | 1d | ---------------------F-----------------TT-HE---AS-V |
| 199 | FR2 | 1f | --X-----XG--XXXXXX--X---XX---X----T---E-HST-DG |
| 200 | HC-J6 | 2a | ------F-------------------------I-T-V--AE-K-ISTG |
| 201 | HC-J8 | 2b | ---I------------------------------V-.-V--VE---ISSS |
| 202 | CH610 | 2c | ---I--------------------S-------IS--V--VE-K-TSTS |

FIGURE 4J

| SEQ ID NO: (continued) | Name | | 151　　　　　　　　　　　　　　　　　　　　　　　　　　　200 |
|---|---|---|---|
| 234 | S83 | 2c | VE-KDTGDS |
| 203 | CH114 | 2c | ------------------IX------M-------------XIS--V--XE---TST- |
| 204 | NE92 | 2d | ------------------I---------------------I---V-GL--K-TSSS |
| 205 | BNL3 | 2e | ---X--------------I--X----------X--------I---V-XVE-K-TSQA |
| 206 | FR4 | 2f | ------------------I----------------------I---V--I--K-NSHF |
| 235 | BNL4 | 2g | ----------------------------------------------V--V-K-TSTM |
| 236 | BNL5 | 2h | ----------------------------------------------V--K-TSHS |
| 237 | BNL6 | 2i | ------------------I--------------------I---V--V-A-RS-S |
| 207 | HD10 | 3a | ------A-----------I--F---------------F--IH--ASLEW--TS- |
| 208 | BR33 | 3a | ------A-----------I--F---------------F--IH--AGLEW--TS- |
| 209 | BR36 | 3a | ------A-----------I--F---------------F--IH--ASLEW--TS- |
| 210 | NZL1 | 3a | ------A-----------I--F---------------F--IH--ASLEW--TS- |
| 211 | HCV-TR | 3b | ------A-G---------I------------------F---C---GLEYT-TS- |
| 212 | GB809_4 | 4a | ------AV----------I----------------------EHY--AS-I |
| 238 | Z4 | 4a | EHY--AS-I |
| 239 | Z1 | 4b | VHY--AS-V |
| 213 | GB116 | 4c | -E----AV---------I-------------S---------T--VNY--AS-V |
| 214 | GB215 | 4c | -E----AV---------I-------------Y---------T--IHY--AS-V |
| 215 | GB358 | 4c | ------AV---------I-----------------------T--VNY--AS-V |
| 240 | Z6 | 4c | VNY--AS-I |
| 241 | Z7 | 4c | VNYH-AS-V |
| 217 | DK13 | 4d | ------L---------------------------------NY---S-V |
| 218 | CAM600 | 4e | ------AV---------I-----------------------T---VNY--AS-I |

FIGURE 4K

```
SEQ ID NO:
(continued)                151                                                                           200
219 GB809        -----AV---I------------------------------------------GVNY--AS-V
220 CAMG22       -----AV---I------------------------------------------VHYH-TS-I
242 CAMG27       -----AV---I------------------------------------------VHYH-TS-I
221 GB549        -----AV---I------------------------------------QHY--IS-I
222 GB438        -----AV---I---------------------------V--R-----QHY--AS-I
223 CAR4/12054i  -----A----I-------------------S--E----------------IHY--ASDG
224 CAR4/901     -----AV---I---------------X-----------------------QHY--VS-I
283 BNL7                   -I-F----------------------------------------INY--VS-I
243 BNL8                   -I--------------------------------------------INY--TS-I
244 BNL9                   -I--------------------------------------------INYH-TS-I
245 BNL10                  -I------I---X-------X---------------------TNY--VS-I
246 BNL11                  -I--------------------------------------------TNY--VS-I
247 BNL12                  -I----------------------I---------------------QHY--VS-I
248 GB724
226 BE95                                        I----------------------VPY--AS-I
227 BE100                                       I----------------------VPY--AS-I
249 SA4                                                                VPY--AS-V
228 HK2          ----AI---I------------------------------T-----LTYG--S--
229 FR1          ----AI---I------------------------------T---I--K-AS-I
230 VN4          -XXI---X------X----XX-X----------------T-----AHYT-KS--
231 VN12         ----AI---I------------------X----------------LNYA-KS--
284 NE98         -X--------I-F----------------------------F---LT-TAGLEY--AS--
```

FIGURE 4L

| SEQ ID NO: (continued) | | | 201 YHVTNDCPNSSIVYEAADAILHTPGCVPCVREGNASRCWVAMTPTVATRD 250 |
|---|---|---|---|
| 180 | HCV-1 | 1a | ------------------------------------------------- |
| 179 | HCV-H | 1a | -----V------------------------------V------------ |
| 181 | HC-J1 | 1a | ------------------------------------------------- |
| 182 | HCVEC1 | 1a | ----------------H--------------------------------- |
| 183 | HCVHCT18 | 1a | ----------------H-----H--------------V----------- |
| 184 | HCVHCT23 | 1a | -----------------------------------V------------ |
| 185 | HCVHCT27 | 1a | -------T--T------A-------------D-V----V---K------ |
| 186 | HCVTH | 1a | -------T---S------A--------------------K--PVA---- |
| 187 | HCV-J | 1b | ----S-------M-M---------------S-F----L------L-A-N |
| 188 | HC-J4.83 | 1b | ----S-------M-M---------------D-S----L------L-A-N |
| 189 | HC-J4.91 | 1b | ----S-------V-M------------------S----L------L-A- |
| 190 | HCV-China1b | 1b | ----S-------L-M------------------S----L------L-A-N |
| 191 | HCV-JTA | 1b | ----S------GM-M---------------N------L------L-A-N |
| 192 | HCV-JTB | 1b | ----S------GM-M---------------N-V----L------L-A-N |
| 193 | HCV-BK | 1b | ----S-A-----L-M---------------S------L------L-A-N |
| 194 | HCV-JK1 | 1b | ----S-------M-M---------------S------L------L-A-N |
| 195 | HCV-T | 1b | ----S-------M-M---------------N-S----L------L-A-N |
| 279 | BNL1 | 1d | ----S----I--MDGM-M-Y----------D-HL---M-L-----L-VKX |
| 280 | BNL2 | 1d | -L--S----I--MSGM----A---------N-S-----MXL----L-VK- |
| 199 | FR2 | 1f | ----S-G---K-I-------X-------I------I---PL---L-A-I |
| 200 | HC-J6 | 2a | -M---T-D--TWQLQA-V--V------EKV-T---IPVS-N--VQQ |
| 201 | HC-J8 | 2b | -YA--S-N--TWQLT--V--L------ENDNGTLH--IQV--N--VKH |
| 202 | CH610 | 2c | -M--S--------WQLEG-V-------EQI-----PVS-N---I-Q |

| SEQ ID NO (continued) | Name | Group | Sequence (201–250) |
|---|---|---|---|
| 234 | S83 | 2c | -MP------S------WQLEG-V-------------E-TA-V-----PVA-NL-ISQ |
| 203 | CH114 | 2c | -M-------S------WQLEG-VX-I---------EWTNTTP----PVS-X--I-Q |
| 204 | NE92 | 2d | -M-------Q------WQLR---V--V--------EEK--I---IPVS-NI-VSQ |
| 205 | BNL3 | 2e | -MA------S-N----WQLX---V--V--------ENSSGRFH--IPIS-NI-VSK |
| 206 | FR4 | 2f | -MA------A-D----WQLR---V--V--------E-S--RTF--T-VS-N--VSR |
| 235 | BNL4 | 2g | -MA------S-N----IWQMQG-V--V--------ELQ--K----IPV---VNQ |
| 236 | BNL5 | 2h | -M-------S------WQLK---V--V--------E-HQ-Q----IPV---VSQ |
| 237 | BNL6 | 2i | -M-------S------WQLEE-V--V---------EWKD-T----IPV-NI-VSQ |
| 207 | HD10 | 3a | -VL------S---------D-V-------------QD---T-A--TPV-----V-Y |
| 208 | BR33 | 3a | -VL------S---------D-V----A--------QD---T-T--TPV-----V-Y |
| 209 | BR36 | 3a | -VL------S---------D-V-------I-----QD---T-T--TPV----VKY |
| 210 | NZL1 | 3a | -VL------S---------D-V-------------QD---T-T--TPV-----V-Y |
| 211 | HCV-TR | 3b | -VL------S-G------E-V-----L--------TT---Q-S--TTVST---V-T |
| 212 | GB809-4 | 4a | --I------------V---TDHH----L-------A----V----TPV----AVS |
| 238 | Z4 | 4a | --I----------------DHH----L--------MT---T----TPV----VAH |
| 239 | Z1 | 4b | --I------T-------TEHH-M-L----------TE---T----PL-----APY |
| 213 | GB116 | 4c | --I----------------DYH----L-L------V----Q----L------APY |
| 214 | GB215 | 4c | --I----------------DHH----L-L------V----Q----LS-----APY |
| 215 | GB358 | 4c | --I---------------TEHH----L-L------V----Q----L------APY |
| 240 | Z6 | 4c | --I----------------EHQ----L-L------V----Q----L------VSY |
| 241 | Z7 | 4c | --I-----M----------EHH----L-L-----------Q----L------APY |
| 217 | DK13 | 4d | --I---------------TDYH----L-----------.K.T---SL-----AQH |
| 218 | CAM600 | 4e | --I-----A---------TENH----L--------T----Q----L------SPY |

FIGURE 40

| SEQ ID NO: (continued) | Name | Code | 201 ——————————————————————— 250 |
|---|---|---|---|
| 219 | GB809 | 4e | --I------A---TDNH--L-----------KT--Q------L-------SPY |
| 220 | CAMG22 | 4f | --L----------F--VHH--L----------T--Q------L-----L-APT |
| 242 | CAMG27 | 4f | --I----------F--EHH--L----------T--Q----I-L-----L-APH |
| 221 | GB549 | 4g | ----------------DHH-M-L---------T--T------PL----L-APY |
| 222 | GB438 | 4h | ----------------DHH-M-L---------T--V------IPL-----VPY |
| 223 | CAR4/12054i | 4? | -YI-------------ENH---L---I-----KT--Q------L-----L-APH |
| 224 | CAR4/901 | 4? | -Y--------------DHH-M-L---I-----T--V------SL------APY |
| 283 | BNL7 | 4k | -Y--------------DHH---L---------T--Q------L-------APY |
| 243 | BNL8 | 4k | ----------------DHH---L------------Q------L-------APY |
| 244 | BNL9 | 4k | --I-------------DHH-AL----------V--Q------L-----I-APY |
| 245 | BNL10 | 4k | ----------------DHH---L---------V--Q------L-------APY |
| 246 | BNL11 | 4k | -------------F--DHH---L---------K--H------L-------API |
| 247 | BNL12 | 4l | ----------------SDHH--L---------KT--T-----L-------API |
| 248 | GB724 | 4? | --I------V---TDHH--L------------T--V------TPV-----AVS |
| 226 | BE95 | 5a | -------------F--DNL---A---------MT--V-----QI----LSAPS |
| 227 | BE100 | 5a | ----------------D-L---A---------KD-V------QI----LSAPS |
| 249 | SA4 | 5a | ----------------DNL---A---------QD-V-K----QI----LSAPN |
| 228 | HK2 | 6a | --L----------L--DAM---L---L-----VDDR-T----H-V----L-IPN |
| 229 | FR1 | 7a | --L---S-N----F--ETM---L---------IKA--E----LPVS---L-VPN |
| 230 | VN4 | 8a | --L----------L--ETL---L---------KXX--Q----QAS----L-VPN |
| 231 | VN12 | 8b | --L----------L--NGM---L---------KT--LTK---LSAS---L-VQN |
| 284 | NE98 | 10a | --M---S-G----L--G-I---L---------S.T.------IPVSX---VKS |

FIGURE 4P

| SEQ ID NO: (continued) | | | 251　　　　　　　　　　　　　　　　　　　　　　　　　300<br>GKLPATQLRRHIDLLVGSATLCSALYVGDLCGSVFLVGQLFTFSPRRHWT |
|---|---|---|---|
| 180 | HCV-1 | 1a | ------------------------------------------------- |
| 179 | HCV-H | 1a | ---T--------------------------------------------H- |
| 181 | HC-J1 | 1a | -------------------------------------I----------- |
| 182 | HCVEC1 | 1a | ---T---------------------------------------------- |
| 183 | HCVHCT18 | 1a | ---T---------------------------------------------- |
| 184 | HCVHCT23 | 1a | ---T---------------------------------------------- |
| 185 | HCVHCT27 | 1a | N-------------------------I---------------------- |
| 186 | HCVTH | 1a | R--T-----------------------I---------------------- |
| 187 | HCV-J | 1b | SSI-T-TI---V---A-A---M--------S-------------YE--- |
| 188 | HC-J4.83 | 1b | ASV-T-TI---V---A-AF--M--------S--------------E--- |
| 189 | HC-J4.91 | 1b | ASV-T-TI---V---T-AF--M--------S----I---------E--- |
| 190 | HCV-China1b | 1b | ATI-TATV---V---A-AFS-M--------S--------------YE--- |
| 191 | HCV-JTA | 1b | TSI-T-TI---V---A-AF--M--------S--------------YE--- |
| 192 | HCV-JTB | 1b | TSI-T-TI---V---A-AF--M--------S--------------YE--- |
| 193 | HCV-BK | 1b | VTI-T-TI---V---A-AF--M--------S--------------V--- |
| 194 | HCV-JK1 | 1b | SSI-T-TI---V---A-AF--M--------S--------------YE--- |
| 195 | HCV-T | 1b | NSV-TATI---V---XX-F--M--X--------------------YE--- |
| 279 | BNL1 | 1d | ASV-TXAI---V---T-AFR-M----------A--------------M-H- |
| 280 | BNL2 | 1d | ANV-TAAI---V---A-VF--M--I-----------------TS--LYH- |
| 199 | FR2 | 1f | ANA-IDEV---V-------M--I----G---------------------- |
| 200 | HC-J6 | 2a | PGALTQG-T---MV-M-----------G-M-AA-M-IV--QH--F |
| 201 | HC-J8 | 2b | RGALTRS---T-V-MI-MA--A-----V---A-MILS-A-MV--Q--NF |
| 202 | CH610 | 2c | PGTLTKG--A-V-VI-M----------V---ALMIAA-AVIA--Q---TF |

| SEQ ID NO: (continued) | | | 251 | | | | | | | 300 |
|---|---|---|---|---|---|---|---|---|---|---|
| 234 | S83 | 2c | PGALTKG--A---II-M---V------V--ALM-AA-VVVV--QH-TF |
| 203 | CH114 | 2c | PGALTKG--A---VI-M---------V--ALMIAA-AVVA--Q--XF |
| 204 | NE92 | 2d | PGALTKG--T---TIIA---F----I------A-M |
| 205 | BNL3 | 2e | PGALTKG--AR--AV-M---------V--A-MIAA-A-IVA-K--YF |
| 206 | FR4 | 2f | PGALTRG--A---TI-M--------I---A-MIAA-VAVV--QY-TF |
| 235 | BNL4 | 2g | PGALTRG--T---TI-MV--------I--V-A-MIAA-VVIV--QH-NF |
| 236 | BNL5 | 2h | PGALTRG--T---TI-A---V-------F--A-M--S-F-MI--QH-IF |
| 237 | BNL6 | 2i | PGAXTKG--T---II-A---F |
| 207 | HD10 | 3a | VGATTASI---V-M---A--M---------M--A-------Q-- |
| 208 | BR33 | 3a | VGATTASI-S-V----A--M---------M--A-------R-- |
| 209 | BR36 | 3a | VGATTASI-S-V----A--M---------M--A-------R-- |
| 210 | NZL1 | 3a | VGATTASI-S-V----A--M---------M--A-------R-- |
| 211 | HCV-TR | 3b | LGVTTASI-T-V-M---ARQ--------AF-A-------R-- |
| 212 | GB809_4 | 4a | MDA-LESF---V--M---A--V--V-------GA--M---Q-- |
| 238 | Z4 | 4a | PGA-LESF---V--M---A--------GA--M--MI--R-- |
| 239 | Z1 | 4b | PNA-LESM---V--M---A--M---F-I-----G----D-R-- |
| 213 | GB116 | 4c | VGA-LES---S-V---M---A--V-----I---G----M-S-Q-- |
| 214 | GB215 | 4c | IGA-VESF---V-MM---A--V-----I---G----M-S-R-- |
| 215 | GB358 | 4c | IGA-LES---S-V---M---A------I---G----M-S-Q-- |
| 240 | Z6 | 4c | IGA-LDS----V---M---A--V-----I---GA---M-S-Q-- |
| 241 | Z7 | 4c | IGA-LESI---V---M---A--V-----I---G----M-S-Q-- |
| 217 | DK13 | 4d | LNA-LES---V---M---G-------I--V-G:---M-S-Q-- |
| 218 | CAM600 | 4e | AGA-LEP---V---M---A--M-------GL---M----Q-- |

FIGURE 4Q

| SEQ ID NO: (continued) | | | 251 | | | | | | | | | 300 |
|---|---|---|---|---|---|---|---|---|---|---|---|---|
| 219 | GB809 | 4e | VGA-LEP- | --V- | -M- | -A- | -V- | -- | -- | -GL- | -- | -M- | --- | -Q- | --- |
| 220 | CAMG22 | 4f | LGA-LESM- | --V- | -M- | -T- | -- | -- | -- | -GI- | -A- | -M- | -R- | -L- |
| 242 | CAMG27 | 4f | IGA-LESM- | --V- | -M- | -T- | -- | -- | -- | -GI- | -- | -M-N | -R- | -L- |
| 221 | GB549 | 4g | VGA-LESM- | --V- | -M- | -A- | -V- | -I- | -- | -G- | -- | -M- | -R- | -- |
| 222 | GB438 | 4h | LGA-L-SV-Q-V- | -M- | -A- | -- | -I- | -H- | -A- | -MVS | -Q- | -- |
| 223 | CAR4/1205 | 4i | LRA-LSS- | -A-V- | -M- | -A- | -A- | -F- | -- | -G- | -A- | -- | -IR- | -I-E |
| 224 | CAR4/901 | 4? | LGA-L-S- | --V- | -M- | -A- | -- | -I- | -- | -G- | -- | -M- | -Q- | -- |
| 283 | BNL7 | 4k | IGA-LES- | -S-V- | -M- | -A- | -V- | -I- | -X- | -XGL- | -- | -M-S | -R- | -- |
| 243 | BNL8 | 4k | IGA-LES- | -S-V- | -M- | -A- | -V- | -I- | -- | -GL- | -- | -M-S | -R- | -- |
| 244 | BNL9 | 4k | IGA-LES- | -S-V- | -M- | -A- | -V- | -I- | -- | -GA- | -- | -M-S | -R- | -- |
| 245 | BNL10 | 4k | TAA-LES- | -S-V- | -M- | -A- | -V- | -I- | -X- | -GL- | -- | -M-SX | -Q- | -- |
| 246 | BNL11 | 4k | IGA-LES- | -S-V-VM- | -A- | -V- | -I- | -- | -GL- | -- | -M-S | -R- | -- |
| 247 | BNL12 | 4l | LSA-LMSV- | --V- | -M- | -A- | -- | -S- | -- | -GA- | -- | -M- | -Q- | -- |
| 248 | GB724 | 4? | VDA-LESF- | --V- | -M- | -A- | -V- | -- | -- | -GA- | -- | -M- | -Q- | -- |
| 226 | BE95 | 5a | LGAVTAP- | -AV-Y-A-G-A- | -- | -- | -A- | -AL- | -- | -M- | -YR- | -Q-A |
| 227 | BE100 | 5a | FGAVTAP- | -AV-Y- | -G-A- | -- | -- | -A- | -AL- | -- | -M- | -YR- | -Q-A |
| 249 | SA4 | 5a | LGAVTAP- | -AV-Y-A-G-A- | -- | -- | -A- | -A- | -- | -M- | -YR- | -Q-T |
| 228 | HK2 | 6a | AST---GF- | --V- | -A-A-VV- | -S- | -I- | -- | -L- | -A- | -- | -Q- | -- |
| 229 | FR1 | 7a | SSV-IHGF- | --V- | -- | -A-AF- | -M-I | -- | -II- | -- | -R-KY | -QV |
| 230 | VN4 | 8a | AST-V-GF-K-V-IM- | -A-AF- | -M- | -- | -GL- | -- | -LR- | -M-QV |
| 231 | VN12 | 8b | ASVSIRGV-E-V- | -- | -A-AF- | -- | -- | -GL- | -- | -R--MYEI |
| 284 | NE98 | 10a | PCAATAS- | -T-V-MM-XA- | -- | -- | -AL--X- | -G-SWRH- | -Q- | -- |

FIGURE 4R

| SEQ ID NO: (continued) | | | 301                                                350 |
|---|---|---|---|
| 180 | HCV-1 | 1a | TQGCNCSIYPGHITGHRMAWDMMMNWSPTTALVMAQLLRIPQAILDMIAG |
| 179 | HCV-H | 1a | ---D--------------------N---------A----M--------- |
| 181 | HC-J1 | 1a | -------------------------------------A----------- |
| 182 | HCVEC1 | 1a | -------------------------------------------------- |
| 183 | HCVHCT18 | 1a | -------------------------------------------------- |
| 184 | HCVHCT23 | 1a | ---D---------------------------------------------- |
| 185 | HCVHCT27 | 1a | -------------------------------------------------- |
| 186 | HCVTH | 1a | ---D---------------------------------------------- |
| 187 | HCV-J | 1b | V-D---------VS---------------------VS-----VV---V- |
| 188 | HC-J4.83 | 1b | ------------LS---------------------VS-----VV---V- |
| 189 | HC-J4.91 | 1b | V-D---------VS---------------------VS-----VV---V- |
| 190 | HCV-China1b | 1b | I-D---------V----------------------VS-----VM--VV- |
| 191 | HCV-JTA | 1b | V-D---------VS---------------------VS-----VV---V- |
| 192 | HCV-JTB | 1b | V-D---------VS---------------------VS-----VV---V- |
| 193 | HCV-BK | 1b | L-D------L--VS---------------------VS-----VV---V- |
| 194 | HCV-JK1 | 1b | V-D---------VS---------------------VS-----VV--VV- |
| 195 | HCV-T | 1b | V-D---------V----------------------VS-----VV--VV- |
| 279 | BNL1 | 1d | --E----------------------------------------------- |
| 280 | BNL2 | 1d | --E----------------------------------------------- |
| 199 | FR2 | 1f | V-D------S----XXX--------------------VS-----VV--VG- |
| 200 | HC-J6 | 2a | V-D---T-------------------------ATMIL-YAM-V-EV-I-G- |
| 201 | HC-J8 | 2b | --E--Q-----------------------LS---LTMIL-YAA-V-ELV-EI-F- |
| 202 | CH610 | 2c | V-E---------X-------------------------------------- |

| SEQ ID NO: (continued) | Name | Label | 301 ... 319 |
|---|---|---|---|
| 234 | S83 | 2c | V-E------R---------- |
| 203 | CH114 | 2c | V-E---------------X |
| 286 | NE92 | 2d | V-D----------------- |
| 205 | BNL3 | 2e | V-E----------------- |
| 206 | FR4 | 2f | V-E---------------X |
| 235 | BNL4 | 2g | S-D----------------- |
| 236 | BNL5 | 2h | V-D----------------- |
| 237 | BNL6 | 2i | -------------------- |
| 207 | HD10 | 3a | V-T------L----LS---- |
| 208 | BR33 | 3a | V-T------L----LS---- |
| 209 | BR36 | 3a | V-T------L----LS---- |
| 210 | NZL1 | 3a | V-T------L----LS---- |
| 211 | HCV-TR | 3b | V-T-----------VS---- |
| 212 | GB809_4 | 4a | --D---T------------- |
| 238 | Z4 | 4a | --E---T------------- |
| 239 | Z1 | 4b | --D-----------VS---- |
| 213 | GB116 | 4c | --D---A--V---------- |
| 214 | GB215 | 4c | --D---A-------G----- |
| 215 | GB358 | 4c | --D---A--V---------- |
| 240 | Z6 | 4c | --D---A------------- |
| 241 | Z7 | 4c | --D---A--V---------- |
| 217 | DK13 | 4d | --D---T------------- |
| 218 | CAM600 | 4e | --D---T------------- |

| SEQ ID NO: (continued) | | | 301 | | | | | | | | | | | | | | | | | | 319 |
|---|---|---|---|---|---|---|---|---|---|---|---|---|---|---|---|---|---|---|---|---|---|
| 219 | GB809 | 4e | - | - | D | - | - | - | - | - | - | - | A | - | - | - | - | - | - | - | - |
| 220 | G22 | 4f | - | - | E | - | - | - | - | - | T | - | - | - | - | - | - | - | - | - | - |
| 242 | G27 | 4f | - | - | E | - | - | - | - | - | - | - | - | - | - | - | - | - | - | - | - |
| 221 | GB549 | 4g | - | - | D | - | - | - | - | - | - | - | - | - | D | - | - | - | - | - | - |
| 222 | GB438 | 4h | - | - | D | - | - | - | - | - | - | - | - | - | V | - | - | - | - | - | - |
| 223 | CAR4/12054i | | - | - | D | - | - | - | - | - | - | - | - | - | S | - | - | X | X | X | X |
| 283 | BNL7 | 4k | - | - | D | - | - | - | - | - | - | - | - | - | - | - | - | - | - | - | - |
| 243 | BNL8 | 4k | A | - | D | - | - | - | - | - | - | - | - | - | - | - | - | - | - | - | - |
| 244 | BNL9 | 4k | - | - | D | - | - | - | - | - | - | - | - | - | - | - | - | - | - | - | - |
| 245 | BNL10 | 4k | - | - | D | - | - | - | - | - | - | - | - | - | - | - | - | - | - | - | - |
| 246 | BNL11 | 4k | - | - | E | - | - | - | - | - | - | - | - | - | - | - | - | - | - | - | - |
| 247 | BNL12 | 4l | V | - | D | - | - | - | - | - | - | - | - | - | V | - | - | - | - | - | - |
| 224 | CAR4/901 | 4? | - | - | D | - | - | - | - | - | - | - | - | - | V | - | - | - | - | - | - |
| 248 | GB724 | 4? | - | - | D | - | - | - | - | - | - | - | T | - | - | - | - | - | - | - | - |
| 226 | BE95 | 5a | V | - | N | - | - | - | - | - | S | - | - | - | V | - | - | - | - | - | - |
| 227 | BE100 | 5a | V | - | D | - | - | - | - | - | S | - | - | - | V | - | - | Q | - | - | - |
| 249 | SA4 | 5a | V | - | D | - | - | - | - | - | S | - | - | - | - | - | - | - | - | - | - |
| 228 | HK2 | 6a | V | - | D | - | - | - | - | - | - | - | T | - | V | - | - | - | - | - | - |
| 229 | FR1 | 7a | - | - | D | - | - | - | X | N | X | - | V | - | - | - | - | - | - | - | - |
| 230 | VN4 | 8a | V | - | E | - | - | - | - | - | - | - | T | - | - | - | - | - | - | - | - |
| 231 | VN12 | 8b | A | - | D | - | - | - | - | - | - | - | - | - | A | - | - | - | - | - | - |
| 284 | NE98 | 10a | V | - | D | - | - | - | - | - | - | - | - | - | - | - | - | - | - | - | - |

| SEQ ID NO: (continued) | | | 351 AHWGVLAGIAYFSMVGNWAKVLVLVVLLLFAGVDA | ETHVTGGSAGHTVSGF 400 |
|---|---|---|---|---|
| 180 | HCV-1 | 1a | ---------------------------------- | ---------------- |
| 179 | HCV-H | 1a | ---------K------------------------ | -----N--R-TA-L |
| 181 | HC-J1 | 1a | ---------------------------------- | ---------------- |
| 182 | HCVEC1 | 1a | ---------------------------------- | ---------------- |
| 183 | HCVHCT18 | 1a | ---------------------------------- | --I-S--Q-ARAM--L |
| 184 | HCVHCT23 | 1a | ---------------------------------- | ---------------- |
| 185 | HCVHCT27 | 1a | ---------------------------------- | ---------------- |
| 186 | HCVTH | 1a | ---------------------------------- | ---------------- |
| 187 | HCV-J | 1b | ------L--Y---------------I-M------G | H-----RVASSTQSL |
| 188 | HC-J4.83 | 1b | ------L--Y---------------I-A------G | --YTS--A-S--T-TL |
| 189 | HC-J4.91 | 1b | ------L--Y---------------I-A------G | A-YTS--V--R-T--- |
| 190 | HCV-China1b | 1b | ------L--YA--------------I-M------G | D-YAS--AQ-RSTL-- |
| 191 | HCV-JTA | 1b | ------L--Y---------------I-M------G | V-YT----QARHTQSV |
| 192 | HCV-JTB | 1b | ------L--Y---------------I-M------G | V-YT----QARHTQ-V |
| 193 | HCV-BK | 1b | ------L--Y--A------------I-M------G | D------AQAK-TNRL |
| 194 | HCV-JK1 | 1b | ------L--Y---------------I-M------G | T-Y-SV-H-SQ-TRRV |
| 195 | HCV-T | 1b | ------L--Y---------------I-M------G | S-I-S--TVAR-THSL |
| 279 | BNL1 | 1d | ---------------------------------- | ---------------- |
| 280 | BNL2 | 1d | ---------------------------------- | ---------------- |
| 199 | FR2 | 1f | ---MF-L----Q-A----V-I---A----- | IQ--TV--TA-NARTL |
| 200 | HC-J6 | 2a | ----VF-L----Q-A----IAI-------V--- | .T-YSS-QE--R--A-- |
| 201 | HC-J8 | 2b | G--------------------------------- | ---------------- |

| SEQ ID NO: (continued) | | | 401                                                    450 |
|---|---|---|---|
| | | | VSLLAPGAKQNVQLINTNGSWHLNSTALNCNDSLNTGWLAGLFYHHKFNSS |
| 180 | HCV-1      | 1a | -G--T-----------I--------------I-------------Q---- |
| 179 | HCV-H      | 1a | ----------------I--------------I-------------Q---- |
| 181 | HC-J1      | 1a | ---FT-----------I------------E--------------I-Q--- |
| 182 | HCVEC1     | 1a | ---FT-----------I------------E-------------------- |
| 183 | HCVHCT18   | 1a | -------------------------------------------------- |
| 184 | HCVHCT23   | 1a | -------------------------------------------------- |
| 185 | HCVHCT27   | 1a | -------------------------------------------------- |
| 186 | HCVTH      | 1a | -------------------------------------------------- |
| 187 | HCV-J      | 1b | --W-SQ-PS-KI---V------I-R-----Q--FI-A----A-R---A-- |
| 188 | HC-J4.83   | 1b | A--FS---S-RI---V------I-R-----H--F--A----T-R------ |
| 189 | HC-J4.91   | 1b | T--FSS--S-KI---V------I-R-----H--F--A----T-------- |
| 190 | HCV-China1b| 1b | T--FT---S-KI---------I-R--------F--A----T-R---A-- |
| 191 | HCV-JTA    | 1b | T-FFTQ-PA-RI----------I-R-----E--FF-A----A-------- |
| 192 | HCV-JTB    | 1b | A-FFT--PA-KI----------I-R-----E--FF-A----A-------- |
| 193 | HCV-BK     | 1b | -MF-S-PS-KI-----------I-R--------F--A----T-S------ |
| 194 | HCV-JK1    | 1b | A-FFS--SA-KI----------I-R-----E-I--FF-A---VK------ |
| 195 | HCV-T      | 1b | A--FTQ--S-KI----------I-R-----Q--F--S----A-R---A-- |
| 279 | BNL1       | 1d | -------------------------------------------------- |
| 280 | BNL2       | 1d | -------------------------------------------------- |
| 199 | FR2        | 1f | -------------------------------------------------- |
| 200 | HC-J6      | 2a | TGMFSL--R-KI---------I-R-------H--F--S----T-S----- |
| 201 | HC-J8      | 2b | AG-FTT----LY---------I-R-------Q--F--S----T------- |

| SEQ ID NO: | | 571 | |
|---|---|---|---|
| 250 | HCV-1 | IGGAGNNT | LHCPTDCFRKHPDATYSRCGSGP |
| 251 | HCV-H | ---V---- | -L-----Y-E------------- |
| 252 | HC-J1 | --G----- | ------------------------ |
| 253 | HCV-J | ---V---- | -V---E---TK------------ |
| 254 | HC-J4.83 | --V-H--- | -T---E---TK------------ |
| 255 | HC-J4.91 | --V-R--- | -I---E---TK------------ |
| 256 | HCV-CHINA | ---V---- | -T---E--T------------- |
| 257 | HCV-JTA | ---V--L- | -T---E---TK------------ |
| 258 | HCV-JTB | ---V--L- | -T---E---TK------------ |
| 259 | HCV-BK | ---V---- | -T---E---TK------------ |
| 260 | HCV-JK1 | -------- | -T---E---TK------------ |
| 261 | HCV-T | ---G---- | -V---E---TK------------ |
| 262 | HC-G9 | ---S---- | -L--------------------- |
| 263 | HC-J6 | -RADF-ASMD-L | -----T--IK------------ |
| 264 | HC-J8 | -RKDY-S-ID-L | -----LK--A------------ |

```
                        604
      WITPRCLVDYPYRLWHYPCTINYTIFKIRMYVGGVEH
SEQ ID NO:
(continued)
250  HCV-1      ------------------------------------
251  HCV-H     R---M-------------------------V------
252  HC-J1     ----M-------------------------V------
253  HCV-J     -L--M----------------V-F-V--V--------
254  HC-J4.83  -L-----------------F-FS--V-----------
255  HC-J4.91  -L-----------------L-FS--V-----------
256  HCV-CHINA -L-----------------V-FA--V-----------
257  HCV-JTA  -L--I----------------V-F---V---------
258  HCV-JTB  -L--I----------------V-F---V---------
259  HCV-BK   -L--M----------------V-F---V---------
260  HCV-JK1  -L--M----------------F-F---V---------
261  HCV-T    -L--M----------------V-F---V---------
262  HC-G9    -L-------------------V------V--------
263  HC-J6    -L--I----------------V--------F------
264  HC-J8    -L-------------------V-F----A--------
```

FIGURE 5B

```
SEQ ID NO:
                              1188          1200
    265  HCV-1            GVAKAVDFIPVEN
    266  HCV-H            -------------
    267  HC-J1            ------------S
    268  HC3-J            ------------S
    178  BE8309           --------V---S
    269  HC-J4.83         ------------S
    270  HC-J4.91         ------------S
    271  HCV-CHINA        ------------T
    272  HCV-JTA          ------------S
    273  HCV-JTB          ------------S
    274  HCV-BK           --------V---S
    275  HCV-JK1          ------------S
    276  HCV-T            --------V---S
    277  HC-J6            ----SI------T
    278  HC-J8            ----SI------S 1201                                              1250
    265  HCV-1           LETTMRSPVFTDNSSPPVVPQSFQVAHLHAPTGSGKSTKVPAAYAAQGYK
    266  HCV-H           ----------------A--------------------------------
    267  HC-J1           ----------------A-----------------------------K--
    268  HCV-J           M---------------A---T----------------------------
    178  BE8309          M---------------A---T----------------------------
    269  HC-J4.83        M---------------A---T----------------------------
    270  HC-J4.91        M---------------A---T----------------------------
    271  HCV-CHINA       M---------------A---T----------------------------
    272  HCV-JTA         M---------------A---T----------------------------
    273  HCV-JTB         M---------------A---T----------------------------
    274  HCV-BK          M---------------A----------------------------X--
    275  HCV-JK1         M---------------A---T----------------------------
    276  HCV-T           M---------------A---T----------------------------
    277  HC-J6           -DIVT---T-S---T--A---TY--GY-------------V--------
    278  HC-J8           -DVAT-T-S-S---T--A----Y--GY-------------S----

1251                                         1300
    265  HCV-1           VLVLNPSVAATLGFGAYMSKAHGIDPNIRTGVRTITTGSPITYSTYGKFL
    266  HCV-H           ------------------------V------------------------
    267  HC-J1           -------------------------------------------------
    268  HCV-J           -------------------E--------------------G--------C---
    178  BE8309          ------------------------V-------------------A--------
    269  HC-J4.83        ------------------P-------------------------G--------
    270  HC-J4.91        -------------------------------------------GS--------
    271  HCV-CHINA       ------------------------V-------------------A--------
    272  HCV-JTA         ---------------------T---------------------A--------
    273  HCV-JTB         ---------------------T---------------------G--------
    274  HCV-BK          -----------------------------------------A-V--------
    275  HCV-JK1         ------------------------V----S--------------A--------
    276  HCV-T           ------------------------V-------------------A--------
    277  HC-J6           ----------------L------N--------------V---A----------
    278  HC-J8           -----------------------N-------------V---DS--------I
```

FIGURE 6A

| SEQ ID NO: | | 1301                                                   1350 |
|---|---|---|
| 265 | HCV-1     | ADGGCSGGAYDIIICDECHSTDATSILGIGTVLDQAETAGARLVVLATAT |
| 266 | HCV-H     | --A---------------------S------------------------ |
| 267 | HC-J1     | -------------------------V------------------------ |
| 268 | HCV-J     | -----------------------S-T------------------------ |
| 178 | BE8309    | -----------------------I-S------------------------ |
| 269 | HC-J4.83  | -----------------------S-T------------------------ |
| 270 | HC-J4.91  | -----------------------S-T------------------------ |
| 271 | HCV-CHINA | -----------------------S-T------------------------ |
| 272 | HCV-JTA   | -----------------------S-T------------------------ |
| 273 | HCV-JTB   | -----------------------S-T------------------------ |
| 274 | HCV-BK    | -----------------------S-T------------------------ |
| 275 | HCV-JK1   | -----------------------S----------------------A-- |
| 276 | HCV-T     | --------------M--------S-T------------------------ |
| 277 | HC-J6     | -----A-----------AV-S-T---------------V--T------- |
| 278 | HC-J8     | -----AA-------------V---T------------------V------ |

| SEQ ID NO: | | 1351                                                   1400 |
|---|---|---|
| 265 | HCV-1     | PPGSVTVPHPNIEEVALSTTGEIPFYGKAIPLEVIKGGRHLIFCHSKKKC |
| 266 | HCV-H     | -------S----------------------------------------- |
| 267 | HC-J1     | ----I----A--------------------A------------------ |
| 268 | HCV-J     | ----I------------N-----------I-A----------------- |
| 178 | BE8309    | ------------------S----------I------------------- |
| 269 | HC-J4.83  | --------------IG--NN---------I-A----------------- |
| 270 | HC-J4.91  | --------------IG--NN---------I-A----------------- |
| 271 | HCV-CHINA | -----------------N-----------I-A-R--------------- |
| 272 | HCV-JTA   | -----------------N-------------A----------------- |
| 273 | HCV-JTB   | -----------------N-----------I------------------- |
| 274 | HCV-BK    | -----------------N-----------I-A-R--------------- |
| 275 | HCV-JK1   | -----------------PN-----------T------------------ |
| 276 | HCV-T     | ------------I---N------------I-T----------------- |
| 277 | HC-J6     | ---T---------GQE---------R----SY----------------- |
| 278 | HC-J8     | ---T--T--S-------GHE-----------AF---------------- |

| SEQ ID NO: | | 1401                                                   1450 |
|---|---|---|
| 265 | HCV-1     | DELAAKLVALGINAVAYYRGLDVSVIPTSGDVVVVATDALMTGYTGDFDS |
| 266 | HCV-H     | ---------------------------------S-------F------- |
| 267 | HC-J1     | -------V---------------------------------------- |
| 268 | HCV-J     | -------TG--L-----------------------------F------- |
| 178 | BE8309    | -------SGF-------------------------------F------- |
| 269 | HC-J4.83  | -------TG--L----------------PI---A-------F------- |
| 270 | HC-J4.91  | -------TG--L----------------PI-----------F------- |
| 271 | HCV-CHINA | -------SS--L----------------S------------F------- |
| 272 | HCV-JTA   | -------SG------------------------I--------------- |
| 273 | HCV-JTB   | -------SG--------------------------------------- |
| 274 | HCV-BK    | -------SG------------------------I--------------- |
| 275 | HCV-JK1   | -------S---V------------------------------------ |
| 276 | HCV-T     | -------S----H---------------A--N---------F------- |
| 277 | HC-J6     | -----A-RGM-L---------------Q-------------F------- |
| 278 | HC-J8     | -----A-RGM-V---------------Q-------------------- |

FIGURE 6B

| SEQ ID NO: | | | |
|---|---|---|---|
| | | 1451 | 1465 |
| 265 | HCV-1 | VIDCNTCVTQTVDFS | |
| 266 | HCV-H | --------------- | |
| 267 | HC-J1 | --------------- | |
| 268 | HCV-J | --------------- | |
| 178 | BE8309 | --------------- | |
| 269 | HC-J4.83 | --------------- | |
| 270 | HC-J4.91 | --------------- | |
| 271 | HCV-CHINA | --------------- | |
| 272 | HCV-JTA | --------------- | |
| 273 | HCV-JTB | --------------- | |
| 274 | HCV-BK | --------------- | |
| 275 | HCV-JK1 | --------------- | |
| 276 | HCV-T | --------------- | |
| 277 | HC-J6 | -----VA---V---- | |
| 278 | HC-J8 | -----VA-S-I---- | |

FIGURE 6C

IMMUNODOMINANT HUMAN T-CELL EPITOPES OF HEPATITIS C VIRUS

The present application is 371 U.S. national phase filing of PCT/EP94/03555, filed Oct. 28, 1994, which claims benefit of EP 93402718.6, filed Nov. 4, 1993.

The present invention describes immunodominant hepatitis C virus T cell epitopes useful in hepatitis C prophylactic and therapeutic vaccines, derived from the HCV core, E1, E2 end NS3 proteins.

TECHNICAL FIELD OF THE INVENTION

The present invention relates to the production of novel synthetic immunogens related to the hepatitis C virus core, E1, E2 and NS3 regions and to the use thereof in the production of vaccines, therapeutic agents and the like. More specifically, the present invention relates to polypeptide compositions containing HCV core, E1, E2 and NS3 T cell determinants.

BACKGROUND OF THE INVENTION

In the few years since its discovery, Hepatitis C virus (HCV) has been shown to be a major cause of acute and chronic liver disease. HCV is a single-stranded RNA virus with a genome of approximately 9400 nucleotides that consists of a 5' untranslated region (5'UR) of 341 nucleotides which precedes a single large open reading frame encoding a precursor polyprotein of about 3010 amino acids (Kato et al., 1990). The genetic organization of the viral genome is related to that of flavi- and pestiviruses, with the putative structural proteins located in the N-terminal region and a variety of non structural proteins located at the C-terminal end of the polyprotein. The structural proteins are the core protein (C, amino acids 1–191) followed by the putative envelope proteins E1 (amino acids 192–383) and E2/NS1 (amino acids 384–746). The terms E2 and NS1 are often used interchangeably. Another form of E2 is composed of amino acids 384 to 809 and a third form is associated with NS2. The non structural proteins are NS2, NS3, NS4 and NS5, of which at least NS4 and NS5 have been shown to be further processed into NS4A, NS4B, NS5A, and NS5B.

Structural analysis of HCV genomes revealed the existence of different genotypes that have been classified into types and subtypes (Stuyver et al., 1993). The sequence diversities are distributed along the whole genome including the 5' untranslated region. The highest sequence variability has been observed in the NS2 and 3' untranslated regions, and in the putative envelope regions encoding the E1 and E2 proteins. The core, NS3, and certain regions of the NS4 proteins displayed markedly less diversity (Okamoto et al., 1992).

HCV Humoral Response

Soon after the discovery of HCV, immunoassays for the detection of circulating antibodies against HCV proteins became widely available. These tools have led to an explosive increase of the knowledge in the field of the human humoral immune response to HCV in different conditions. Once it was demonstrated that HCV was the major cause of posttransfusional non-A, non-B hepatitis, the search for antibodies to HCV was added to the safety screening panel of blood products. This procedure not only increased the safety of blood transfusions but also enhanced the knowledge of the epidemiology of the virus. The fact that HCV is responsible for a large proportion of chronic hepatic infections in which blood transfusion or parenteral inoculation are excluded remains a major challenge for further epidemiological studies. The widespread use of the assays for the detection of antibodies to HCV has also led to the recognition of the regions with humoral antigenicity of the virus. The relationship between the kinetics and magnitude of the humoral immune response to the different proteins of HCV and the course and outcome of the disease remains to be established.

HCV T Cell Epitopes

The immune response to viral antigens is almost entirely T cell dependent. T cells are required both for antibody production and for some cytotoxic reactions. HCV-encoded proteins are immunogenic not only at the B cell level, but also at the T cell level.

Studies describing the cellular immune response to HCV are scarce. Lin et al. (1993) describe candidate T cell epitopes within absolutely conserved regions of HCV gene obtained by means of a computer search revealing a large number of potential T cell epitopes. It has also been reported that peripheral blood cell monocytes (PBMC) from HCV-infected individuals proliferate in response to HCV recombinant proteins and that peripheral responses to core protein correlate with a benign course of infection (Botarelli et al., 1993). In the liver of patients with chronic HCV infection HCV-specific, HLA class I-restricted cytotoxic T lymphocytes (CTL) have been identified and cloned that recognize epitopes in E1 and NS2 proteins. These investigators have mainly focused on obtaining T cell clones from individual patients, and on the localization of the immunoreactive domain for the single CTL clones. Such studies led to the discovery of the epitope ASRCWVAM (aa 235–242) (SEQ ID NO:167) (in the aminoterminal part of the E1 protein, and of the epitope LMALTLSPYYKRY (aa 826–838) (SEQ ID NO:168) from the NS2 region (Koziel et al., 1992). In patients with chronic HCV hepatitis intrahepatic $CD4^+$ T cells which specifically recognized the NS4 protein of HCV were observed. The clonotype of these T lymphocytes was not detectable in the PBMC from these subjects (Minutello et al., 1993). These studies demonstrate that in patients with HCV hepatitis, HCV-specific T lymphocytes can be isolated from the infected liver and the peripheral blood. Their role in the pathogenesis of the liver damage in HCV hepatitis and their relevance for the clearance or persistence of the virus remains to be established.

Although neutralization of certain viral infections is possible by humoral immunity only, most microbiological agents can only be cleared from the host with the aid of cellular immunity. Even when the neutralizing capacity of circulating antibodies is established in certain infections, T helper cell activity is generally required to allow B cells to produce the required levels of circulating antibodies, for achievement of neutralization and clearance of the infectious agent. However, certain infectious agents can only be neutralized by means of cellular immunity.

In the case of hepatitis C virus, it can be anticipated that T cell immunity may be required for clearance of the virus, since most patients enter into a chronic course of the disease, and since most patients infected with HCV have developed humoral immunity to most of the HCV antigens which can be employed for diagnosis of HCV infection, as described in patent applications no. EP-A-0 318 216, EP-A-0 388 232, EP-A-0 442 394, EP-A-0 484 787, EP-A-0 489 968. However, most of the antibody-positive patients have not been able to clear the virus from the circulation since they remain HCV-PCR positive and, consequently, the detected antibodies have not been protective neither sufficient to neutralize the virus. Possibly, antibodies to other epitopes which are currently not included in HCV diagnostic assays may be capable of neutralizing HCV infection. Such epitopes may be located on the viral membrane proteins E1 and E2, but protection against a wide range of different HCV species may be hampered by the hypervariability of HCV envelope regions.

The aim of the present invention is to provide T cell stimulating polypeptides and peptides derived from the HCV structural and NS3 regions.

Another aim of the present invention is to provide T cell stimulating polypeptides and peptides as defined above for use in the preparation of an HCV immunogenic composition.

Another aim of the present invention is to provide T cell stimulating peptides or polypeptides derived from the core region, the E1 region, the E2 region, or the NS3 region of HCV.

Another aim of the present invention is to provide T cell stimulating peptides or polypeptides from HCV as specified above which contain either T helper cell (CD4$^+$) epitopes and/or CTL (CD8$^+$) epitopes.

Another aim of the present invention is to provide recombinant polypeptides containing the same.

Another aim of the present invention is to provide therapeutic as well as prophylactic compositions comprising the same.

Another aim of the present invention is to provide prophylactic or therapeutic compositions comprising said polypeptides.

Another aim of the present invention is to provide methods for preventing or treating HCV infection based on the same.

DETAILED DESCRIPTION OF THE INVENTION

More particularly, the present invention describes a polypeptide of about 8 to about 100 amino acids comprising or consisting of at least 8 contiguous amino acids selected from the core and/or E1 and/or E2 and/or NS3 regions of the HCV polyprotein, with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes. Such polypeptides and peptides are for instance mentioned in EP-A-0 318 216, EP-A-0 388 232, EP-A-0 442 394, EP-A-0 484 787, EP-A-0 489 968, WO 92/22571, Lesniewski et al., 1993; Weiner et al., 1993; etc. The content of these applications is hereby incorporated by reference.

Even more particularly, the present invention relates to the use of polypeptides as described above for the preparation of an HCV immunogenic composition.

The expression "HCV immunogenic composition" refers to the prevention or treatment of HCV infection.

Preferentially said polypeptide is different from RALAHGVRVLEDG, RMAWDMM, PTDCFRKHP, YPYRLWH, GKSTKVP, PSVMT, IGTVLDQAE, AVAYYR, ASRCWVAM and TGDFDSVID (SEQ ID NOs: 169–176, 167 and 177, respectively).

The term "HCV polyprotein" refers to any HCV polyprotein disclosed in the art and is reviewed in Okamoto et al. 1992, such as the type 1a HCV polyprotein of the HC-J1 isolate, such as the HCV polyprotein of the type 2a HC-J6 isolate (Okamoto et al., 1991), the type 2b HC-J8 isolate (Okamoto et al., 1992). According to this definition, any variation already observed within any of the described regions of HCV is to be considered as part of a the definition of HCV polyprotein. For example, numerous types and subtypes are disclosed in Bukh et al., 1993, Bukh et al., 1994, Stuyver et al., 1993a, Stuyver et al., 1993b, Stuyver et al., 1994a, Stuyver et al., 1994c. Moreover, conservative substitutions may be introduced in these HCV polyproteins according to the present invention. The term "conservative substitution" as used herein denotes that one amino acid residue has been replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that antibodies raised to such a polypeptide also immunoreact with the corresponding polypeptide having the unsubstituted amino acid.

The term "antibody" refers to a molecule that is a member of a family of glycosylated proteins called immunoglobulins, which can specifically combine with an antigen.

The word "antigen" has been used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

The term "corresponds" in its various grammatical forms as used in relation to peptide sequences means the peptide described plus or minus up to three amino acid residues at either or both of the amino- and carboxy-termini and containing only conservative substitutions in particular amino acid residues along the polypeptide sequence.

"Epitope" refers to that portion of a molecule that is specifically bound by a T cell antigen receptor or an antibody combining site.

The term "immunoreact" in its various forms means binding between an antigen as a ligand and a molecule containing an antibody combining site such as a Fab portion of a whole antibody.

The expression "T-cell stimulating epitope" or T cell epitope according to the present invention refers to an epitope capable of stimulating T-cells. A T-cell stimulating epitope may be selected according to the present invention by monitoring the lymphoproliferative response (as detailed in the Examples section) towards polypeptides containing in their amino acid sequence at least 8 contiguous amino acids derived from the core, and/or the E1, and/or the E2, and/or the NS3 region of any HCV polyprotein. Said lymphoproliferative response may be measured by either a T-helper assay comprising in vitro stimulation of PMBC from patients with hepatitis C infection with varying concentrations of peptides to be tested for T-cell stimulating activity and counting the amount of radiolabelled thymidine uptake.

Said lymphoproliferative response may also be measured by means of a CTL assay measuring the lytic activity of cytotoxic cells using $^{51}$Cr release. Proliferation is considered positive when the stimulation index (mean cpm of antigen-stimulated cultures/mean cpm of controle cultures) is more than 1, preferably more than 2, most preferably more than 3. In order to select a T-cell stimulating epitope containing peptide, the results of these lymphoproliferative assays are compared and immunodominant T-cell epitope containing polypeptides or peptides are selected. The results of the lymphoproliferative assays against certain peptides may also be compared between clinical non-responders and responders to Interferon-a treatment. The lymphoproliferative response towards a series of synthetic, overlapping peptides representing the HCV core, E1 and E2/NS1 sequences and a recombinant NS3 protein was monitored in 32 patients with chronic HCV hepatitis as disclosed in the Examples section of the present invention.

Consequently, the present invention represents a selection of immunodominant T cell epitopes from a series of antigens covering the core, E1, E2 and NS3 regions. From the examples section, it is clear that not only peptide pools 2 and 3 and peptides NS1–5* and NS1–7* but also, pools 4, 5, 6 and 9 and NS3, reacted frequently with hepatitis C patients (Table 4) while infrequent reactivity could only be observed in normal controls with the same polypeptides (Table 5). It is obvious from the data presented in Table 4 that large areas of the HCV structural region, such as pool 1 (amino acids 5–72) and pools 7 and 8 (amino acids 427–578) show little reactivity with T cells of infected patients, even with patients with a response to IFN-α treatment. Most strikingly, however, it was found that while the dominant B cell response to hepatitis C in general is located to the core aminoterminus (see also Table 3), the dominant T cell response is directed towards the core carboxyterminal region (see Table 4). In the literature, ample evidence can be found that the core carboxyterminal half contains little or no B cell-reactive epitopes. Based on the present invention, it may be desirable to yet include for instance parts of the core carboxyterminal region (spanning amino acids 73–176) into prophylactic or therapeutic vaccine compositions.

The words "polypeptide" and "peptide" are used interchangeably throughout the specification and designate a linear series of amino acids connected one to the other by peptide bonds between the alpha-amino and carboxy groups of adjacent amino acids. Polypeptides can be a variety of lengths, either in their natural (uncharged) forms or in forms which are salts, and either free of modifications such as glycosylation, side chain oxidation, or phosphorylation or containing these modifications. It is well understod in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acids side chains, such as glycosyl units, lipids, or inorganic ions such as phosphates, as well as modifications relating to chemical conversions of the chains, such as oxidation of sulfhydryl groups. Thus, "polypeptide" or its equivalent terms is intended to include the appropriate amino acid sequence referenced, subject to those of the foregoing modifications which do not destroy its functionality.

The polypeptides of the invention, and particularly the shorter peptides amongst them, can be prepared by classical chemical synthesis. The synthesis can be carried out in homogeneous solution or in solid phase.

For instance, the synthesis technique in homogeneous solution which can be used is the one described by Houben-weyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can also be prepared by means of recombinant DNA techniques as documented below.

The polypeptides or peptides according to the present invention may, as specified above, vary in lenght. The peptides according to the invention contain at least 3, preferably at least 4, 5, 6, 7, most preferably however al least 8 contiguous HCV amino acids. Preferred lengths of peptides are 6, 7, 8, 9, 10, or more (for instance 15, 20, 25, 30, etc.) amino acid residues. The polypeptides of the present invention may be up till 150 to 200 amino acids long, but are preferably less than 100 amino acids.

Further contemplated according to the present invention is a polypeptide as defined above, comprising or consisting of at least 8 contiguous amino acids selected from the region comprised between amino acids 73 to 176 in the core region of HCV, between amino acids 192 to 234 and 243 to 392 of the E1 region of HCV, between amino acids 397 and 428 and amino acids 571 to 638 of the E2 region of HCV, or between amino acids 1188 to 1463 of the NS3 region of HCV, and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The expression "comprised between amino acids X to Y" includes the amino acid X and the amino acid Y.

The numbering of the HCV polyprotein used in the present invention refers to the numbering as used for the HCV-J isolate according to Kato et al., 1990. All other HCV isolates known in the art may be aligned to this sequence to obtain the referred HCV polyprotein numbering for each individual HCV isolate. For instance, it is known that type 2 isolates can contain 4 extra codons/amino acids in their E2 sequence, while type 3 sequences have an insertion of 2 amino acids compared to type 1 sequences.

The Examples section of the present invention describes T cell epitopes in, amongst other regions of the HCV structural region: the carboxyterminal region of the core protein (aa 73–176), amino acids 192 to 383 of the E1 region, amino acids 397 and 428 and amino acids 571 to 638 of the E2 region, amino acids 1188 to 1463 of the NS3 region. Groups of peptides covering parts of the structural proteins core and E2, and covering the complete E1 protein, as well as a recombinant NS3 protein have been studied. Peptides were tested as group 1 (aa 5–80), group 2 (aa 73–140), group 3 (aa 133–200), group 4 (aa 193–260), group 5 (aa 253–332), group 6 (325–392), group 7 (aa 427–494), group 8 (aa 487–578), and group 9 (aa 571–638) as shown in Table 1.

Recombinant NS3 encompassed amino acids 1188 to 1463 of the isolate IG8309, belonging to the 1b subtype group of HCV.

The T cell response to the group 3 peptides, as well as to the individual peptides NS1–7* and NS1–5* shows a statistically relevant correlation with a decrease in alanine aminotransferase (ALT) and viral RNA levels, which are generally accepted to indicate a more benign course of the disease. A correlation between response to 'a recombinant HCV core protein' and a more benign course of the disease has been described by Botarelli et al. 1993. However, no epitopes have been mapped nor has the sequence and exact position of the recombinant core protein been described in Botarelli et al., 1993. In the present invention, a similar T cell response has been observed to the group 2 peptides (aa 73–140) both in patients responding to IFN-α and in patients non-responding to the same. On the contrary, T cell reactivity to the group 3 peptides (aa 133–200) was observed in responders to interferon-α and differed from the T cell reactivity observed to this region in non-responders to IFN-α treatment. Furthermore, after investigating the reactivity of individual peptides from groups 2 and 3, this specific response correlating with a more benign course of HCV infection, could be further mapped to specific individual peptides termed CORE 23, CORE 25, and CORE 27. Peptide CORE 19, belonging to the group 2 peptides, was also recognized by some of the responders to IFN-α treatment (see FIG. 1).

The present invention thus also contemplates a polypeptide as defined above comprising or consisting of at least 8 to about 104 contiguous amino acids selected from the region comprised between amino acids 73 to 176, more particularly comprising or consisting of 8 to about 68 contiguous amino acids selected from the region comprised between amino acids 109 to 176 in the core region of HCV characterized by the following sequences:

$NH_2$-$GX_1X_2WX_3X_4PGX_5PWPLYX_6NX_7GX_8GX_9$
$AGWLLSPRGSRPX_{10}WGX_{11}$-$X_{12}DPRX_{13}$
$X_{14}SRNX_{15}GX_{16}VIDTX_{17}TCGX_{18}ADLX_{19}X_{20}$
$YIPX_{21}X_{22}G$-$X_{23}PX_{24}GGX_{25}X_{26}X_{27}X_{28}LX_{29}$
$HGVRX_{30}$ $X_{31}X_{32}DGX_{33}NX_{34}X_{35}TGN$-$X_{36}$
PGCSFSI-COOH (SEQ ID NO 58, spanning positions 73 to 176)

wherein $X_1$ represents R or K, $X_2$ represents A, S or T, $X_3$ represents A or G, $X_4$ represents Q, K or R, $X_2$ represents Y or H, $X_6$ represents G or A, $X_7$ represents E or K, $X_8$ represents C, M or L, $X_9$ represents W or L, $X_{10}$ represents S, N, T, D or H, $X_{11}$ represents P or Q, $X_{12}$ represents N or T, $X_{13}$ represents R or H, $X_{14}$ represents R or K, $X_{15}$ represents L or V or F, $X_{16}$ represents K or R, $X_{17}$ represents L or I, $X_{18}$ represents F or L, $X_{19}$ represents M or I, $X_{20}$ represents G or E, $X_{21}$ represents L or V or I, $X_{22}$ represents V or L, $X_{23}$ represents A or G, $X_{24}$ represents L, V, or I, $X_{25}$ represents A or V, $X_{26}$ represents A or S, $X_{27}$ represents R or A, $X_{28}$ represents A or T or E, $X_{29}$ represents A or E, $X_{30}$ represents V or A or L, $X_{31}$ represents L or V or I, $X_{32}$ represents E or G, $X_{33}$ represents V or I, and $X_{34}$ represents F or Y, $X_{35}$ represents A or P, $X_{36}$ represents L or I, and, $NH_2$-$X_{11}X_{12}DPRX_{13}X_{14}SRNX_{15}GX_{16}VIDTX_{17}$
$TCGX_{18}ADLX_{19}X_{20}YIPX_{21}X_{22}G$-$X_{23}PX_{24}$
$GGX_{25}X_{26}GX_{27}X_{28}LX_{29}HGVRX_{30}X_{31}X_{32}DGX_{33}$
$NX_{34}X_{35}TGN$-$X_{36}PGCSFSI$-COOH (SEQ ID NO 48, spanning positions 109 to 176)

wherein said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes, $X_{11}$ to $X_{16}$ having the meanings above-mentioned.

It is to be underlined that in the present text, $X_1$, $X_2$, $X_3$, $X_4$, $X_5$, $X_6$, $X_7$, $X_8$, $X_9$, $X_{10}$, $X_{11}$, $X_{12}$, X13, $X_{14}$, $X_{15}$, $X_{16}$, $X_{17}$, $X_{18}$, $X_{19}$, $X_{20}$, $X_{21}$, $X_{22}$, $X_{23}$, $X_{24}$, $X_{25}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$ have always the same meaning as the one which is defined for SEQ ID NO 58.

Preferentially said polypeptide is different from RALAH-GVRVLEDG (SEQ ID NO:169) spanning positions 149 to 161 of the core region of HCV.

More particularly, the present invention relates to a polypeptide as defined above comprising or consisting of at least 8 to about 76 contiguous amino acids selected from the regions comprised between amino acids 73 to 148, or comprising or consisting of 8 to about 15 contiguous amino acids selected from the region comprised between amino acids 162 to 176, or comprising or consisting of 8 to about 16 contiguous amino acids selected from the region comprised between amino acids 129 to 144 in the core region of HCV characterized by the following sequences:

$NH_2$-$GX_1X_2WX_3X_4PGX_5PWPLYX_6NX_7GX_8GX_9$
$AGWLLSPRGSRPX_{10}WGX_{11}$-$X_{12}DPRX_{13}X_{14}$
$SRNX_{15}GX_{16}VIDTX_{17}TCGX_{18}ADLX_{19}X_{20}YIPX_{21}$
$X_{22}G$-$X_{23}PX_{24}GGX_{25}X_{26}$-COOH (SEQ ID NO 59, spanning positions 73 to 148), $NH_2$-$X_{33}NX_{34}X_{35}$
$TGNX_{36}PGCSFSI$-COOH (SEQ ID NO 60, spanning positions 162 to 176), and, $NH_2GX_{28}ADLX_{19}X_{20}YIPX_{21}X_{22}GX_{23}PX_{24}$ (SEQ ID NO 61, spanning positions 129 to 149). Particularly preferred is peptide ALMGYIPLV (SEQ ID NO 163).

Even more particularly, the present invention relates to the use of polypeptides as described above for the preparation of an HCV immunogenic composition.

The present invention thus also contemplates a polypeptide as defined above comprising or consisting of at least 8 to about 44 contiguous amino acids selected from the region comprised between amino acid positions 133 to 176 of the core region of HCV:

$NH_2$-$LX_{19}X_{21}YIPX_{21}X_{22}GX_{23}PX_{24}GGX_{25}X_{26}X_{27}$
$X_{28}LX_{29}HGVR_{30}X_{31}X_{32}DGX_{33}NX_{34}X_{35}TGN$-$X_{36}$
PGCSFSI-COOH (SEQ ID NO 50), and more particularly selected from peptide LMGYIPLVGAPLG-GAARALAHGVRVLEDGVNYATGNLPGCSFSI (SEQ ID NO 67), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 157 to 176 of the core region of HCV:

$NH_2$-$X_{30}X_{31}X_{32}DGX_{33}NX_{34}X_{35}TGNX_{36}PGCSFSI$-COOH (SEQ ID NO 51), and more particularly selected from VLEDGVNYATGN-LPGCSFSI (SEQ ID NO 13=peptide CORE 27) or VLEDIVNYATGNLPGCSFSI (SEQ ID NO 73), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes. Preferentially said peptides are further chosen from the following list of peptides:

$NH_2$-$GX_{33}NX_{34}X_{35}TGNX_{36}$-COOH (SEQ ID NO 74),
$NH_2$-$X_{33}NX_{34}X_{35}TGNX_{36}$-COOH (SEQ ID NO 75),
$NH_2$-$NX_{36}$PGCSFSI-COOH (SEQ ID NO 76) and
$NH_2$-$X_{36}$PGCSFSI-COOH (SEQ ID NO 77). Particularly preferred peptides include : GVNYATGNL (SEQ ID NO 78), GVNYATGNL (SEQ ID NO 79), NLPGCSFSI (SEQ ID NO 80) and LPGCSFSI (SEQ ID NO 81).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 145 to 164 of the core region of HCV:

$NH_2$-$GGX_{25}X_{26}X_{27}X_{28}LX_{29}HGVRX_{30}X_{31}X_{32}DGX_{33}NX_{34}$-COOH (SEQ ID NO 52), and more particularly selected from GGAARALAHGVRVLEDGVNY (SEQ ID NO 12=peptide CORE 25) or GGVAARALAHGVRVLEDGVNY (SEQ ID NO 118), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes. Prefererntially said peptides according to the invention are chosen from the following list of peptides:

$NH_2$-$X_{28}LX_{29}HGVRX_{30}X_{31}$-COOH (SEQ ID NO 82),
$NH_2$-$LX_{29}HGVR_{30}X_{31}$-COOH (SEQ ID NO 83),
$NH_2$-$GVRX_{30}X_{31}X_{32}DGX_{33}$-COOH (SEQ ID NO 84),
$NH_2$-$VRX_{30}X_{31}X_{32}DGX_{33}$-COOH (SEQ ID NO 85),
$NH_2$-$RX_{30}X_{31}X_{32}DGX_{33}NX_{34}$-COOH (SEQ ID NO 86), and
$NH_2$-$X_{30}X_{31}X_{32}DGX_{33}NX_{34}$-COOH (SEQ ID NO 87).

Particularly preferred peptides include: ALAHGVRVL (SEQ ID NO 88), LAHGVRVL (SEQ ID NO 89), VRVLEDGV (SEQ ID NO 90), RVLEDGV (SEQ ID NO 91), VLEDGVNY (SEQ ID NO 92), and LEDGVNY (SEQ ID NO 93).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 133 to 152 of the core region of HCV:

NH2-$LX_{19}X_{21}YIPX_{21}X_{22}GX_{23}PX_{24}GGX_{25}X_{26}X_{27}X_{28}LX_{29}$-COOH (SEQ ID NO 53), and more particularly selected from LMGYIPLVGAPLGGAARALA (SEQ ID NO 11=peptide CORE 23), and provided that said polypeptide is different from any known T cell epitope containing HCV peptide or polypeptide described from any of the above-mentioned regions. The latter known HCV polypeptides and peptides are described for screening for B cell epitopes. Preferentially said peptides according to the invention are chosen from the following list of peptides:

$NH_2$-$LX_{19}X_{20}YIPX_{21}X_{22}GX_{23}PX_{24}GGX_{25}$-COOH (SEQ ID NO 62),
$NH_2$-$X_{19}X_{20}YIPX_{21}X_{22}GX_{23}PX_{24}GGX_{25}$-COOH (SEQ ID NO 63),
$NH_2$-$YIPX_{21}X_{22}GX_{23}PX_{24}$-COOH (SEQ ID NO 64),
$NH_2$-$IPX_{21}X_{22}GX_{23}PX_{24}$-COOH (SEQ ID NO 65),
$NH_2$-$X_{21}X_{22}GX_{23}PX_{24}GGX_{25}$-COOH (SEQ ID NO 66), and
NH2-$X_{22}GX_{23}PX_{24}GGX_{25}$-COOH (SEQ ID NO 68).
Prefered peptides chosen from this list include:
LMGYIPLV (SEQ ID NO 69), MGYIPLV (SEQ ID NO 70), YIPLVGAPL (SEQ ID NO 71), IPLVGAPL (SEQ ID NO 72), LVGAPLGGA (SEQ ID NO 94), and VGAPLGGA (SEQ ID NO 95).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 109 to 128 of the core region of HCV:

$NH_2$-$X_{11}X_{12}DPRX_{13}X_{14}SRNX_{15}GX_{16}VIDTX_{17}TC$-COOH (SEQ ID NO 54), and more particularly selected from PTDPRRRSRNLGKVIDTLTC (SEQ ID NO 9=peptide CORE 19), and provided that said polypeptide is different from any known T cell epitope containing HCV peptide or polypeptide described from any of the above-mentioned regions. The latter known HCV polypeptides and peptides are described for screening for B cell epitopes. Preferentially said peptides according to the present invention are chosen from the following peptides:

$NH_2$-$NX_{15}GX_{16}VIDTX_{17}$-COOH (SEQ ID NO 96) or
$NH_2$-$X_{15}GX_{16}VIDTX_{17}$-COOH (SEQ ID NO 97). Preferential peptides are for instance NLGKVIDTL (SEQ ID NO 98) and LGKVIDTL (SEQ ID NO 117).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 73 to 92 of the core region of HCV:

$NH_2$-$GX_1X_2WX_3X_4PGX_5PWPLYX_6NX_7GX_8G$-COOH (SEQ ID NO 99), and more particularly selected from GRTWAQPGYPWPLYGNEGCG (SEQ ID NO 6=peptide CORE 13), and provided that said polypeptide is different from any known T cell epitope containing HCV peptide or polypeptide described from any of the above-mentioned regions. The latter known HCV polypeptides and peptides are described for screening for B cell epitopes. Preferred peptides according to the present invention include for instance peptides further selected from:

$NH_2$-$X_2WX_3X_4PGX_5PW$-COOH (SEQ ID NO 100) and
$NH_2$-$WX_3X_4PGX_5PW$-COOH (SEQ ID NO 101), such as the peptides: TWAQPGYPW (SEQ ID NO 102) and WAQPGYPW (SEQ ID NO 103).

Even more particularly, the present invention relates to the use of polypeptides as described above for the preparation of an HCV immunogenic composition.

The present invention thus also contemplates a polypeptide as defined above comprising or consisting of at least 8 contiguous amino acids selected from the region comprised between amino acids 192 to 234 and 243 to 392 of HCV, more particularly selected from the region comprised between amino acids 192 to 234 and 243 to 383 in the E1 region of HCV characterized by the following sequences:

$NH_2$-YQVRNSTGLYHVTNDCPNSSIVYEAHDAI LHTPGCVPCVREGN (SEQ ID NO 164, spanning positions 192 to 234), and, TPTVATTRDGKLPATQLR RHIDLLVGSATLCSALYVGDLCGSVQLFTFSP RRHWTTQGCNCSIYPGHITGHRMAWDMMMN WSPTAALVMAQLLRIPQAILDMIAGAHWGVLA GIAYFSMVGNWAKVLVVLLLFAGVDAETIVSG GQA-COOH (SEQ ID NO 104, spanning positions 243 to 392), or any variant to this sequence derived from another type of HCV as depicted in FIG. 4, wherein said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

With said peptide being preferentially different from RMAWDMM (SEQ ID NO:170) spanning positions 317 to 323 and ASRCWVAM (SEQ ID NO:167) spanning positions 235–242.

Even more particularly, the present invention relates to the use of polypeptides as described above for the preparation of an HCV immunogenic composition.

The present invention thus also contemplates a polypeptide as defined above comprising or consisting of at least 8 to about 68 contiguous amino acids selected from the region comprised between amino acids 193 to 234 and 243 to 260 in the E1 region of HCV characterized by the following sequence:

QVRNSTGLYHVTNDCPNSSIVYEAHDAI-LHTPGCVPCVREGN (SEQ ID NO 165, spanning positions 193 to 234), and, TPTVATTRDGKLPATQLR (SEQ ID NO 105, spanning positions 243 to 260), or any variant to this sequence derived from another type of HCV as depicted in FIG. 4, wherein said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Particularly preferred peptides according to the invention include:

QVRNSTGLYHVTNDCPNSSI (SEQ ID NO 16),
NDCPNSSIVYEAHDAILHTP (SEQ ID NO 17),
HDAILHTPGCVPCVREGNVS (SEQ ID NO 18),
CVREGNVSRCWVAMTPTVAT (SEQ ID NO 19), and,
AMTPTVATRDGKLPPATQLRR (SEQ ID NO 20).

Even more particularly, the present invention relates to the use of polypeptides as described above for the preparation of an HCV immunogenic composition.

The present invention thus also contemplates a polypeptide as defined above comprising or consisting of at least 8 to about 80 contiguous amino acids selected from the region comprised between amino acids 253 to 332 in the E1 region of HCV characterized by the following sequence:

NH2-LPATQLRRHIDLLVGSATLCSALYVGDLCG SVQLFTFSPRRHWTTQGCNCSIYPGHITGHRM AWDMMMNWSPTAAL-COOH (SEQ ID NO 106), or any variant to this sequence derived from another type of HCV as depicted in FIG. 4, wherein said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Particularly preferred peptides according to the invention include:

LPATQLRRHIDLLVGSATLC (SEQ ID NO 21),
LVGSATLCSALYVGDLCGSV (SEQ ID NO 22),
QLFTFSPRRHWTTQGCNCSI (SEQ ID NO 23),
TQGCNCSIYPGHITGHRMAW (SEQ ID NO 24), and,
ITGHRMAWDMMMNWSPTAAL (SEQ ID NO 25).

Even more particularly, the present invention relates to the use of polypeptides as described above for the preparation of an HCV immunogenic composition.

The present invention thus also contemplates a polypeptide as defined above comprising or consisting of at least 8 to about 68 contiguous amino acids selected from the region comprised between amino acids 325 to 392 in the E1 region of HCV characterized by the following sequence:

$NH_2$-MNWSPTAALVMAQLLRIPQAILDMIAGA HWGVLAGIAYFSMVGNWAKVLVVLLLFAGVD AETIVSGGQA-COOH (SEQ ID NO 107), or any variant to this sequence derived from another type of HCV as depicted in FIG. 4, wherein said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Particularly preferred peptides according to the present invention include:

NWSPTAALVMAQLLRIPQAI (SEQ ID NO 26),
LLRIPQAILDMIAGAHWGVL (SEQ ID NO 27),
AGAHWGVLAGIAYFSMVGNW (SEQ ID NO 28), and,
VVLLLFAGVDAETIVSGGQA (SEQ ID NO 29).

Even more particularly, the present invention relates to the use of polypeptides as described above for the preparation of an HCV immunogenic composition.

The present invention also contemplates a polypeptide as defined above comprising or consisting of at least 8 to about 32 contiguous amino acids selected from the region between amino acids 397 to 428, or comprising or consisting of at least 8 to about 68 contiguous amino acids selected from the region between amino acids 571 to 638 in the E2 region of HCV characterized by the following sequences:

$NH_2$-$X_{37}X_{38}X_{39}X_{40}X_{41}X_{42}X_{43}X_{44}X_{45}GX_{46}X_{47}$ $QX_{48}X_{49}X_{50}LX_{51}NX_{52}NGSWHX_{53}NX_{54}$TALN-COOH (SEQ ID NO 49, spanning positions 397 to 428, see FIG. 4), and, $NH_2$-$IX_{55}X_{56}X_{57}X_{58}NX_{59}X_{60}Z_1Z_2LX_{61}$CPTDCF $RKX_{62}PX_{63}X_{64}TYX_{65}X_{66}CGX_{67}GPX_{68}X_{69}$-TP $RCX_{70}X_{71}$DYPYRLWHYPCT$X_{72}NX_{73}X_{74}X_{75}$ FKX$_{76}$RMX$_{77}$VGGVEH-COOH (SEQ ID NO 108, spanning positions 571 to 638, see FIG. 5).

wherein X$_{37}$ represents S, A, Q, L, N, Y, R, Y or H, X$_{38}$ represents G, S, T, A or R, X$_{39}$ represents F, I, L, or V; X$_{40}$ represents V, A, or T; X$_{41}$ represents S, D or G; X$_{42}$ represents L, I, W, F, or M; X$_{43}$ represents L, I or F, X$_{44}$ represents A, T, D or S; X$_{45}$ represents P, Q, S, R, L, I or T; X$_{46}$ represents A, P, or S; X47 represents K, S, Q, A, or R; X$_{48}$ represents N, K, D, or R; X$_{49}$ represents V, I, or L; X$_{50}$ represents Q, S or Y; X$_{51}$ represents I or V; X$_{52}$ represents L or I; X$_{53}$ represents S or R; and X$_{54}$ represents T or S; X$_{55}$ represents G or R; X$_{56}$ represents G, A, or K, X$_{57}$ represents A, V, G, S, or D; X$_{58}$ represents G, F, or Y; X$_{59}$ represents N, H, R, L, A, or S; X$_{60}$ represents T or S; Z$_1$ represents no amino acids or represents M or I; Z$_2$ represents no amino acid or D; X$_{61}$ represents H, L, V, T, or I; X$_{62}$ represents H or Y; X$_{63}$ represents D or E; X$_{64}$ represents A or T; X$_{65}$ represents S, T, I, or L; X$_{66}$ represents R or K; X$_{76}$ represents S or A, X$_{68}$ represents W or L; X$_{69}$ represents I or L; X$_{70}$ represents L, M or I, X$_{71}$ represents V or I; X$_{72}$ represents I, V, F, or L; X$_{73}$ represents Y or F; X$_{74}$ represents T, S or A; X$_{75}$ represents I or V; X$_{76}$ represents I, V or A, X$_{77}$ represents Y or F, and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 397 to 416 of the E2 region of HCV:

NH$_2$-X$_{37}$X$_{38}$X$_{39}$X$_{40}$X$_{41}$X$_{42}$X$_{43}$X$_{44}$X$_{45}$GX$_{46}$X$_{47}$QX$_{48}$X$_{49}$X$_{50}$LX$_{51}$NX$_{54}$-COOH (SEQ ID NO 55), and more particularly selected from SGLVSLFTPGAKQ-NIQLINT (SEQ ID NO 46 or peptide NS1–7*), and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 409 to 428 of the E2 region of HCV:

NH$_2$-QX$_{48}$X$_{49}$X$_{50}$DLX$_{51}$NX$_{54}$NGSWHX$_{52}$NX$_{53}$TALN-COOH (SEQ ID NO 56) and more particularly selected from QNIQLINTNGSWHINSTALN (SEQ ID NO 47 or peptide NS1–5*), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes. Preferentially, the peptides according to the present invention are selected from the following list of peptides:

NH$_2$-X$_{50}$LX$_{51}$NX$_{54}$NGSW-COOH (SEQ ID NO 109),
NH$_2$-LX$_{51}$NX$_{54}$NGSW-COOH (SEQ ID NO 110),
NH$_2$-SWHX$_{52}$NX$_{53}$TAL-COOH (SEQ ID NO 111), and
NH$_2$-SWHX$_{52}$NX$_{53}$TAL-COOH (SEQ ID NO 112).

Prefered peptides include for instance: QLINTNGSW (SEQ ID NO 113), LINTNGSW (SEQ ID NO 114), SWHINSTAL (SEQ ID NO 115) and WHINSTAL (SEQ ID NO 116).

Even more particularly, the present invention relates the use of to polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 571 to 638 of the E2 region of HCV:

NH$_2$-IX$_{55}$X$_{56}$X$_{57}$X$_{58}$NX$_{59}$X$_{60}$Z$_1$Z$_2$LX$_{61}$CPTDCFR KX$_{62}$PX$_{63}$X$_{64}$TYX$_{65}$X$_{66}$CGX$_{67}$GPX$_{68}$X$_{69}$-TPRCX$_{70}$X$_{71}$DYPYRLWHYPCTX$_{72}$NX$_{73}$X$_{74}$X$_{75}$FKX$_{76}$RMX$_{77}$VGGVEH-COOH (SEQ ID NO 108), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Preferred peptides according to the invention are chosen from the following list of peptides:

X$_{60}$Z$_1$Z$_2$LX$_{61}$CPTDCF (SEQ ID NO 119),
FRKX$_{62}$PX$_{63}$X$_{64}$TY (SEQ ID NO 120),
X$_{66}$X$_{69}$-TPRCX$_{70}$X$_{71}$ (SEQ ID NO 121),
X$_{70}$X$_{71}$DYPYRL (SEQ ID NO 122),
X$_{71}$DYPYRLW (SEQ ID NO 123),
YPYRLWHY (SEQ ID NO 124),
LWHYPCTX$_{72}$ (SEQ ID NO 125),
X$_{72}$NX$_{73}$X$_{74}$X$_{75}$FKX$_{76}$ (SEQ ID NO 126),
X$_{73}$X$_{74}$X$_{75}$FKX$_{76}$RM (SEQ ID NO 127),
X$_{75}$FKX$_{76}$RMX$_{77}$V (SEQ ID NO 128),
X$_{76}$RMX$_{77}$VGGV (SEQ ID NO 129),
IX$_{55}$X$_{56}$X$_{57}$X$_{58}$NX$_{59}$X$_{60}$Z$_1$Z$_2$LX$_{61}$CPTDCFRKX$_{62}$P (SEQ ID NO 130),
TDCFRKX$_{62}$PX$_{63}$X$_{64}$TYX$_{65}$X$_{66}$CGX$_{67}$GPX$_{68}$ (SEQ ID NO 131),
X$_{65}$X$_{66}$CGX$_{67}$GPX$_{68}$X$_{69}$TPRCX$_{70}$X$_{71}$DYPYR (SEQ ID NO 132),
CX$_{70}$X$_{71}$DYPYRLWHYPCTX$_{72}$NX$_{73}$X$_{74}$X$_{75}$ (SEQ ID NO 133),
PCTX$_{72}$NX$_{73}$X$_{74}$X$_{75}$FKX$_{76}$RMX$_{77}$VGGVEH (SEQ ID NO 134).

More preferentially, the peptides according to the present invention are selected from the following list of peptides:

IGGAGNNTLHCPTDCFRKHP (SEQ ID NO 41),
TDCFRKHPDATYSRCGSGPW (SEQ ID NO 42),
SRCGSGPWITPRCLVDYPYR (SEQ ID NO 43),
CLVDYPYRLWHYPCTINYTI (SEQ ID NO 44), and,
PCTINYTIFKIRMYVGGVEH (SEQ ID NO 45).

With said peptides being preferentially different from PTDCFRKHP (SEQ ID NO: 171) spanning positions 582 to 590 and YPYRLWH (SEQ ID NO: 172) spanning positions 611 to 617.

Even more particularly, the present invention relates the use of to polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 1188 to 1463 of the NS3 region of HCV characterized by the following sequence:

NH$_2$-GVAKAVDFVPVESMETTMRSPVFTDNSSP PAVPQTFQVAHLHAPTGSGKSTKVPAAYAAQG YKVLVLNPSVAATLGFGAYMSKAHGVDPNIRT GVRTITTGAPITYSTYGKFLADGGCSGGAYDIII CDECHSIDSTSILGIGTVLDQAETAGARLVVLAT ATPPGSVTVPHPNIEEVALSSTGEIPFYGKAIPIE VIKGGRHLIFCHSKKKCDELAAKLSGFGINAVA YYRGLDVSVIPTSGDVVVVATDALMTGFTGDF DSVIDCNTCTQTVDFS-COOH (SEQ ID NO 57), or any variant of said sequence as can be deduced from FIG. 6, and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Preferentially said peptides are chosen from the following list of peptides:

VAKAVDFV (SEQ ID NO 135), VAKAVDFI (SEQ ID NO 136), VESMETTM (SEQ ID NO.137), AVPQT-FQV (SEQ ID NO 138), YAAQGYKV (SEQ ID NO 139), VLVLNPSVA (SEQ ID NO 140), YMSKAHGV (SEQ ID NO 141), IRTGVRTI (SEQ ID NO 142), YSTYGKFL (SEQ ID NO 143), ILGIGTVL (SEQ ID NO 144), VTVPHPNI (SEQ ID NO 145), IPFYGKAI (SEQ ID NO 146), FYGKAIPI (SEQ ID NO 147), VIKGGRHL (SEQ ID NO 148), IKGGRHLI (SEQ ID NO 149), FCHSKKKC (SEQ ID NO 150), CDE-LAAKL (SEQ ID NO 151), LAAKLSGFG (SEQ ID NO 152), SGFGINAV (SEQ ID NO 153), FGINAVAY (SEQ ID NO 154), YRGLDVSV (SEQ ID NO 155), VIPTSGDV (SEQ ID NO 156), IPTSGDVV (SEQ ID NO 157), VVVATDAL (SEQ ID NO 158), VVAT-DALM (SEQ ID NO 159), MTGFTGDF (SEQ ID NO 160), FTGDFDSV (SEQ ID NO 161), KLVALGINAV (SEQ ID NO 166), VIDCNTCV (SEQ ID NO 162), or any variant of said sequence as can be deduced from FIG. 6.

With said peptides being preferentially different from GKSTKVP, PSVMT, IGTVLDQAE, AVAYYR and TGD-FDSVID (SEQ ID NOs: 173–176 and 177, respectively).

The present invention relates more particularly to any of the above-mentioned polypeptides wherein said T cell stimulating epitope is a T cell helper epitope.

According to another embodiment, the present invention relates to any of the above-mentioned polypeptides wherein said T cell stimulating epitope is a CTL epitope.

The present invention also relates to the incorporation of any of the above-mentioned polypeptides into a prophylactic vaccine composition.

According to another embodiment, the present invention relates to the incorporation of any of the above-mentioned polypeptides into a therapeutic vaccine composition.

Moreover, the present invention also contemplates a polypeptide comprising or consisting of multiple repeats of any of the polypeptides as defined above, combinations of any of the polypeptides as defined above, or mimotopes of the peptides as defined above.

The term "mimotopes" refers to peptides which mimic the polypeptides as defined above immunologically. Since sequence variability has been observed fro HCV, it may be desirable to vary one or more amino acids so as to better mimic the epitopes of different strains. It should be understood that such mimotopes need not be identical to any particular HCV sequence as long as the subject compounds are capable of providing for immunological stimulation after which the T cells are reactive with at least one strain of HCV. The polypeptides as described above, may therefore be subject to insertions, deletions and conservative as well as non-conservative amino acid subtitutions where such changes might provide for certain advantages in their use. The peptides will preferably be as short as possible while still maintaining all of their sensitivity of the larger sequence. In certain cases, it may be desirable to join two or more peptides into a single structure. The formation of such a composite may involve covalent or non-covalent linkages.

The present invention also contemplates a polypeptide as defined above, with said polypeptide being a recombinant polypeptide expressed by means of an expression vector comprising a nucleic acid insert encoding a polypeptide as defined above.

In order to carry out the expression of the T-cell containing polypeptides of the invention in bacteria such as *E. coli* or in eukaryotic cells such as in *S. cerevisiae*, or in cultured vertebrate or invertebrate hosts such as insect cells, Chinese Hamster Ovary (CHO), COSI, BHK, and MDCK cells, the following steps are carried out:

transformation of an appropriate cellular host with a recombinant vector, or by means of adenoviruses, influenza viruses, BCG, and any other live carrier systems, in which a nucleotide sequence coding for one of the polypeptides of the invention has been inserted under the control of the appropriate regulatory elements, particularly a promoter recognized by the polymerases of the cellular host or of the live carrier system and in the case of a prokaryotic host, an appropriate ribosome binding site (RBS), enabling the expression in said cellular host of said nucleotide sequence, culture of said transformed cellular host under conditions enabling the expression of said insert. Recombinant virus or live carrier vectors may also be directly used as live vaccines in humans.

According to a preferred embodiment, the present invention contemplates a polypeptide as defined above which is operably linked to a pathogen related immunogen such as the HCV core protein, the HCV envelope proteins E1 and E2, or the HCV NS3, NS4 or NS5 immunogens, or a HCV peptide containing a B cell epitope.

The phrase "operatively linked" as used herein means that the linkage does not interfere with the ability of either of the linked groups to function as described; e.g., to function as a T or B cell determinant. Thus, operatively linking not only includes covalent linkages, but also includes linkages capable of inducing T cell function.

The phrase "pathogen related" as used herein designates a polypeptide that is capable of inducing the T cell function that immunoreacts with a pathogen in native form.

The defined polypeptides can be employed as such or in combination with HCV B cell epitopes, HBsAg or HBcAg particles, HIV immunogens, HTLV immunogens. HCV peptides containing preferred B cell epitopes are detailed in for instance EP-A-0 489 968 and WO 93/18054.

Methods for operatively linking individual polypeptides through an amino acid residue side chain to form an immunogenic conjugate, i.e., a branched-chain polypeptide polymer, are well known in the art. Those methods include linking through one or more types of functional groups on various side chains and result in the respective polypeptide backbones being covalently linked (coupled) but separated by at least one side chain.

Useful side chain functional groups include epsilon-amino groups, beta- or gamma-carboxyl groups, thiol (—SH) groups and aromatic rings (e.g. tyrosine and histidine). Methods for linking polypeptides using each of the above functional groups are described in Erlanger (1980), Auramcas et al. (1978) and U.S. Pat. No. 4,493,795 to Nestor et al. In addition, a site-directed coupling reaction, as described in Rodwell et al. (1985), can be carried out so that the biological activity of the polypeptides is not substantially diminished.

Furthermore, as is well known in the art, the HBcAg protein and polypeptide immunogen can be used in their native form or their functional group content may be modified by succinylation of lysine residues or reaction with cysteine-thiolactone. A sulfhydryl group may also be incorporated into either polypeptide by reaction of amino functions with 2-iminothiolane or the N-hydroxysuccinimide ester of 3-(3-dithiopyridyl) propionate. The polypeptides can also be modified to incorporate spacer arms, such as hexamethylene diamine or other bifunctional molecules of similar size, to facilitate linking.

Any polypeptide immunogen against which antibody production is desired can be linked to the polypeptide of the present invention protein to form an immunogenic conjugate of this invention. In preferred embodiments the polypeptide immunogen is a pathogen related immunogen and the conjugate has the capacity to induce the production of antibodies that immunoreact with the pathogen when injected in an effective amount into an animal. Exemplary immunogens of particular importance are derived from bacteria such as *B. pertussis. S. typosa, S. Paratyphoid* A and B, *C. diptheriae, C. tetani, C. botulinum, C. perfrincens, B. anthracis, P. restis, P. multocida, V. cholerae, N. meningitides, N. gonorrhea, H. influenzae, T. palladium*, and the like; immunogens derived from viruses such as polio virus, adenovirus, parainfluenza virus, measles, mumps, respiratory syncytical virus, influenza virus, equine encephalomyeitis virus, hog chloera virus, Newcastle virus, fowl pox virus, rabies virus, feline and canine distemper viruses, foot and mouth disease virus, human and simian immunodeficiency viruses, and the like; rickettsiae immunogen such as epidemic and endemic typhus, and the spotted fever groups, and the like. Immunogens are well known to the prior art in numerous references such as U.S. Pat. Nos. 3,149,036, 3,983,228, and 4,069,313; in Essential Immunology, 3rd Ed., by Roit, published by Blackwell Scientific Publications; in *Fundamentals of Clinical Immunology*, by Alexander and Good, published by W. B. Saunders; and in *Immunology*, by Bellanti, published by W. B. Saunders. Particularly preferred pathogen related immunogens are those described in U.S. Pat. Nos. 4,625,015, 4,544,500, 4,545,931, 4,663,436, 4,631,191, 4,629,783 and in Patent Cooperation Treaty International Publication No. WO87/02775 and No. WO87/02892, all of whose disclosures are incorporated herein by reference.

The present invention relates particularly to any of the following peptides or any peptide comprised in the sequence of any of the following peptides, with said peptides containing a T cell epitope:

$NH_2-X_{30}X_{31}X_{32}DGX_{33}NX_{34}X_{35}TGNX_{36}PGCSFSI-COOH$ (SEQ ID NO 51),

VLEDGVNYATGNLPGCSFSI (SEQ ID NO 13 peptide CORE 27),

VLEDIVNYATGNLPGCSFSI (SEQ ID NO 73), $NH_2-GX_{33}NX_{34}X_{35}TGNX_{36}-COOH$ (SEQ ID NO 74), $NH_2-X_{33}NX_{34}X_{35}TGNX_{36}-COOH$ (SEQ ID NO 75), $NH_2-NX_{36}PGCSFSI-COOH$ (SEQ ID NO 76), $NH_2-X_{36}PGCSFSI-COOH$ (SEQ ID NO 77),

GVNYATGNL (SEQ ID NO 78), GVNYATGNL (SEQ ID NO 79),

NLPGCSFSI (SEQ ID NO 80), LPGCSFSI (SEQ ID NO 81), $NH_2GGX_{25}X_{26}X_{27}X_{28}LX_{29}HGVRX_{30}X_{31}X_{32}DGX_{33}NX_{34}-COOH$ (SEQ ID NO 52),

GGAARALAHGVRVLEDGVNY (SEQ ID NO 12=peptide CORE 25),

GGVAARALAHGVRVLEDGVNY (SEQ ID NO 118), $NH_2-X_{28}LX_{29}HGVR_{30}X_{31}-COOH$ (SEQ ID NO 82), $NH_2-LX_{29}HGVRX_{30}X_{31}-COOH$ (SEQ ID NO 83), $NH_2-GVRX_{30}X_{31}X_{32}DGX_{33}-COOH$ (SEQ ID NO 84), $NH_2-VRX_{30}X_{31}X_{32}DGX_{33}-COOH$ (SEQ ID NO 85), $NH_2-RX_{30}X_{31}X_{32}DGX_{33}NX_{34}-COOH$ (SEQ ID NO 86), $NH_2-X_{30}X_{31}X_{32}DGX_{33}NX_{34}-COOH$ (SEQ ID NO 87),

ALAHGVRVL (SEQ ID NO 88), LAHGVRVL (SEQ ID NO 89),

VRVLEDGV (SEQ ID NO 90), RVLEDGV (SEQ ID NO 91), VLEDGVNY (SEQ ID NO 92), LEDGVNY (SEQ ID NO 93), $NH_2-LX_{19}X_{20}YIPX_{21}X_{22}GX_{23}PX_{24}GGX_{25}X_{26}X_{27}X_{28}LX_{29}-COOH$ (SEQ ID NO 53),

LMGYIPLVGAPLGGAARALA (SEQ ID NO 11=peptide CORE 23), $NH_2-LX_{19}X_{20}YIPX_{20}X_{22}GX_{23}PX_{24}GGX_{25}-COOH$ (SEQ ID NO 62), $NH_2-X_{19}X_{20}YIPX_{21}X_{22}GX_{23}PX_{24}GGX_{25}-COOH$ (SEQ ID NO 63), $NH_2-YIPX_{21}X_{22}GX_{23}PX_{24}-COOH$ (SEQ ID NO 64), $NH_2-IPX_{21}X_{22}GX_{23}PX_{24}-COOH$ (SEQ ID NO 65), $NH_2-X_{21}X_{22}GX_{23}PX_{24}GGX_{25}-COOH$ (SEQ ID NO 66), $NH_2-X_{22}GX_{23}PX_{24}GGX_{25}-COOH$ (SEQ ID NO 68),

LMGYIPLV (SEQ ID NO 69), MGYIPLV (SEQ ID NO 70),

YIPLVGAPL (SEQ ID NO 71), IPLVGAPL (SEQ ID NO 72),

LVGAPLGGA (SEQ ID NO 94), VGAPLGGA (SEQ ID NO 95), $NH_2-X_{11}X_{12}DPRX_{13}X_{14}SRNX_{15}GX_{16}VIDTX_{17}TCCOOH$ (SEQ ID NO 54),

PTDPRRRSRNLGKVIDTLTC (SEQ ID NO 9=peptide CORE 19), $NH_2-NX_{15}GX_{16}VIDTX_{17}-COOH$ (SEQ ID NO 96), $NH_2-X_{15}GX_{16}VIDTX_{17}-COOH$ (SEQ ID NO 97), NLGKVIDTL (SEQ ID NO 98), LGKVIDTL (SEQ ID NO 117), $NH_2-GX_1X_2WX_3X_4PGX_5PWPLYX_6NX_7GX_8G-COOH$ (SEQ ID NO 99), GRTWAQPGYPWPLYGNEGCG (SEQ ID NO 6=peptide CORE 13), $NH_2-X_2WX_3X_4PGX_5PW-COOH$ (SEQ ID NO 100), $NH_2-WX_3X_4PGX_5PW-COOH$ (SEQ ID NO 101), TWAQPGYPW (SEQ ID NO 102), WAQPGYPW (SEQ ID NO 103),
QVRNSTGLYHVINDCPNSSI (SEQ ID NO 16),
NDCPNSSIVYEAHDAILHTP (SEQ ID NO 17),
HDAILHTPGCVPCVREGNVS (SEQ ID NO 18),
CVREGNVSRCWVAMTPTVAT (SEQ ID NO 19),
AMTPTVATRDGKLPPATQLRR (SEQ ID NO 20),
LPATQLRRHIDLLVGSATLC (SEQ ID NO 21),
LVGSATLCSALYVGDLCGSV (SEQ ID NO 22),
QLFTFSPRRHWTTQGCNCSI (SEQ ID NO 23),
TQGCNCSIYPGHITGHRMAW (SEQ ID NO 24),
ITGHRMAWDMMMNWSPTAAL (SEQ ID NO 25),
NWSPTAALVMAQLLRIPQAI (SEQ ID NO 26),
LLRIPQAILDMIAGAHWGVL (SEQ ID NO 27),
AGAHWGVLAGIAYFSMVGNW (SEQ ID NO 28),
VVLLLFAGVDAETIVSGGQA (SEQ ID NO 29),
$NH_2$-$X_{37}X_{38}X_{39}X_{40}X_{41}X_{42}X_{43}X_{44}X_{45}GX_{46}X_{47}QX_{47}QX_{48}X_{49}X_{50}LX_{51}NX_{54}$-COOH (SEQ ID NO 55),
SGLVSLFTPGAKQNIQLINT (SEQ ID NO 46),
$NH_2$-$QX_{48}X_{49}X_{50}LX_{51}NX_{54}NGSWHX_{52}NX_{53}TALN$-COOH (SEQ ID NO 56),
$NH_2$-$X_{50}LX_{51}NX_{54}NGSW$-COOH (SEQ ID NO 109),
$NH_2$-$LX_{51}NX_{54}NGSW$-COOH (SEQ ID NO 110),
$NH_2$-$SWHX_{52}NX_{53}TAL$-COOH (SEQ ID NO 111),
$NH_2$-$SWHX_{52}NX_{53}TAL$-COOH (SEQ ID NO 112),
QLINTNGSW (SEQ ID NO 113),
LINTNGSW (SEQ ID NO 114), SWHINSTAL (SEQ ID NO 115), WHINSTAL (SEQ ID NO 116),
GGAGNNTLHCPTDCFRKHP (SEQ ID NO 41),
TDCFRKHPDATYSRCGSGPW (SEQ ID NO 42), 1SRCGSGPWITPRCLVDYPYR (SEQ ID NO 43),
CLVDYPYRLWHYPCTINYTI (SEQ ID NO 44),
PCTINYTIFKIRMYVGGVEH (SEQ ID NO 45),
$X_{60}Z_1Z_2LX_{61}CPTDCF$ (SEQ ID NO 119),
$FRKX_{62}PX_{63}X_{64}TY$ (SEQ ID NO 120),
$X_{68}X_{69}$-$TPRCX_{70}X_{71}$ (SEQ ID NO 121),
$X_{70}X_{71}DYPYRL$ (SEQ ID NO 122),
$X_{71}DYPYRLW$ (SEQ ID NO 123),
YPYRLWHY (SEQ ID NO 124),
$LWHYPCTX_{72}$ (SEQ ID NO 125),
$X_{72}NX_{73}X_{74}X_{75}FKX_{76}$ (SEQ ID NO 126),
$X_{73}X_{74}X_{75}FKX_{76}RM$ (SEQ ID NO 127),
$X_{75}FKX_{76}RMX_{77}V$ (SEQ ID NO 128),
$X_{76}RMX_{77}VGGV$ (SEQ ID NO 129),
$IX_{55}X_{56}X_{57}X_{58}NX_{59}X_{60}Z_1Z_2LX_{61}CPTDCFRKX_{62}P$ (SEQ ID NO 130),
$TDCFRKX_{62}PX_{63}X_{64}TYX_{65}X_{66}CGX_{67}GPX_{68}$ (SEQ ID NO 131),
$X_{65}X_{66}CGX_{67}GPX_{68}X_{69}TPRCX_{70}X_{71}DYPYR$ (SEQ ID NO 132),
$CX_{70}X_{71}DYPYRLWHYPCTX_{72}NX_{73}X_{74}X_{75}$ (SEQ ID NO 133),
$PCTX_{72}NX_{73}X_{74}X_{75}FKX_{76}RM_{77}VGGVEH$ (SEQ ID NO 134) VAKAVDFV (SEQ ID NO 135), VAKAVDFI (SEQ ID NO 136), VESMETTM (SEQ ID NO 137), AVPQTFQV (SEQ ID NO 138), YAAQGYKV (SEQ ID NO 139), VLVLNPSVA (SEQ ID NO 140), YMSKAHGV (SEQ ID NO 141), IRTGVRTI (SEQ ID NO 142), YSTYGKFL (SEQ ID NO 143), ILGIGTVL (SEQ ID NO 144), VTVPHPNI (SEQ ID NO 145), IPFYGKAI (SEQ ID NO 146), FYGKAIPI (SEQ ID NO 147), VIKGGRHL (SEQ ID NO 148), IKGGRHLI (SEQ ID NO 149), FCHSKKKC (SEQ ID NO 150), CDELAAKL (SEQ ID NO 151), LAAKLSGFG (SEQ ID NO 152), SGFGINAV (SEQ ID NO 153), FGINAVAY (SEQ ID NO 154), YRGLDVSV (SEQ ID NO 155), VIPTSGDV (SEQ ID NO 156), IPTSGDVV (SEQ ID NO 157), VVVATDAL (SEQ ID NO 158), VVATDALM (SEQ ID NO 159), MTGFTGDF (SEQ ID NO 160), FTGDFDSV (SEQ ID NO 161), VIDCNTCV (SEQ ID NO 162).

Moreover, the present invention contemplates an immunogenic composition consisting of or comprising at least one of the polypeptides as defined above mixed with a pharmaceutical acceptable excipient.

Before administration to patients, formulants may be added to the polypeptides or peptides of the invention. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. Sucrose is most preferred. "Sugar alcohol" is defined as a C4 to C8 hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP patent applications No. EP 0 270 799 and EP 0 268 110.

Additionally, polypeptides can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). PEG is soluble in water at room temperature and has the general formula: R(O—$CH_2$—$CH_2$)$_n$O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated. However, it will be understood that the type and amount of the reactive groups may be varied to achieve a covalently conjugated PEG/polypeptide of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, and a discussion of POG/IL-2 conjugates is found in U.S. Pat. No. 4,766,106.

Another drug delivery system for increasing circulatory half-life is the liposome. Methods of preparing liposome delivery systems are discussed in Gabizon et al., 1982; and Szoka, 1980. Other drug delivery systems are known in the art and are described in, e.g. Poznansky, 1984.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the polypeptides and compositions of this invention are used to treat human patients to prevent or treat any of the above-defined disease states. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonacueous vehicles such as fixed oils and ethyl oleate may also be used. A preferred vehicle is 5% dexerose in saline. The vehicle may contain minor amounts of additives such as substances that enhance isotonicity and chemical stability, including buffers and preservatives.

The dosage and mode of administration will depend on the individual.

More particularly, the present invention contemplates a composition as defined above for use in a method of immunizing against HCV, comprising administrating a sufficient amount of at least one of the polypeptides as defined above, possibly accompanied by pharmaceutically acceptable adjuvants, to produce an immune response.

More particularly, said immunogenic composition is a vaccine composition. Even more particularly, said vaccine composition is a prophylactic vaccine composition. Alternatively, said vaccine composition may also be a therapeutic vaccine composition.

The prophylactic vaccine composition refers to a vaccine composition aimed for preventing HCV infection and to be administered to normal persons who are not yet infected with HCV.

The therapeutic vaccine composition refers to a vaccine composition aimed for treatment of HCV infection and to be administered to patients being infected with HCV.

The polypeptides described in the present invention can be modified with lipid (lipopeptides, e.g. PAM$_3$Cys), and formulated with alum, monophosphoryl lipid A, pluronics, SAF1, Ribi, trehalose-6,6-dimycolate or other immunostimulating compounds known to those skilled in the art, as to enhance their immunogenicity.

Also, the present invention contemplates according to a preferred embodiment, a composition as defined above, with said composition comprising in addition to any of the T cell-stimulating polypeptides as defined above, a peptide or polypeptide containing at least one B-cell epitope of HCV, and/or a structural HCV polypetide, and/or a non-structural HCV polypeptide.

According to a yet other preferred embodiment, the present invention contemplates a composition as defined above for use in a method of treatment of HCV, comprising administrating a sufficient amount of at least one of the polypeptides as defined above, possibly accompanied by pharmaceutically acceptable adjuvants, to allow treatment of HCV infection. In this case the polypeptides of the present invention can be employed in the form of therapeutic vaccine, aiming at the induction of a sufficient level of T cell function for clearance of Hepatitis C virus infection.

According to yet another preferred embodiment, the present invention contemplates a composition as defined above, with said composition comprising in addition to any of the polypeptides as defined above, a peptide or polypeptide containing at least one B-cell epitope of HCV, and/or a structural HCV dpolypeptide, and/or a non-structural HCV polypeptide.

According to yet another embodiment, the present invention contemplates a composition wherein said polypeptides as defined above are mixed with HBsAg or HBcAg paricles, HBV immunogens, HIV immunogens and/or HTLV immunogens.

FIGURE LEGENDS

FIG. 1: Evolution of the lymphoproliferative responses and transaminase activities in HCV patient No. 632. AST depicts aspartate aminotransferase, ALT depicts alanine aminotransferase; SI: simulation index; P1 to P6 refers to the groups of peptides 1 to 6 as disclosed in Table 1.

FIG. 2: Frequencies of lymphoproliferation responses to peptide pools 1–9, single peptides NS1–7*, NS1–5* and recombinant NS3 protein in healthy controls, interferon (IFN) responders and IFN non-responders.

FIG. 3: represents the part of the sequence of the isolate IG8309 which has been tested, with said part extending from with Gly at position 41 to Ser at position 318 (SEQ ID NO 57).

Figure 4H:
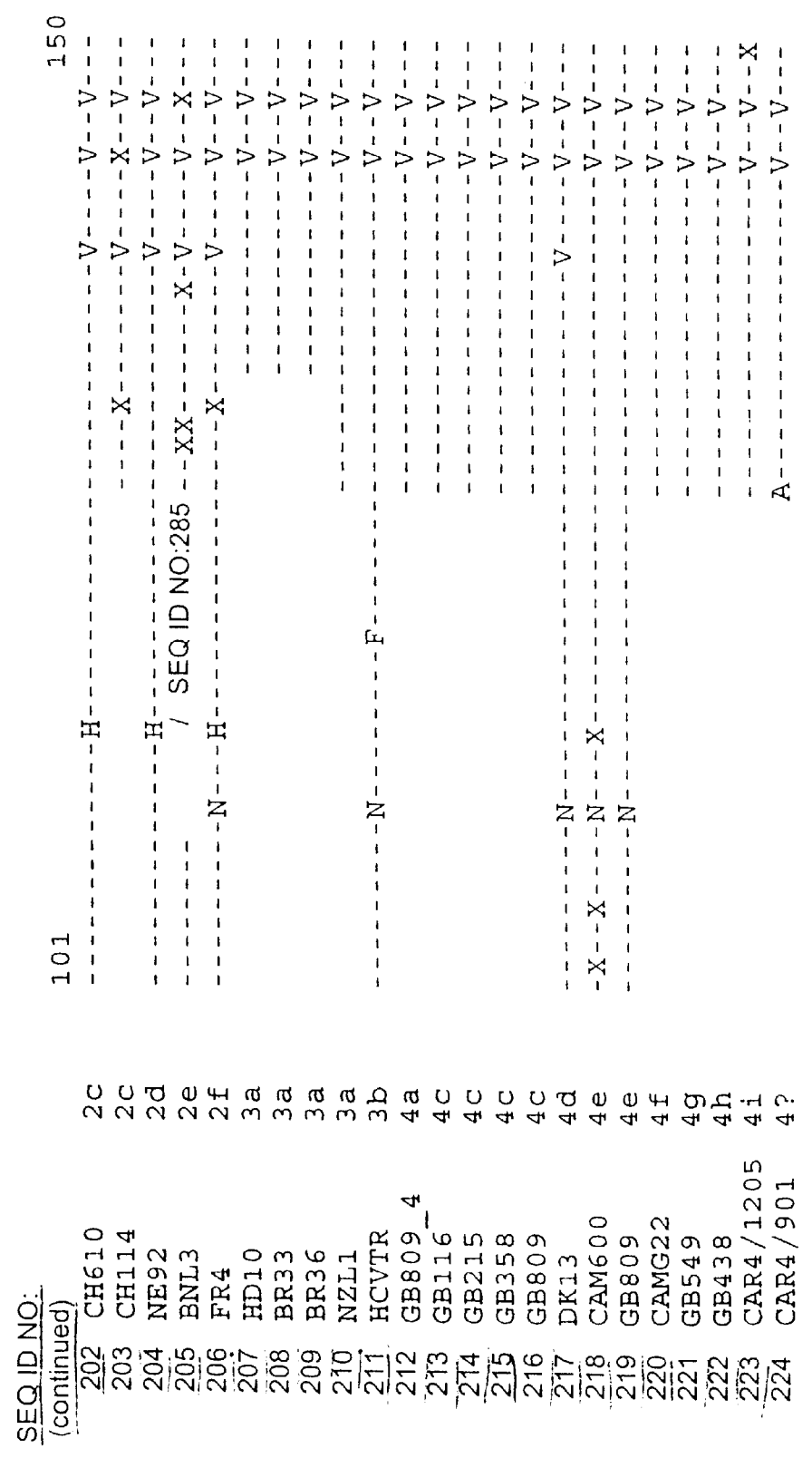

FIG. 4A represents an alignment of the HCV structural regions.

FIG. 4B represents an alignment of the HCV structural regions.

FIG. 4C represents an alignment of the HCV structural regions.

FIG. 4D represents an alignment of the HCV structural regions.

FIG. 4E represents an alignment of the HCV structural regions.

FIG. 4F represents an alignment of the HCV structural regions.

FIG. 4G represents an alignment of the HCV structural regions.

FIG. 4H represents an alignment of the HCV structural regions.

FIG. 4I represents an alignment of the HCV structural regions.

FIG. 4J represents an alignment of the HCV structural regions.

FIG. 4K represents an alignment of the HCV structural regions.

FIG. 4L represents an alignment of the HCV structural regions.

FIG. 4M represents an alignment of the HCV structural regions.

FIG. 4N represents an alignment of the HCV structural regions.

FIG. 4O represents an alignment of the HCV structural regions.

FIG. 4P represents an alignment of the HCV structural regions.

FIG. 4Q represents an alignment of the HCV structural regions.

FIG. 4R represents an alignment of the HCV structural regions.

FIG. 4S represents an alignment of the HCV structural regions.

FIG. 4T represents an alignment of the HCV structural regions.

FIG. 4U represents an alignment of the HCV structural regions.

FIG. 4V represents an alignment of the HCV structural regions.

FIG. 4W represents an alignment of the HCV structural regions.

Figure 1:
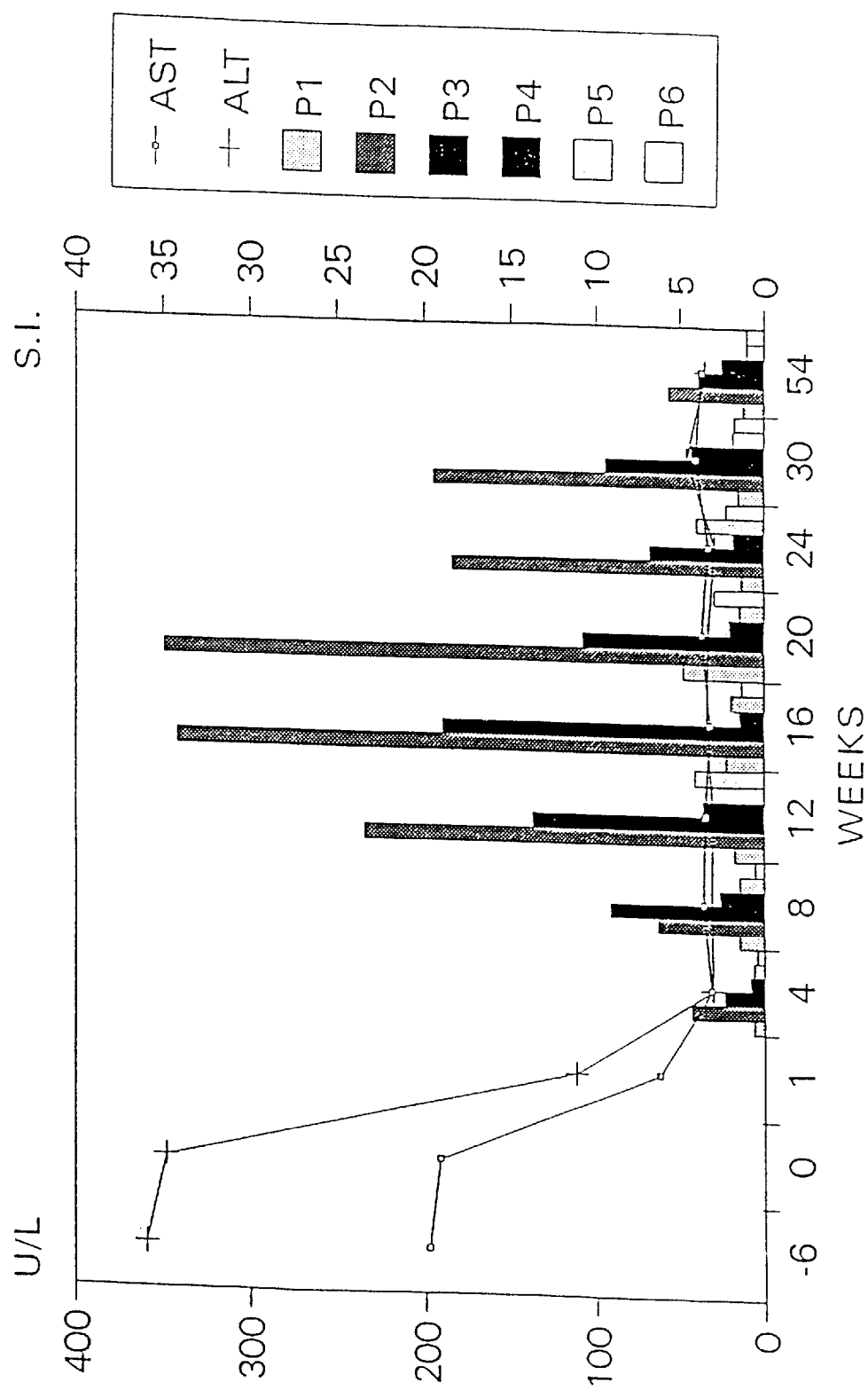

FIG. 5A. Alignment of E2 regions spanning amino acid positions 571 to 638.

FIG. 5B. Alignment of E2 regions spanning amino acid positions 571 to 638.

FIG. 6A. Alignment of NS3 sequences spanning amino acid positions 1188 to 1465.

FIG. 6B. Alignment of NS3 sequences spanning amino acid positions 1188 to 1465.

FIG. 6C. Alignment of NS3 sequences spanning amino acid positions 1188 to 1465.

EXAMPLES

Example 1

Patients Studied

The patients studied consisted of 19 males and 13 females, aged between 27 and 71 (mean age: 49.9 years). The diagnosis of chronic HCV hepatitis was based on a) a documented elevation of alanine aminotransferase of 2 times the upper limit of normal for at least six months; b) the presence of HCV-specific serum antibodies detected by two second generation enzyme immunoassay tests (UBI test and Innotest HCV AbII, Innogenetics, Antwerp Belgium) and c) absence of clinical, histological or serological signs of other viral, toxic, metabolic, hereditary or auto-immune hepatitis. The patients were randomized to receive either the standard treatment consisting of 3 million units Interferon α-2b (INTRON A) given thrice weekly for 24 weeks or an experimental treatment consisting of an induction phase of 6 million units Interferon a-2b thrice weekly for eight weeks, followed by a maintenance phase of titrated doses of interferon of 6 to 1 million units thrice weekly until biochemical and virological remission (alanine aminotransferase activity normal, plasma hepatitis C virus-RNA undetectable) was achieved. Patients were considered clinical responders when a normalization of alanine aminotransferase activity was observed on at least two successive control visits during treatment with al least one month interval.

As controls for the specificity of the lymphoproliferative responses, 18 healthy individuals aged 25–58 years (mean 38.6), 10 males and 8 females were selected. These subjects were negative for HCV antibodies and HCV-RNA. One subject had a history of past hepatitis B virus infection and 7 had antibodies to HBsAg as a result of vaccination.

A liver biopsy was performed in all patients prior to the initiation of Interferon-a therapy. The histological status was defined according to conventional histological classification (Knodell et al., 1981).

Based on the definition of clinical responders given above, 18 subjects could be considered clinical responders to Interferon-α. The most relevant clinical, pathological and virological data of both groups are summarized in Table 2. Although the responder group contained more women and the non-responder group more men than theoretically expected, the observed imbalances were not significant ($X^2$-test). The duration of the disease in each subject was estimated based on anamnestic data (surgery with multiple transfusions, intravenous drug abuse, professional exposure through needle stick accident, etc.) or patient file data displaying chronically fluctuating and elevated transaminase levels. The disease duration varied from one to 32 years. The mean disease duration was 9.2±9.2 years in responders and 6.8±5.4 years in non-responders. Although the responder group contained more subjects treated with the experimental protocol and the non-responder group more subjects treated with the standard protocol, the imbalance was not significant $X^2$-test). Twenty six out of 32 patients (81%) were infected with HCV of genotype 1b. The genotypes 3a, 4a and 5a were found in 4, 1 and 1 subject, respectively. Anamnestic data allowed us to retrieve the source of infection. Blood transfusions are the possible source of the HCV infection in 14 subjects, IV drug abuse in 3 patients and needle stick accidents in 3 others. No source of infection could be traced back in 12 subjects. Most patients (20 out of 32) showed pathological lesions compatible with chronic active hepatitis in a mild, moderate or severe form. Seven patients displayed signs of chronic persistent hepatitis. In two subjects the biopsy showed only aspecific lesions and in two others signs of liver cirrhosis were observed.

Example 2

Analysis of the Humoral Immune Response

INNO-LIA HCV AbII (Innogenetics, Belgium) was employed to detect antibodies to peptide epitopes from the core, NS4a+b and NS5a region. From each patient a serum sample obtained before the start of the interferon therapy was examined and sometimes, additional follow-up samples were also tested. All 32 patients studied had circulating antibodies towards HCV demonstrated by two commercially available enzyme immunoassays. Using a peptide-based immunoblot assay (INNO-LIA HCV AbII) we were able to partially define the specificities of these antibodies. Sera from 31 patients were examined at least once with this assay and in 20 subjects the assay was applied on two sera taken with an interval of 4 (Patient 635) to 124 weeks (Patient 606). Table 3 shows the results of this survey. Apart from the reactivity pattern with the antigens employed (4 individually spotted core peptides, a mixture of NS4 peptides defining a fifth line and a selection of NS5 peptides creating a sixth line), Table 3 also shows the HCV genotype and the moment at which the serum was taken with respect to the start of the interferon therapy. The data clearly indicate that the antibody recognition pattern of an individual patient hardly changes over time. The only differences observed in the 20 paired samples were single step alterations in the intensity of the reactions. As well in responders as in non-responders to interferon we observed the same hierarchy in the serological reaction patterns. When indeterminate or weak reactions are not taken into consideration, the following hierarchy appears: Core2>NS4>NS5>Core1>Core4>Core3.

Example 3

Detection of HCV RNA and HCV Genotyping

Reverse transcription and PCR was performed as described previously (Stuyver et al, 1993). PCR products were further processed for genotyping by means of the Inno-LiPA genotyping assay (Stuyver et al., 1993). The results of the genotyping assays are included in Table 3.

Example 4

Analysis of the Cellular Immune Response 4.1. Synthesis of ECV Antigens

Nine groups of peptides (pools) corresponding to Core, E1 and E2/NS1 sequences, two single peptides not included in these pools corresponding to E2/NS1, and a recombinant protein representing the central part of NS3-HCV genotype 1b, were used for in vitro stimulation of PBMC. Each group pooled 4–6 different 20-mer peptides which overlapped 8 amino acids. Groups 1, 2 and 3 included mainly core peptides with amino acid positions 5–80, 73–140 and 133–200, respectively (Table 1). Groups 4, 5 and 6 predominantly encompassed E1 peptides with amino acid positions 193–260, 253–332 and 325–392, respectively. Groups 7, 8 and 9 comprised E2/NS1 peptides with amino acid positions 427–494, 487–578 and 571–638, respectively. The two additional single peptides (NS1–7*, and NS1–5*) covered amino acids from 397 to 428 of the E2 sequence (Table 1). A fusion protein containing the NS3 sequence was expressed in E. coli and covered HCV amino acids 1188 to 1463 of the Belgian isolate IG8309.

Peptides were dissolved in the buffers shown in Table 1 and added to the cultures at a final concentration of 10 $\mu$g/ml. At this peptide concentration, the concentration of dissolving buffers in the cell cultures was not toxic or inhibitory. Preliminary experiments were performed to ascertain this. NS3 protein was used at a final concentration of 1.5 $\mu$g/ml. Tetanus toxoid (WHO, Copenhagen, Denmark), used as a positive control antigen, was added to the culture media at a final concentration of 10 $\mu$g/ml.

All the peptides were synthesized on either PepSyn K resin (Millipore) functionalized with the acid labile linker 4-(a-Fmoc-amino-2',4',-dimethoxybenzyl) phenoxyacetic acid, or TentaGel S-RAM resin (Rapp Polymere) functionalized with the same linker which yields peptide amides upon cleavage. t-Butyl-based side chain protection and Fmoc-a-amino protected amino acid derivatives were used. The guanidino group of arginine was 2,2,5,7,8-pentamethylchroman-6-sulfonyl-protected. The imidazole group of histidine was protected with either t-Boc or trityl and the sulfhydryl group of cysteine was protected with a trityl group. Couplings were carried out using preformed O-pentafluorophenyl esters except in the case of arginine where TBTU (O-(1H-benzotriazol-1-yl)-N,N,N',N',-tetramethyluronium tetrafluoroborate, Novabiochem) was used as the activating agent in the presence of 2 equivalents of the base N-methylmorpholine and 1 equivalent of 1-hydroxybenzotriazole. Occasionally, glutamine, asparagine, and tryptophan were also coupled using TBTU activation. In these cases, the trityl-protected derivatives of glutamine and asparagine (Millipore), and the t-Boc-protected derivative of tryptophan (Novabiochem) were used. All syntheses were carried out on a Milligen 9050 PepSynthesizer (Millipore) using continuous flow procedures. Following cleavage of the peptides with trifluoroacetic acid in the presence of appropriate scavengers and precipitation with diethylether, all peptides were analyzed by $C_{18}$-reverse phase chromatography.

HCV amino acid sequences corresponding to the viral nucleocapsid (core) and E1 proteins were based on the HC-J1 sequence described by Okamoto et al. (1990) Japan. J. Exp. Med. (1990) 60:167–177). HCV sequences starting at amino acid residue $Gly_{451}$ were taken from the sequences reported by Choo et al. (1991) Proc. Natl. Acad. Sci. USA (1991) 88:2451–2455. Most peptide sequences were chosen such that the peptides would overlap each other by 8 amino acid residues.

4.2. T Cell Proliferation Assays

The medium used for all cell cultures consisted of RPMI 1640 supplemented with 25 mM HEPES, 2 mM L-glutamine, 50 U/ml penicillin and 50 $\mu$g/ml streptomycin (all from Gibco Europe, Gent, Belgium), $5\times10^{-5}$ M 2-mercaptoethanol (Sigma, St. Louis, Mo.) and 10% heat-inactivated pooled human AB serum. This AB serum was obtained from healthy blood donors with blood group $AB^+$ and was only used when antibodies to HCV and HCV-RNA were absent. This "complemented" RPMI 1640 medium will hereafter be designated "complete medium".

PBMC were isolated from heparinized venous blood by isopycnic density centrifugation on Ficoll Hypaque (Lymphoprep, Nyegaard, Denmark) and suspended in complete medium. $4\times10^{-5}$ PBMC in 200 $\mu$l of complete medium were cultured in 96 well round-bottomed microplates (Falcon Plastics) in the absence (unstimulated controls) or presence of varying concentrations of antigens for 5 days at 37° C. in an atmosphere of 5% $CO_2$ in air. 0.5 $\mu$Ci ($^3$H)-thymidine was then added to each well and 16 to 20 h later the cultures were harvested onto glass fiber filters using a multichannel cell harvester (PHD, Cambridge, Mass.) to measure the incorporation of ($^3$H)-thymidine by liquid scintillation counting in an LKB-Wallac 8100 counter (LKB, Bromma, Sweden). Results are expressed as stimulation index (SI; mean cpm of antigen-stimulated cultures/mean cpm of control cultures). Proliferation was considered positive when stimulation index was >3. In some figures the results are expressed as cpm (mean cpm of antigen-stimulated cultures—mean cpm of control cultures). Standard deviations of the mean cpm of triplicate cultures were consistently below 10%.

The occurrence of in vivo primed HCV-specific memory T lymphocytes was examined using a lymphoproliferation assay. PBMC from 32 patients with chronic HCV were stimulated in vitro with pools of 4 to 6 partially overlapping, synthetic peptides representing the core, E1 and E2/NS1 regions of HCV type 1a, with 2 overlapping, single peptides from the amino-terminus of HCV type 1a and with a recombinant fusion protein containing the NS3 sequence of HCV type 1b. In all but 2 patients (#610 and #636) at least 2 and up to 11 (#633) assays were performed. In patient # 632 for example lymphoproliferation was examined on 8 different occasions between week 4 and 54 following the start (week 0) of the Interferon therapy. FIG. 1 shows the results of these assays in correlation with the biochemical (ALT/AST) response to therapy. Four weeks after the start of Intron-A (Schering Plough) a normalization of the transaminase levels was observed. PBMC's from the patient consistently and vigorously proliferate upon stimulation with peptide pools 2 and 3. The responses to the other antigen preparations were less vigorous and less reproducible, suggesting that the number of memory cells recognizing these epitopes is lower. Antigens that did not induce a proliferative response with a stimulation index (SI) 3 at any time are not represented in the graph.

Figure 2:
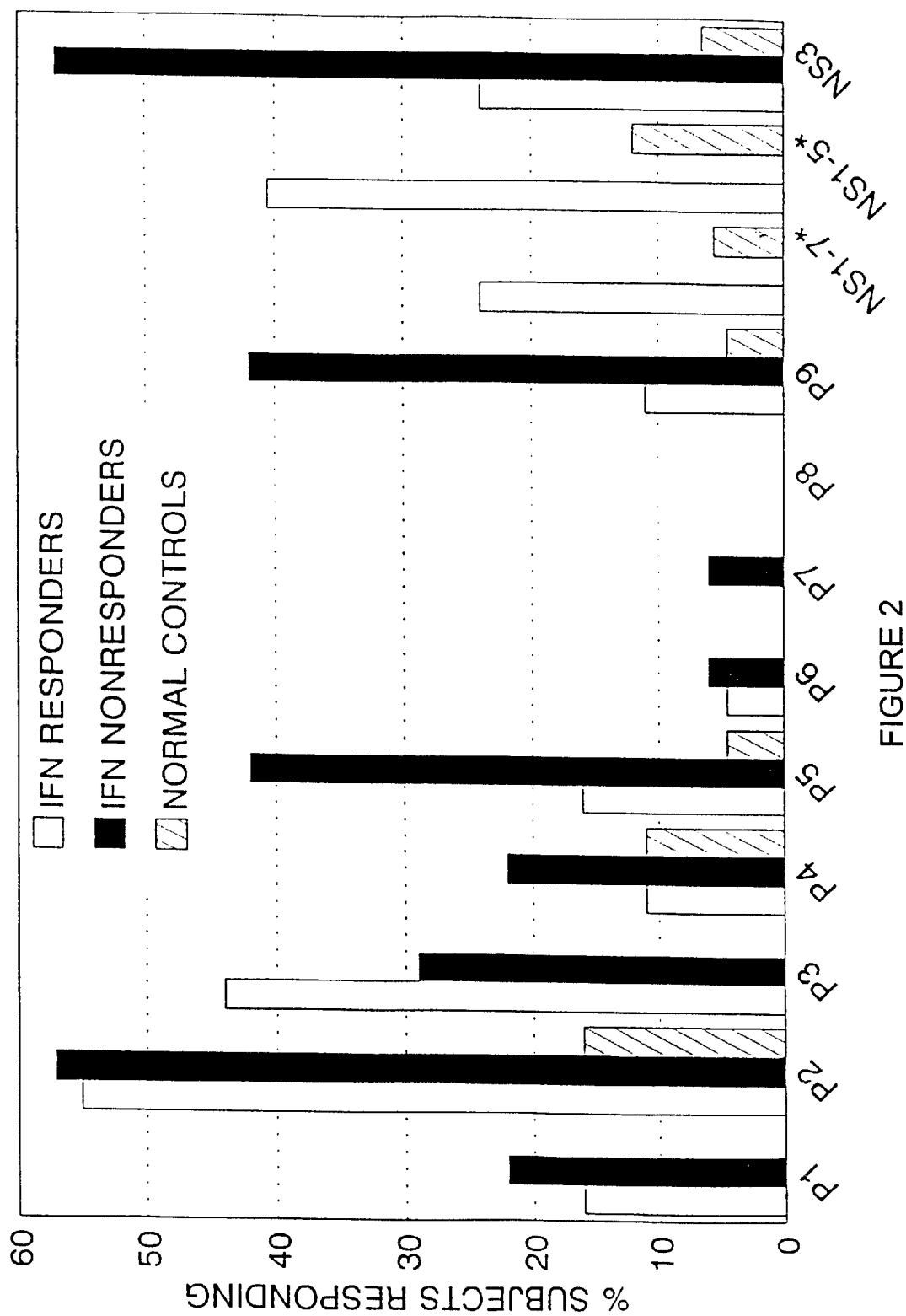

To analyze and summarize the results of 135 assays performed in the 32 HCV patients, we have chosen to consider the response of an individual patient to a particular antigen preparation (peptide pools 1 to 9, NS1–5*, NS1–7* or NS3 protein) as significant when it induces SI's 3 in at least half of the assays performed. The results shown in Table 4 have been obtained using this scoring method. The Table shows the antigen recognition pattern of chronic HCV patients towards the 12 antigen preparations standardly used. Apart from the individual patient number and the number of assays performed with PBMC's from each subject, Table 4 also shows the time frame wherein these assays were executed. The start of the Interferon therapy serves as the reference point, week 0. None of the patients responded to all the antigens. PBMC's from 13 of 18 (72%) clinical responders and 12 of 14 (85%) non-responders proliferated in response to at least one antigen preparation. All but one antigen preparation, peptide pool 8, induced a proliferative response in at least one subject. The most frequent responses were to peptide pools 2 and 3. Whereas both interferon-responders and non-responders proliferated equally well to peptide pool 2 (56% and 57%, respectively), non-responders reacted less well to peptide pool 3 (29% or 4 of 14) than responders (44% or 8 of 18). Similar imbalances were observed for the reactions to peptide pools 5 and 9, that were more frequently recognized by non-responders (43% and 43%, respectively) than by responders (17% and 11%, respectively). Clinical non-responders to interferon therapy also reacted more frequently (57 or 8 of 14) upon stimulation with the NS3 protein than responders (24% or 4 of 17). However, none of these differences in proliferative response rates to peptide pools 3, 5 and 9 or to NS3 protein reached statistical significance (p<0.05 in $^2$-test). A striking and significant difference (p=0.01 in $^2$-test) was observed for the response rate of responders and non-responders to peptides NS1–5* and NS1–7*. Indeed, 8 of 17 responders recognized one or both peptides while none of the non-responders did so. A summary of the results of all these proliferation assays is provided in FIG. 2, in which the response rates of the HCV patients as well as 18 healthy control subjects towards the 12 antigen preparations. Indeed, to establish the relevance of the proliferative responses observed in HCV patients, PBMC's from 18 healthy control subjects were stimulated with the same antigen preparations. Overall, 27 assays were performed: a single assay in 10 subjects, two in 7 volunteers and 3 in one individual. In 12 control subjects none of the antigens induced a proliferative response. In 6 subjects one or more antigens induced a proliferative response with an SI 3 in a unique assay or in at least half of the assays performed. Table 5 shows the antigens that induced the proliferation in these subjects. Although FIG. 2 suggests that proliferative responses occur more frequently in HCV patients than in healthy controls, these differences do not always reach statistical significance (p<0.05). Peptide pools 2 and 3 and the NS3 protein clearly (p<0.05) induce more frequent proliferative responses in the whole group of HCV patients than in healthy controls. Most of these differences are also significant when interferon responders and non-responders are each compared to the healthy control group. Only for the proliferative response to NS3 of interferon responders this is no longer valid. Although the frequency of proliferative response to peptide pool 5 in healthy controls and HCV patients were not significantly different, they turned out to be so (p<0.03) when only the non-responders were compared to the control subjects. All other differences did not reach the p<0.05 level.

Example 5

Fine Specificity of the Recognition of the HCV Core Region by PBMC from Clinical Responders: T Cell Epitope Localization in the Core Carboxyterminal Region Since peptide pools 2 and 3 elicited proliferative responses in a large fraction of HCV patients, we have examined which peptides from these pools were inducing these responses. The stimulatory capacity of single peptides on PBMC's from healthy control subjects was tested as well. Twenty-three proliferation assays were performed with PBMC's from 17 control subjects. Peptides core C17, core C21 and core C31 were recognized by 2, 1 and 1 subject or 12%i, 6% and 6% of subjects, respectively. PBMC's were prepared from 11 HCV patients that responded to interferon therapy. Eight subjects had displayed a proliferative response to either one or both peptide pools 2 and 3, whereas 3 patients had not. Nineteen assays were performed. The scoring system for positive reactions was as described in example 4. Table 6 summarizes the results of these 19 assays and demonstrates the consistency of the assay results. Indeed, PBMC's from the patients that had not reacted to the peptide pools did not proliferate upon stimulation with any of the individual peptides. The PBMC's from the patients that had displayed a proliferative response before, also reacted upon stimulation with one or several peptides from these pools. At least one and up to five of these peptides were recognized by these patients. The most immunogenic region of the HCV core sequence seems to be located between amino acids 109 and 176. Peptides C27 (AA 157–176), recognized by 6 of the 8 proliferative responders, turns out to be the most immunodominant one, followed by C25 which is recognized by 5 patients, and C23 and C19 which are recognized by 3 subjects.

Example 6

The fine specificity of the lymphoproliferative responses was tested again with new samples, the majority of which was obtained from other patients than those analyzed in example 5. Five patients (two αIFN responders and three αIFN non-responders) and 16 normal controls were examined. Table 7 shows the results of the assays performed in chronic hepatitis C patients. The highest LPR observed in both AIFN responders tested was towards aa positions: 73–92 (C13); 109–128 (C19); 121–140 (C21); 145–164 (C25); 157–176 (C27). Only aa residues 121–140 (C21) and 133–152 (C23) elicited a high PLR in two αIFN non-responders. Therefore, the use of peptides C13, C19, C25 and/or C27 in prophylactic or therapeutic vaccine compositions may be particularly advantageous.

REFERENCES

Maertens, G., Ducatteeuw, A., Stuyver, L., Vandeponseele, P., Venneman, A., Wyseur, A., Bosman, F., Heijtink, R. & de Martynoff, G. (1994) Low prevalence of anti-E1 antibodies reactive to recombinant type 1b E1 envelope protein in type 2, 3, and 4 sera, but high prevalence in subtypes 1a and-1b. In: Viral Hepatitis and Liver Disease, Proceedings of the International Symposium on Viral Hepatitis and Liver Disease (Eds. Nishioka, K., Suzuki, H., Mishiro, S., and Oda, T.), pp 314–316, Springer-Verlag Tokyo.

Simmonds, P., Rose, K. A., Graham, S., Chan, S.-W., McOmish, F., Dow, B. C., Follett, E. A. C., Yap, P. L., & Marsden, H. (1993b) Mapping of serotype-specific, immunodominant epitopes in the NS4 region of hepatitis C virus (HCV): Use of type-specific peptides to serologically discriminate infections with HCV type 1, 2, and 3. *J. Clin. Microbiol.* 31, 1493–1503.

Simmonds, P., Holmes, E. C., Cha, T.-A., Chan, S.-W., McOmish, F., Irvine, B., Beall, E., Yap, P. L., Kolberg, J., & Urdea, M. S. (1993c) *J. Gen. Virol.* 74, 2391–2399.

Stuyver, L., Van Arnhem, W., Wyseur, A. & Maertens, G. (1994) Cloning and phylogenetic analysis of the Core, E2, and NS3/4 regions of hepatitis C virus type 5a. Biochem. Biophys. Res. Comm. 202, 1308–1314.

Simmonds, P., Alberti, A., Alter, H., Bonino, F., Bradley, D. W., Bréchot, C., Brouwer, J., Chan, S.-W., Chayama K., Chen, D.-S., Choo, Q.-L., Colombo, M., Cuypers, T., Date, T., Dusheiko, G., Esteban, J. I., Fay, O., Hadziyannis, S., Han, J., Hatzakis, A., Holmes, E. C., Hotta, H., Houghton, M., Irvine, B., Kohara, M., Kolberg, J. A., Kuo, G., Lau, J. Y. N., Lelie, P. N., Maertens. G., McOmish, F., Miyamura, T., Mizokami, M., Nomoto, A., Prince A. M., Reesink, H. W., Rice, C., Roggendorf, M., Schalm, S., Shikata, T., Shimotohno, K., Stuyver, L., Trepo, C., Weiner, A., Yap, P. L. & Urdea, M. S. (1994) A proposed system for the nomenclature of hepatitis C virus genotypes. *Hepatology* 19, 1321–1324.

Stuyver, L., Van Arnhem, W., Wyseur, A., DeLeys, R. & Maertens, G. (1993a) Analysis of the putative E1 envelope and NS4a epitope regions of HCV type 3. Biochem. Biophys. Res. Comm. 192, 635–641.

Stuyver, L., Rossau, R., Wyseur, A., Duhamel, M., Vanderborght, B., Van Heuverswyn, H. & Maertens, G. (1993b) Typing of hepatitis C virus isolates and characterization of new subtypes using a line probe assay. J. Gen Virol. 74, 1093–1102.

Stuyver, L., Wyseur, A., Van Arnhem, W., Rossau, R., Delaporte, E., Dazza, M.-C., Van Doorn, L.-J., Kleter, B. & Maertens, G. (1994a) The use of a line probe assay as a tool to detect new types or subtypes of hepatitis C virus. In: Viral Hepatitis and Liver Disease, Proceedings of the International Symposium on Viral Hepatitis and Liver Disease (Eds. Nishioka, K., Suzuki, H., Mishiro, S., and Oda, T.), pp 317–319, Springer-Verlag Tokyo.

Stuyver, L., Van Arnhem, W., Wyseur, A. & Maertens, G. (1994b) Cloning and Phylogenetic analysis of the Core, E2, and NS3/4 regions of the hepatitis C virus type 5a. Biochem. Biophys. Res. Comm. 202, 1308–1314.

Stuyver, L., Van Arnhem, W., Wyseur, A., Hernandez, F., Delaporte, E., & Maertens, G. (1994c) Classification of hepatitis C viruses based on phylogenetics analysis of the E1 and NS5B regions and identification of 5 new subtypes. Proc. Natl. Acad. Sci. USA 91, in press.

Knauf M, Bell D P, Hirtzer P, Luo Z, Young J, Katre N (1988) Relationship of effective molecular size to systemic clearance in rate of recombinant interleukin-2 chemically modified with water-soluble polymers. J Biol Chem.263: 15064–15070.

Poznansky M, Juliano R (1984) Biological approaches to the controlled delivery of drugs: a critical review. Pharmacol Rev.36: 277–336.

Szoka F Jr, Papahadjopoulos D (1980) Comparative properties and methods of preparation of lipid vesicles (liposomes). Annu-Rev-Biophys-Bioeng 9: 467–508.

Aurameas et al., Scand J Immunol, Vol. 8, Suppl. 7, 7–23 (1978).

Botarelli P, Brunetto M, Minutello M, Calvo P, Unutmaz D, Weiner A, Choo Q, Shuster J, Kuo G, Bonino F, Houghton M, Abrignani S (1993) T-lymphocyte response to hepatitis C virus in different clinical courses of infection. Gastroenterology 104: 580–587.

Bukh J, Purcell R, Miller R (1992). Sequence analysis of the 5' noncoding region of hepatitis C virus. Proc Natl Acad Sci USA 89:4942–4946.

Cha T, Beal E, Irvine B, Kolberg J, Chien D, Kuo G, Urdea M (1992) At least five related, but distinct, hepatitis C viral genotypes exist. Proc Natl Acad Sci USA 89:7144–7148.

Chan S, Simmonds P, McOmish F, Yap P, Mitchell R, Dow B, Follett E (1991) Serological responses to infection with three different types of hepatitis C virus. Lancet 338:1991.

Chan S, McOmish F, Holmes E, Dow B, Peutherer J, Follett E, Yap P, Sinmonds P (1992) Analysis of a new hepatitis C virus type and its phylogenetic relationship to existing variants. J Gen Virol 73:1131–1141.

Choo Q, Richman K, Han J, Berger K, Lee C, Dong C, Gallegos C, Coit D, Medina-Selby A, Barr P, Weiner A, Bradley D, Kuo G, Houghton M (1991) Genetic organization and diversity of the hepatitis C virus. Proc Natl Acad Sci USA 88:2451–2455.

Davies G, Balard L, Schiffer E (1989) Treatment of chronic hepatitis with recombinant interferon alpha: a multicenter radomnized, controlled trial. N Engl Med 321: 1501–1506.

Erlanger, Method of Enzymology, 70: 85 (1980).

Gabizon A, Dagan A, Goren D, Barenholz Y, Fuks Z (1982) Liposbmes as in vivo carriers of adriamycin: reduced cardiac uptake and preserved antitumor activity in mice. Cancer Res 42: 4734–4739.

Hoofnagle J, Lullen K, Jones D (1986) Treatment of chronic non-A, non-B hepatitis with recombinant human alpha interferon., N Engl J Med 315: 1575–1578.

Kato N, Hijikata M, Ootsuyama Y, Nakagawa M, Ohkoshi S, Sugimura T, Shimotohno K (1990) Molecular cloning of the human hepatitis C virus genome from Japanese patients with non-A, non-B hepatitis. Proc Natl Acad Sci USA 87: 9524–9528.

Koziel M, Dudley D, Wong J, Dienstag J, Houghton M, Ralston R, Walker B (1992). Intrahepatic cytotoxic T lymphocytes specific for hepatitis C virus in persons with chronic hepatitis. J Immunology 149: 3339–3344.

Minutello M, Pileri P, Unutmaz D, Censini S, Kuo G, Houghton M, Brunetto M, Bonino F. Abrignani S (1993). Compartimentalization of T lymphocytes to the site of disease: intrahepatic CD4+ T cells specific for the protein NS4 of Hepatitis C Virus in patients with Chronic hepatitis C. J Exp Med 178: 17–25.

Mori S, Kato N, Yagyu A, Tanaka T, Ikeda Y, Petchclai B, Chiewsilp P, Kurimura T, Shimotohno K (1992) A new type of hepatitis C virus in patients in Thailand. Biochem Biophys Res Comm 183: 334–342.

Okamoto H, Okada S, Sugiyama Y, Yotsumoto S, Tanaka T, Yoshizawa H, Tsuda F, Miyakawa Y, Mayumi M (1990). The 5' terminal sequence of the hepatitis C virus genome. Jap J Exp Med 60: 167–177.

Okamoto H, Okada S, Sugiyama Y, Kurai K, Iizuka H, Machida A, Miyakawa Y, Mayumi M (1991) Nucleotide sequence of the genomic RNA of hepatitis C virus isolated from a human carrier: comparison with reported isolates for conserved and divergent regions. J Gen Virol 72: 2697–2704.

Okamoto H, Kurai K, Okada S, Yamamoto K, Lizuka H, Tanaka T, Fukuda S, Tsuda F, Mishiro S (1992) Full-length sequences of a hepatitis C virus genome having poor homology to reported isolates: comparative study of four distinct genotypes. Virology 188: 331–341.

Rodwell et al., Biotech 3, 889–894 (1985).

Stuyver L, Rossau R, Wyseur A, Duhamel M, Vanderborght B, Van Heuverswyn H, Maertens G (1993) Typing of hepatitis C virus (HCV) isolates and characterization of new (sub)types using a Line Probe Assay. J Gen Virology, 74: 1093–1102.

*Essential Immunology*, 3rd Ed., by Roit, published by Blackwell Scientific Publications; *Fundamentals of Clinical Immunology*, by Alexander and Good, published by W. B. Saunders; *Immunology*, by Bellanti, published by W. B. Saunders.

TABLE 1

Synthetic peptides used as antigens in the lymphoproliferative assays.

| HCV REGION | POOL | PEPTIDE NAME | AMINO ACID (AA) SEQUENCE | AA POSITION | SEQ ID NO | SOLVENT |
|---|---|---|---|---|---|---|
| CORE | 1 | CORE 2 | PKPQRKTKRNTNRRP | 5–19 | 1 | A |
| | | CORE 3 | RNTNRRPQDVKFPGGGQIVG | 13–32 | 2 | A |
| | | CORE 5 | PGGGQIVGGVYLLPRRGPRL | 25–44 | 3 | B |
| | | CORE 9 | TRKTSERSQPRGRRQPIPKV | 49–68 | 4 | A |
| | | CORE 11 | RRQPIPKVRRPEGRTWAQPG | 61–80 | 5 | A |
| | 2 | CORE 13 | GRTWAQPGYPWPLYGNEGCG | 73–92 | 6 | B |
| | | CORE 15 | LYGNEGCGWAGWLLSPRGSR | 85–104 | 7 | C |
| | | CORE 17 | LLSPRGSRPSWGPTDPRRRS | 97–116 | 8 | A |
| | | CORE 19 | PTDPRRRSRNLGKVIDTLTC | 109–128 | 9 | A |
| | | CORE 21 | KVIDTLTCGFADLMGYIPLV | 121–140 | 10 | D |
| | 3 | CORE 23 | LMGYIPLVGAPLGGAARALA | 133–152 | 11 | A |
| | | CORE 25 | GGAARALAHGVRVLEDGVNY | 145–164 | 12 | A |
| | | CORE 27 | VLEDGVNYATGNLPGCSFSI | 157–176 | 13 | E |
| | | CORE 29 | LPGCSFSIFLLALLSCLTVP | 169–188 | 14 | O |
| | | CORE 31 | LLSCLTVPASAYQVRNSTGL | 181–200 | 15 | C |
| E1 | 4 | E1-33 | QVRNSTGLYHVTNDCFNSSI | 193–212 | 16 | O |
| | | E1-35 | NDCPNSSIVYEAHDAILHTP | 205–224 | 17 | C |
| | | E1-37 | HDAILHTPGCVPCVREGNVS | 217–236 | 18 | A |
| | | E1-39 | CVREGNVSRCWVAMTPTVAT | 229–248 | 19 | H |
| | | E1-41 | AMTPTVATRDGKLPPATQLRR | 241–260 | 20 | A |
| | 5 | E1-43 | LPATQLRRHIDLLVGSATLC | 253–272 | 21 | H |
| | | E1-45 | LVGSATLCSALYVGDLCGSV | 265–284 | 22 | E |
| | | E1-49 | QTFLTSPRRHWTTQGCNCSI | 289–308 | 23 | H |
| | | E1-51 | TQGCNCSTYPGHITGHRMAW | 301–320 | 24 | B |
| | | E1-53 | ITGHRMAWDMMMNWSPTAAL | 313–332 | 25 | H |
| | 6 | E1-55 | NWSPTAALVMAQLLRIPQAI | 325–344 | 26 | H |
| | | E1-57 | LLRIPQAILDMAIAGAHWGVL | 337–356 | 27 | H |
| | | E1-59 | AGAHWGVLAGIAYFSMVGNW | 349–368 | 28 | I |
| | | E1-63 | VVLLLFAGVDAETTIVSGGQA | 373–392 | 29 | E |
| E2/NS1 | 7 | NS1-3' | LNCNESLNTGWWLAGLIYQHK | 427–446 | 30 | C |
| | | NS1-1' | AGLIYQHKFNSSGCPERLAS | 439–458 | 31 | B |
| | | NS1-1 | GCPERLASCRPLTDFDQGWG | 451–470 | 32 | B |
| | | NS1-3 | TDFDQGWGPISYANGSGPDQ | 463–482 | 33 | A |
| | | NS1-5 | ANGSGPDQRFYCHWHYPPKPC | 475–494 | 34 | A |
| | 8 | NS1-7 | WHYPPKPCGIVPAKSVCGPV | 487–506 | 35 | B |
| | | NS1-9 | AKSVCGPVYCFTPSPVVVGT | 499–518 | 36 | O |
| | | NS1-11 | PSPVVVGTTDRSGAPTYSWG | 511–530 | 37 | C |
| | | NS1-13 | GAPTYSWGENDTDVFVLNNT | 523–542 | 38 | E |
| | | NS1-17 | GNWFGCTWMNSTGFTKVCGA | 547–566 | 39 | O |
| | | NS1-19 | GFTKVCGAPPVCIGGAGNNT | 559–578 | 40 | A |
| | 9 | NS1-21 | IGGAGNNTLHCPTDCFRKHP | 571–590 | 41 | A |
| | | NS1-23 | TDCFRKHPDATYSRCGSGPW | 583–602 | 42 | A |
| | | NS1-25 | SRCGSGPWITPRCLVDYPYR | 595–614 | 43 | B |
| | | NS1-27 | CLVDYPYRLWHYPCTINYTI | 607–626 | 44 | C |
| | | NS1-29 | PCTINYTIFKIRMYVGGVEH | 619–638 | 45 | A |
| | | NS1-7' | SGLVSLFTPGAKQNIQLINT | 397–416 | 46 | C |
| | | NS1-5' | QNIQLINTNGSWHINSTALN | 409–428 | 47 | C |

Solvents used:
Solvent A: 0.1% trifluoroacetic acid;
Solvent B: 0.1% trifluoroacetic acid, 25% acetonitrile;
Solvent C: 0.1% trifluoroacetic acid, 30% acetonitrile;
Solvent D: 0.1% trifluoroacetic acid, 50% acetonitrile;
Solvent E: 0.005 ammonia buffer;
Solvent O: 50% dimethyl sulfoxide;
Solvent H: 0.1% trifluoroacetic acid, 40% acetonitrile.

TABLE 2

General data from HCV patients.

| Patient | Gender | Age | AP Diagnosis | Source | Duration (Years) | Genotype | IFN Scheme | ALT before therapy |
|---|---|---|---|---|---|---|---|---|
| | | | | CLINICAL RESPONDERS | | | | |
| 604 | F | 30 | CAH: mod | IVDA | 10 | 1b | 2 | 150 |
| 607 | M | 39 | CPH | Unknown | 2 | 1b | 1 | 182 |
| 608 | M | 61 | CAH: mild | Transfusion | 7 | 3a | 1 | 196 |
| 610 | F | 27 | Non spec | Unknown | 2 | 1b | 2 | 219 |
| 614 | M | 56 | CAH: mild | Tranfusion | 10 | 1b | 2 | 425 |
| 615 | M | 71 | CAH: mod | Unknown | 2 | 1b | 1 | 201 |
| 616 | F | 52 | Non spec | Transfusion | 5 | 1b | 1 | 152 |
| 618 | F | 37 | CPH | Needle stick | 5 | 1b | 2 | 60 |
| 621 | M | 48 | CAH: mod | Unknown | 8 | 1b | 1 | 63 |
| 624 | M | 31 | CPH | Needle stick | 15 | 1b | 2 | 158 |
| 626 | F | 34 | CAH: sev | Transfusion | 6 | 3a | 2 | 168 |
| 630 | M | 30 | CPH | Needle stick | 5 | 1b | 2 | 9 |
| 632 | M | 57 | CPH | Unknown | 1 | 4a or 5a | 2 | 359 |
| 633 | F | 30 | CAH: mod | Transfusion | 2 | 1b | 2 | 292 |
| 634 | F | 67 | CAH: mod | Unknown | 32 | 1b | 2 | 481 |
| 635 | F | 47 | prob cirrh | Tranfusion | 14 | 1b | 2 | 100 |
| 636 | F | 54 | CAH: mod | Unknown | 7 | 5a | 1 | 90 |
| 639 | F | 62 | CAH | Transfusion | 32 | 1b | 1 | 79 |
| | | | | CLINICAL NON-RESPONDERS | | | | |
| 601 | M | 32 | CAH: mod | Transfusion | 3 | 1b | 2 | 141 |
| 602 | M | 66 | CAH: mod | Transfusion | 3 | 1b | 1 | 349 |
| 603 | M | 45 | CAH: sev | Transfusion | 17 | 1b | 2 | 157 |
| 606 | F | 53 | CAH: mod | Unknown | 2 | 1b | 1 | 299 |
| 611 | M | 51 | CPH | Transfusion | 7 | 1b | 1 | 195 |
| 613 | F | 38 | CAH: mod | IVDA | 17 | 3a | 1 | 178 |
| 617 | M | 71 | CAH: sev | Transfusion | 3 | 1b | 1 | 447 |
| 620 | M | 67 | CAH: mod | Unknown | 2 | 1b | 1 | 138 |
| 622 | M | 40 | CAH: sev | Transfusion | 11 | 1b | 1 | 291 |
| 625 | M | 70 | CAH: mod | Unknown | 1 | 1b | 1 | 134 |
| 627 | M | 44 | CAH: mod | IVDA | 8 | 3a | 1 | 254 |
| 629 | F | 61 | Cirrh | Transfusion | 11 | 1b | 1 | 179 |
| 631 | M | 69 | CPH | Unknown | 5 | 1b | 2 | 358 |
| 637 | F | 59 | Cirrh | Unknown | 5 | 1b | 2 | 118 |

CAH = CHRONIC ACTIVE HEPATITIS.
CPH = CHRONIC PERSISTENT HEPATITIS.
CIRRH = CIRRHOSIS.
NON SPEC = NOT DONE OR NOT SPECIFIC ABNORMALITIES

TABLE 3

Antibody reactivities to 6 HCV antigens of the Line Immuno-Assay in 32 chronic HCV patients.

| Patient | Weeks | Genotype | NS4 | NS5 | C1 | C2 | C3 | C4 |
|---|---|---|---|---|---|---|---|---|
| | | CLINICAL RESPONDERS | | | | | | |
| 604 | −6 | 1b | 3 | 3 | 2 | 2 | − | − |
| | 90 | | 3 | 3 | 3 | 3 | − | 2 |
| 607 | −11 | 1b | 2 | 3 | 2 | − | − | − |
| | 84 | | 3 | 3 | 3 | − | − | − |
| 608 | −6 | 3a | − | 3 | − | − | − | − |
| 610 | −6 | 1b | 3 | − | 2 | 3 | − | − |
| 614 | 30 | 1b | 3 | 3 | 2 | 2 | − | − |
| | 60 | | 2 | 3 | 3 | 3 | − | − |
| 615 | −2 | 1b | 3 | − | − | 2 | − | − |
| 616 | −6 | 1b | 3 | − | 2 | 3 | 2 | 2 |
| 618 | −6 | 1b | − | − | − | 3 | − | − |
| | 54 | | − | − | − | 2 | − | − |
| 621 | −3 | 1b | 3 | 3 | 2 | − | − | − |
| | 30 | | 3 | 3 | 2 | − | − | − |
| 624 | −5 | 1b | 3 | 3 | 2 | 2 | − | − |
| | 20 | | 3 | 3 | 2 | 3 | 2 | 2 |
| 626 | 2 | 3a | − | 2 | 2 | 3 | − | − |
| | 20 | | 2 | 2 | 3 | 3 | − | 2 |
| 630 | −12 | 1b | 3 | − | 2 | 2 | − | − |
| | 8 | | 3 | − | 2 | 2 | − | − |
| 632 | −6 | 4a or 5a | − | 3 | 2 | 3 | 2 | 2 |
| | 8 | | − | 3 | 2 | 3 | 2 | 2 |
| 633 | −6 | 1b | 3 | 3 | − | 2 | − | 2 |

"−" denotes negative, indeterminate or weak reactions.
2, moderate reaction.
3, strong reaction.

TABLE 4

T-cell recognition of 12 HCV antigens in 32 chronic hepatitis C patients under alpha-interferon therapy.

| Patient | Genotype | N°, Assays | Time of assays | P1 | P2 | P3 | P4 | P5 | P6 | P7 | P8 | P9 | NS1-7* | NS1-5* | NS3 |
|---|---|---|---|---|---|---|---|---|---|---|---|---|---|---|---|
| CLINICAL RESPONDERS | | | | | | | | | | | | | | | |
| 604 | 1b | 2 | w90–108 | | + | + | + | + | + | | + | + | + | + |
| 607 | 1b | 2 | w84–120 | | + | | | + | | | | + | ND | ND | ND |
| 608 | 3a | 2 | w90–108 | | + | + | | | | | | | | | |
| 610 | 1b | 1 | w84 | | | | | | | | | | | | |
| 614 | 1b | 4 | w60–108 | | | | | | | | | | | + | |
| 615 | 1b | 2 | w66–84 | + | + | + | + | + | | | | | | | + |
| 616 | 1b | 3 | w78–108 | | | | | | | | | | | + | |
| 618 | 1b | 4 | w54–84 | + | + | | | | | | | | | | + |
| 621 | 1b | 4 | w30–60 | | | + | | | | | | | + | + | |
| 624 | 1b | 9 | w20–90 | | | | | | | | | | | | |
| 626 | 3a | 9 | w16–60 | | + | + | | | | | | | + | | |
| 630 | 1b | 6 | w8–75 | | | | | | | | | | | | |
| 632 | 4a or 5a | 8 | w4–54 | | + | + | | | | | | | | | |
| 633 | 1b | 11 | w0–48 | | | | | | | | | | | | |
| 634 | 1b | 3 | w0–24 | | + | | | | | | | | | + | + |
| 635 | 1b | 7 | w-6–54 | + | + | + | | | | | | | | | |
| 636 | 5a | 1 | w24 | | + | + | | | | | | | | + | |
| 639 | 1b | 4 | w-3–19 | + | + | + | | | | | | | + | + | |
| CLINICAL NON-RESPONDERS | | | | | | | | | | | | | | | |
| 601 | 1b | 4 | w90–140 | | + | | | + | + | | + | | | | + |
| 602 | 1b | 2 | w96–108 | + | + | + | + | | | | + | | | | + |
| 603 | 1b | 2 | w78–93 | | + | + | + | + | | | | | | | + |
| 606 | 1b | 3 | w84–96 | | + | | | + | | | | | | | + |
| 611 | 1b | 2 | w66–84 | + | + | | | + | | | | | | | |
| 613 | 3a | 8 | w60–96 | | | | | | | | | | | | + |
| 617 | 1b | 5 | w60–108 | | | | | | | | | | | | |
| 620 | 1b | 3 | w42–66 | | | | | | | | + | | | | + |
| 622 | 1b | 3 | w30–54 | | | | | | + | | | | | | + |
| 625 | 1b | 4 | w20–66 | + | + | | | | | | + | | | | |
| 627 | 3a | 3 | w16–24 | | + | | | | | | | | + | | |
| 629 | 1b | 2 | w20–48 | + | + | | + | + | | + | + | | | | + |
| 631 | 1b | 5 | w4–w16 | | | | | | | | | | | | |
| 637 | 1b | 7 | w-6–16 | | | | + | | | | | | | | |

P1–3 corresponds to Core,
P4–6 represents E1.
P7–9 comprises E2/NS1.
(+) denotes lymphoproliferative response.
ND- Not done.

TABLE 5

Antigens recognized by 6 control subjects displaying significant* lymphoproliferation responses.

| SUBJECTS | N° ASSAYS | P1 | P2 | P3 | P4 | P5 | P6 | P7 | P8 | P9 | NS1-7* | NS1-5* | NS3 |
|---|---|---|---|---|---|---|---|---|---|---|---|---|---|
| CAE | 3 | | | | | | | | + | | | | |
| IDS | 1 | + | | | | | | | | | | + | |
| LCE | 1 | | | | | | | | | | + | | |
| MVH | 1 | + | + | + | | | | + | | + | | | |
| PDG | 2 | | | + | | | | | | | | | |
| RDB | 2 | + | | | | | | | | | | | |

*A response is considered significant when a S.I. equal or greater than 3 in a single peptide assay or in at least half of the assays performed.

TABLE 6

The lymphoproliferative responses to peptide pools are consistent with lymphoproliferative responses to single peptides fr.

| Patient | PEPTIDE N° assays | POOLS Pool 2 | Pool 3 | N° assays | C13 | C15 | SINGLE P2 C17 | C19 | C21 | PEPTIDES C23 | C25 | C27 | P3 C29 | C31 |
|---|---|---|---|---|---|---|---|---|---|---|---|---|---|---|
| LPR TO POOLS 2 AND/OR 3 | | | | | | | | | | | | | | |
| 604 | 2 | + | + | 1 | - | - | - | - | - | + | - | - | - | - |
| 615 | 2 | + | + | 1 | - | - | - | - | - | + | - | + | - | - |
| 618 | 4 | + | - | 1 | - | - | - | - | - | - | + | + | - | - |
| 621 | 4 | - | + | 1 | - | - | - | - | - | - | + | + | - | - |
| 626 | 9 | + | + | 5 | - | - | - | - | - | - | + | + | - | - |
| 632 | 8 | + | + | 4 | - | - | - | + | + | + | + | + | - | - |
| 634 | 2 | + | - | 1 | - | - | - | + | - | - | - | + | - | - |
| 639 | 4 | + | + | 2 | - | - | - | + | - | - | + | + | - | + |
| NO LPR TO POOLS 2 AND 3 | | | | | | | | | | | | | | |
| 614 | 3 | - | - | 1 | - | - | - | - | - | - | - | - | - | - |
| 616 | 3 | - | - | 1 | - | - | - | - | - | - | - | - | - | - |
| 633 | 1 | - | - | 1 | - | - | - | - | - | - | - | - | - | - |

TABLE 7

Fine specificity of T-cell recognition of P2 and P3 Core individual peptides

| Patient N° | Clinical response to αIFN[a] | Week[b] | Blank[e] | TT[d] | P2 peptides C13[e] | C15 | C17 | C19 | C21 | C23 | C25 | C27 | C29 | P3 peptides C31 |
|---|---|---|---|---|---|---|---|---|---|---|---|---|---|---|
| 626 | R | 14 | 750 | 14.5 | 4.4 | — | — | — | 3.3 | — | 6 | 8.2 | — | — |
| 636 | R | 28 | 1032 | 3.6 | 6.3 | — | — | 7.1 | — | — | 9.7 | 5.8 | — | — |
| 620 | NR | 20 | 5047 | 4.1 | ND | ND | ND | ND | ND | 4.1 | — | — | — | — |
| 627 | NR | 54 | 928 | 19.1 | — | — | — | — | 3.6 | — | — | — | — | — |
| 637 | NR | 45 | 2370 | 4.2 | — | — | — | — | — | — | — | — | — | — |

[a]R: responder; NR: Not responder.
[b]Time points of αIFN therapy on which LPA were performed.
[c]Values express cpm.
[d]TT: Tetanus toxoid. Values denote SI.
[e]C13–C21 and C23–C31 are the individual peptides of P2 and P3 Core peptide pools. Only SI equal or greater than 3 are shown.
[f]ND: Not done.

What is claimed is:

1. A composition comprising a poptide selected from the group consisting of at least 7 to less than 25 contiguous amino acids of the amino acid sequence represented by SEQ ID NO:58 and at least 44 to at most 104 contiguous amino acids of the amino acid sequence represented by SEQ ID NO:58; wherin said peptide contains a T cell stimulating epitope.

2. The composition according to claim 1 wherein said amino acid sequence is selected from the group consisting of SEQ ID NO:s 48, 50, 51, 52, 53, 54 and 99.

3. The composition according to claim 1 wherein said amino acid sequence is selected from the group consisting of SEQ ID NO:s 13, 73, 74, 75, 76, 77, 78, 79, 80 and 81.

4. The composition according to claim 1 wherein said amino acid sequence is selected from the group consisting of SEQ ID NO:s 12, 118, 82, 83, 84, 85, 86, 87, 88, 89, 90, 91, 92 and 93.

5. The composition according to claim 1 wherein said amino acid sequence is selected from the group consisting of SEQ ID NO:s 11, 62, 63, 64, 65, 66, 68, 69, 70, 71, 72, 94 and 95.

6. The composition according to claim 1 wherein said amino acid sequence is selected from the group consisting of SEQ ID NO:s 9, 96, 97, 98 and 117.

7. The composition according to claim 1 wherein said amino acid sequence is selected from the group consisting of SEQ ID NO:s 100, 101, 102 and 103.

8. A method of treating a person infected with HCV comprising administering thc composition of claim 1.

9. A method of inducing T cell function in a person comprising administering the composition of claim 1 to a person.

10. A composition comprising a peptide having the sequence of SEQ ID NO:67.

11. A method of treating a person infected with HCV comprising administering to a person in need of said treatment a composition comprising a peitide of at least 7 to at most 104 contiguous amino acids of the amino acid sequence represented by SEQ ID NO:58; said peptide containing a T cell-stimulating epitope.

12. A method of inducing T cell function comprising administering a composition comprising a peptide of at least 7 contiguous amino acids to at most 104 contiguous amino acids of the amino acid sequence represented by SEQ ID NO:58 in an amount sufficient to induce T cell activity.

13. A method of immunizing a person comprising administering to a person a composition comprising a peptide of at least 7 to at most 104 contiguous amino acids of the amino acid sequence represented by SEQ ID NO:58; said peptide containing a T cell stimulating epitope.

14. The composition of claim 1, further comprising a pharmaceutically acceptable excipient.

15. The composition of claim 1, wherein said peptide is a recombinant peptide expressed by an expression vector comprising a nucleic acid insert encoding for said peptide.

* * * * *

UNITED STATES PATENT AND TRADEMARK OFFICE
CERTIFICATE OF CORRECTION

PATENT NO. : 6,555,114 B1
DATED : April 29, 2003
INVENTOR(S) : Leroux-Roels et al.

It is certified that error appears in the above-identified patent and that said Letters Patent is hereby corrected as shown below:

Column 2,
Line 34, delete "(in" and insert therefor -- in --.

Column 3,
Line 63, delete "PSVMT" and insert therefor -- PSVAAT --.

Column 5,
Line 13, delete "Interferon-a" and insert therefor -- Interferon-α --.
Line 49, delete "understod" and insert therefore -- understood --.

Column 6,
Line 15, delete "lenght" and insert therefor -- length --.
Line 17, delete "al" and insert therefor -- at --.

Column 7,
Line 61, delete "$X_{26}GX_{27}$" and insert therefor -- $X_{26}X_{27}$ --.

Column 8,
Line 4, delete "$X_{16}$" and insert therefor -- $X_{36}$ --.
Line 6, delete "X13" and insert therefor -- $X_{13}$ --.
Line 7, delete "$_{X18}$" and insert therefor -- $X_{18}$ --.

Column 9,
Line 37, delete "Prefererntially" and insert therefor -- Preferentially --.
Line 41, delete "$R_{30}X_{31}$" and insert therefor -- $RX_{30} X_{31}$ --.
Line 60, delete "$X_{19}X_{21}$" and insert therefor -- $X_{19}X_{20}$ --.

Column 10,
Line 14, delete "NH2" and insert therefor -- $NH_2$ --.

Column 12,
Line 62, delete "$X_{52}NGSWHX_{53}NX_{54}$" and insert therefor
-- $X_{54}NGSWHX_{52}NX_{53}$ --.

UNITED STATES PATENT AND TRADEMARK OFFICE
CERTIFICATE OF CORRECTION

PATENT NO. : 6,555,114 B1
DATED : April 29, 2003
INVENTOR(S) : Leroux-Roels et al.

It is certified that error appears in the above-identified patent and that said Letters Patent is hereby corrected as shown below:

Column 13,
Line 20, delete "$X_{76}$" and insert therefor -- $X_{67}$ --.

Column 14,
Line 14, delete "to" and insert therefor -- the --.

Column 15,
Line 18, delete "TCTQ" and insert therefor -- TCVTQ --.
Line 49, delete "PSVMT" and insert therefor -- PSVAAT --.

Column 16,
Line 3, delete "fro" and insert therefor -- for --.
Line 28, delete "COSI" and insert therefor -- COS1 --.

Column 17,
Line 38, delete "*perfrincens*" and insert therefor -- *perfringens* --.
Line 39, delete "*restis*" and insert therefor -- *pestis* --.
Line 43, delete "encephalomyeitis" and insert therefor -- encephalomyelitis --.
Line 44, delete "chloera" and insert therefor -- cholera --.

Column 18,
Line 1, delete "13 peptide" and insert therefor -- 13 = peptide --.
Line 36, delete "$PX_{20}$" and insert therefor -- $PX_{21}$ --.
Line 60, delete "NO 117), N" and insert therefor -- NO 117), --.
Line 61, delete "$H_2$" and insert therefor -- $NH_2$ --:

Column 19,
Line 3, delete "VIND" and insert therefor -- VTND --.
Line 20, delete "$QX_{47}$".
Line 36, delete "1".

Column 21,
Line 45, delete "Nonacueous" and insert therefor -- Nonaqueous --.
Line 47, delete "dexerose" and insert therefor -- dextrose --.

UNITED STATES PATENT AND TRADEMARK OFFICE
CERTIFICATE OF CORRECTION

PATENT NO. : 6,555,114 B1
DATED : April 29, 2003
INVENTOR(S) : Leroux-Roels et al.

It is certified that error appears in the above-identified patent and that said Letters Patent is hereby corrected as shown below:

Column 24,
Line 2, delete "Interferon a-2b" and insert therefor -- Interferon α-2b --.
Line 10, delete "al" and insert therefor -- at --.

Column 25,
Line 31, delete "ECV" and insert therefor -- HCV --.

Column 26,
Line 43, delete "$10^{-5}$" and insert therefor -- $10^5$ --.

Column 28,
Line 61, delete "AIFN" and insert therefor -- αIFN --.

Columns 31/32,
Table 1, amino acid sequence of peptide E1-33: delete "CFN" and insert therefor -- CPN --.
Table 1, amino acid sequence of peptide E1-49: delete "QTFLT" and insert therefor -- QLFTF --.
Table 1, amino acid sequence of peptide E1-51: delete "STY" and insert therefor -- SIY --.
Table 1, amino acid sequence of peptide E1-57: delete "MAIA" and insert therefor -- MIA --.
Table 1, amino acid sequence of peptide E1-63: delete "ETTI" and insert therefor -- ETI --.
Table 1, amino acid sequence of peptide NS1-5: delete "FYCH" and insert therefor -- PYC --.

Columns 35/36,
Table 4, line of Patient 635: delete "+" in columns P1, P2 and P3.
Table 4, line of Patient 627: add "+" in column P9.
Table 4, line of Patient 627: delete "+" in column NS1-7*.

Columns 37/38,
Table 7, line of Patient 620: delete "ND" and insert therefor -- $ND^f$ -- in column $C13^e$

UNITED STATES PATENT AND TRADEMARK OFFICE
CERTIFICATE OF CORRECTION

PATENT NO.    : 6,555,114 B1
DATED         : April 29, 2003
INVENTOR(S)   : Leroux-Roels et al.

It is certified that error appears in the above-identified patent and that said Letters Patent is hereby corrected as shown below:

Column 283,
Line 15, delete "7" and insert therefor -- 8 --.
Line 42, delete "thc" and insert therefor -- the --.

Column 284,
Line 20, delete "7" and insert therefor -- 8 --.
Line 27, delete "7" and insert therefor -- 8 --.
Line 32, delete "7" and insert therefor -- 8 --.

Signed and Sealed this

Twenty-ninth Day of June, 2004

JON W. DUDAS
*Acting Director of the United States Patent and Trademark Office*

SEQUENCE LISTING

<160> NUMBER OF SEQ ID NOS: 286

<210> SEQ ID NO 1
<211> LENGTH: 15
<212> TYPE: PRT
<213> ORGANISM: hepatitis C virus

<400> SEQUENCE: 1

Pro Lys Pro Gln Arg Lys Thr Lys Arg Asn Thr Asn Arg Arg Pro
1               5                   10                  15

<210> SEQ ID NO 2
<211> LENGTH: 20
<212> TYPE: PRT
<213> ORGANISM: hepatitis C virus

<400> SEQUENCE: 2

Arg Asn Thr Asn Arg Arg Pro Gln Asp Val Lys Phe Pro Gly Gly Gly
1               5                   10                  15

Gln Ile Val Gly
            20

<210> SEQ ID NO 3
<211> LENGTH: 20
<212> TYPE: PRT
<213> ORGANISM: hepatitis C virus

<400> SEQUENCE: 3

Pro Gly Gly Gly Gln Ile Val Gly Gly Val Tyr Leu Leu Pro Arg Arg
1               5                   10                  15

Gly Pro Arg Leu
            20

<210> SEQ ID NO 4
<211> LENGTH: 20
<212> TYPE: PRT
<213> ORGANISM: hepatitis C virus

<400> SEQUENCE: 4

Thr Arg Lys Thr Ser Glu Arg Ser Gln Pro Arg Gly Arg Arg Gln Pro
1               5                   10                  15

Ile Pro Lys Val
            20

<210> SEQ ID NO 5
<211> LENGTH: 20
<212> TYPE: PRT
<213> ORGANISM: hepatitis C virus

<400> SEQUENCE: 5

Arg Arg Gln Pro Ile Pro Lys Val Arg Arg Pro Glu Gly Arg Thr Trp
1               5                   10                  15

Ala Gln Pro Gly
            20

<210> SEQ ID NO 6
<211> LENGTH: 20
<212> TYPE: PRT
<213> ORGANISM: hepatitis C virus

<400> SEQUENCE: 6

Gly Arg Thr Trp Ala Gln Pro Gly Tyr Pro Trp Pro Leu Tyr Gly Asn
1               5                   10                  15

Glu Gly Cys Gly
            20

<210> SEQ ID NO 7
<211> LENGTH: 20
<212> TYPE: PRT
<213> ORGANISM: hepatitis C virus

<400> SEQUENCE: 7

Leu Tyr Gly Asn Glu Gly Cys Gly Trp Ala Gly Trp Leu Leu Ser Pro
1               5                   10                  15

Arg Gly Ser Arg
            20

<210> SEQ ID NO 8

```
<211> LENGTH: 20
<212> TYPE: PRT
<213> ORGANISM: hepatitis C virus

<400> SEQUENCE: 8

Leu Leu Ser Pro Arg Gly Ser Arg Pro Ser Trp Gly Pro Thr Asp Pro
1               5                   10                  15

Arg Arg Arg Ser
            20

<210> SEQ ID NO 9
<211> LENGTH: 20
<212> TYPE: PRT
<213> ORGANISM: hepatitis C virus

<400> SEQUENCE: 9

Pro Thr Asp Pro Arg Arg Arg Ser Arg Asn Leu Gly Lys Val Ile Asp
1               5                   10                  15

Thr Leu Thr Cys
            20

<210> SEQ ID NO 10
<211> LENGTH: 20
<212> TYPE: PRT
<213> ORGANISM: hepatitis C virus

<400> SEQUENCE: 10

Lys Val Ile Asp Thr Leu Thr Cys Gly Phe Ala Asp Leu Met Gly Tyr
1               5                   10                  15

Ile Pro Leu Val
            20

<210> SEQ ID NO 11
<211> LENGTH: 20
<212> TYPE: PRT
<213> ORGANISM: hepatitis C virus

<400> SEQUENCE: 11

Leu Met Gly Tyr Ile Pro Leu Val Gly Ala Pro Leu Gly Gly Ala Ala
1               5                   10                  15

Arg Ala Leu Ala
            20

<210> SEQ ID NO 12
<211> LENGTH: 20
<212> TYPE: PRT
<213> ORGANISM: hepatitis C virus

<400> SEQUENCE: 12

Gly Gly Ala Ala Arg Ala Leu Ala His Gly Val Arg Val Leu Glu Asp
1               5                   10                  15

Gly Val Asn Tyr
            20

<210> SEQ ID NO 13
<211> LENGTH: 20
<212> TYPE: PRT
<213> ORGANISM: hepatitis C virus

<400> SEQUENCE: 13

Val Leu Glu Asp Gly Val Asn Tyr Ala Thr Gly Asn Leu Pro Gly Cys
1               5                   10                  15
```

Ser Phe Ser Ile
            20

<210> SEQ ID NO 14
<211> LENGTH: 20
<212> TYPE: PRT
<213> ORGANISM: hepatitis C virus

<400> SEQUENCE: 14

Leu Pro Gly Cys Ser Phe Ser Ile Phe Leu Ala Leu Leu Ser Cys
1               5                   10                  15

Leu Thr Val Pro
            20

<210> SEQ ID NO 15
<211> LENGTH: 20
<212> TYPE: PRT
<213> ORGANISM: hepatitis C virus

<400> SEQUENCE: 15

Leu Leu Ser Cys Leu Thr Val Pro Ala Ser Ala Tyr Gln Val Arg Asn
1               5                   10                  15

Ser Thr Gly Leu
            20

<210> SEQ ID NO 16
<211> LENGTH: 20
<212> TYPE: PRT
<213> ORGANISM: hepatitis C virus

<400> SEQUENCE: 16

Gln Val Arg Asn Ser Thr Gly Leu Tyr His Val Thr Asn Asp Cys Pro
1               5                   10                  15

Asn Ser Ser Ile
            20

<210> SEQ ID NO 17
<211> LENGTH: 20
<212> TYPE: PRT
<213> ORGANISM: hepatitis C virus

<400> SEQUENCE: 17

Asn Asp Cys Pro Asn Ser Ser Ile Val Tyr Glu Ala His Asp Ala Ile
1               5                   10                  15

Leu His Thr Pro
            20

<210> SEQ ID NO 18
<211> LENGTH: 20
<212> TYPE: PRT
<213> ORGANISM: hepatitis C virus

<400> SEQUENCE: 18

His Asp Ala Ile Leu His Thr Pro Gly Cys Val Pro Cys Val Arg Glu
1               5                   10                  15

Gly Asn Val Ser
            20

<210> SEQ ID NO 19
<211> LENGTH: 20
<212> TYPE: PRT
<213> ORGANISM: hepatitis C virus

```
<400> SEQUENCE: 19

Cys Val Arg Glu Gly Asn Val Ser Arg Cys Trp Val Ala Met Thr Pro
1               5                   10                  15

Thr Val Ala Thr
            20

<210> SEQ ID NO 20
<211> LENGTH: 21
<212> TYPE: PRT
<213> ORGANISM: hepatitis C virus

<400> SEQUENCE: 20

Ala Met Thr Pro Thr Val Ala Thr Arg Asp Gly Lys Leu Pro Pro Ala
1               5                   10                  15

Thr Gln Leu Arg Arg
            20

<210> SEQ ID NO 21
<211> LENGTH: 20
<212> TYPE: PRT
<213> ORGANISM: hepatitis C virus

<400> SEQUENCE: 21

Leu Pro Ala Thr Gln Leu Arg Arg His Ile Asp Leu Leu Val Gly Ser
1               5                   10                  15

Ala Thr Leu Cys
            20

<210> SEQ ID NO 22
<211> LENGTH: 20
<212> TYPE: PRT
<213> ORGANISM: hepatitis C virus

<400> SEQUENCE: 22

Leu Val Gly Ser Ala Thr Leu Cys Ser Ala Leu Tyr Val Gly Asp Leu
1               5                   10                  15

Cys Gly Ser Val
            20

<210> SEQ ID NO 23
<211> LENGTH: 20
<212> TYPE: PRT
<213> ORGANISM: hepatitis C virus

<400> SEQUENCE: 23

Gln Leu Phe Thr Phe Ser Pro Arg Arg His Trp Thr Thr Gln Gly Cys
1               5                   10                  15

Asn Cys Ser Ile
            20

<210> SEQ ID NO 24
<211> LENGTH: 20
<212> TYPE: PRT
<213> ORGANISM: hepatitis C virus

<400> SEQUENCE: 24

Thr Gln Gly Cys Asn Cys Ser Ile Tyr Pro Gly His Ile Thr Gly His
1               5                   10                  15

Arg Met Ala Trp
            20
```

-continued

```
<210> SEQ ID NO 25
<211> LENGTH: 20
<212> TYPE: PRT
<213> ORGANISM: hepatitis C virus

<400> SEQUENCE: 25

Ile Thr Gly His Arg Met Ala Trp Asp Met Met Met Asn Trp Ser Pro
1               5                   10                  15

Thr Ala Ala Leu
            20

<210> SEQ ID NO 26
<211> LENGTH: 20
<212> TYPE: PRT
<213> ORGANISM: hepatitis C virus

<400> SEQUENCE: 26

Asn Trp Ser Pro Thr Ala Ala Leu Val Met Ala Gln Leu Leu Arg Ile
1               5                   10                  15

Pro Gln Ala Ile
            20

<210> SEQ ID NO 27
<211> LENGTH: 20
<212> TYPE: PRT
<213> ORGANISM: hepatitis C virus

<400> SEQUENCE: 27

Leu Leu Arg Ile Pro Gln Ala Ile Leu Asp Met Ile Ala Gly Ala His
1               5                   10                  15

Trp Gly Val Leu
            20

<210> SEQ ID NO 28
<211> LENGTH: 20
<212> TYPE: PRT
<213> ORGANISM: hepatitis C virus

<400> SEQUENCE: 28

Ala Gly Ala His Trp Gly Val Leu Ala Gly Ile Ala Tyr Phe Ser Met
1               5                   10                  15

Val Gly Asn Trp
            20

<210> SEQ ID NO 29
<211> LENGTH: 20
<212> TYPE: PRT
<213> ORGANISM: hepatitis C virus

<400> SEQUENCE: 29

Val Val Leu Leu Leu Phe Ala Gly Val Asp Ala Glu Thr Ile Val Ser
1               5                   10                  15

Gly Gly Gln Ala
            20

<210> SEQ ID NO 30
<211> LENGTH: 21
<212> TYPE: PRT
<213> ORGANISM: hepatitis C virus

<400> SEQUENCE: 30

Leu Asn Cys Asn Glu Ser Leu Asn Thr Gly Trp Trp Leu Ala Gly Leu
1               5                   10                  15
```

Ile Tyr Gln His Lys
            20

<210> SEQ ID NO 31
<211> LENGTH: 20
<212> TYPE: PRT
<213> ORGANISM: hepatitis C virus

<400> SEQUENCE: 31

Ala Gly Leu Ile Tyr Gln His Lys Phe Asn Ser Ser Gly Cys Pro Glu
1               5                   10                  15

Arg Leu Ala Ser
            20

<210> SEQ ID NO 32
<211> LENGTH: 20
<212> TYPE: PRT
<213> ORGANISM: hepatitis C virus

<400> SEQUENCE: 32

Gly Cys Pro Glu Arg Leu Ala Ser Cys Arg Pro Leu Thr Asp Phe Asp
1               5                   10                  15

Gln Gly Trp Gly
            20

<210> SEQ ID NO 33
<211> LENGTH: 20
<212> TYPE: PRT
<213> ORGANISM: hepatitis C virus

<400> SEQUENCE: 33

Thr Asp Phe Asp Gln Gly Trp Gly Pro Ile Ser Tyr Ala Asn Gly Ser
1               5                   10                  15

Gly Pro Asp Gln
            20

<210> SEQ ID NO 34
<211> LENGTH: 20
<212> TYPE: PRT
<213> ORGANISM: hepatitis C virus

<400> SEQUENCE: 34

Ala Asn Gly Ser Gly Pro Asp Gln Arg Pro Tyr Cys Trp His Tyr Pro
1               5                   10                  15

Pro Lys Pro Cys
            20

<210> SEQ ID NO 35
<211> LENGTH: 20
<212> TYPE: PRT
<213> ORGANISM: hepatitis C virus

<400> SEQUENCE: 35

Trp His Tyr Pro Pro Lys Pro Cys Gly Ile Val Pro Ala Lys Ser Val
1               5                   10                  15

Cys Gly Pro Val
            20

<210> SEQ ID NO 36
<211> LENGTH: 20
<212> TYPE: PRT
<213> ORGANISM: hepatitis C virus -continued

```
<400> SEQUENCE: 36

Ala Lys Ser Val Cys Gly Pro Val Tyr Cys Phe Thr Pro Ser Pro Val
1               5                   10                  15

Val Val Gly Thr
            20

<210> SEQ ID NO 37
<211> LENGTH: 20
<212> TYPE: PRT
<213> ORGANISM: hepatitis C virus

<400> SEQUENCE: 37

Pro Ser Pro Val Val Val Gly Thr Thr Asp Arg Ser Gly Ala Pro Thr
1               5                   10                  15

Tyr Ser Trp Gly
            20

<210> SEQ ID NO 38
<211> LENGTH: 20
<212> TYPE: PRT
<213> ORGANISM: hepatitis C virus

<400> SEQUENCE: 38

Gly Ala Pro Thr Tyr Ser Trp Gly Glu Asn Asp Thr Asp Val Phe Val
1               5                   10                  15

Leu Asn Asn Thr
            20

<210> SEQ ID NO 39
<211> LENGTH: 20
<212> TYPE: PRT
<213> ORGANISM: hepatitis C virus

<400> SEQUENCE: 39

Gly Asn Trp Phe Gly Cys Thr Trp Met Asn Ser Thr Gly Phe Thr Lys
1               5                   10                  15

Val Cys Gly Ala
            20

<210> SEQ ID NO 40
<211> LENGTH: 20
<212> TYPE: PRT
<213> ORGANISM: hepatitis C virus

<400> SEQUENCE: 40

Gly Phe Thr Lys Val Cys Gly Ala Pro Pro Val Cys Ile Gly Gly Ala
1               5                   10                  15

Gly Asn Asn Thr
            20

<210> SEQ ID NO 41
<211> LENGTH: 20
<212> TYPE: PRT
<213> ORGANISM: hepatitis C virus

<400> SEQUENCE: 41

Ile Gly Gly Ala Gly Asn Asn Thr Leu His Cys Pro Thr Asp Cys Phe
1               5                   10                  15

Arg Lys His Pro
            20
```

<210> SEQ ID NO 42
<211> LENGTH: 20
<212> TYPE: PRT
<213> ORGANISM: hepatitis C virus

<400> SEQUENCE: 42

Thr Asp Cys Phe Arg Lys His Pro Asp Ala Thr Tyr Ser Arg Cys Gly
1               5                   10                  15

Ser Gly Pro Trp
            20

<210> SEQ ID NO 43
<211> LENGTH: 20
<212> TYPE: PRT
<213> ORGANISM: hepatitis C virus

<400> SEQUENCE: 43

Ser Arg Cys Gly Ser Gly Pro Trp Ile Thr Pro Arg Cys Leu Val Asp
1               5                   10                  15

Tyr Pro Tyr Arg
            20

<210> SEQ ID NO 44
<211> LENGTH: 20
<212> TYPE: PRT
<213> ORGANISM: hepatitis C virus

<400> SEQUENCE: 44

Cys Leu Val Asp Tyr Pro Tyr Arg Leu Trp His Tyr Pro Cys Thr Ile
1               5                   10                  15

Asn Tyr Thr Ile
            20

<210> SEQ ID NO 45
<211> LENGTH: 20
<212> TYPE: PRT
<213> ORGANISM: hepatitis C virus

<400> SEQUENCE: 45

Pro Cys Thr Ile Asn Tyr Thr Ile Phe Lys Ile Arg Met Tyr Val Gly
1               5                   10                  15

Gly Val Glu His
            20

<210> SEQ ID NO 46
<211> LENGTH: 20
<212> TYPE: PRT
<213> ORGANISM: hepatitis C virus

<400> SEQUENCE: 46

Ser Gly Leu Val Ser Leu Phe Thr Pro Gly Ala Lys Gln Asn Ile Gln
1               5                   10                  15

Leu Ile Asn Thr
            20

<210> SEQ ID NO 47
<211> LENGTH: 20
<212> TYPE: PRT
<213> ORGANISM: hepatitis C virus

<400> SEQUENCE: 47

Gln Asn Ile Gln Leu Ile Asn Thr Asn Gly Ser Trp His Ile Asn Ser

```
1               5                   10                  15

Thr Ala Leu Asn
            20
```

<210> SEQ ID NO 48
<211> LENGTH: 68
<212> TYPE: PRT
<213> ORGANISM: hepatitis C virus
<220> FEATURE:
<221> NAME/KEY: MISC_FEATURE
<222> LOCATION: (1)
<223> OTHER INFORMATION: Xaa is Pro or Gln
<220> FEATURE:
<221> NAME/KEY: MISC_FEATURE
<222> LOCATION: (2)
<223> OTHER INFORMATION: Xaa is Asn or Thr
<220> FEATURE:
<221> NAME/KEY: MISC_FEATURE
<222> LOCATION: (6)
<223> OTHER INFORMATION: Xaa is Arg or His
<220> FEATURE:
<221> NAME/KEY: MISC_FEATURE
<222> LOCATION: (7)
<223> OTHER INFORMATION: Xaa is Arg or Lys
<220> FEATURE:
<221> NAME/KEY: MISC_FEATURE
<222> LOCATION: (11)
<223> OTHER INFORMATION: Xaa is Leu, Val or Phe
<220> FEATURE:
<221> NAME/KEY: MISC_FEATURE
<222> LOCATION: (13)
<223> OTHER INFORMATION: Xaa is Lys or Arg
<220> FEATURE:
<221> NAME/KEY: MISC_FEATURE
<222> LOCATION: (18)
<223> OTHER INFORMATION: Xaa is Leu or Ile
<220> FEATURE:
<221> NAME/KEY: MISC_FEATURE
<222> LOCATION: (22)
<223> OTHER INFORMATION: Xaa is Phe or Leu
<220> FEATURE:
<221> NAME/KEY: MISC_FEATURE
<222> LOCATION: (26)
<223> OTHER INFORMATION: Xaa is Met or Ile
<220> FEATURE:
<221> NAME/KEY: MISC_FEATURE
<222> LOCATION: (27)
<223> OTHER INFORMATION: Xaa is Gly or Glu
<220> FEATURE:
<221> NAME/KEY: MISC_FEATURE
<222> LOCATION: (31)
<223> OTHER INFORMATION: Xaa is Leu, Val or Ile
<220> FEATURE:
<221> NAME/KEY: MISC_FEATURE
<222> LOCATION: (32)
<223> OTHER INFORMATION: Xaa is Val or Leu
<220> FEATURE:
<221> NAME/KEY: MISC_FEATURE
<222> LOCATION: (34)
<223> OTHER INFORMATION: Xaa is Ala or Gly
<220> FEATURE:
<221> NAME/KEY: MISC_FEATURE
<222> LOCATION: (36)
<223> OTHER INFORMATION: Xaa is Leu, Val or Ile
<220> FEATURE:
<221> NAME/KEY: MISC_FEATURE
<222> LOCATION: (39)
<223> OTHER INFORMATION: Xaa is Ala or Val
<220> FEATURE:
<221> NAME/KEY: MISC_FEATURE
<222> LOCATION: (40)
<223> OTHER INFORMATION: Xaa is Ala or Ser
<220> FEATURE:
<221> NAME/KEY: MISC_FEATURE
<222> LOCATION: (41)
<223> OTHER INFORMATION: Xaa is Arg or Ala
<220> FEATURE:

```
<221> NAME/KEY: MISC_FEATURE
<222> LOCATION: (42)
<223> OTHER INFORMATION: Xaa is Ala, Thr or Glu
<220> FEATURE:
<221> NAME/KEY: MISC_FEATURE
<222> LOCATION: (44)
<223> OTHER INFORMATION: Xaa is Ala or Glu
<220> FEATURE:
<221> NAME/KEY: MISC_FEATURE
<222> LOCATION: (49)
<223> OTHER INFORMATION: Xaa is Val, Ala or Leu
<220> FEATURE:
<221> NAME/KEY: MISC_FEATURE
<222> LOCATION: (50)
<223> OTHER INFORMATION: Xaa is Leu, Val or Ile
<220> FEATURE:
<221> NAME/KEY: MISC_FEATURE
<222> LOCATION: (51)
<223> OTHER INFORMATION: Xaa is Glu or Gly
<220> FEATURE:
<221> NAME/KEY: MISC_FEATURE
<222> LOCATION: (54)
<223> OTHER INFORMATION: Xaa is Val or Ile
<220> FEATURE:
<221> NAME/KEY: MISC_FEATURE
<222> LOCATION: (56)
<223> OTHER INFORMATION: Xaa is Phe or Tyr
<220> FEATURE:
<221> NAME/KEY: MISC_FEATURE
<222> LOCATION: (57)
<223> OTHER INFORMATION: Xaa is Ala or Pro
<220> FEATURE:
<221> NAME/KEY: MISC_FEATURE
<222> LOCATION: (61)
<223> OTHER INFORMATION: Xaa is Leu or Ile

<400> SEQUENCE: 48

Xaa Xaa Asp Pro Arg Xaa Xaa Ser Arg Asn Xaa Gly Xaa Val Ile Asp
 1               5                  10                  15

Thr Xaa Thr Cys Gly Xaa Ala Asp Leu Xaa Xaa Tyr Ile Pro Xaa Xaa
             20                  25                  30

Gly Xaa Pro Xaa Gly Gly Xaa Xaa Xaa Xaa Leu Xaa His Gly Val Arg
         35                  40                  45

Xaa Xaa Xaa Asp Gly Xaa Asn Xaa Xaa Thr Gly Asn Xaa Pro Gly Cys
     50                  55                  60

Ser Phe Ser Ile
65

<210> SEQ ID NO 49
<211> LENGTH: 32
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ser, Ala, Gln, Leu, Asn, Tyr, Arg or His
<220> FEATURE:
<221> NAME/KEY: MISC_FEATURE
<222> LOCATION: (2)..(2)
<223> OTHER INFORMATION: Xaa is Gly, Ser, Thr, Ala or Arg
<220> FEATURE:
<221> NAME/KEY: MISC_FEATURE
<222> LOCATION: (3)..(3)
<223> OTHER INFORMATION: Xaa is Phe, Ile, Leu or Val
<220> FEATURE:
<221> NAME/KEY: MISC_FEATURE
<222> LOCATION: (4)..(4)
<223> OTHER INFORMATION: Xaa is Val, Ala or Thr
<220> FEATURE:
<221> NAME/KEY: MISC_FEATURE
<222> LOCATION: (5)..(5)
<223> OTHER INFORMATION: Xaa is Ser, Asp or Gly
<220> FEATURE:
```

```
<221> NAME/KEY: MISC_FEATURE
<222> LOCATION: (6)..(6)
<223> OTHER INFORMATION: Xaa is Leu, Ile, Trp, Phe or Met
<220> FEATURE:
<221> NAME/KEY: MISC_FEATURE
<222> LOCATION: (7)..(7)
<223> OTHER INFORMATION: Xaa is Leu, Ile or Phe
<220> FEATURE:
<221> NAME/KEY: MISC_FEATURE
<222> LOCATION: (8)..(8)
<223> OTHER INFORMATION: Xaa is Ala, Thr, Asp or Ser
<220> FEATURE:
<221> NAME/KEY: MISC_FEATURE
<222> LOCATION: (9)..(9)
<223> OTHER INFORMATION: Xaa is Pro, Gln, Ser, Arg, Leu, Ile or Thr
<220> FEATURE:
<221> NAME/KEY: MISC_FEATURE
<222> LOCATION: (11)..(11)
<223> OTHER INFORMATION: Xaa is Ala, Pro or Ser
<220> FEATURE:
<221> NAME/KEY: MISC_FEATURE
<222> LOCATION: (12)..(12)
<223> OTHER INFORMATION: Xaa is Lys, Ser, Gln, Ala or Arg
<220> FEATURE:
<221> NAME/KEY: MISC_FEATURE
<222> LOCATION: (14)..(14)
<223> OTHER INFORMATION: Xaa is Asn, Lys, Asp or Arg
<220> FEATURE:
<221> NAME/KEY: MISC_FEATURE
<222> LOCATION: (15)..(15)
<223> OTHER INFORMATION: Xaa is Val, Ile or Leu
<220> FEATURE:
<221> NAME/KEY: MISC_FEATURE
<222> LOCATION: (16)..(16)
<223> OTHER INFORMATION: Xaa is Gln, Ser or Tyr
<220> FEATURE:
<221> NAME/KEY: MISC_FEATURE
<222> LOCATION: (18)..(18)
<223> OTHER INFORMATION: Xaa is Ile or Val
<220> FEATURE:
<221> NAME/KEY: MISC_FEATURE
<222> LOCATION: (20)..(20)
<223> OTHER INFORMATION: Xaa is Thr or Ser
<220> FEATURE:
<221> NAME/KEY: MISC_FEATURE
<222> LOCATION: (26)..(26)
<223> OTHER INFORMATION: Xaa is Leu or Ile
<220> FEATURE:
<221> NAME/KEY: MISC_FEATURE
<222> LOCATION: (28)..(28)
<223> OTHER INFORMATION: Xaa is Ser or Arg

<400> SEQUENCE: 49

Xaa Xaa Xaa Xaa Xaa Xaa Xaa Xaa Xaa Gly Xaa Xaa Gln Xaa Xaa Xaa
 1               5                  10                  15

Leu Xaa Asn Xaa Asn Gly Ser Trp His Xaa Asn Xaa Thr Ala Leu Asn
             20                  25                  30

<210> SEQ ID NO 50
<211> LENGTH: 44
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Met or Ile
<220> FEATURE:
<221> NAME/KEY: MISC_FEATURE
<222> LOCATION: (3)..(3)
<223> OTHER INFORMATION: Xaa is Gly or Glu
<220> FEATURE:
<221> NAME/KEY: MISC_FEATURE
<222> LOCATION: (7)..(7)
<223> OTHER INFORMATION: Xaa is Leu, Val or Ile
<220> FEATURE:
<221> NAME/KEY: MISC_FEATURE
```

```
<222> LOCATION: (8)..(8)
<223> OTHER INFORMATION: Xaa is Val or Leu
<220> FEATURE:
<221> NAME/KEY: MISC_FEATURE
<222> LOCATION: (10)..(10)
<223> OTHER INFORMATION: Xaa is Ala or Gly
<220> FEATURE:
<221> NAME/KEY: MISC_FEATURE
<222> LOCATION: (12)..(12)
<223> OTHER INFORMATION: Xaa is Leu, Val or Ile
<220> FEATURE:
<221> NAME/KEY: MISC_FEATURE
<222> LOCATION: (15)..(15)
<223> OTHER INFORMATION: Xaa is Ala or Val
<220> FEATURE:
<221> NAME/KEY: MISC_FEATURE
<222> LOCATION: (16)..(16)
<223> OTHER INFORMATION: Xaa is Ala or Ser
<220> FEATURE:
<221> NAME/KEY: MISC_FEATURE
<222> LOCATION: (17)..(17)
<223> OTHER INFORMATION: Xaa is Arg or Ala
<220> FEATURE:
<221> NAME/KEY: MISC_FEATURE
<222> LOCATION: (18)..(18)
<223> OTHER INFORMATION: Xaa is Ala, Thr or Glu
<220> FEATURE:
<221> NAME/KEY: MISC_FEATURE
<222> LOCATION: (20)..(20)
<223> OTHER INFORMATION: Xaa is Ala or Glu
<220> FEATURE:
<221> NAME/KEY: MISC_FEATURE
<222> LOCATION: (25)..(25)
<223> OTHER INFORMATION: Xaa is Val, Ala or Leu
<220> FEATURE:
<221> NAME/KEY: MISC_FEATURE
<222> LOCATION: (26)..(26)
<223> OTHER INFORMATION: Xaa is Leu, Val or Ile
<220> FEATURE:
<221> NAME/KEY: MISC_FEATURE
<222> LOCATION: (27)..(27)
<223> OTHER INFORMATION: Xaa is Glu or Gly
<220> FEATURE:
<221> NAME/KEY: MISC_FEATURE
<222> LOCATION: (30)..(30)
<223> OTHER INFORMATION: Xaa is Val or Ile
<220> FEATURE:
<221> NAME/KEY: MISC_FEATURE
<222> LOCATION: (32)..(32)
<223> OTHER INFORMATION: Xaa is Phe or Tyr
<220> FEATURE:
<221> NAME/KEY: MISC_FEATURE
<222> LOCATION: (33)..(33)
<223> OTHER INFORMATION: Xaa is Ala or Pro
<220> FEATURE:
<221> NAME/KEY: MISC_FEATURE
<222> LOCATION: (37)..(37)
<223> OTHER INFORMATION: Xaa is Leu or Ile

<400> SEQUENCE: 50

Leu Xaa Xaa Tyr Ile Pro Xaa Xaa Gly Xaa Pro Xaa Gly Gly Xaa Xaa
1               5                   10                  15

Xaa Xaa Leu Xaa His Gly Val Arg Xaa Xaa Xaa Asp Gly Xaa Asn Xaa
            20                  25                  30

Xaa Thr Gly Asn Xaa Pro Gly Cys Ser Phe Ser Ile
        35                  40

<210> SEQ ID NO 51
<211> LENGTH: 20
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Val, Ala or Leu
```

```
<220> FEATURE:
<221> NAME/KEY: MISC_FEATURE
<222> LOCATION: (2)..(2)
<223> OTHER INFORMATION: Xaa is Leu, Val or Ile
<220> FEATURE:
<221> NAME/KEY: MISC_FEATURE
<222> LOCATION: (3)..(3)
<223> OTHER INFORMATION: Xaa is Glu or Gly
<220> FEATURE:
<221> NAME/KEY: MISC_FEATURE
<222> LOCATION: (6)..(6)
<223> OTHER INFORMATION: Xaa is Val or Ile
<220> FEATURE:
<221> NAME/KEY: MISC_FEATURE
<222> LOCATION: (8)..(8)
<223> OTHER INFORMATION: Xaa is Phe or Tyr
<220> FEATURE:
<221> NAME/KEY: MISC_FEATURE
<222> LOCATION: (9)..(9)
<223> OTHER INFORMATION: Xaa is Ala or Pro
<220> FEATURE:
<221> NAME/KEY: MISC_FEATURE
<222> LOCATION: (13)..(13)
<223> OTHER INFORMATION: Xaa is Leu or Ile

<400> SEQUENCE: 51

Xaa Xaa Xaa Asp Gly Xaa Asn Xaa Xaa Thr Gly Asn Xaa Pro Gly Cys
 1               5                  10                  15

Ser Phe Ser Ile
            20

<210> SEQ ID NO 52
<211> LENGTH: 20
<212> TYPE: PRT
<213> ORGANISM: hepatitis C virus
<220> FEATURE:
<221> NAME/KEY: MISC_FEATURE
<222> LOCATION: (3)..(3)
<223> OTHER INFORMATION: Xaa is Ala or Val
<220> FEATURE:
<221> NAME/KEY: MISC_FEATURE
<222> LOCATION: (4)..(4)
<223> OTHER INFORMATION: Xaa is Ala or Ser
<220> FEATURE:
<221> NAME/KEY: MISC_FEATURE
<222> LOCATION: (5)..(5)
<223> OTHER INFORMATION: Xaa is Arg or Ala
<220> FEATURE:
<221> NAME/KEY: MISC_FEATURE
<222> LOCATION: (6)..(6)
<223> OTHER INFORMATION: Xaa is Ala, Thr or Glu
<220> FEATURE:
<221> NAME/KEY: MISC_FEATURE
<222> LOCATION: (8)..(8)
<223> OTHER INFORMATION: Xaa is Ala or Glu
<220> FEATURE:
<221> NAME/KEY: MISC_FEATURE
<222> LOCATION: (13)..(13)
<223> OTHER INFORMATION: Xaa is Val, Ala or Leu
<220> FEATURE:
<221> NAME/KEY: MISC_FEATURE
<222> LOCATION: (14)..(14)
<223> OTHER INFORMATION: Xaa is Leu, Val or Ile
<220> FEATURE:
<221> NAME/KEY: MISC_FEATURE
<222> LOCATION: (15)..(15)
<223> OTHER INFORMATION: Xaa is Glu or Gly
<220> FEATURE:
<221> NAME/KEY: MISC_FEATURE
<222> LOCATION: (18)..(18)
<223> OTHER INFORMATION: Xaa is Val or Ile
<220> FEATURE:
<221> NAME/KEY: MISC_FEATURE
<222> LOCATION: (20)..(20)
<223> OTHER INFORMATION: Xaa is Phe or Tyr
```

-continued

<400> SEQUENCE: 52

Gly Gly Xaa Xaa Xaa Xaa Leu Xaa His Gly Val Arg Xaa Xaa Xaa Asp
1               5                   10                  15

Gly Xaa Asn Xaa
            20

<210> SEQ ID NO 53
<211> LENGTH: 20
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Met or Ile
<220> FEATURE:
<221> NAME/KEY: MISC_FEATURE
<222> LOCATION: (3)..(3)
<223> OTHER INFORMATION: Xaa is Gly or Glu
<220> FEATURE:
<221> NAME/KEY: MISC_FEATURE
<222> LOCATION: (7)..(7)
<223> OTHER INFORMATION: Xaa is Leu, Val or Ile
<220> FEATURE:
<221> NAME/KEY: MISC_FEATURE
<222> LOCATION: (8)..(8)
<223> OTHER INFORMATION: Xaa is Val or Leu
<220> FEATURE:
<221> NAME/KEY: MISC_FEATURE
<222> LOCATION: (10)..(10)
<223> OTHER INFORMATION: Xaa is Ala or Gly
<220> FEATURE:
<221> NAME/KEY: MISC_FEATURE
<222> LOCATION: (12)..(12)
<223> OTHER INFORMATION: Xaa is Leu, Val or Ile
<220> FEATURE:
<221> NAME/KEY: MISC_FEATURE
<222> LOCATION: (15)..(15)
<223> OTHER INFORMATION: Xaa is Ala or Val
<220> FEATURE:
<221> NAME/KEY: MISC_FEATURE
<222> LOCATION: (16)..(16)
<223> OTHER INFORMATION: Xaa is Ala or Ser
<220> FEATURE:
<221> NAME/KEY: MISC_FEATURE
<222> LOCATION: (17)..(17)
<223> OTHER INFORMATION: Xaa is Arg or Ala
<220> FEATURE:
<221> NAME/KEY: MISC_FEATURE
<222> LOCATION: (18)..(18)
<223> OTHER INFORMATION: Xaa is Ala, Thr or Glu
<220> FEATURE:
<221> NAME/KEY: MISC_FEATURE
<222> LOCATION: (20)..(20)
<223> OTHER INFORMATION: Xaa is Ala or Glu

<400> SEQUENCE: 53

Leu Xaa Xaa Tyr Ile Pro Xaa Xaa Gly Xaa Pro Xaa Gly Gly Xaa Xaa
1               5                   10                  15

Xaa Xaa Leu Xaa
            20

<210> SEQ ID NO 54
<211> LENGTH: 20
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Pro or Gln
<220> FEATURE:
<221> NAME/KEY: MISC_FEATURE
<222> LOCATION: (2)..(2)
<223> OTHER INFORMATION: Xaa is Asn or Thr

```
<220> FEATURE:
<221> NAME/KEY: MISC_FEATURE
<222> LOCATION: (6)..(6)
<223> OTHER INFORMATION: Xaa is Arg or His
<220> FEATURE:
<221> NAME/KEY: MISC_FEATURE
<222> LOCATION: (7)..(7)
<223> OTHER INFORMATION: Xaa is Arg or Lys
<220> FEATURE:
<221> NAME/KEY: MISC_FEATURE
<222> LOCATION: (11)..(11)
<223> OTHER INFORMATION: Xaa is Leu, Val or Phe
<220> FEATURE:
<221> NAME/KEY: MISC_FEATURE
<222> LOCATION: (13)..(13)
<223> OTHER INFORMATION: Xaa is Lys or Arg
<220> FEATURE:
<221> NAME/KEY: MISC_FEATURE
<222> LOCATION: (18)..(18)
<223> OTHER INFORMATION: Xaa is Leu or Ile

<400> SEQUENCE: 54

Xaa Xaa Asp Pro Arg Xaa Xaa Ser Arg Asn Xaa Gly Xaa Val Ile Asp
1               5                   10                  15

Thr Xaa Thr Cys
            20

<210> SEQ ID NO 55
<211> LENGTH: 20
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ser, Ala, Gln, Leu, Asn, Tyr, Arg or His
<220> FEATURE:
<221> NAME/KEY: MISC_FEATURE
<222> LOCATION: (2)..(2)
<223> OTHER INFORMATION: Xaa is Gly, Ser, Thr, Ala or Arg
<220> FEATURE:
<221> NAME/KEY: MISC_FEATURE
<222> LOCATION: (3)..(3)
<223> OTHER INFORMATION: Xaa is Phe, Ile, Leu or Val
<220> FEATURE:
<221> NAME/KEY: MISC_FEATURE
<222> LOCATION: (4)..(4)
<223> OTHER INFORMATION: Xaa is Val, Ala or Thr
<220> FEATURE:
<221> NAME/KEY: MISC_FEATURE
<222> LOCATION: (5)..(5)
<223> OTHER INFORMATION: Xaa is Ser, Asp or Gly
<220> FEATURE:
<221> NAME/KEY: MISC_FEATURE
<222> LOCATION: (6)..(6)
<223> OTHER INFORMATION: Xaa is Leu, Ile, Trp, Phe or Met
<220> FEATURE:
<221> NAME/KEY: MISC_FEATURE
<222> LOCATION: (7)..(7)
<223> OTHER INFORMATION: Xaa is Leu, Ile or Phe
<220> FEATURE:
<221> NAME/KEY: MISC_FEATURE
<222> LOCATION: (8)..(8)
<223> OTHER INFORMATION: Xaa is Ala, Thr, Asp or Ser
<220> FEATURE:
<221> NAME/KEY: MISC_FEATURE
<222> LOCATION: (9)..(9)
<223> OTHER INFORMATION: Xaa is Pro, Gln, Ser, Arg, Leu, Ile or Thr
<220> FEATURE:
<221> NAME/KEY: MISC_FEATURE
<222> LOCATION: (11)..(11)
<223> OTHER INFORMATION: Xaa is Ala, Pro or Ser
<220> FEATURE:
<221> NAME/KEY: MISC_FEATURE
<222> LOCATION: (12)..(12)
<223> OTHER INFORMATION: Xaa is Lys, Ser, Gln, Ala or Arg
<220> FEATURE:
```

-continued

```
<221> NAME/KEY: MISC_FEATURE
<222> LOCATION: (14)..(14)
<223> OTHER INFORMATION: Xaa is Asn, Lys, Asp or Arg
<220> FEATURE:
<221> NAME/KEY: MISC_FEATURE
<222> LOCATION: (15)..(15)
<223> OTHER INFORMATION: Xaa is Val, Ile or Leu
<220> FEATURE:
<221> NAME/KEY: MISC_FEATURE
<222> LOCATION: (16)..(16)
<223> OTHER INFORMATION: Xaa is Gln, Ser or Tyr
<220> FEATURE:
<221> NAME/KEY: MISC_FEATURE
<222> LOCATION: (18)..(18)
<223> OTHER INFORMATION: Xaa is Ile or Val
<220> FEATURE:
<221> NAME/KEY: MISC_FEATURE
<222> LOCATION: (20)..(20)
<223> OTHER INFORMATION: Xaa is Thr or Ser

<400> SEQUENCE: 55

Xaa Xaa Xaa Xaa Xaa Xaa Xaa Xaa Xaa Gly Xaa Xaa Gln Xaa Xaa Xaa
1               5                   10                  15

Leu Xaa Asn Xaa
            20

<210> SEQ ID NO 56
<211> LENGTH: 20
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Asn, Lys, Asp or Arg
<220> FEATURE:
<221> NAME/KEY: MISC_FEATURE
<222> LOCATION: (3)..(3)
<223> OTHER INFORMATION: Xaa is Val, Ile or Leu
<220> FEATURE:
<221> NAME/KEY: MISC_FEATURE
<222> LOCATION: (4)..(4)
<223> OTHER INFORMATION: Xaa is Gln, Ser or Tyr
<220> FEATURE:
<221> NAME/KEY: MISC_FEATURE
<222> LOCATION: (6)..(6)
<223> OTHER INFORMATION: Xaa is Ile or Val
<220> FEATURE:
<221> NAME/KEY: MISC_FEATURE
<222> LOCATION: (8)..(8)
<223> OTHER INFORMATION: Xaa is Thr or Ser
<220> FEATURE:
<221> NAME/KEY: MISC_FEATURE
<222> LOCATION: (14)..(14)
<223> OTHER INFORMATION: Xaa is Leu or Ile
<220> FEATURE:
<221> NAME/KEY: MISC_FEATURE
<222> LOCATION: (16)..(16)
<223> OTHER INFORMATION: Xaa is Ser or Arg

<400> SEQUENCE: 56

Gln Xaa Xaa Xaa Leu Xaa Asn Xaa Asn Gly Ser Trp His Xaa Asn Xaa
1               5                   10                  15

Thr Ala Leu Asn
            20

<210> SEQ ID NO 57
<211> LENGTH: 278
<212> TYPE: PRT
<213> ORGANISM: hepatitis C virus

<400> SEQUENCE: 57

Gly Val Ala Lys Ala Val Asp Phe Val Pro Val Glu Ser Met Glu Thr
```

-continued

```
1               5                   10                  15
Thr Met Arg Ser Pro Val Phe Thr Asp Asn Ser Ser Pro Pro Ala Val
                20                  25                  30
Pro Gln Thr Phe Gln Val Ala His Leu His Ala Pro Thr Gly Ser Gly
                35                  40                  45
Lys Ser Thr Lys Val Pro Ala Ala Tyr Ala Ala Gln Gly Tyr Lys Val
 50                  55                  60
Leu Val Leu Asn Pro Ser Val Ala Ala Thr Leu Gly Phe Gly Ala Tyr
 65                  70                  75                  80
Met Ser Lys Ala His Gly Val Asp Pro Asn Ile Arg Thr Gly Val Arg
                85                  90                  95
Thr Ile Thr Thr Gly Ala Pro Ile Thr Tyr Ser Thr Tyr Gly Lys Phe
                100                 105                 110
Leu Ala Asp Gly Gly Cys Ser Gly Gly Ala Tyr Asp Ile Ile Ile Cys
                115                 120                 125
Asp Glu Cys His Ser Ile Asp Ser Thr Ser Ile Leu Gly Ile Gly Thr
                130                 135                 140
Val Leu Asp Gln Ala Glu Thr Ala Gly Ala Arg Leu Val Val Leu Ala
145                 150                 155                 160
Thr Ala Thr Pro Pro Gly Ser Val Thr Val Pro His Pro Asn Ile Glu
                165                 170                 175
Glu Val Ala Leu Ser Ser Thr Gly Glu Ile Pro Phe Tyr Gly Lys Ala
                180                 185                 190
Ile Pro Ile Glu Val Ile Lys Gly Gly Arg His Leu Ile Phe Cys His
                195                 200                 205
Ser Lys Lys Lys Cys Asp Glu Leu Ala Ala Lys Leu Ser Gly Phe Gly
                210                 215                 220
Ile Asn Ala Val Ala Tyr Tyr Arg Gly Leu Asp Val Ser Val Ile Pro
225                 230                 235                 240
Thr Ser Gly Asp Val Val Val Ala Thr Asp Ala Leu Met Thr Gly
                245                 250                 255
Phe Thr Gly Asp Phe Asp Ser Val Ile Asp Cys Asn Thr Cys Val Thr
                260                 265                 270
Gln Thr Val Asp Phe Ser
                275

<210> SEQ ID NO 58
<211> LENGTH: 104
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(3)
<223> OTHER INFORMATION: Xaa is Ala, Ser or Thr
<220> FEATURE:
<221> NAME/KEY: MISC_FEATURE
<222> LOCATION: (5)..(5)
<223> OTHER INFORMATION: Xaa is Ala or Gly
<220> FEATURE:
<221> NAME/KEY: MISC_FEATURE
<222> LOCATION: (6)..(6)
<223> OTHER INFORMATION: Xaa is Gln, Lys or Arg
<220> FEATURE:
<221> NAME/KEY: MISC_FEATURE
<222> LOCATION: (9)..(9)
<223> OTHER INFORMATION: Xaa is Tyr or His
<220> FEATURE:
```

-continued

```
<221> NAME/KEY: MISC_FEATURE
<222> LOCATION: (15)..(15)
<223> OTHER INFORMATION: Xaa is Gly or Ala
<220> FEATURE:
<221> NAME/KEY: MISC_FEATURE
<222> LOCATION: (17)..(17)
<223> OTHER INFORMATION: Xaa is Glu or Lys
<220> FEATURE:
<221> NAME/KEY: MISC_FEATURE
<222> LOCATION: (19)..(19)
<223> OTHER INFORMATION: Xaa is Cys, Met or Leu
<220> FEATURE:
<221> NAME/KEY: MISC_FEATURE
<222> LOCATION: (21)..(21)
<223> OTHER INFORMATION: Xaa is Trp or Leu
<220> FEATURE:
<221> NAME/KEY: MISC_FEATURE
<222> LOCATION: (34)..(34)
<223> OTHER INFORMATION: Xaa is Ser, Asn, Thr, Asp or His
<220> FEATURE:
<221> NAME/KEY: MISC_FEATURE
<222> LOCATION: (37)..(37)
<223> OTHER INFORMATION: Xaa is Pro or Gln
<220> FEATURE:
<221> NAME/KEY: MISC_FEATURE
<222> LOCATION: (38)..(38)
<223> OTHER INFORMATION: Xaa is Asn or Thr
<220> FEATURE:
<221> NAME/KEY: MISC_FEATURE
<222> LOCATION: (42)..(42)
<223> OTHER INFORMATION: Xaa is Arg or His
<220> FEATURE:
<221> NAME/KEY: MISC_FEATURE
<222> LOCATION: (43)..(43)
<223> OTHER INFORMATION: Xaa is Arg or His
<220> FEATURE:
<221> NAME/KEY: MISC_FEATURE
<222> LOCATION: (47)..(47)
<223> OTHER INFORMATION: Xaa is Leu, Val or Phe
<220> FEATURE:
<221> NAME/KEY: MISC_FEATURE
<222> LOCATION: (49)..(49)
<223> OTHER INFORMATION: Xaa is Lys or Arg
<220> FEATURE:
<221> NAME/KEY: MISC_FEATURE
<222> LOCATION: (54)..(54)
<223> OTHER INFORMATION: Xaa is Leu or Ile
<220> FEATURE:
<221> NAME/KEY: MISC_FEATURE
<222> LOCATION: (58)..(58)
<223> OTHER INFORMATION: Xaa is Phe or Leu
<220> FEATURE:
<221> NAME/KEY: MISC_FEATURE
<222> LOCATION: (62)..(62)
<223> OTHER INFORMATION: Xaa is Met or Ile
<220> FEATURE:
<221> NAME/KEY: MISC_FEATURE
<222> LOCATION: (63)..(63)
<223> OTHER INFORMATION: Xaa is Gly or Glu
<220> FEATURE:
<221> NAME/KEY: MISC_FEATURE
<222> LOCATION: (67)..(67)
<223> OTHER INFORMATION: Xaa is Leu, Val or Ile
<220> FEATURE:
<221> NAME/KEY: MISC_FEATURE
<222> LOCATION: (68)..(68)
<223> OTHER INFORMATION: Xaa is Val or Leu
<220> FEATURE:
<221> NAME/KEY: MISC_FEATURE
<222> LOCATION: (70)..(70)
<223> OTHER INFORMATION: Xaa is Ala or Gly
<220> FEATURE:
<221> NAME/KEY: MISC_FEATURE
<222> LOCATION: (72)..(72)
<223> OTHER INFORMATION: Xaa is Leu, Val or Ile
<220> FEATURE:
<221> NAME/KEY: MISC_FEATURE
<222> LOCATION: (75)..(75)
<223> OTHER INFORMATION: Xaa is Ala or Val
```

```
<220> FEATURE:
<221> NAME/KEY: MISC_FEATURE
<222> LOCATION: (76)..(76)
<223> OTHER INFORMATION: Xaa is Ala or Ser
<220> FEATURE:
<221> NAME/KEY: MISC_FEATURE
<222> LOCATION: (77)..(77)
<223> OTHER INFORMATION: Xaa is Arg or Ala
<220> FEATURE:
<221> NAME/KEY: MISC_FEATURE
<222> LOCATION: (78)..(78)
<223> OTHER INFORMATION: Xaa is Ala, Thr or Glu
<220> FEATURE:
<221> NAME/KEY: MISC_FEATURE
<222> LOCATION: (80)..(80)
<223> OTHER INFORMATION: Xaa is Ala or Glu
<220> FEATURE:
<221> NAME/KEY: MISC_FEATURE
<222> LOCATION: (85)..(85)
<223> OTHER INFORMATION: Xaa is Val, Ala or Leu
<220> FEATURE:
<221> NAME/KEY: MISC_FEATURE
<222> LOCATION: (86)..(86)
<223> OTHER INFORMATION: Xaa is Leu, Val or Ile
<220> FEATURE:
<221> NAME/KEY: MISC_FEATURE
<222> LOCATION: (87)..(87)
<223> OTHER INFORMATION: Xaa is Glu or Gly
<220> FEATURE:
<221> NAME/KEY: MISC_FEATURE
<222> LOCATION: (90)..(90)
<223> OTHER INFORMATION: Xaa is Val or Ile
<220> FEATURE:
<221> NAME/KEY: MISC_FEATURE
<222> LOCATION: (92)..(92)
<223> OTHER INFORMATION: Xaa is Phe or Tyr
<220> FEATURE:
<221> NAME/KEY: MISC_FEATURE
<222> LOCATION: (93)..(93)
<223> OTHER INFORMATION: Xaa is Ala or Pro
<220> FEATURE:
<221> NAME/KEY: MISC_FEATURE
<222> LOCATION: (97)..(97)
<223> OTHER INFORMATION: Xaa is Leu or Ile

<400> SEQUENCE: 58

Gly Xaa Xaa Trp Xaa Xaa Pro Gly Xaa Pro Trp Pro Leu Tyr Xaa Asn
1               5                   10                  15

Xaa Gly Xaa Gly Xaa Ala Gly Trp Leu Leu Ser Pro Arg Gly Ser Arg
            20                  25                  30

Pro Xaa Trp Gly Xaa Xaa Asp Pro Arg Xaa Xaa Ser Arg Asn Xaa Gly
        35                  40                  45

Xaa Val Ile Asp Thr Xaa Thr Cys Gly Xaa Ala Asp Leu Xaa Xaa Tyr
    50                  55                  60

Ile Pro Xaa Xaa Gly Xaa Pro Xaa Gly Gly Xaa Xaa Xaa Xaa Leu Xaa
65                  70                  75                  80

His Gly Val Arg Xaa Xaa Xaa Asp Gly Xaa Asn Xaa Xaa Thr Gly Asn
                85                  90                  95

Xaa Pro Gly Cys Ser Phe Ser Ile
            100

<210> SEQ ID NO 59
<211> LENGTH: 76
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
```

```
<222> LOCATION: (3)..(3)
<223> OTHER INFORMATION: Xaa is Ala, Ser or Thr
<220> FEATURE:
<221> NAME/KEY: MISC_FEATURE
<222> LOCATION: (5)..(5)
<223> OTHER INFORMATION: Xaa is Ala or Gly
<220> FEATURE:
<221> NAME/KEY: MISC_FEATURE
<222> LOCATION: (6)..(6)
<223> OTHER INFORMATION: Xaa is Gln, Lys or Arg
<220> FEATURE:
<221> NAME/KEY: MISC_FEATURE
<222> LOCATION: (9)..(9)
<223> OTHER INFORMATION: Xaa is Tyr or His
<220> FEATURE:
<221> NAME/KEY: MISC_FEATURE
<222> LOCATION: (15)..(15)
<223> OTHER INFORMATION: Xaa is Gly or Ala
<220> FEATURE:
<221> NAME/KEY: MISC_FEATURE
<222> LOCATION: (17)..(17)
<223> OTHER INFORMATION: Xaa is Glu or Lys
<220> FEATURE:
<221> NAME/KEY: MISC_FEATURE
<222> LOCATION: (19)..(19)
<223> OTHER INFORMATION: Xaa is Cys, Met or Leu
<220> FEATURE:
<221> NAME/KEY: MISC_FEATURE
<222> LOCATION: (21)..(21)
<223> OTHER INFORMATION: Xaa is Trp or Leu
<220> FEATURE:
<221> NAME/KEY: MISC_FEATURE
<222> LOCATION: (34)..(34)
<223> OTHER INFORMATION: Xaa is Ser, Asn, Thr, Asp or His
<220> FEATURE:
<221> NAME/KEY: MISC_FEATURE
<222> LOCATION: (37)..(37)
<223> OTHER INFORMATION: Xaa is Pro or Gln
<220> FEATURE:
<221> NAME/KEY: MISC_FEATURE
<222> LOCATION: (38)..(38)
<223> OTHER INFORMATION: Xaa is Asn or Thr
<220> FEATURE:
<221> NAME/KEY: MISC_FEATURE
<222> LOCATION: (42)..(42)
<223> OTHER INFORMATION: Xaa is Arg or His
<220> FEATURE:
<221> NAME/KEY: MISC_FEATURE
<222> LOCATION: (43)..(43)
<223> OTHER INFORMATION: Xaa is Arg or Lys
<220> FEATURE:
<221> NAME/KEY: MISC_FEATURE
<222> LOCATION: (47)..(47)
<223> OTHER INFORMATION: Xaa is Leu, Val or Phe
<220> FEATURE:
<221> NAME/KEY: MISC_FEATURE
<222> LOCATION: (49)..(49)
<223> OTHER INFORMATION: Xaa is Lys or Arg
<220> FEATURE:
<221> NAME/KEY: MISC_FEATURE
<222> LOCATION: (54)..(54)
<223> OTHER INFORMATION: Xaa is Leu or Ile
<220> FEATURE:
<221> NAME/KEY: MISC_FEATURE
<222> LOCATION: (58)..(58)
<223> OTHER INFORMATION: Xaa is Phe or Leu
<220> FEATURE:
<221> NAME/KEY: MISC_FEATURE
<222> LOCATION: (62)..(62)
<223> OTHER INFORMATION: Xaa is Met or Ile
<220> FEATURE:
<221> NAME/KEY: MISC_FEATURE
<222> LOCATION: (63)..(63)
<223> OTHER INFORMATION: Xaa is Gly or Glu
<220> FEATURE:
<221> NAME/KEY: MISC_FEATURE
<222> LOCATION: (67)..(67)
<223> OTHER INFORMATION: Xaa is Leu, Val or Ile
<220> FEATURE:
```

```
<221> NAME/KEY: MISC_FEATURE
<222> LOCATION: (68)..(68)
<223> OTHER INFORMATION: Xaa is Val or Leu
<220> FEATURE:
<221> NAME/KEY: MISC_FEATURE
<222> LOCATION: (70)..(70)
<223> OTHER INFORMATION: Xaa is Ala or Gly
<220> FEATURE:
<221> NAME/KEY: MISC_FEATURE
<222> LOCATION: (72)..(72)
<223> OTHER INFORMATION: Xaa is Leu, Val or Ile
<220> FEATURE:
<221> NAME/KEY: MISC_FEATURE
<222> LOCATION: (75)..(75)
<223> OTHER INFORMATION: Xaa is Ala or Val
<220> FEATURE:
<221> NAME/KEY: MISC_FEATURE
<222> LOCATION: (76)..(76)
<223> OTHER INFORMATION: Xaa is Ala or Ser

<400> SEQUENCE: 59

Gly Xaa Xaa Trp Xaa Xaa Pro Gly Xaa Pro Trp Pro Leu Tyr Xaa Asn
1               5                   10                  15

Xaa Gly Xaa Gly Xaa Ala Gly Trp Leu Leu Ser Pro Arg Gly Ser Arg
            20                  25                  30

Pro Xaa Trp Gly Xaa Xaa Asp Pro Arg Xaa Xaa Ser Arg Asn Xaa Gly
        35                  40                  45

Xaa Val Ile Asp Thr Xaa Thr Cys Gly Xaa Ala Asp Leu Xaa Xaa Tyr
    50                  55                  60

Ile Pro Xaa Xaa Gly Xaa Pro Xaa Gly Gly Xaa Xaa
65                  70                  75

<210> SEQ ID NO 60
<211> LENGTH: 15
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Val or Ile
<220> FEATURE:
<221> NAME/KEY: MISC_FEATURE
<222> LOCATION: (3)..(3)
<223> OTHER INFORMATION: Xaa is Phe or Tyr
<220> FEATURE:
<221> NAME/KEY: MISC_FEATURE
<222> LOCATION: (4)..(4)
<223> OTHER INFORMATION: Xaa is Ala or Pro
<220> FEATURE:
<221> NAME/KEY: MISC_FEATURE
<222> LOCATION: (8)..(8)
<223> OTHER INFORMATION: Xaa is Leu or Ile

<400> SEQUENCE: 60

Xaa Asn Xaa Xaa Thr Gly Asn Xaa Pro Gly Cys Ser Phe Ser Ile
1               5                   10                  15

<210> SEQ ID NO 61
<211> LENGTH: 16
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Phe or Leu
<220> FEATURE:
<221> NAME/KEY: MISC_FEATURE
<222> LOCATION: (6)..(6)
<223> OTHER INFORMATION: Xaa is Met or Ile
<220> FEATURE:
<221> NAME/KEY: MISC_FEATURE
```

```
<222> LOCATION: (7)..(7)
<223> OTHER INFORMATION: Xaa is Gly or Glu
<220> FEATURE:
<221> NAME/KEY: MISC_FEATURE
<222> LOCATION: (11)..(11)
<223> OTHER INFORMATION: Xaa is Leu, Val or Ile
<220> FEATURE:
<221> NAME/KEY: MISC_FEATURE
<222> LOCATION: (12)..(12)
<223> OTHER INFORMATION: Xaa is Val or Leu
<220> FEATURE:
<221> NAME/KEY: MISC_FEATURE
<222> LOCATION: (14)..(14)
<223> OTHER INFORMATION: Xaa is Ala or Gly
<220> FEATURE:
<221> NAME/KEY: MISC_FEATURE
<222> LOCATION: (16)..(16)
<223> OTHER INFORMATION: Xaa is Leu, Val or Ile

<400> SEQUENCE: 61

Gly Xaa Ala Asp Leu Xaa Xaa Tyr Ile Pro Xaa Xaa Gly Xaa Pro Xaa
1               5                   10                  15

<210> SEQ ID NO 62
<211> LENGTH: 15
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Met or Ile
<220> FEATURE:
<221> NAME/KEY: MISC_FEATURE
<222> LOCATION: (3)..(3)
<223> OTHER INFORMATION: Xaa is Gly or Glu
<220> FEATURE:
<221> NAME/KEY: MISC_FEATURE
<222> LOCATION: (7)..(7)
<223> OTHER INFORMATION: Xaa is Leu, Val or Ile
<220> FEATURE:
<221> NAME/KEY: MISC_FEATURE
<222> LOCATION: (8)..(8)
<223> OTHER INFORMATION: Xaa is Val or Leu
<220> FEATURE:
<221> NAME/KEY: MISC_FEATURE
<222> LOCATION: (10)..(10)
<223> OTHER INFORMATION: Xaa is Ala or Gly
<220> FEATURE:
<221> NAME/KEY: MISC_FEATURE
<222> LOCATION: (12)..(12)
<223> OTHER INFORMATION: Xaa is Leu, Val or Ile
<220> FEATURE:
<221> NAME/KEY: MISC_FEATURE
<222> LOCATION: (15)..(15)
<223> OTHER INFORMATION: Xaa is Ala or Val

<400> SEQUENCE: 62

Leu Xaa Xaa Tyr Ile Pro Xaa Xaa Gly Xaa Pro Xaa Gly Gly Xaa
1               5                   10                  15

<210> SEQ ID NO 63
<211> LENGTH: 14
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Met or Ile
<220> FEATURE:
<221> NAME/KEY: MISC_FEATURE
<222> LOCATION: (2)..(2)
<223> OTHER INFORMATION: Xaa is Gly or Glu
<220> FEATURE:
<221> NAME/KEY: MISC_FEATURE
<222> LOCATION: (6)..(6)
```

-continued

<223> OTHER INFORMATION: Xaa is Leu, Val or Ile
<220> FEATURE:
<221> NAME/KEY: MISC_FEATURE
<222> LOCATION: (7)..(7)
<223> OTHER INFORMATION: Xaa is Val or Leu
<220> FEATURE:
<221> NAME/KEY: MISC_FEATURE
<222> LOCATION: (9)..(9)
<223> OTHER INFORMATION: Xaa is Ala or Gly
<220> FEATURE:
<221> NAME/KEY: MISC_FEATURE
<222> LOCATION: (11)..(11)
<223> OTHER INFORMATION: Xaa is Leu, Val or Ile
<220> FEATURE:
<221> NAME/KEY: MISC_FEATURE
<222> LOCATION: (14)..(14)
<223> OTHER INFORMATION: Xaa is Ala or Val

<400> SEQUENCE: 63

Xaa Xaa Tyr Ile Pro Xaa Xaa Gly Xaa Pro Xaa Gly Gly Xaa
1               5                   10

<210> SEQ ID NO 64
<211> LENGTH: 9
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: Xaa is Leu, Val or Ile
<220> FEATURE:
<221> NAME/KEY: MISC_FEATURE
<222> LOCATION: (5)..(5)
<223> OTHER INFORMATION: Xaa is Val or Leu
<220> FEATURE:
<221> NAME/KEY: MISC_FEATURE
<222> LOCATION: (7)..(7)
<223> OTHER INFORMATION: Xaa is Ala or Gly
<220> FEATURE:
<221> NAME/KEY: MISC_FEATURE
<222> LOCATION: (9)..(9)
<223> OTHER INFORMATION: Xaa is Leu, Val or Ile

<400> SEQUENCE: 64

Tyr Ile Pro Xaa Xaa Gly Xaa Pro Xaa
1               5

<210> SEQ ID NO 65
<211> LENGTH: 8
<212> TYPE: PRT
<213> ORGANISM: hepatitis C virus
<220> FEATURE:
<221> NAME/KEY: MISC_FEATURE
<222> LOCATION: (3)..(3)
<223> OTHER INFORMATION: Xaa is Leu, Val or Ile
<220> FEATURE:
<221> NAME/KEY: MISC_FEATURE
<222> LOCATION: (4)..(4)
<223> OTHER INFORMATION: Xaa is Val or Leu
<220> FEATURE:
<221> NAME/KEY: MISC_FEATURE
<222> LOCATION: (6)..(6)
<223> OTHER INFORMATION: Xaa is Ala or Gly
<220> FEATURE:
<221> NAME/KEY: MISC_FEATURE
<222> LOCATION: (8)..(8)
<223> OTHER INFORMATION: Xaa is Leu, Val or Ile

<400> SEQUENCE: 65

Ile Pro Xaa Xaa Gly Xaa Pro Xaa
1               5

<210> SEQ ID NO 66

```
<211> LENGTH: 9
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Leu, Val or Ile
<220> FEATURE:
<221> NAME/KEY: MISC_FEATURE
<222> LOCATION: (2)..(2)
<223> OTHER INFORMATION: Xaa is Val or Leu
<220> FEATURE:
<221> NAME/KEY: MISC_FEATURE
<222> LOCATION: (4)..(4)
<223> OTHER INFORMATION: Xaa is Ala or Gly
<220> FEATURE:
<221> NAME/KEY: MISC_FEATURE
<222> LOCATION: (6)..(6)
<223> OTHER INFORMATION: Xaa is Leu, Val or Ile
<220> FEATURE:
<221> NAME/KEY: MISC_FEATURE
<222> LOCATION: (9)..(9)
<223> OTHER INFORMATION: Xaa is Ala or Val

<400> SEQUENCE: 66

Xaa Xaa Gly Xaa Pro Xaa Gly Gly Xaa
1               5

<210> SEQ ID NO 67
<211> LENGTH: 44
<212> TYPE: PRT
<213> ORGANISM: hepatitis C virus

<400> SEQUENCE: 67

Leu Met Gly Tyr Ile Pro Leu Val Gly Ala Pro Leu Gly Gly Ala Ala
1               5                   10                  15

Arg Ala Leu Ala His Gly Val Arg Val Leu Glu Asp Gly Val Asn Tyr
            20                  25                  30

Ala Thr Gly Asn Leu Pro Gly Cys Ser Phe Ser Ile
        35                  40

<210> SEQ ID NO 68
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Val or Leu
<220> FEATURE:
<221> NAME/KEY: MISC_FEATURE
<222> LOCATION: (3)..(3)
<223> OTHER INFORMATION: Xaa is Ala or Gly
<220> FEATURE:
<221> NAME/KEY: MISC_FEATURE
<222> LOCATION: (5)..(5)
<223> OTHER INFORMATION: Xaa is Leu, Val or Ile
<220> FEATURE:
<221> NAME/KEY: MISC_FEATURE
<222> LOCATION: (8)..(8)
<223> OTHER INFORMATION: Xaa is Ala or Val

<400> SEQUENCE: 68

Xaa Gly Xaa Pro Xaa Gly Gly Xaa
1               5

<210> SEQ ID NO 69
<211> LENGTH: 8
<212> TYPE: PRT
<213> ORGANISM: hepatitis C virus
```

```
<400> SEQUENCE: 69

Leu Met Gly Tyr Ile Pro Leu Val
1               5

<210> SEQ ID NO 70
<211> LENGTH: 7
<212> TYPE: PRT
<213> ORGANISM: hepatitis C virus

<400> SEQUENCE: 70

Met Gly Tyr Ile Pro Leu Val
1               5

<210> SEQ ID NO 71
<211> LENGTH: 9
<212> TYPE: PRT
<213> ORGANISM: hepatitis C virus

<400> SEQUENCE: 71

Tyr Ile Pro Leu Val Gly Ala Pro Leu
1               5

<210> SEQ ID NO 72
<211> LENGTH: 8
<212> TYPE: PRT
<213> ORGANISM: hepatitis C virus

<400> SEQUENCE: 72

Ile Pro Leu Val Gly Ala Pro Leu
1               5

<210> SEQ ID NO 73
<211> LENGTH: 20
<212> TYPE: PRT
<213> ORGANISM: hepatitis C virus

<400> SEQUENCE: 73

Val Leu Glu Asp Ile Val Asn Tyr Ala Thr Gly Asn Leu Pro Gly Cys
1               5                   10                  15

Ser Phe Ser Ile
            20

<210> SEQ ID NO 74
<211> LENGTH: 9
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Val or Ile
<220> FEATURE:
<221> NAME/KEY: MISC_FEATURE
<222> LOCATION: (4)..(4)
<223> OTHER INFORMATION: Xaa is Phe or Tyr
<220> FEATURE:
<221> NAME/KEY: MISC_FEATURE
<222> LOCATION: (5)..(5)
<223> OTHER INFORMATION: Xaa is Ala or Pro
<220> FEATURE:
<221> NAME/KEY: MISC_FEATURE
<222> LOCATION: (9)..(9)
<223> OTHER INFORMATION: Xaa is Leu or Ile

<400> SEQUENCE: 74

Gly Xaa Asn Xaa Xaa Thr Gly Asn Xaa
1               5
```

```
<210> SEQ ID NO 75
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Val or Ile
<220> FEATURE:
<221> NAME/KEY: MISC_FEATURE
<222> LOCATION: (3)..(3)
<223> OTHER INFORMATION: Xaa is Phe or Tyr
<220> FEATURE:
<221> NAME/KEY: MISC_FEATURE
<222> LOCATION: (4)..(4)
<223> OTHER INFORMATION: Xaa is Ala or Pro
<220> FEATURE:
<221> NAME/KEY: MISC_FEATURE
<222> LOCATION: (8)..(8)
<223> OTHER INFORMATION: Xaa is Leu or Ile

<400> SEQUENCE: 75

Xaa Asn Xaa Xaa Thr Gly Asn Xaa
1               5

<210> SEQ ID NO 76
<211> LENGTH: 9
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Leu or Ile

<400> SEQUENCE: 76

Asn Xaa Pro Gly Cys Ser Phe Ser Ile
1               5

<210> SEQ ID NO 77
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Leu or Ile

<400> SEQUENCE: 77

Xaa Pro Gly Cys Ser Phe Ser Ile
1               5

<210> SEQ ID NO 78
<211> LENGTH: 9
<212> TYPE: PRT
<213> ORGANISM: hepatitis C virus

<400> SEQUENCE: 78

Gly Val Asn Tyr Ala Thr Gly Asn Leu
1               5

<210> SEQ ID NO 79
<211> LENGTH: 9
<212> TYPE: PRT
<213> ORGANISM: hepatitis C virus

<400> SEQUENCE: 79

Gly Val Asn Tyr Ala Thr Gly Asn Leu
1               5
```

```
<210> SEQ ID NO 80
<211> LENGTH: 9
<212> TYPE: PRT
<213> ORGANISM: hepatitis C virus

<400> SEQUENCE: 80

Asn Leu Pro Gly Cys Ser Phe Ser Ile
1               5

<210> SEQ ID NO 81
<211> LENGTH: 8
<212> TYPE: PRT
<213> ORGANISM: hepatitis C virus

<400> SEQUENCE: 81

Leu Pro Gly Cys Ser Phe Ser Ile
1               5

<210> SEQ ID NO 82
<211> LENGTH: 9
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ala, Thr or Glu
<220> FEATURE:
<221> NAME/KEY: MISC_FEATURE
<222> LOCATION: (3)..(3)
<223> OTHER INFORMATION: Xaa is Ala or Glu
<220> FEATURE:
<221> NAME/KEY: MISC_FEATURE
<222> LOCATION: (8)..(8)
<223> OTHER INFORMATION: Xaa is Val, Ala or Leu
<220> FEATURE:
<221> NAME/KEY: MISC_FEATURE
<222> LOCATION: (9)..(9)
<223> OTHER INFORMATION: Xaa is Leu, Val or Ile

<400> SEQUENCE: 82

Xaa Leu Xaa His Gly Val Arg Xaa Xaa
1               5

<210> SEQ ID NO 83
<211> LENGTH: 8
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Ala or Glu
<220> FEATURE:
<221> NAME/KEY: MISC_FEATURE
<222> LOCATION: (7)..(7)
<223> OTHER INFORMATION: Xaa is Val, Ala or Leu
<220> FEATURE:
<221> NAME/KEY: MISC_FEATURE
<222> LOCATION: (8)..(8)
<223> OTHER INFORMATION: Xaa is Leu, Val or Ile

<400> SEQUENCE: 83

Leu Xaa His Gly Val Arg Xaa Xaa
1               5

<210> SEQ ID NO 84
<211> LENGTH: 9
<212> TYPE: PRT
<213> ORGANISM: hepatitis C virus
<220> FEATURE:
<221> NAME/KEY: MISC_FEATURE
```

```
<222> LOCATION: (4)..(4)
<223> OTHER INFORMATION: Xaa is Val, Ala or Leu
<220> FEATURE:
<221> NAME/KEY: MISC_FEATURE
<222> LOCATION: (5)..(5)
<223> OTHER INFORMATION: Xaa is Leu, Val or Ile
<220> FEATURE:
<221> NAME/KEY: MISC_FEATURE
<222> LOCATION: (6)..(6)
<223> OTHER INFORMATION: Xaa is Glu or Gly
<220> FEATURE:
<221> NAME/KEY: MISC_FEATURE
<222> LOCATION: (9)..(9)
<223> OTHER INFORMATION: Xaa is Val or Ile

<400> SEQUENCE: 84

Gly Val Arg Xaa Xaa Xaa Asp Gly Xaa
1               5

<210> SEQ ID NO 85
<211> LENGTH: 8
<212> TYPE: PRT
<213> ORGANISM: hepatitis C virus
<220> FEATURE:
<221> NAME/KEY: MISC_FEATURE
<222> LOCATION: (3)..(3)
<223> OTHER INFORMATION: Xaa is Val, Ala or Leu
<220> FEATURE:
<221> NAME/KEY: MISC_FEATURE
<222> LOCATION: (4)..(4)
<223> OTHER INFORMATION: Xaa is Leu, Val or Ile
<220> FEATURE:
<221> NAME/KEY: MISC_FEATURE
<222> LOCATION: (5)..(5)
<223> OTHER INFORMATION: Xaa is Glu or Gly
<220> FEATURE:
<221> NAME/KEY: MISC_FEATURE
<222> LOCATION: (8)..(8)
<223> OTHER INFORMATION: Xaa is Val or Ile

<400> SEQUENCE: 85

Val Arg Xaa Xaa Xaa Asp Gly Xaa
1               5

<210> SEQ ID NO 86
<211> LENGTH: 9
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Val, Ala or Leu
<220> FEATURE:
<221> NAME/KEY: MISC_FEATURE
<222> LOCATION: (3)..(3)
<223> OTHER INFORMATION: Xaa is Leu, Val or Ile
<220> FEATURE:
<221> NAME/KEY: MISC_FEATURE
<222> LOCATION: (4)..(4)
<223> OTHER INFORMATION: Xaa is Glu or Gly
<220> FEATURE:
<221> NAME/KEY: MISC_FEATURE
<222> LOCATION: (7)..(7)
<223> OTHER INFORMATION: Xaa is Val or Ile
<220> FEATURE:
<221> NAME/KEY: MISC_FEATURE
<222> LOCATION: (9)..(9)
<223> OTHER INFORMATION: Xaa is Phe or Tyr

<400> SEQUENCE: 86

Arg Xaa Xaa Xaa Asp Gly Xaa Asn Xaa
1               5
```

-continued

```
<210> SEQ ID NO 87
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Val, Ala or Leu
<220> FEATURE:
<221> NAME/KEY: MISC_FEATURE
<222> LOCATION: (2)..(2)
<223> OTHER INFORMATION: Xaa is Leu, Val or Ile
<220> FEATURE:
<221> NAME/KEY: MISC_FEATURE
<222> LOCATION: (3)..(3)
<223> OTHER INFORMATION: Xaa is Glu or Gly
<220> FEATURE:
<221> NAME/KEY: MISC_FEATURE
<222> LOCATION: (6)..(6)
<223> OTHER INFORMATION: Xaa is Val or Ile
<220> FEATURE:
<221> NAME/KEY: MISC_FEATURE
<222> LOCATION: (8)..(8)
<223> OTHER INFORMATION: Xaa is Phe or Tyr

<400> SEQUENCE: 87

Xaa Xaa Xaa Asp Gly Xaa Asn Xaa
1               5

<210> SEQ ID NO 88
<211> LENGTH: 9
<212> TYPE: PRT
<213> ORGANISM: hepatitis C virus

<400> SEQUENCE: 88

Ala Leu Ala His Gly Val Arg Val Leu
1               5

<210> SEQ ID NO 89
<211> LENGTH: 8
<212> TYPE: PRT
<213> ORGANISM: hepatitis C virus

<400> SEQUENCE: 89

Leu Ala His Gly Val Arg Val Leu
1               5

<210> SEQ ID NO 90
<211> LENGTH: 8
<212> TYPE: PRT
<213> ORGANISM: hepatitis C virus

<400> SEQUENCE: 90

Val Arg Val Leu Glu Asp Gly Val
1               5

<210> SEQ ID NO 91
<211> LENGTH: 7
<212> TYPE: PRT
<213> ORGANISM: hepatitis C virus

<400> SEQUENCE: 91

Arg Val Leu Glu Asp Gly Val
1               5

<210> SEQ ID NO 92
<211> LENGTH: 8
<212> TYPE: PRT
<213> ORGANISM: hepatitis C virus
```

```
<400> SEQUENCE: 92

Val Leu Glu Asp Gly Val Asn Tyr
1               5

<210> SEQ ID NO 93
<211> LENGTH: 7
<212> TYPE: PRT
<213> ORGANISM: hepatitis C virus

<400> SEQUENCE: 93

Leu Glu Asp Gly Val Asn Tyr
1               5

<210> SEQ ID NO 94
<211> LENGTH: 9
<212> TYPE: PRT
<213> ORGANISM: hepatitis C virus

<400> SEQUENCE: 94

Leu Val Gly Ala Pro Leu Gly Gly Ala
1               5

<210> SEQ ID NO 95
<211> LENGTH: 8
<212> TYPE: PRT
<213> ORGANISM: hepatitis C virus

<400> SEQUENCE: 95

Val Gly Ala Pro Leu Gly Gly Ala
1               5

<210> SEQ ID NO 96
<211> LENGTH: 9
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Leu, Val or Phe
<220> FEATURE:
<221> NAME/KEY: MISC_FEATURE
<222> LOCATION: (4)..(4)
<223> OTHER INFORMATION: Xaa is Lys or Arg
<220> FEATURE:
<221> NAME/KEY: MISC_FEATURE
<222> LOCATION: (9)..(9)
<223> OTHER INFORMATION: Xaa is Leu or Ile

<400> SEQUENCE: 96

Asn Xaa Gly Xaa Val Ile Asp Thr Xaa
1               5

<210> SEQ ID NO 97
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Leu, Val or Phe
<220> FEATURE:
<221> NAME/KEY: MISC_FEATURE
<222> LOCATION: (3)..(3)
<223> OTHER INFORMATION: Xaa is Lys or Arg
<220> FEATURE:
<221> NAME/KEY: MISC_FEATURE
<222> LOCATION: (8)..(8)
<223> OTHER INFORMATION: Xaa is Leu or Ile
```

```
<400> SEQUENCE: 97

Xaa Gly Xaa Val Ile Asp Thr Xaa
1               5

<210> SEQ ID NO 98
<211> LENGTH: 9
<212> TYPE: PRT
<213> ORGANISM: hepatitis C virus

<400> SEQUENCE: 98

Asn Leu Gly Lys Val Ile Asp Thr Leu
1               5

<210> SEQ ID NO 99
<211> LENGTH: 20
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(3)
<223> OTHER INFORMATION: Xaa is Ala, Ser or Thr
<220> FEATURE:
<221> NAME/KEY: MISC_FEATURE
<222> LOCATION: (5)..(5)
<223> OTHER INFORMATION: Xaa is Ala or Gly
<220> FEATURE:
<221> NAME/KEY: MISC_FEATURE
<222> LOCATION: (6)..(6)
<223> OTHER INFORMATION: Xaa is Gln, Lys or Arg
<220> FEATURE:
<221> NAME/KEY: MISC_FEATURE
<222> LOCATION: (9)..(9)
<223> OTHER INFORMATION: Xaa is Tyr or His
<220> FEATURE:
<221> NAME/KEY: MISC_FEATURE
<222> LOCATION: (15)..(15)
<223> OTHER INFORMATION: Xaa is Gly or Ala
<220> FEATURE:
<221> NAME/KEY: MISC_FEATURE
<222> LOCATION: (17)..(17)
<223> OTHER INFORMATION: Xaa is Glu or Lys
<220> FEATURE:
<221> NAME/KEY: MISC_FEATURE
<222> LOCATION: (19)..(19)
<223> OTHER INFORMATION: Xaa is Cys, Met or Leu

<400> SEQUENCE: 99

Gly Xaa Xaa Trp Xaa Xaa Pro Gly Xaa Pro Trp Pro Leu Tyr Xaa Asn
1               5                   10                  15

Xaa Gly Xaa Gly
            20

<210> SEQ ID NO 100
<211> LENGTH: 9
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ala, Ser or Thr
<220> FEATURE:
<221> NAME/KEY: MISC_FEATURE
<222> LOCATION: (3)..(3)
<223> OTHER INFORMATION: Xaa is Ala or Gly
<220> FEATURE:
<221> NAME/KEY: MISC_FEATURE
<222> LOCATION: (4)..(4)
```

```
<223> OTHER INFORMATION: Xaa is Gln, Lys or Arg
<220> FEATURE:
<221> NAME/KEY: MISC_FEATURE
<222> LOCATION: (7)..(7)
<223> OTHER INFORMATION: Xaa is Tyr or His

<400> SEQUENCE: 100

Xaa Trp Xaa Xaa Pro Gly Xaa Pro Trp
1               5

<210> SEQ ID NO 101
<211> LENGTH: 8
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Ala or Gly
<220> FEATURE:
<221> NAME/KEY: MISC_FEATURE
<222> LOCATION: (3)..(3)
<223> OTHER INFORMATION: Xaa is Gln, Lys or Arg
<220> FEATURE:
<221> NAME/KEY: MISC_FEATURE
<222> LOCATION: (6)..(6)
<223> OTHER INFORMATION: Xaa is Tyr or His

<400> SEQUENCE: 101

Trp Xaa Xaa Pro Gly Xaa Pro Trp
1               5

<210> SEQ ID NO 102
<211> LENGTH: 9
<212> TYPE: PRT
<213> ORGANISM: hepatitis C virus

<400> SEQUENCE: 102

Thr Trp Ala Gln Pro Gly Tyr Pro Trp
1               5

<210> SEQ ID NO 103
<211> LENGTH: 8
<212> TYPE: PRT
<213> ORGANISM: hepatitis C virus

<400> SEQUENCE: 103

Trp Ala Gln Pro Gly Tyr Pro Trp
1               5

<210> SEQ ID NO 104
<211> LENGTH: 147
<212> TYPE: PRT
<213> ORGANISM: hepatitis C virus

<400> SEQUENCE: 104

Thr Pro Thr Val Ala Thr Thr Arg Asp Gly Lys Leu Pro Ala Thr Gln
1               5                   10                  15

Leu Arg Arg His Ile Asp Leu Leu Val Gly Ser Ala Thr Leu Cys Ser
                20                  25                  30

Ala Leu Tyr Val Gly Asp Leu Cys Gly Ser Val Gln Leu Phe Thr Phe
            35                  40                  45

Ser Pro Arg Arg His Trp Thr Thr Gln Gly Cys Asn Cys Ser Ile Tyr
        50                  55                  60

Pro Gly His Ile Thr Gly His Arg Met Ala Trp Asp Met Met Met Asn
65                  70                  75                  80
```

```
Trp Ser Pro Thr Ala Ala Leu Val Met Ala Gln Leu Leu Arg Ile Pro
                85                  90                  95

Gln Ala Ile Leu Asp Met Ile Ala Gly Ala His Trp Gly Val Leu Ala
            100                 105                 110

Gly Ile Ala Tyr Phe Ser Met Val Gly Asn Trp Ala Lys Val Leu Val
        115                 120                 125

Val Leu Leu Leu Phe Ala Gly Val Asp Ala Glu Thr Ile Val Ser Gly
    130                 135                 140

Gly Gln Ala
145

<210> SEQ ID NO 105
<211> LENGTH: 18
<212> TYPE: PRT
<213> ORGANISM: hepatitis C virus

<400> SEQUENCE: 105

Thr Pro Thr Val Ala Thr Thr Arg Asp Gly Lys Leu Pro Ala Thr Gln
1               5                   10                  15

Leu Arg

<210> SEQ ID NO 106
<211> LENGTH: 76
<212> TYPE: PRT
<213> ORGANISM: hepatitis C virus

<400> SEQUENCE: 106

Leu Pro Ala Thr Gln Leu Arg Arg His Ile Asp Leu Leu Val Gly Ser
1               5                   10                  15

Ala Thr Leu Cys Ser Ala Leu Tyr Val Gly Asp Leu Cys Gly Ser Val
            20                  25                  30

Gln Leu Phe Thr Phe Ser Pro Arg Arg His Trp Thr Thr Gln Gly Cys
        35                  40                  45

Asn Cys Ser Ile Tyr Pro Gly His Ile Thr Gly His Arg Met Ala Trp
    50                  55                  60

Asp Met Met Met Asn Trp Ser Pro Thr Ala Ala Leu
65                  70                  75

<210> SEQ ID NO 107
<211> LENGTH: 69
<212> TYPE: PRT
<213> ORGANISM: hepatitis C virus

<400> SEQUENCE: 107

Met Asn Trp Ser Pro Thr Ala Ala Leu Val Met Ala Gln Leu Leu Arg
1               5                   10                  15

Ile Pro Gln Ala Ile Leu Asp Met Ile Ala Gly Ala His Trp Gly Val
            20                  25                  30

Leu Ala Gly Ile Ala Tyr Phe Ser Met Val Gly Asn Trp Ala Lys Val
        35                  40                  45

Leu Val Val Leu Leu Leu Phe Ala Gly Val Asp Ala Glu Thr Ile Val
    50                  55                  60

Ser Gly Gly Gln Ala
65

<210> SEQ ID NO 108
<211> LENGTH: 70
<212> TYPE: PRT
<213> ORGANISM: hepatitis C virus
```

```
<220> FEATURE:
<221> NAME/KEY: MISC_FEATURE
<222> LOCATION: (2)..(2)
<223> OTHER INFORMATION: Xaa is Gly or Arg
<220> FEATURE:
<221> NAME/KEY: MISC_FEATURE
<222> LOCATION: (3)..(3)
<223> OTHER INFORMATION: Xaa is Gly, Ala or Lys
<220> FEATURE:
<221> NAME/KEY: MISC_FEATURE
<222> LOCATION: (4)..(4)
<223> OTHER INFORMATION: Xaa is Ala, Val, Gly, Ser or Asp
<220> FEATURE:
<221> NAME/KEY: MISC_FEATURE
<222> LOCATION: (5)..(5)
<223> OTHER INFORMATION: Xaa is Gly, Phe or Tyr
<220> FEATURE:
<221> NAME/KEY: MISC_FEATURE
<222> LOCATION: (7)..(7)
<223> OTHER INFORMATION: Xaa is Asn, His, Arg, Leu, Ala or Ser
<220> FEATURE:
<221> NAME/KEY: MISC_FEATURE
<222> LOCATION: (8)..(8)
<223> OTHER INFORMATION: Xaa is Thr or Ser
<220> FEATURE:
<221> NAME/KEY: MISC_FEATURE
<222> LOCATION: (9)..(9)
<223> OTHER INFORMATION: Xaa is no amino acid or Met or Ile
<220> FEATURE:
<221> NAME/KEY: MISC_FEATURE
<222> LOCATION: (10)..(10)
<223> OTHER INFORMATION: Xaa is no amino acid or Asp
<220> FEATURE:
<221> NAME/KEY: MISC_FEATURE
<222> LOCATION: (12)..(12)
<223> OTHER INFORMATION: Xaa is His, Leu, Val, Thr or Ile
<220> FEATURE:
<221> NAME/KEY: MISC_FEATURE
<222> LOCATION: (21)..(21)
<223> OTHER INFORMATION: Xaa is His or Tyr
<220> FEATURE:
<221> NAME/KEY: MISC_FEATURE
<222> LOCATION: (23)..(23)
<223> OTHER INFORMATION: Xaa is Asp or Glu
<220> FEATURE:
<221> NAME/KEY: MISC_FEATURE
<222> LOCATION: (24)..(24)
<223> OTHER INFORMATION: Xaa is Ala or Thr
<220> FEATURE:
<221> NAME/KEY: MISC_FEATURE
<222> LOCATION: (27)..(27)
<223> OTHER INFORMATION: Xaa is Ser, Thr, Ile or Leu
<220> FEATURE:
<221> NAME/KEY: MISC_FEATURE
<222> LOCATION: (28)..(28)
<223> OTHER INFORMATION: Xaa is Arg or Lys
<220> FEATURE:
<221> NAME/KEY: MISC_FEATURE
<222> LOCATION: (31)..(31)
<223> OTHER INFORMATION: Xaa is Ser or Ala
<220> FEATURE:
<221> NAME/KEY: MISC_FEATURE
<222> LOCATION: (34)..(34)
<223> OTHER INFORMATION: Xaa is Trp or Leu
<220> FEATURE:
<221> NAME/KEY: MISC_FEATURE
<222> LOCATION: (35)..(35)
<223> OTHER INFORMATION: Xaa is Ile or Leu
<220> FEATURE:
<221> NAME/KEY: MISC_FEATURE
<222> LOCATION: (40)..(40)
<223> OTHER INFORMATION: Xaa is Leu, Met or Ile
<220> FEATURE:
<221> NAME/KEY: MISC_FEATURE
<222> LOCATION: (41)..(41)
<223> OTHER INFORMATION: Xaa is Val or Ile
<220> FEATURE:
<221> NAME/KEY: MISC_FEATURE
<222> LOCATION: (54)..(54)
```

```
<223> OTHER INFORMATION: Xaa is Ile, Val, Phe or Leu
<220> FEATURE:
<221> NAME/KEY: MISC_FEATURE
<222> LOCATION: (56)..(56)
<223> OTHER INFORMATION: Xaa is Tyr or Phe
<220> FEATURE:
<221> NAME/KEY: MISC_FEATURE
<222> LOCATION: (57)..(57)
<223> OTHER INFORMATION: Xaa is Thr, Ser or Ala
<220> FEATURE:
<221> NAME/KEY: MISC_FEATURE
<222> LOCATION: (58)..(58)
<223> OTHER INFORMATION: Xaa is Ile or Val
<220> FEATURE:
<221> NAME/KEY: MISC_FEATURE
<222> LOCATION: (61)..(61)
<223> OTHER INFORMATION: Xaa is Ile, Val or Ala
<220> FEATURE:
<221> NAME/KEY: MISC_FEATURE
<222> LOCATION: (64)..(64)
<223> OTHER INFORMATION: Xaa is Tyr or Phe

<400> SEQUENCE: 108

Ile Xaa Xaa Xaa Xaa Asn Xaa Xaa Xaa Xaa Leu Xaa Cys Pro Thr Asp
1               5                   10                  15

Cys Phe Arg Lys Xaa Pro Xaa Xaa Thr Tyr Xaa Xaa Cys Gly Xaa Gly
            20                  25                  30

Pro Xaa Xaa Thr Pro Arg Cys Xaa Xaa Asp Tyr Pro Tyr Arg Leu Trp
        35                  40                  45

His Tyr Pro Cys Thr Xaa Asn Xaa Xaa Xaa Phe Lys Xaa Arg Met Xaa
    50                  55                  60

Val Gly Gly Val Glu His
65                  70

<210> SEQ ID NO 109
<211> LENGTH: 9
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Gln, Ser or Tyr
<220> FEATURE:
<221> NAME/KEY: MISC_FEATURE
<222> LOCATION: (3)..(3)
<223> OTHER INFORMATION: Xaa is Ile or Val
<220> FEATURE:
<221> NAME/KEY: MISC_FEATURE
<222> LOCATION: (5)..(5)
<223> OTHER INFORMATION: Xaa is Thr or Ser

<400> SEQUENCE: 109

Xaa Leu Xaa Asn Xaa Asn Gly Ser Trp
1               5

<210> SEQ ID NO 110
<211> LENGTH: 8
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Ile or Val
<220> FEATURE:
<221> NAME/KEY: MISC_FEATURE
<222> LOCATION: (4)..(4)
<223> OTHER INFORMATION: Xaa is Thr or Ser

<400> SEQUENCE: 110

Leu Xaa Asn Xaa Asn Gly Ser Trp
```

1               5

<210> SEQ ID NO 111
<211> LENGTH: 9
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: Xaa is Leu or Ile
<220> FEATURE:
<221> NAME/KEY: MISC_FEATURE
<222> LOCATION: (6)..(6)
<223> OTHER INFORMATION: Xaa is Ser or Arg

<400> SEQUENCE: 111

Ser Trp His Xaa Asn Xaa Thr Ala Leu
1               5

<210> SEQ ID NO 112
<211> LENGTH: 9
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: Xaa is Leu or Ile
<220> FEATURE:
<221> NAME/KEY: MISC_FEATURE
<222> LOCATION: (6)..(6)
<223> OTHER INFORMATION: Xaa is Ser or Arg

<400> SEQUENCE: 112

Ser Trp His Xaa Asn Xaa Thr Ala Leu
1               5

<210> SEQ ID NO 113
<211> LENGTH: 9
<212> TYPE: PRT
<213> ORGANISM: hepatitis C virus

<400> SEQUENCE: 113

Gln Leu Ile Asn Thr Asn Gly Ser Trp
1               5

<210> SEQ ID NO 114
<211> LENGTH: 8
<212> TYPE: PRT
<213> ORGANISM: hepatitis C virus

<400> SEQUENCE: 114

Leu Ile Asn Thr Asn Gly Ser Trp
1               5

<210> SEQ ID NO 115
<211> LENGTH: 9
<212> TYPE: PRT
<213> ORGANISM: hepatitis C virus

<400> SEQUENCE: 115

Ser Trp His Ile Asn Ser Thr Ala Leu
1               5

<210> SEQ ID NO 116
<211> LENGTH: 8
<212> TYPE: PRT
<213> ORGANISM: hepatitis C virus

```
<400> SEQUENCE: 116

Trp His Ile Asn Ser Thr Ala Leu
1               5

<210> SEQ ID NO 117
<211> LENGTH: 8
<212> TYPE: PRT
<213> ORGANISM: hepatitis C virus

<400> SEQUENCE: 117

Leu Gly Lys Val Ile Asp Thr Leu
1               5

<210> SEQ ID NO 118
<211> LENGTH: 21
<212> TYPE: PRT
<213> ORGANISM: hepatitis C virus

<400> SEQUENCE: 118

Gly Gly Val Ala Ala Arg Ala Leu Ala His Gly Val Arg Val Leu Glu
1               5                  10                  15

Asp Gly Val Asn Tyr
            20

<210> SEQ ID NO 119
<211> LENGTH: 11
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Thr or Ser
<220> FEATURE:
<221> NAME/KEY: MISC_FEATURE
<222> LOCATION: (2)..(2)
<223> OTHER INFORMATION: Xaa is no amino acid or Met or Ile
<220> FEATURE:
<221> NAME/KEY: MISC_FEATURE
<222> LOCATION: (3)..(3)
<223> OTHER INFORMATION: Xaa is no amino acid or Asp
<220> FEATURE:
<221> NAME/KEY: MISC_FEATURE
<222> LOCATION: (5)..(5)
<223> OTHER INFORMATION: Xaa is His, Leu, Val, Thr or Ile

<400> SEQUENCE: 119

Xaa Xaa Xaa Leu Xaa Cys Pro Thr Asp Cys Phe
1               5                   10

<210> SEQ ID NO 120
<211> LENGTH: 9
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: Xaa is His or Tyr
<220> FEATURE:
<221> NAME/KEY: MISC_FEATURE
<222> LOCATION: (6)..(6)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Ala or Thr

<400> SEQUENCE: 120

Phe Arg Lys Xaa Pro Xaa Xaa Thr Tyr
1               5
```

<210> SEQ ID NO 121
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Trp or Leu
<220> FEATURE:
<221> NAME/KEY: MISC_FEATURE
<222> LOCATION: (2)..(2)
<223> OTHER INFORMATION: Xaa is Ile or Leu
<220> FEATURE:
<221> NAME/KEY: MISC_FEATURE
<222> LOCATION: (7)..(7)
<223> OTHER INFORMATION: Xaa is Leu, Met or Ile
<220> FEATURE:
<221> NAME/KEY: MISC_FEATURE
<222> LOCATION: (8)..(8)
<223> OTHER INFORMATION: Xaa is Val or Ile

<400> SEQUENCE: 121

Xaa Xaa Thr Pro Arg Cys Xaa Xaa
1               5

<210> SEQ ID NO 122
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Leu, Met or Ile
<220> FEATURE:
<221> NAME/KEY: MISC_FEATURE
<222> LOCATION: (2)..(2)
<223> OTHER INFORMATION: Xaa is Val or Ile

<400> SEQUENCE: 122

Xaa Xaa Asp Tyr Pro Tyr Arg Leu
1               5

<210> SEQ ID NO 123
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Val or Ile

<400> SEQUENCE: 123

Xaa Asp Tyr Pro Tyr Arg Leu Trp
1               5

<210> SEQ ID NO 124
<211> LENGTH: 8
<212> TYPE: PRT
<213> ORGANISM: hepatitis C virus

<400> SEQUENCE: 124

Tyr Pro Tyr Arg Leu Trp His Tyr
1               5

<210> SEQ ID NO 125
<211> LENGTH: 8
<212> TYPE: PRT
<213> ORGANISM: hepatitis C virus
<220> FEATURE:

<221> NAME/KEY: MISC_FEATURE
<222> LOCATION: (8)..(8)
<223> OTHER INFORMATION: Xaa is Ile, Val, Phe or Leu

<400> SEQUENCE: 125

Leu Trp His Tyr Pro Cys Thr Xaa
1               5

<210> SEQ ID NO 126
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ile, Val, Phe or Leu
<220> FEATURE:
<221> NAME/KEY: MISC_FEATURE
<222> LOCATION: (3)..(3)
<223> OTHER INFORMATION: Xaa is Tyr or Phe
<220> FEATURE:
<221> NAME/KEY: MISC_FEATURE
<222> LOCATION: (4)..(4)
<223> OTHER INFORMATION: Xaa is Thr, Ser or Ala
<220> FEATURE:
<221> NAME/KEY: MISC_FEATURE
<222> LOCATION: (5)..(5)
<223> OTHER INFORMATION: Xaa is Ile or Val
<220> FEATURE:
<221> NAME/KEY: MISC_FEATURE
<222> LOCATION: (8)..(8)
<223> OTHER INFORMATION: Xaa is Ile, Val or Ala

<400> SEQUENCE: 126

Xaa Asn Xaa Xaa Xaa Phe Lys Xaa
1               5

<210> SEQ ID NO 127
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Tyr or Phe
<220> FEATURE:
<221> NAME/KEY: MISC_FEATURE
<222> LOCATION: (2)..(2)
<223> OTHER INFORMATION: Xaa is Thr, Ser or Ala
<220> FEATURE:
<221> NAME/KEY: MISC_FEATURE
<222> LOCATION: (3)..(3)
<223> OTHER INFORMATION: Xaa is Ile or Val
<220> FEATURE:
<221> NAME/KEY: MISC_FEATURE
<222> LOCATION: (6)..(6)
<223> OTHER INFORMATION: Xaa is Ile, Val or Ala

<400> SEQUENCE: 127

Xaa Xaa Xaa Phe Lys Xaa Arg Met
1               5

<210> SEQ ID NO 128
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ile or Val
<220> FEATURE:
<221> NAME/KEY: MISC_FEATURE
<222> LOCATION: (4)..(4)

```
<223> OTHER INFORMATION: Xaa is Ile, Val or Ala
<220> FEATURE:
<221> NAME/KEY: MISC_FEATURE
<222> LOCATION: (7)..(7)
<223> OTHER INFORMATION: Xaa is Tyr or Phe

<400> SEQUENCE: 128

Xaa Phe Lys Xaa Arg Met Xaa Val
1               5

<210> SEQ ID NO 129
<211> LENGTH: 8
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ile, Val or Ala
<220> FEATURE:
<221> NAME/KEY: MISC_FEATURE
<222> LOCATION: (4)..(4)
<223> OTHER INFORMATION: Xaa is Tyr or Phe

<400> SEQUENCE: 129

Xaa Arg Met Xaa Val Gly Gly Val
1               5

<210> SEQ ID NO 130
<211> LENGTH: 22
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Gly or Arg
<220> FEATURE:
<221> NAME/KEY: MISC_FEATURE
<222> LOCATION: (3)..(3)
<223> OTHER INFORMATION: Xaa is Gly, Ala or Lys
<220> FEATURE:
<221> NAME/KEY: MISC_FEATURE
<222> LOCATION: (4)..(4)
<223> OTHER INFORMATION: Xaa is Ala, Val, Gly, Ser or Asp
<220> FEATURE:
<221> NAME/KEY: MISC_FEATURE
<222> LOCATION: (5)..(5)
<223> OTHER INFORMATION: Xaa is Gly, Phe or Tyr
<220> FEATURE:
<221> NAME/KEY: MISC_FEATURE
<222> LOCATION: (7)..(7)
<223> OTHER INFORMATION: Xaa is Asn, His, Arg, Leu, Ala or Ser
<220> FEATURE:
<221> NAME/KEY: MISC_FEATURE
<222> LOCATION: (8)..(8)
<223> OTHER INFORMATION: Xaa is Thr or Ser
<220> FEATURE:
<221> NAME/KEY: MISC_FEATURE
<222> LOCATION: (9)..(9)
<223> OTHER INFORMATION: Xaa is no amino acid or Met or Ile
<220> FEATURE:
<221> NAME/KEY: MISC_FEATURE
<222> LOCATION: (10)..(10)
<223> OTHER INFORMATION: Xaa is no amino acid or Asp
<220> FEATURE:
<221> NAME/KEY: MISC_FEATURE
<222> LOCATION: (12)..(12)
<223> OTHER INFORMATION: Xaa is His, Leu, Val, Thr or Ile
<220> FEATURE:
<221> NAME/KEY: MISC_FEATURE
<222> LOCATION: (21)..(21)
<223> OTHER INFORMATION: Xaa is His or Tyr

<400> SEQUENCE: 130

Ile Xaa Xaa Xaa Xaa Asn Xaa Xaa Xaa Xaa Leu Xaa Cys Pro Thr Asp
```

-continued

```
                  1               5              10              15

Cys Phe Arg Lys Xaa Pro
                20

<210> SEQ ID NO 131
<211> LENGTH: 20
<212> TYPE: PRT
<213> ORGANISM: hepatitis C virus
<220> FEATURE:
<221> NAME/KEY: MISC_FEATURE
<222> LOCATION: (7)..(7)
<223> OTHER INFORMATION: Xaa is His or Tyr
<220> FEATURE:
<221> NAME/KEY: MISC_FEATURE
<222> LOCATION: (9)..(9)
<223> OTHER INFORMATION: Xaa is Asp or Glu
<220> FEATURE:
<221> NAME/KEY: MISC_FEATURE
<222> LOCATION: (10)..(10)
<223> OTHER INFORMATION: Xaa is Ala or Thr
<220> FEATURE:
<221> NAME/KEY: MISC_FEATURE
<222> LOCATION: (13)..(13)
<223> OTHER INFORMATION: Xaa is Ser, Thr, Ile or Leu
<220> FEATURE:
<221> NAME/KEY: MISC_FEATURE
<222> LOCATION: (14)..(14)
<223> OTHER INFORMATION: Xaa is Arg or Lys
<220> FEATURE:
<221> NAME/KEY: MISC_FEATURE
<222> LOCATION: (17)..(17)
<223> OTHER INFORMATION: Xaa is Ser or Ala
<220> FEATURE:
<221> NAME/KEY: MISC_FEATURE
<222> LOCATION: (20)..(20)
<223> OTHER INFORMATION: Xaa is Trp or Leu

<400> SEQUENCE: 131

Thr Asp Cys Phe Arg Lys Xaa Pro Xaa Xaa Thr Tyr Xaa Xaa Cys Gly
1               5                  10                  15

Xaa Gly Pro Xaa
                20

<210> SEQ ID NO 132
<211> LENGTH: 20
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is Ser, Thr, Ile or Leu
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (5)..(5)
<223> OTHER INFORMATION: Xaa is Ser or Ala
<220> FEATURE:
<221> NAME/KEY: MISC_FEATURE
<222> LOCATION: (8)..(8)
<223> OTHER INFORMATION: Xaa is Trp or Leu
<220> FEATURE:
<221> NAME/KEY: MISC_FEATURE
<222> LOCATION: (9)..(9)
<223> OTHER INFORMATION: Xaa is Ile or Leu
<220> FEATURE:
<221> NAME/KEY: MISC_FEATURE
<222> LOCATION: (14)..(14)
<223> OTHER INFORMATION: Xaa is Leu, Met or Ile
<220> FEATURE:
<221> NAME/KEY: MISC_FEATURE
<222> LOCATION: (15)..(15)
```

<223> OTHER INFORMATION: Xaa is Val or Ile

<400> SEQUENCE: 132

Xaa Xaa Cys Gly Xaa Gly Pro Xaa Xaa Thr Pro Arg Cys Xaa Xaa Asp
1               5                   10                  15

Tyr Pro Tyr Arg
            20

<210> SEQ ID NO 133
<211> LENGTH: 20
<212> TYPE: PRT
<213> ORGANISM: hepatitis C virus
<220> FEATURE:
<221> NAME/KEY: MISC_FEATURE
<222> LOCATION: (2)..(2)
<223> OTHER INFORMATION: Xaa is Leu, Met or Ile
<220> FEATURE:
<221> NAME/KEY: MISC_FEATURE
<222> LOCATION: (3)..(3)
<223> OTHER INFORMATION: Xaa is Val or Ile
<220> FEATURE:
<221> NAME/KEY: MISC_FEATURE
<222> LOCATION: (16)..(16)
<223> OTHER INFORMATION: Xaa is Ile, Val, Phe or Leu
<220> FEATURE:
<221> NAME/KEY: MISC_FEATURE
<222> LOCATION: (18)..(18)
<223> OTHER INFORMATION: Xaa is Tyr or Phe
<220> FEATURE:
<221> NAME/KEY: MISC_FEATURE
<222> LOCATION: (19)..(19)
<223> OTHER INFORMATION: Xaa is Thr, Ser or Ala
<220> FEATURE:
<221> NAME/KEY: MISC_FEATURE
<222> LOCATION: (20)..(20)
<223> OTHER INFORMATION: Xaa is Ile or Val

<400> SEQUENCE: 133

Cys Xaa Xaa Asp Tyr Pro Tyr Arg Leu Trp His Tyr Pro Cys Thr Xaa
1               5                   10                  15

Asn Xaa Xaa Xaa
            20

<210> SEQ ID NO 134
<211> LENGTH: 20
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: Xaa is Ile, Val, Phe or Leu
<220> FEATURE:
<221> NAME/KEY: MISC_FEATURE
<222> LOCATION: (6)..(6)
<223> OTHER INFORMATION: Xaa is Tyr or Phe
<220> FEATURE:
<221> NAME/KEY: MISC_FEATURE
<222> LOCATION: (7)..(7)
<223> OTHER INFORMATION: Xaa is Thr, Ser or Ala
<220> FEATURE:
<221> NAME/KEY: MISC_FEATURE
<222> LOCATION: (8)..(8)
<223> OTHER INFORMATION: Xaa is Ile or Val
<220> FEATURE:
<221> NAME/KEY: MISC_FEATURE
<222> LOCATION: (11)..(11)
<223> OTHER INFORMATION: Xaa is Ile, Val or Ala
<220> FEATURE:
<221> NAME/KEY: MISC_FEATURE
<222> LOCATION: (14)..(14)
<223> OTHER INFORMATION: Xaa is Tyr or Phe

<400> SEQUENCE: 134

Pro Cys Thr Xaa Asn Xaa Xaa Xaa Phe Lys Xaa Arg Met Xaa Val Gly
1               5                   10                  15

Gly Val Glu His
            20

<210> SEQ ID NO 135
<211> LENGTH: 8
<212> TYPE: PRT
<213> ORGANISM: hepatitis C virus

<400> SEQUENCE: 135

Val Ala Lys Ala Val Asp Phe Val
1               5

<210> SEQ ID NO 136
<211> LENGTH: 8
<212> TYPE: PRT
<213> ORGANISM: hepatitis C virus

<400> SEQUENCE: 136

Val Ala Lys Ala Val Asp Phe Ile
1               5

<210> SEQ ID NO 137
<211> LENGTH: 8
<212> TYPE: PRT
<213> ORGANISM: hepatitis C virus

<400> SEQUENCE: 137

Val Glu Ser Met Glu Thr Thr Met
1               5

<210> SEQ ID NO 138
<211> LENGTH: 8
<212> TYPE: PRT
<213> ORGANISM: hepatitis C virus

<400> SEQUENCE: 138

Ala Val Pro Gln Thr Phe Gln Val
1               5

<210> SEQ ID NO 139
<211> LENGTH: 8
<212> TYPE: PRT
<213> ORGANISM: hepatitis C virus

<400> SEQUENCE: 139

Tyr Ala Ala Gln Gly Tyr Lys Val
1               5

<210> SEQ ID NO 140
<211> LENGTH: 9
<212> TYPE: PRT
<213> ORGANISM: hepatitis C virus

<400> SEQUENCE: 140

Val Leu Val Leu Asn Pro Ser Val Ala
1               5

<210> SEQ ID NO 141
<211> LENGTH: 8
<212> TYPE: PRT
<213> ORGANISM: hepatitis C virus

```
<400> SEQUENCE: 141

Tyr Met Ser Lys Ala His Gly Val
1               5

<210> SEQ ID NO 142
<211> LENGTH: 8
<212> TYPE: PRT
<213> ORGANISM: hepatitis C virus

<400> SEQUENCE: 142

Ile Arg Thr Gly Val Arg Thr Ile
1               5

<210> SEQ ID NO 143
<211> LENGTH: 8
<212> TYPE: PRT
<213> ORGANISM: hepatitis C virus

<400> SEQUENCE: 143

Tyr Ser Thr Tyr Gly Lys Phe Leu
1               5

<210> SEQ ID NO 144
<211> LENGTH: 8
<212> TYPE: PRT
<213> ORGANISM: hepatitis C virus

<400> SEQUENCE: 144

Ile Leu Gly Ile Gly Thr Val Leu
1               5

<210> SEQ ID NO 145
<211> LENGTH: 8
<212> TYPE: PRT
<213> ORGANISM: hepatitis C virus

<400> SEQUENCE: 145

Val Thr Val Pro His Pro Asn Ile
1               5

<210> SEQ ID NO 146
<211> LENGTH: 8
<212> TYPE: PRT
<213> ORGANISM: hepatitis C virus

<400> SEQUENCE: 146

Ile Pro Phe Tyr Gly Lys Ala Ile
1               5

<210> SEQ ID NO 147
<211> LENGTH: 8
<212> TYPE: PRT
<213> ORGANISM: hepatitis C virus

<400> SEQUENCE: 147

Phe Tyr Gly Lys Ala Ile Pro Ile
1               5

<210> SEQ ID NO 148
<211> LENGTH: 8
<212> TYPE: PRT
<213> ORGANISM: hepatitis C virus

<400> SEQUENCE: 148
```

```
Val Ile Lys Gly Gly Arg His Leu
1               5

<210> SEQ ID NO 149
<211> LENGTH: 8
<212> TYPE: PRT
<213> ORGANISM: hepatitis C virus

<400> SEQUENCE: 149

Ile Lys Gly Gly Arg His Leu Ile
1               5

<210> SEQ ID NO 150
<211> LENGTH: 8
<212> TYPE: PRT
<213> ORGANISM: hepatitis C virus

<400> SEQUENCE: 150

Phe Cys His Ser Lys Lys Lys Cys
1               5

<210> SEQ ID NO 151
<211> LENGTH: 8
<212> TYPE: PRT
<213> ORGANISM: hepatitis C virus

<400> SEQUENCE: 151

Cys Asp Glu Leu Ala Ala Lys Leu
1               5

<210> SEQ ID NO 152
<211> LENGTH: 9
<212> TYPE: PRT
<213> ORGANISM: hepatitis C virus

<400> SEQUENCE: 152

Leu Ala Ala Lys Leu Ser Gly Phe Gly
1               5

<210> SEQ ID NO 153
<211> LENGTH: 8
<212> TYPE: PRT
<213> ORGANISM: hepatitis C virus

<400> SEQUENCE: 153

Ser Gly Phe Gly Ile Asn Ala Val
1               5

<210> SEQ ID NO 154
<211> LENGTH: 8
<212> TYPE: PRT
<213> ORGANISM: hepatitis C virus

<400> SEQUENCE: 154

Phe Gly Ile Asn Ala Val Ala Tyr
1               5

<210> SEQ ID NO 155
<211> LENGTH: 8
<212> TYPE: PRT
<213> ORGANISM: hepatitis C virus

<400> SEQUENCE: 155

Tyr Arg Gly Leu Asp Val Ser Val
1               5
```

<210> SEQ ID NO 156
<211> LENGTH: 8
<212> TYPE: PRT
<213> ORGANISM: hepatitis C virus

<400> SEQUENCE: 156

Val Ile Pro Thr Ser Gly Asp Val
1               5

<210> SEQ ID NO 157
<211> LENGTH: 8
<212> TYPE: PRT
<213> ORGANISM: hepatitis C virus

<400> SEQUENCE: 157

Ile Pro Thr Ser Gly Asp Val Val
1               5

<210> SEQ ID NO 158
<211> LENGTH: 8
<212> TYPE: PRT
<213> ORGANISM: hepatitis C virus

<400> SEQUENCE: 158

Val Val Val Ala Thr Asp Ala Leu
1               5

<210> SEQ ID NO 159
<211> LENGTH: 8
<212> TYPE: PRT
<213> ORGANISM: hepatitis C virus

<400> SEQUENCE: 159

Val Val Ala Thr Asp Ala Leu Met
1               5

<210> SEQ ID NO 160
<211> LENGTH: 8
<212> TYPE: PRT
<213> ORGANISM: hepatitis C virus

<400> SEQUENCE: 160

Met Thr Gly Phe Thr Gly Asp Phe
1               5

<210> SEQ ID NO 161
<211> LENGTH: 8
<212> TYPE: PRT
<213> ORGANISM: hepatitis C virus

<400> SEQUENCE: 161

Phe Thr Gly Asp Phe Asp Ser Val
1               5

<210> SEQ ID NO 162
<211> LENGTH: 8
<212> TYPE: PRT
<213> ORGANISM: hepatitis C virus

<400> SEQUENCE: 162

Val Ile Asp Cys Asn Thr Cys Val
1               5

<210> SEQ ID NO 163
<211> LENGTH: 9
<212> TYPE: PRT
<213> ORGANISM: hepatitis C virus

<400> SEQUENCE: 163

Ala Leu Met Gly Tyr Ile Pro Leu Val
1               5

<210> SEQ ID NO 164
<211> LENGTH: 43
<212> TYPE: PRT
<213> ORGANISM: hepatitis C virus

<400> SEQUENCE: 164

Tyr Gln Val Arg Asn Ser Thr Gly Leu Tyr His Val Thr Asn Asp Cys
1               5                   10                  15

Pro Asn Ser Ser Ile Val Tyr Glu Ala His Asp Ala Ile Leu His Thr
            20                  25                  30

Pro Gly Cys Val Pro Cys Val Arg Glu Gly Asn
        35                  40

<210> SEQ ID NO 165
<211> LENGTH: 42
<212> TYPE: PRT
<213> ORGANISM: hepatitis C virus

<400> SEQUENCE: 165

Gln Val Arg Asn Ser Thr Gly Leu Tyr His Val Thr Asn Asp Cys Pro
1               5                   10                  15

Asn Ser Ser Ile Val Tyr Glu Ala His Asp Ala Ile Leu His Thr Pro
            20                  25                  30

Gly Cys Val Pro Cys Val Arg Glu Gly Asn
        35                  40

<210> SEQ ID NO 166
<211> LENGTH: 10
<212> TYPE: PRT
<213> ORGANISM: hepatitis C virus

<400> SEQUENCE: 166

Lys Leu Val Ala Leu Gly Ile Asn Ala Val
1               5                   10

<210> SEQ ID NO 167
<211> LENGTH: 8
<212> TYPE: PRT
<213> ORGANISM: hepatitis C virus

<400> SEQUENCE: 167

Ala Ser Arg Cys Trp Val Ala Met
1               5

<210> SEQ ID NO 168
<211> LENGTH: 13
<212> TYPE: PRT
<213> ORGANISM: hepatitis C virus

<400> SEQUENCE: 168

Leu Met Ala Leu Thr Leu Ser Pro Tyr Tyr Lys Arg Tyr
1               5                   10

<210> SEQ ID NO 169

-continued

```
<211> LENGTH: 13
<212> TYPE: PRT
<213> ORGANISM: hepatitis C virus

<400> SEQUENCE: 169

Arg Ala Leu Ala His Gly Val Arg Val Leu Glu Asp Gly
1               5                   10

<210> SEQ ID NO 170
<211> LENGTH: 7
<212> TYPE: PRT
<213> ORGANISM: hepatitis C virus

<400> SEQUENCE: 170

Arg Met Ala Trp Asp Met Met
1               5

<210> SEQ ID NO 171
<211> LENGTH: 9
<212> TYPE: PRT
<213> ORGANISM: hepatitis C virus

<400> SEQUENCE: 171

Pro Thr Asp Cys Phe Arg Lys His Pro
1               5

<210> SEQ ID NO 172
<211> LENGTH: 7
<212> TYPE: PRT
<213> ORGANISM: hepatitis C virus

<400> SEQUENCE: 172

Tyr Pro Tyr Arg Leu Trp His
1               5

<210> SEQ ID NO 173
<211> LENGTH: 7
<212> TYPE: PRT
<213> ORGANISM: hepatitis C virus

<400> SEQUENCE: 173

Gly Lys Ser Thr Lys Val Pro
1               5

<210> SEQ ID NO 174
<211> LENGTH: 6
<212> TYPE: PRT
<213> ORGANISM: hepatitis C virus

<400> SEQUENCE: 174

Pro Ser Val Ala Ala Thr
1               5

<210> SEQ ID NO 175
<211> LENGTH: 9
<212> TYPE: PRT
<213> ORGANISM: hepatitis C virus

<400> SEQUENCE: 175

Ile Gly Thr Val Leu Asp Gln Ala Glu
1               5

<210> SEQ ID NO 176
<211> LENGTH: 6
<212> TYPE: PRT
```

```
<213> ORGANISM: hepatitis C virus

<400> SEQUENCE: 176

Ala Val Ala Tyr Tyr Arg
1               5

<210> SEQ ID NO 177
<211> LENGTH: 9
<212> TYPE: PRT
<213> ORGANISM: hepatitis C virus

<400> SEQUENCE: 177

Thr Gly Asp Phe Asp Ser Val Ile Asp
1               5

<210> SEQ ID NO 178
<211> LENGTH: 278
<212> TYPE: PRT
<213> ORGANISM: hepatitis C virus

<400> SEQUENCE: 178

Gly Val Ala Lys Ala Val Asp Phe Val Pro Val Glu Ser Met Glu Thr
1               5                   10                  15

Thr Met Arg Ser Pro Val Phe Thr Asp Asn Ser Ser Pro Pro Ala Val
                20                  25                  30

Pro Gln Thr Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
        50                  55                  60

Leu Val Leu Asn Pro Ser Val Ala Ala Thr Leu Gly Phe Gly Ala Tyr
65                  70                  75                  80

Met Ser Lys Ala His Gly Val Asp Pro Asn Ile Arg Thr Gly Val Arg
                85                  90                  95

Thr Ile Thr Thr Gly Ala Pro Ile Thr Tyr Ser Thr Tyr Gly Lys Phe
            100                 105                 110

Leu Ala Asp Gly Gly Cys Ser Gly Gly Ala Tyr Asp Ile Ile Ile Cys
        115                 120                 125

Asp Glu Cys His Ser Ile Asp Ser Thr Ser Ile Leu Gly Ile Gly Thr
130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Val Ala Leu Ser Ser Thr Gly Glu Ile Pro Phe Tyr Gly Lys Ala
            180                 185                 190

Ile Pro Ile Glu Val Ile Lys Gly Gly Arg His Leu Ile Phe Cys His
        195                 200                 205

Ser Lys Lys Lys Cys Asp Glu Leu Ala Ala Lys Leu Ser Gly Phe Gly
    210                 215                 220

Ile Asn Ala Val Ala Tyr Tyr Arg Gly Leu Asp Val Ser Val Ile Pro
225                 230                 235                 240

Thr Ser Gly Asp Val Val Val Ala Thr Asp Ala Leu Met Thr Gly
                245                 250                 255

Phe Thr Gly Asp Phe Asp Ser Val Ile Asp Cys Asn Thr Cys Val Thr
            260                 265                 270

Gln Thr Val Asp Phe Ser
        275
```

```
<210> SEQ ID NO 179
<211> LENGTH: 450
<212> TYPE: PRT
<213> ORGANISM: hepatitis C virus

<400> SEQUENCE: 179

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
            195                 200                 205

Asn Ser Ser Val Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg His His Trp Thr Thr Gln Asp Cys
290                 295                 300

Asn Cys Ser Ile Tyr Pro Gly His Ile Thr Gly His Arg Met Ala Trp
305                 310                 315                 320

Asn Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Lys Tyr Phe Ser Met Val Gly Asn Trp
            355                 360                 365

Ala Lys Val Leu Val Val Leu Leu Leu Phe Ala Gly Val Asp Ala Glu
```

```
              370                 375                 380
Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
                435                 440                 445

Ser Ser
    450

<210> SEQ ID NO 180
<211> LENGTH: 450
<212> TYPE: PRT
<213> ORGANISM: hepatitis C virus

<400> SEQUENCE: 180

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
            50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Thr Gly Leu Tyr His Val Thr Asn Asp Cys Pro
            195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
            275                 280                 285
```

```
Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser
    450

<210> SEQ ID NO 181
<211> LENGTH: 450
<212> TYPE: PRT
<213> ORGANISM: hepatitis C virus

<400> SEQUENCE: 181

Met Ser Thr Ile Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Val Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205
```

-continued

```
Asn Ser Ser Ile Val Tyr Glu Ala His Asp Ala Ile Leu His Thr Pro
    210                 215                 220
Gly Cys Val Pro Cys Val Arg Glu Gly Asn Val Ser Arg Cys Trp Val
225                 230                 235                 240
Ala Met Thr Pro Thr Val Ala Thr Arg Asp Gly Lys Leu Pro Ala Thr
                245                 250                 255
Gln Leu Arg Arg His Ile Asp Leu Leu Val Gly Ser Ala Thr Leu Cys
            260                 265                 270
Ser Ala Leu Tyr Val Gly Asp Leu Cys Gly Ser Val Phe Leu Ile Gly
        275                 280                 285
Gln Leu Phe Thr Phe Ser Pro Arg Arg His Trp Thr Thr Gln Gly Cys
    290                 295                 300
Asn Cys Ser Ile Tyr Pro Gly His Ile Thr Gly His Arg Met Ala Trp
305                 310                 315                 320
Asp Met Met Met Asn Trp Ser Pro Thr Ala Ala Leu Val Met Ala Gln
                325                 330                 335
Leu Leu Arg Ile Pro Gln Ala Ile Leu Asp Met Ile Ala Gly Ala His
            340                 345                 350
Trp Gly Val Leu Ala Gly Ile Ala Tyr Phe Ser Met Val Gly Asn Trp
        355                 360                 365
Ala Lys Val Leu Val Val Leu Leu Leu Phe Ala Gly Val Asp Ala Glu
    370                 375                 380
Thr Ile Val Ser Gly Gly Gln Ala Ala Arg Ala Met Ser Gly Leu Val
385                 390                 395                 400
Ser Leu Phe Thr Pro Gly Ala Lys Gln Asn Ile Gln Leu Ile Asn Thr
                405                 410                 415
Asn Gly Ser Trp His Ile Asn Ser Thr Ala Leu Asn Cys Asn Glu Ser
            420                 425                 430
Leu Asn Thr Gly Trp Leu Ala Gly Leu Ile Tyr Gln His Lys Phe Asn
        435                 440                 445
Ser Ser
    450

<210> SEQ ID NO 182
<211> LENGTH: 181
<212> TYPE: PRT
<213> ORGANISM: hepatitis C virus

<400> SEQUENCE: 182

Thr Cys Gly Phe Ala Asp Leu Met Gly Tyr Ile Pro Leu Val Gly Ala
1               5                   10                  15
Pro Leu Gly Gly Ala Ala Arg Ala Leu Ala His Gly Val Arg Val Leu
                20                  25                  30
Glu Asp Gly Val Asn Tyr Ala Thr Gly Asn Leu Pro Gly Cys Ser Phe
            35                  40                  45
Ser Ile Phe Leu Leu Ala Leu Leu Ser Cys Leu Thr Val Pro Ala Ser
        50                  55                  60
Ala Tyr Gln Val Arg Asn Ser Ser Gly Leu Tyr His Val Thr Asn Asp
65                  70                  75                  80
Cys Pro Asn Ser Ser Ile Val Tyr Glu Ala Ala Asp Ala Ile Leu His
                85                  90                  95
Thr Pro Gly Cys Val Pro Cys His Arg Glu Gly Val Ala Ser Arg Cys
            100                 105                 110
Trp Val Ala Met Thr Pro Thr Val Ala Thr Arg Asp Gly Lys Leu Thr
```

```
                115                 120                 125
Ala Thr Gln Leu Arg Arg His Ile Asp Leu Leu Val Gly Ser Ala Thr
    130                 135                 140

Leu Cys Ser Ala Leu Tyr Val Gly Asp Leu Cys Gly Ser Val Phe Leu
145                 150                 155                 160

Val Gly Gln Leu Phe Thr Phe Ser Pro Arg Arg His Trp Thr Thr Gln
                165                 170                 175

Gly Cys Asn Cys Ser
            180

<210> SEQ ID NO 183
<211> LENGTH: 192
<212> TYPE: PRT
<213> ORGANISM: hepatitis C virus

<400> SEQUENCE: 183

Thr Cys Gly Phe Ala Asp Leu Met Gly Tyr Ile Pro Leu Val Gly Ala
1               5                   10                  15

Pro Leu Gly Gly Ala Ala Arg Ala Leu Ala His Gly Val Arg Val Leu
                20                  25                  30

Glu Asp Gly Val Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
    50                  55                  60

Ala His Gln Val Arg Asn Ser Thr Gly Leu Tyr His Val Thr Asn Asp
65                  70                  75                  80

Cys Pro Asn Ser Ser Ile Val Tyr Glu Ala Ala Asp Ala Ile Leu His
                85                  90                  95

Thr Pro Gly Cys Val Pro Cys His Arg Glu Gly Val Ala Ser Arg Cys
            100                 105                 110

Trp Val Val Met Thr Pro Thr Val Ala Thr Arg Asp Gly Lys Leu Thr
    115                 120                 125

Ala Thr Gln Leu Arg Arg His Ile Asp Leu Leu Val Gly Ser Ala Thr
    130                 135                 140

Leu Cys Ser Ala Leu Tyr Val Gly Asp Leu Cys Gly Ser Val Phe Leu
145                 150                 155                 160

Val Gly Gln Leu Phe Thr Phe Ser Pro Arg Arg His Trp Thr Thr Gln
                165                 170                 175

Gly Cys Asn Cys Ser Ile Tyr Pro Gly His Ile Thr Gly His Arg Met
            180                 185                 190

<210> SEQ ID NO 184
<211> LENGTH: 191
<212> TYPE: PRT
<213> ORGANISM: hepatitis C virus

<400> SEQUENCE: 184

Gly Phe Ala Asp Leu Met Gly Tyr Ile Pro Leu Val Gly Ala Pro Leu
1               5                   10                  15

Gly Gly Arg Ala Arg Ala Leu Ala His Gly Val Arg Val Leu Glu Asp
                20                  25                  30

Gly Val Asn Tyr Ala Thr Gly Asn Leu Pro Gly Cys Ser Phe Ser Ile
            35                  40                  45

Phe Leu Leu Ala Leu Leu Ser Cys Leu Thr Val Pro Ala Ser Ala Tyr
    50                  55                  60

Gln Val Arg Asn Ser Thr Gly Leu Tyr His Val Thr Asn Asp Cys Pro
```

-continued

```
65                  70                  75                  80
Asn Ser Ser Ile Val Tyr Glu Ala Ala Asp Ala Ile Leu His Ala Pro
                85                  90                  95
Gly Cys Val Pro Cys Val Arg Asp Gly Val Ala Ser Arg Cys Trp Val
            100                 105                 110
Val Met Thr Pro Thr Val Ala Lys Arg Asp Gly Lys Leu Thr Ala Thr
            115                 120                 125
Gln Leu Arg Arg His Ile Asp Leu Leu Val Gly Ser Ala Thr Leu Cys
        130                 135                 140
Ser Ala Leu Tyr Val Gly Asp Leu Cys Gly Ile Val Phe Leu Val Gly
145                 150                 155                 160
Gln Leu Phe Thr Phe Ser Pro Arg Arg His Trp Thr Thr Gln Asp Cys
                165                 170                 175
Asn Cys Ser Ile Tyr Pro Gly His Ile Thr Gly His Arg Met Ala
                180                 185                 190

<210> SEQ ID NO 185
<211> LENGTH: 191
<212> TYPE: PRT
<213> ORGANISM: hepatitis C virus

<400> SEQUENCE: 185

Gly Phe Ala Asp Leu Met Gly Tyr Ile Pro Leu Val Gly Ala Pro Leu
1               5                   10                  15
Gly Gly Ala Ala Arg Ala Leu Ala His Gly Val Arg Val Leu Glu Asp
                20                  25                  30
Gly Val Asn Tyr Ala Thr Gly Asn Leu Pro Gly Cys Ser Phe Ser Ile
            35                  40                  45
Phe Leu Leu Ala Leu Leu Ser Cys Leu Thr Val Pro Ala Ser Ala Tyr
        50                  55                  60
Gln Val Arg Asn Ser Ser Gly Ile Tyr His Val Thr Asn Asp Cys Pro
65                  70                  75                  80
Asn Ser Ser Ile Val Tyr Glu Thr Ala Asp Thr Ile Leu His Ser Pro
                85                  90                  95
Gly Cys Val Pro Cys Val Arg Glu Gly Asn Ala Lys Arg Cys Trp Pro
            100                 105                 110
Val Ala Thr Pro Thr Val Ala Thr Arg Asp Asn Lys Leu Pro Ala Thr
            115                 120                 125
Gln Leu Arg Arg His Ile Asp Leu Leu Val Gly Ser Ala Thr Leu Cys
        130                 135                 140
Ser Ala Leu Tyr Val Gly Asp Leu Cys Gly Ser Val Phe Leu Val Gly
145                 150                 155                 160
Gln Leu Phe Thr Phe Ser Pro Arg Arg His Trp Thr Thr Gln Asp Cys
                165                 170                 175
Asn Cys Ser Ile Tyr Pro Gly His Ile Thr Gly His Arg Met Ala
                180                 185                 190

<210> SEQ ID NO 186
<211> LENGTH: 192
<212> TYPE: PRT
<213> ORGANISM: hepatitis C virus

<400> SEQUENCE: 186

Thr Cys Gly Phe Ala Asp Leu Met Gly Tyr Ile Pro Leu Val Gly Ala
1               5                   10                  15
Pro Leu Gly Gly Ala Ala Arg Ala Leu Ala His Gly Val Arg Val Leu
```

```
                    20                  25                  30
Glu Asp Gly Val Asn Tyr Ala Thr Gly Asn Leu Pro Gly Cys Ser Phe
             35                  40                  45

Ser Leu Phe Leu Leu Ala Leu Leu Ser Cys Leu Thr Val Pro Ala Ser
 50                  55                  60

Ala Tyr Gln Val Arg Asn Ser Thr Gly Leu Tyr His Val Thr Asn Asp
 65                  70                  75                  80

Cys Pro Asn Ser Ser Ile Val Tyr Glu Ala Asp Ala Ile Leu His
                 85                  90                  95

Ala Pro Gly Cys Val Pro Cys Val Arg Glu Gly Asn Ala Ser Arg Cys
                100                 105                 110

Trp Val Ala Met Thr Pro Thr Val Ala Thr Arg Asp Arg Lys Leu Thr
                115                 120                 125

Ala Thr Gln Leu Arg Arg His Ile Asp Leu Leu Val Gly Ser Ala Thr
                130                 135                 140

Leu Cys Ser Ala Leu Tyr Val Gly Asp Leu Cys Gly Ile Val Phe Leu
145                 150                 155                 160

Val Gly Gln Leu Phe Thr Phe Ser Pro Arg Arg His Trp Thr Thr Gln
                165                 170                 175

Gly Cys Asn Cys Ser Ile Tyr Pro Gly His Ile Thr Gly His Arg Met
                180                 185                 190

<210> SEQ ID NO 187
<211> LENGTH: 450
<212> TYPE: PRT
<213> ORGANISM: hepatitis C virus

<400> SEQUENCE: 187

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
                130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Ile Tyr His Val Thr Asn Asp Cys Ser
                195                 200                 205
```

-continued

```
Asn Ser Ser Ile Val Tyr Glu Ala Ala Asp Met Ile Met His Thr Pro
        210                 215                 220

Gly Cys Val Pro Cys Val Arg Glu Ser Asn Phe Ser Arg Cys Trp Val
225                 230                 235                 240

Ala Leu Thr Pro Thr Leu Ala Ala Arg Asn Ser Ser Ile Pro Thr Thr
                    245                 250                 255

Thr Ile Arg Arg His Val Asp Leu Leu Val Gly Ala Ala Ala Leu Cys
                260                 265                 270

Ser Ala Met Tyr Val Gly Asp Leu Cys Gly Ser Val Phe Leu Val Ser
            275                 280                 285

Gln Leu Phe Thr Phe Ser Pro Arg Arg Tyr Glu Thr Val Gln Asp Cys
        290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                    325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly His
        370                 375                 380

Thr His Val Thr Gly Gly Arg Val Ala Ser Ser Thr Gln Ser Leu Val
385                 390                 395                 400

Ser Trp Leu Ser Gln Gly Pro Ser Gln Lys Ile Gln Leu Val Asn Thr
                    405                 410                 415

Asn Gly Ser Trp His Ile Asn Arg Thr Ala Leu Asn Cys Asn Asp Ser
                420                 425                 430

Leu Gln Thr Gly Phe Ile Ala Ala Leu Phe Tyr Ala His Arg Phe Asn
            435                 440                 445

Ala Ser
    450
```

<210> SEQ ID NO 188
<211> LENGTH: 450
<212> TYPE: PRT
<213> ORGANISM: hepatitis C virus

<400> SEQUENCE: 188

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Trp Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                    85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125
```

```
Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Ile Tyr His Val Thr Asn Asp Cys Ser
                195                 200                 205

Asn Ser Ser Ile Val Tyr Glu Ala Ala Asp Met Ile Met His Thr Pro
    210                 215                 220

Gly Cys Val Pro Cys Val Arg Glu Asp Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Ala Phe Cys
                260                 265                 270

Ser Ala Met Tyr Val Gly Asp Leu Cys Gly Ser Val Phe Leu Val Ser
                275                 280                 285

Gln Leu Phe Thr Phe Ser Pro Arg Arg His Glu Thr Val Gln Asp Cys
    290                 295                 300

Asn Cys Ser Ile Tyr Pro Gly His Leu Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Val Gly Asn Trp
                355                 360                 365

Ala Lys Val Leu Ile Val Ala Leu Leu Phe Ala Gly Val Asp Gly Glu
    370                 375                 380

Thr Tyr Thr Ser Gly Gly Ala Ala Ser His Thr Thr Ser Thr Leu Ala
385                 390                 395                 400

Ser Leu Phe Ser Pro Gly Ala Ser Gln Arg Ile Gln Leu Val Asn Thr
                405                 410                 415

Asn Gly Ser Trp His Ile Asn Arg Thr Ala Leu Asn Cys Asn Asp Ser
                420                 425                 430

Leu His Thr Gly Phe Leu Ala Ala Leu Phe Tyr Thr His Arg Phe Asn
    435                 440                 445

Ser Ser
    450

<210> SEQ ID NO 189
<211> LENGTH: 450
<212> TYPE: PRT
<213> ORGANISM: hepatitis C virus

<400> SEQUENCE: 189

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
```

-continued

```
            35                  40                  45
Thr Arg Lys Thr Ser Glu Arg Ser Gln Pro Arg Gly Arg Arg Gln Pro
            50                  55                  60
Ile Pro Lys Ala Arg Gln Pro Glu Gly Arg Ala Trp Ala Gln Pro Gly
 65                  70                  75                  80
Tyr Pro Trp Pro Leu Tyr Gly Asn Glu Gly Leu Gly Trp Ala Gly Trp
                 85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
            130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Ile Pro Ala Ser Ala Tyr
            180                 185                 190
Glu Val Arg Asn Val Ser Gly Ile Tyr His Val Thr Asn Asp Cys Ser
            195                 200                 205
Asn Ser Ser Ile Val Tyr Glu Ala Ala Asp Val Ile Met His Thr Pro
210                 215                 220
Gly Cys Val Pro Cys Val Arg Glu Gly Asn Ser Ser Arg Cys Trp Val
225                 230                 235                 240
Ala Leu Thr Pro Thr Leu Ala Ala Arg Asp Ala Ser Val Pro Thr Thr
            245                 250                 255
Thr Ile Arg Arg His Val Asp Leu Leu Val Gly Thr Ala Ala Phe Cys
            260                 265                 270
Ser Ala Met Tyr Val Gly Asp Leu Cys Gly Ser Ile Phe Leu Val Ser
            275                 280                 285
Gln Leu Phe Thr Phe Ser Pro Arg Arg His Glu Thr Val Gln Asp Cys
            290                 295                 300
Asn Cys Ser Ile Tyr Pro Gly His Val Ser Gly His Arg Met Ala Trp
305                 310                 315                 320
Asp Met Met Met Asn Trp Ser Pro Thr Thr Ala Leu Val Val Ser Gln
                325                 330                 335
Leu Leu Arg Ile Pro Gln Ala Val Val Asp Met Val Ala Gly Ala His
            340                 345                 350
Trp Gly Val Leu Ala Gly Leu Ala Tyr Tyr Ser Met Val Gly Asn Trp
            355                 360                 365
Ala Lys Val Leu Ile Val Ala Leu Leu Phe Ala Gly Val Asp Gly Ala
            370                 375                 380
Thr Tyr Thr Ser Gly Gly Val Ala Gly Arg Thr Thr Ser Gly Phe Thr
385                 390                 395                 400
Ser Leu Phe Ser Ser Gly Ala Ser Gln Lys Ile Gln Leu Val Asn Thr
                405                 410                 415
Asn Gly Ser Trp His Ile Asn Arg Thr Ala Leu Asn Cys Asn Asp Ser
                420                 425                 430
Leu His Thr Gly Phe Leu Ala Ala Leu Phe Tyr Thr His Lys Phe Asn
            435                 440                 445
Ser Ser
450
```

```
<210> SEQ ID NO 190
<211> LENGTH: 450
<212> TYPE: PRT
<213> ORGANISM: hepatitis C virus

<400> SEQUENCE: 190

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Phe Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val Arg Asn Val Ser Gly Ile Tyr His Val Thr Asn Asp Cys Ser
            195                 200                 205

Asn Ser Ser Ile Val Tyr Glu Ala Ala Asp Leu Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ala Thr Ile Pro Thr Ala
                245                 250                 255

Thr Val Arg Arg His Val Asp Leu Leu Val Gly Ala Ala Ala Phe Ser
            260                 265                 270

Ser Ala Met Tyr Val Gly Asp Leu Cys Gly Ser Val Phe Leu Val Ser
            275                 280                 285

Gln Leu Phe Thr Phe Ser Pro Arg Arg Tyr Glu Thr Ile Gln Asp Cys
        290                 295                 300

Asn Cys Ser Ile Tyr Pro Gly His Val Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Met Asp Met Val Val Gly Ala His
            340                 345                 350

Trp Gly Val Leu Ala Gly Leu Ala Tyr Tyr Ala Met Val Gly Asn Trp
        355                 360                 365

Ala Lys Val Leu Ile Val Met Leu Leu Phe Ala Gly Val Asp Gly Asp
```

```
                    370                 375                 380
Thr Tyr Ala Ser Gly Gly Ala Gln Gly Arg Ser Thr Leu Gly Phe Thr
385                 390                 395                 400

Ser Leu Phe Thr Pro Gly Ala Ser Gln Lys Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Thr His Arg Phe Asn
                435                 440                 445

Ala Ser
    450

<210> SEQ ID NO 191
<211> LENGTH: 450
<212> TYPE: PRT
<213> ORGANISM: hepatitis C virus

<400> SEQUENCE: 191

Met Ser Thr Asn Pro Lys Pro Gln Arg Lys Thr Lys Arg Asn Thr Tyr
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Thr Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Gln Val Arg Asn Ala Ser Gly Leu Tyr His Val Thr Asn Asp Cys Ser
                195                 200                 205

Asn Ser Ser Ile Val Tyr Glu Ala Ala Gly Met Ile Met His Thr Pro
210                 215                 220

Gly Cys Val Pro Cys Val Arg Glu Asn Asn Ala Ser Arg Cys Trp Val
225                 230                 235                 240

Ala Leu Thr Pro Thr Leu Ala Ala Arg Asn Thr Ser Ile Pro Thr Thr
                245                 250                 255

Thr Ile Arg Arg His Val Asp Leu Leu Val Gly Ala Ala Ala Phe Cys
                260                 265                 270

Ser Ala Met Tyr Val Gly Asp Leu Cys Gly Ser Val Phe Leu Val Ser
                275                 280                 285
```

```
Gln Leu Phe Thr Phe Ser Pro Arg Arg Tyr Glu Thr Val Gln Asp Cys
        290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                    325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly Val
        370                 375                 380

Thr Tyr Thr Thr Gly Gly Ser Gln Ala Arg His Thr Gln Ser Val Thr
385                 390                 395                 400

Ser Phe Phe Thr Gln Gly Pro Ala Gln Arg Ile Gln Leu Ile Asn Thr
                405                 410                 415

Asn Gly Ser Trp His Ile Asn Arg Thr Ala Leu Asn Cys Asn Glu Ser
                420                 425                 430

Leu Asn Thr Gly Phe Phe Ala Ala Leu Phe Tyr Ala His Lys Phe Asn
            435                 440                 445

Ser Ser
    450

<210> SEQ ID NO 192
<211> LENGTH: 450
<212> TYPE: PRT
<213> ORGANISM: hepatitis C virus

<400> SEQUENCE: 192

Met Ser Thr Asn Pro Lys Pro Gln Arg Lys Thr Lys Arg Asn Thr Tyr
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Thr Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Gln Val Arg Asn Arg Ser Gly Leu Tyr His Val Thr Asn Asp Cys Ser
        195                 200                 205
```

-continued

```
Asn Ser Ser Ile Val Tyr Glu Ala Ala Gly Met Ile Met His Thr Pro
    210                 215                 220
Gly Cys Val Pro Cys Val Arg Glu Asn Val Ser Arg Cys Trp Val
225                 230                 235                 240
Ala Leu Thr Pro Thr Leu Ala Ala Arg Asn Thr Ser Ile Pro Thr Thr
                245                 250                 255
Thr Ile Arg Arg His Val Asp Leu Leu Val Gly Ala Ala Phe Cys
            260                 265                 270
Ser Ala Met Tyr Val Gly Asp Leu Cys Gly Ser Val Phe Leu Val Ser
            275                 280                 285
Gln Leu Phe Thr Phe Ser Pro Arg Arg Tyr Glu Thr Val Gln Asp Cys
    290                 295                 300
Asn Cys Ser Ile Tyr Pro Gly His Val Ser Gly His Arg Met Ala Trp
305                 310                 315                 320
Asp Met Met Met Asn Trp Ser Pro Thr Thr Ala Leu Val Val Ser Gln
                325                 330                 335
Leu Leu Arg Ile Pro Gln Ala Val Val Asp Met Val Ala Gly Ala His
            340                 345                 350
Trp Gly Val Leu Ala Gly Leu Ala Tyr Tyr Ser Met Val Gly Asn Trp
            355                 360                 365
Ala Lys Val Leu Ile Val Met Leu Leu Phe Ala Gly Val Asp Gly Val
    370                 375                 380
Thr Tyr Thr Thr Gly Gly Ser Gln Ala Arg His Thr Gln Gly Val Ala
385                 390                 395                 400
Ser Phe Phe Thr Pro Gly Pro Ala Gln Lys Ile Gln Leu Ile Asn Thr
                405                 410                 415
Asn Gly Ser Trp His Ile Asn Arg Thr Ala Leu Asn Cys Asn Glu Ser
            420                 425                 430
Leu Asn Thr Gly Phe Phe Ala Ala Leu Phe Tyr Ala His Lys Phe Asn
            435                 440                 445
Ser Ser
    450

<210> SEQ ID NO 193
<211> LENGTH: 450
<212> TYPE: PRT
<213> ORGANISM: hepatitis C virus

<400> SEQUENCE: 193

Met Ser Thr Asn Pro Lys Pro Gln Arg Lys Thr Lys Arg Asn Thr Asn
1               5                   10                  15
Arg Arg Pro Gln Asp Val Lys Phe Pro Gly Gly Gly Gln Ile Val Gly
                20                  25                  30
Gly Val Tyr Leu Leu Pro Arg Arg Gly Pro Arg Leu Gly Val Arg Ala
            35                  40                  45
Pro Arg Lys Thr Ser Glu Arg Ser Gln Pro Arg Gly Arg Arg Gln Pro
    50                  55                  60
Ile Pro Lys Ala Arg Arg Pro Glu Gly Arg Thr Trp Ala Gln Pro Gly
65                  70                  75                  80
Tyr Pro Trp Pro Leu Tyr Gly Asn Glu Gly Leu Gly Trp Ala Gly Trp
                85                  90                  95
Leu Leu Ser Pro Arg Gly Ser Arg Pro Ser Trp Gly Pro Thr Asp Pro
            100                 105                 110
Arg Arg Arg Ser Arg Asn Leu Gly Lys Val Ile Asp Thr Leu Thr Cys
```

```
                 115                 120                 125
Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val His Asn Val Ser Gly Ile Tyr His Val Thr Asn Asp Cys Ser
                195                 200                 205

Asn Ala Ser Ile Val Tyr Glu Ala Ala Asp Leu Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Val Thr Ile Pro Thr Thr
                245                 250                 255

Thr Ile Arg Arg His Val Asp Leu Leu Val Gly Ala Ala Ala Phe Cys
                260                 265                 270

Ser Ala Met Tyr Val Gly Asp Leu Cys Gly Ser Val Phe Leu Val Ser
            275                 280                 285

Gln Leu Phe Thr Phe Ser Pro Arg Arg His Val Thr Leu Gln Asp Cys
290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Ala Gly Asn Trp
            355                 360                 365

Ala Lys Val Leu Ile Val Met Leu Leu Phe Ala Gly Val Asp Gly Asp
370                 375                 380

Thr His Val Thr Gly Gly Ala Gln Ala Lys Thr Thr Asn Arg Leu Val
385                 390                 395                 400

Ser Met Phe Ala Ser Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Thr His Ser Phe Asn
            435                 440                 445

Ser Ser
    450

<210> SEQ ID NO 194
<211> LENGTH: 450
<212> TYPE: PRT
<213> ORGANISM: hepatitis C virus

<400> SEQUENCE: 194

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30
```

-continued

Gly Val Tyr Leu Leu Pro Arg Arg Gly Pro Arg Leu Gly Val Arg Ala
         35                  40                  45
Thr Arg Lys Thr Ser Glu Arg Ser Gln Pro Arg Gly Arg Arg Gln Pro
     50                  55                  60
Ile Pro Lys Ala Arg Gln Pro Glu Gly Arg Ala Trp Ala Gln Pro Gly
 65              70                  75                  80
Tyr Pro Trp Pro Leu Tyr Gly Asn Glu Gly Leu Gly Trp Ala Gly Trp
                 85                  90                  95
Leu Leu Ser Pro Tyr Gly Ser Arg Pro Arg Trp Gly Pro Thr Asp Pro
                100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Leu
        130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Val Ser Thr Tyr
                180                 185                 190
Glu Val Arg Asn Val Ser Gly Val Tyr His Val Thr Asn Asp Cys Ser
            195                 200                 205
Asn Ser Ser Ile Val Tyr Glu Ala Ala Asp Met Ile Met His Thr Pro
210                 215                 220
Gly Cys Val Pro Cys Val Arg Glu Gly Asn Ser Ser Arg Cys Trp Val
225                 230                 235                 240
Ala Leu Thr Pro Thr Leu Ala Ala Arg Asn Ser Ser Ile Pro Thr Thr
                245                 250                 255
Thr Ile Arg Arg His Val Asp Leu Leu Val Gly Ala Ala Ala Leu Cys
                260                 265                 270
Ser Ala Met Tyr Val Gly Asp Leu Cys Gly Ser Val Phe Leu Val Ser
            275                 280                 285
Gln Leu Phe Thr Phe Ser Pro Arg Arg Tyr Glu Thr Val Gln Asp Cys
        290                 295                 300
Asn Cys Ser Leu Tyr Pro Gly His Val Ser Gly His Arg Met Ala Trp
305                 310                 315                 320
Asp Met Met Met Asn Trp Ser Pro Thr Thr Ala Leu Val Val Ser Gln
                325                 330                 335
Leu Leu Arg Ile Pro Gln Ala Val Val Asp Met Val Val Gly Ala His
                340                 345                 350
Trp Gly Val Leu Ala Gly Leu Ala Tyr Tyr Ser Met Val Gly Asn Trp
            355                 360                 365
Ala Lys Val Leu Ile Val Met Leu Leu Phe Ala Gly Val Asp Gly Thr
        370                 375                 380
Thr Tyr Val Ser Val Gly His Ala Ser Gln Thr Thr Arg Arg Val Ala
385                 390                 395                 400
Ser Phe Phe Ser Pro Gly Ser Ala Gln Lys Ile Gln Leu Val Asn Thr
                405                 410                 415
Asn Gly Ser Trp His Ile Asn Arg Thr Ala Leu Asn Cys Asn Glu Ser
            420                 425                 430
Ile Asn Thr Gly Phe Phe Ala Ala Leu Phe Tyr Val Lys Lys Phe Asn
        435                 440                 445
Ser Ser

-continued

```
                450

<210> SEQ ID NO 195
<211> LENGTH: 450
<212> TYPE: PRT
<213> ORGANISM: hepatitis C virus

<400> SEQUENCE: 195

Met Ser Thr Asn Gly Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
                35                  40                  45

Thr Arg Lys Thr Trp Glu Arg Ser Gln Pro Arg Gly Arg Arg Gln Pro
50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Val Ser Pro Arg Gly Ser Arg Pro Asn Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val His Asn Val Ser Gly Ile Tyr His Val Thr Asn Asp Cys Ser
        195                 200                 205

Asn Ser Ser Ile Val Tyr Glu Ala Ala Asp Met Ile Met His Thr Pro
210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Asn Ser Val Pro Thr Ala
                245                 250                 255

Thr Ile Arg Arg His Val Asp Leu Leu Val Gly Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg Tyr Glu Thr Val Gln Asp Cys
    290                 295                 300

Asn Cys Ser Ile Tyr Pro Gly His Val Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Gly Gly Ala His
            340                 345                 350

Trp Gly Val Leu Ala Gly Leu Ala Tyr Tyr Ser Met Val Gly Asn Trp
        355                 360                 365
```

```
Ala Lys Val Leu Ile Val Met Leu Leu Phe Ala Gly Val Asp Gly Ser
        370                 375                 380

Thr Ile Val Ser Gly Gly Thr Val Ala Arg Thr Thr His Ser Leu Ala
385                 390                 395                 400

Ser Leu Phe Thr Gln Gly Ala Ser Gln Lys Ile Gln Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Leu Ala Ser Leu Phe Tyr Ala His Arg Phe Asn
                435                 440                 445

Ala Ser
    450

<210> SEQ ID NO 196
<211> LENGTH: 258
<212> TYPE: PRT
<213> ORGANISM: hepatitis C virus
<220> FEATURE:
<221> NAME/KEY: MISC_FEATURE
<222> LOCATION: (71)..(71)
<223> OTHER INFORMATION: Xaa is any amino acid
<220> FEATURE:
<221> NAME/KEY: MISC_FEATURE
<222> LOCATION: (139)..(139)
<223> OTHER INFORMATION: Xaa is any amino acid
<220> FEATURE:
<221> NAME/KEY: MISC_FEATURE
<222> LOCATION: (200)..(200)
<223> OTHER INFORMATION: Xaa is any amino acid
<220> FEATURE:
<221> NAME/KEY: MISC_FEATURE
<222> LOCATION: (206)..(206)
<223> OTHER INFORMATION: Xaa is any amino acid
<220> FEATURE:
<221> NAME/KEY: MISC_FEATURE
<222> LOCATION: (218)..(218)
<223> OTHER INFORMATION: Xaa is any amino acid
<220> FEATURE:
<221> NAME/KEY: MISC_FEATURE
<222> LOCATION: (219)..(219)
<223> OTHER INFORMATION: Xaa is any amino acid
<220> FEATURE:
<221> NAME/KEY: MISC_FEATURE
<222> LOCATION: (228)..(228)
<223> OTHER INFORMATION: Xaa is any amino acid

<400> SEQUENCE: 196

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Ala Arg Arg Xaa Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Asn Trp Gly Pro Asp Gly Val
            100                 105                 110

Asn Tyr Ala Thr Gly Asn Leu Pro Gly Cys Ser Phe Ser Ile Phe Leu
        115                 120                 125

Leu Ala Leu Leu Ser Cys Leu Thr Val Pro Xaa Thr Ala His Glu Val
```

```
              130                 135                 140
Arg Asn Ala Ser Gly Val Tyr His Val Thr Asn Asp Cys Ser Asn Ser
145                 150                 155                 160

Ser Ile Ile Tyr Glu Met Asp Gly Met Ile Met His Tyr Pro Gly Cys
                165                 170                 175

Val Pro Cys Val Arg Glu Asp Asn His Leu Arg Cys Trp Met Ala Leu
            180                 185                 190

Thr Pro Thr Leu Ala Val Lys Xaa Ala Ser Val Pro Thr Xaa Ala Ile
        195                 200                 205

Arg Arg His Val Asp Leu Leu Val Gly Xaa Xaa Thr Phe Cys Ser Ala
    210                 215                 220

Met Tyr Val Xaa Asp Leu Cys Gly Ser Val Phe Leu Ala Gly Gln Leu
225                 230                 235                 240

Phe Thr Phe Ser Pro Arg Met His His Thr Thr Gln Glu Cys Asn Cys
                245                 250                 255

Ser Ile

<210> SEQ ID NO 197
<211> LENGTH: 258
<212> TYPE: PRT
<213> ORGANISM: hepatitis C virus
<220> FEATURE:
<221> NAME/KEY: MISC_FEATURE
<222> LOCATION: (75)..(75)
<223> OTHER INFORMATION: Xaa is any amino acid
<220> FEATURE:
<221> NAME/KEY: MISC_FEATURE
<222> LOCATION: (191)..(191)
<223> OTHER INFORMATION: Xaa is any amino acid

<400> SEQUENCE: 197

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Asp Arg Arg Gln Pro
        50                  55                  60

Ile Pro Lys Ala Arg Gln Ser Asp Gly Arg Xaa Trp Ala Gln Pro Gly
65                  70                  75                  80

His Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asp Gly Val
            100                 105                 110

Asn Tyr Ala Thr Gly Asn Leu Pro Gly Cys Ser Phe Ser Ile Phe Leu
        115                 120                 125

Leu Ala Phe Leu Ser Cys Leu Thr Val Pro Thr Thr Ala His Glu Val
130                 135                 140

Arg Asn Ala Ser Gly Val Tyr His Leu Thr Asn Asp Cys Ser Asn Ser
145                 150                 155                 160

Ser Ile Ile Tyr Glu Met Ser Gly Met Ile Leu His Ala Pro Gly Cys
                165                 170                 175

Val Pro Cys Val Arg Glu Asn Asn Ser Ser Arg Cys Trp Met Xaa Leu
            180                 185                 190

Thr Pro Thr Leu Ala Val Lys Asp Ala Asn Val Pro Thr Ala Ala Ile
        195                 200                 205
```

```
Arg Arg His Val Asp Leu Leu Val Gly Thr Ala Ala Phe Arg Ser Ala
    210                 215                 220

Met Tyr Val Gly Asp Leu Cys Gly Ser Val Phe Leu Val Gly Gln Leu
225                 230                 235                 240

Phe Thr Phe Ser Pro Arg Leu Tyr His Thr Thr Gln Glu Cys Asn Cys
                245                 250                 255

Ser Ile

<210> SEQ ID NO 198
<211> LENGTH: 74
<212> TYPE: PRT
<213> ORGANISM: hepatitis C virus

<400> SEQUENCE: 198

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Ala Arg Lys Thr Ser Glu Arg Ser Gln Pro Arg Gly Arg Arg Gln Pro
    50                  55                  60

Ile Pro Lys Glu Arg Arg Pro Glu Gly Arg
65                  70

<210> SEQ ID NO 199
<211> LENGTH: 319
<212> TYPE: PRT
<213> ORGANISM: hepatitis C virus
<220> FEATURE:
<221> NAME/KEY: MISC_FEATURE
<222> LOCATION: (152)..(152)
<223> OTHER INFORMATION: Xaa is any amino acid
<220> FEATURE:
<221> NAME/KEY: MISC_FEATURE
<222> LOCATION: (159)..(159)
<223> OTHER INFORMATION: Xaa is any amino acid
<220> FEATURE:
<221> NAME/KEY: MISC_FEATURE
<222> LOCATION: (163)..(163)
<223> OTHER INFORMATION: Xaa is any amino acid
<220> FEATURE:
<221> NAME/KEY: MISC_FEATURE
<222> LOCATION: (164)..(164)
<223> OTHER INFORMATION: Xaa is any amino acid
<220> FEATURE:
<221> NAME/KEY: MISC_FEATURE
<222> LOCATION: (165)..(165)
<223> OTHER INFORMATION: Xaa is any amino acid
<220> FEATURE:
<221> NAME/KEY: MISC_FEATURE
<222> LOCATION: (166)..(166)
<223> OTHER INFORMATION: Xaa is any amino acid
<220> FEATURE:
<221> NAME/KEY: MISC_FEATURE
<222> LOCATION: (167)..(167)
<223> OTHER INFORMATION: Xaa is any amino acid
<220> FEATURE:
<221> NAME/KEY: MISC_FEATURE
<222> LOCATION: (170)..(170)
<223> OTHER INFORMATION: Xaa is any amino acid
<220> FEATURE:
<221> NAME/KEY: MISC_FEATURE
<222> LOCATION: (174)..(174)
<223> OTHER INFORMATION: Xaa is any amino acid
<220> FEATURE:
<221> NAME/KEY: MISC_FEATURE
<222> LOCATION: (175)..(175)
```

-continued

```
<223> OTHER INFORMATION: Xaa is any amino acid
<220> FEATURE:
<221> NAME/KEY: MISC_FEATURE
<222> LOCATION: (180)..(180)
<223> OTHER INFORMATION: Xaa is any amino acid
<220> FEATURE:
<221> NAME/KEY: MISC_FEATURE
<222> LOCATION: (226)..(226)
<223> OTHER INFORMATION: Xaa is any amino acid
<220> FEATURE:
<221> NAME/KEY: MISC_FEATURE
<222> LOCATION: (317)..(317)
<223> OTHER INFORMATION: Xaa is any amino acid
<220> FEATURE:
<221> NAME/KEY: MISC_FEATURE
<222> LOCATION: (318)..(318)
<223> OTHER INFORMATION: Xaa is any amino acid
<220> FEATURE:
<221> NAME/KEY: MISC_FEATURE
<222> LOCATION: (319)..(319)
<223> OTHER INFORMATION: Xaa is any amino acid

<400> SEQUENCE: 199
```

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Ala Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ser Arg Thr Leu Xaa His Gly Val Arg Val Leu Xaa Gly
145                 150                 155                 160

Gly Val Xaa Xaa Xaa Xaa Asn Leu Xaa Gly Cys Ser Xaa Xaa Ile
                165                 170                 175

Phe Leu Leu Xaa Leu Leu Ser Cys Leu Thr Val Pro Thr Ser Ala Tyr
            180                 185                 190

Glu Val His Ser Thr Thr Asp Gly Tyr His Val Thr Asn Asp Cys Ser
        195                 200                 205

Asn Gly Ser Ile Val Tyr Glu Ala Lys Asp Ile Ile Leu His Thr Pro
    210                 215                 220

Gly Xaa Val Pro Cys Ile Arg Glu Gly Asn Ile Ser Arg Cys Trp Val
225                 230                 235                 240

Pro Leu Thr Pro Thr Leu Ala Ala Arg Ile Ala Asn Ala Pro Ile Asp
                245                 250                 255

Glu Val Arg His Val Asp Leu Leu Val Gly Ala Ala Val Phe Cys
            260                 265                 270

Ser Ala Met Tyr Ile Gly Asp Leu Cys Gly Gly Val Phe Leu Val Gly
    275                 280                 285

Gln Leu Phe Thr Phe Thr Ser Arg Arg His Trp Thr Val Gln Asp Cys

```
                    290                 295                 300
Asn Cys Ser Ile Tyr Ser Gly His Ile Thr Gly His Xaa Xaa Xaa
305                 310                 315

<210> SEQ ID NO 200
<211> LENGTH: 450
<212> TYPE: PRT
<213> ORGANISM: hepatitis C virus

<400> SEQUENCE: 200

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Pro Val Val Gly Ala Pro Leu
                130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
                180                 185                 190

Glu Val Lys Asn Ile Ser Thr Gly Tyr Met Val Thr Asn Asp Cys Thr
                195                 200                 205

Asn Asp Ser Ile Thr Trp Gln Leu Gln Ala Ala Val Leu His Val Pro
210                 215                 220

Gly Cys Val Pro Cys Glu Lys Val Gly Asn Thr Ser Arg Cys Trp Ile
225                 230                 235                 240

Pro Val Ser Pro Asn Val Ala Val Gln Gln Pro Gly Ala Leu Thr Gln
                245                 250                 255

Gly Leu Arg Thr His Ile Asp Met Val Val Met Ser Ala Thr Leu Cys
                260                 265                 270

Ser Ala Leu Tyr Val Gly Asp Leu Cys Gly Gly Val Met Leu Ala Ala
                275                 280                 285

Gln Met Phe Ile Val Ser Pro Gln His His Trp Phe Val Gln Asp Cys
                290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Gly Gly Ala His
                340                 345                 350
```

-continued

```
Trp Gly Val Met Phe Gly Leu Ala Tyr Phe Ser Met Gln Gly Ala Trp
            355                 360                 365

Ala Lys Val Val Val Ile Leu Leu Ala Ala Gly Val Asp Ala Gln
    370                 375                 380

Thr His Thr Val Gly Gly Ser Thr Ala His Asn Ala Arg Thr Leu Thr
385                 390                 395                 400

Gly Met Phe Ser Leu Gly Ala Arg Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Leu Ala Ser Leu Phe Tyr Thr His Ser Phe Asn
            435                 440                 445

Ser Ser
    450

<210> SEQ ID NO 201
<211> LENGTH: 450
<212> TYPE: PRT
<213> ORGANISM: hepatitis C virus

<400> SEQUENCE: 201

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Asn Ser Ile Thr Trp Gln Leu Thr Asp Ala Val Leu His Leu Pro
    210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270
```

-continued

```
Ser Ala Leu Tyr Val Gly Asp Val Cys Gly Ala Val Met Ile Leu Ser
            275                 280                 285

Gln Ala Phe Met Val Ser Pro Gln Arg His Asn Phe Thr Gln Glu Cys
        290                 295                 300

Asn Cys Ser Ile Tyr Gln Gly His Ile Thr Gly His Arg Met Ala Trp
305                 310                 315                 320

Asp Met Met Leu Ser Trp Ser Pro Thr Leu Thr Met Ile Leu Ala Tyr
                325                 330                 335

Ala Ala Arg Val Pro Glu Leu Val Leu Glu Ile Ile Phe Gly Gly His
            340                 345                 350

Trp Gly Val Val Phe Gly Leu Ala Tyr Phe Ser Met Gln Gly Ala Trp
        355                 360                 365

Ala Lys Val Ile Ala Ile Leu Leu Leu Val Ala Gly Val Asp Ala Thr
370                 375                 380

Thr Tyr Ser Ser Gly Gln Glu Ala Gly Arg Thr Val Ala Gly Phe Ala
385                 390                 395                 400

Gly Leu Phe Thr Thr Gly Ala Lys Gln Asn Leu Tyr Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Leu Ala Ser Leu Phe Tyr Thr His Lys Phe Asn
        435                 440                 445

Ser Ser
    450

<210> SEQ ID NO 202
<211> LENGTH: 319
<212> TYPE: PRT
<213> ORGANISM: hepatitis C virus
<220> FEATURE:
<221> NAME/KEY: MISC_FEATURE
<222> LOCATION: (319)..(319)
<223> OTHER INFORMATION: Xaa is any amino acid

<400> SEQUENCE: 202

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Thr Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160
```

```
Gly Ile Asn Tyr Ala Thr Gly Asn Leu Pro Gly Cys Ser Phe Ser Ile
                165                 170                 175

Phe Leu Ser Ala Leu Leu Ser Cys Ile Ser Val Pro Val Ser Ala Val
            180                 185                 190

Glu Val Lys Asn Thr Ser Thr Ser Tyr Met Val Thr Asn Asp Cys Ser
        195                 200                 205

Asn Ser Ser Ile Val Trp Gln Leu Glu Gly Ala Val Leu His Thr Pro
    210                 215                 220

Gly Cys Val Pro Cys Glu Gln Ile Gly Asn Ala Ser Arg Cys Trp Val
225                 230                 235                 240

Pro Val Ser Pro Asn Val Ala Ile Arg Gln Pro Gly Thr Leu Thr Lys
                245                 250                 255

Gly Leu Arg Ala His Val Asp Val Ile Val Met Ser Ala Thr Leu Cys
            260                 265                 270

Ser Ala Leu Tyr Val Gly Asp Val Cys Gly Ala Leu Met Ile Ala Ala
        275                 280                 285

Gln Ala Val Ile Ala Ser Pro Gln Arg His Thr Phe Val Gln Glu Cys
    290                 295                 300

Asn Cys Ser Ile Tyr Pro Gly His Ile Thr Gly His Arg Met Xaa
305                 310                 315

<210> SEQ ID NO 203
<211> LENGTH: 193
<212> TYPE: PRT
<213> ORGANISM: hepatitis C virus
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is any amino acid
<220> FEATURE:
<221> NAME/KEY: MISC_FEATURE
<222> LOCATION: (95)..(95)
<223> OTHER INFORMATION: Xaa is any amino acid
<220> FEATURE:
<221> NAME/KEY: MISC_FEATURE
<222> LOCATION: (119)..(119)
<223> OTHER INFORMATION: Xaa is any amino acid
<220> FEATURE:
<221> NAME/KEY: MISC_FEATURE
<222> LOCATION: (173)..(173)
<223> OTHER INFORMATION: Xaa is any amino acid
<220> FEATURE:
<221> NAME/KEY: MISC_FEATURE
<222> LOCATION: (193)..(193)
<223> OTHER INFORMATION: Xaa is any amino acid

<400> SEQUENCE: 203

Thr Cys Gly Phe Xaa Asp Leu Met Gly Tyr Ile Pro Val Val Gly Ala
1               5                   10                  15

Pro Xaa Gly Gly Val Ala Arg Ala Leu Ala His Gly Val Arg Val Leu
            20                  25                  30
```

-continued

```
Glu Asp Gly Ile Xaa Tyr Ala Thr Gly Asn Met Pro Gly Cys Ser Phe
             35                  40                  45

Ser Ile Phe Leu Leu Ala Leu Leu Ser Xaa Ile Ser Val Pro Val Ser
 50                  55                  60

Ala Xaa Glu Val Arg Asn Thr Ser Thr Leu Tyr Met Val Thr Asn Asp
 65                  70                  75                  80

Cys Ser Asn Ser Ser Ile Val Trp Gln Leu Glu Gly Ala Val Xaa His
                 85                  90                  95

Ile Pro Gly Cys Val Pro Cys Glu Trp Thr Asn Thr Thr Pro Arg Cys
                100                 105                 110

Trp Val Pro Val Ser Pro Xaa Val Ala Ile Arg Gln Pro Gly Ala Leu
                115                 120                 125

Thr Lys Gly Leu Arg Ala His Ile Asp Val Ile Val Met Ser Ala Thr
                130                 135                 140

Leu Cys Ser Ala Leu Tyr Val Gly Asp Val Cys Gly Ala Leu Met Ile
145                 150                 155                 160

Ala Ala Gln Ala Val Val Ala Ser Pro Gln Arg His Xaa Phe Val Gln
                165                 170                 175

Glu Cys Asn Cys Ser Ile Tyr Pro Gly His Ile Thr Gly His Arg Met
                180                 185                 190

Xaa
```

<210> SEQ ID NO 204
<211> LENGTH: 304
<212> TYPE: PRT
<213> ORGANISM: hepatitis C virus

<400> SEQUENCE: 204

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Asp Arg Arg Pro Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg His Arg Ser Arg Asn Leu Gly Lys Val Ile Asp Thr Leu Thr Cys
                115                 120                 125

Gly Phe Ala Asp Leu Met Gly Tyr Ile Pro Val Val Gly Ala Pro Val
                130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Gly Leu
                180                 185                 190

Gln Val Lys Asn Thr Ser Ser Ser Tyr Met Val Thr Asn Asp Cys Gln
                195                 200                 205
```

```
Asn Ser Ser Ile Val Trp Gln Leu Arg Asp Ala Val Leu His Val Pro
    210                 215                 220

Gly Cys Val Pro Cys Glu Glu Lys Gly Asn Ile Ser Arg Cys Trp Ile
225                 230                 235                 240

Pro Val Ser Pro Asn Ile Ala Val Ser Gln Pro Gly Ala Leu Thr Lys
                245                 250                 255

Gly Leu Arg Thr His Ile Asp Thr Ile Ile Ala Ser Ala Thr Phe Cys
            260                 265                 270

Ser Ala Leu Tyr Ile Gly Asp Leu Cys Gly Ala Val Met Val Gln Asp
            275                 280                 285

Cys Asn Cys Ser Ile Tyr Pro Gly His Ile Thr Gly His Arg Met Ala
    290                 295                 300
```

```
<210> SEQ ID NO 205
<211> LENGTH: 277
<212> TYPE: PRT
<213> ORGANISM: hepatitis C virus
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (136)..(136)
<223> OTHER INFORMATION: Xaa is any amino acid
<220> FEATURE:
<221> NAME/KEY: MISC_FEATURE
<222> LOCATION: (149)..(149)
<223> OTHER INFORMATION: Xaa is any amino acid
<220> FEATURE:
<221> NAME/KEY: MISC_FEATURE
<222> LOCATION: (175)..(175)
<223> OTHER INFORMATION: Xaa is any amino acid

<400> SEQUENCE: 205

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Asp Arg Xaa Ala Thr Gly Arg Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Leu Ala Xaa Gly
                100                 105                 110

Val Arg Val Leu Glu Asp Gly Ile Asn Tyr Xaa Thr Gly Asn Leu Pro
            115                 120                 125

Gly Cys Ser Phe Ser Ile Phe Xaa Leu Ala Leu Leu Ser Cys Val Thr
    130                 135                 140

Val Pro Val Ser Xaa Val Glu Val Lys Asn Thr Ser Gln Ala Tyr Met
```

```
                145                 150                 155                 160
Ala Thr Asn Asp Cys Ser Asn Ser Ile Val Trp Gln Leu Xaa Asp
                    165                 170                 175

Ala Val Leu His Val Pro Gly Cys Val Pro Cys Glu Asn Ser Ser Gly
            180                 185                 190

Arg Phe His Cys Trp Ile Pro Ile Ser Pro Asn Ile Ala Val Ser Lys
        195                 200                 205

Pro Gly Ala Leu Thr Lys Gly Leu Arg Ala Arg Ile Asp Ala Val Val
    210                 215                 220

Met Ser Ala Thr Leu Cys Ser Ala Leu Tyr Val Gly Asp Val Cys Gly
225                 230                 235                 240

Ala Val Met Ile Ala Ala Gln Ala Phe Ile Val Ala Pro Lys Arg His
                245                 250                 255

Tyr Phe Val Gln Glu Cys Asn Cys Ser Ile Tyr Pro Gly His Ile Thr
            260                 265                 270

Gly His Arg Met Ala
            275

<210> SEQ ID NO 206
<211> LENGTH: 319
<212> TYPE: PRT
<213> ORGANISM: hepatitis C virus
<220> FEATURE:
<221> NAME/KEY: MISC_FEATURE
<222> LOCATION: (131)..(131)
<223> OTHER INFORMATION: Xaa is any amino acid
<220> FEATURE:
<221> NAME/KEY: MISC_FEATURE
<222> LOCATION: (319)..(319)
<223> OTHER INFORMATION: Xaa is any amino acid

<400> SEQUENCE: 206

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Asp Arg Arg Ala Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Leu Gly Lys Val Ile Asp Thr Leu Thr Cys
        115                 120                 125

Gly Phe Xaa Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Ile
            180                 185                 190

Gln Val Lys Asn Asn Ser His Phe Tyr Met Ala Thr Asn Asp Cys Ala
```

```
                195                 200                 205
Asn Asp Ser Ile Val Trp Gln Leu Arg Asp Ala Val Leu His Val Pro
    210                 215                 220

Gly Cys Val Pro Cys Glu Arg Ser Gly Asn Arg Thr Phe Cys Trp Thr
225                 230                 235                 240

Ala Val Ser Pro Asn Val Ala Val Ser Arg Pro Gly Ala Leu Thr Arg
                245                 250                 255

Gly Leu Arg Ala His Ile Asp Thr Ile Val Met Ser Ala Thr Leu Cys
                260                 265                 270

Ser Ala Leu Tyr Ile Gly Asp Leu Cys Gly Ala Val Met Ile Ala Ala
                275                 280                 285

Gln Val Ala Val Ser Pro Gln Tyr His Thr Phe Val Gln Glu Cys
    290                 295                 300

Asn Cys Ser Ile Tyr Pro Gly His Ile Thr Gly His Arg Met Xaa
305                 310                 315

<210> SEQ ID NO 207
<211> LENGTH: 187
<212> TYPE: PRT
<213> ORGANISM: hepatitis C virus

<400> SEQUENCE: 207

Leu Met Gly Tyr Ile Pro Leu Val Gly Ala Pro Val Gly Gly Val Ala
1               5                   10                  15

Arg Ala Leu Ala His Gly Val Arg Ala Leu Glu Asp Gly Ile Asn Phe
            20                  25                  30

Ala Thr Gly Asn Leu Pro Gly Cys Ser Phe Ser Ile Phe Leu Leu Ala
        35                  40                  45

Leu Phe Ser Cys Leu Ile His Pro Ala Ala Ser Leu Glu Trp Arg Asn
50                  55                  60

Thr Ser Gly Leu Tyr Val Leu Thr Asn Asp Cys Ser Asn Ser Ser Ile
65                  70                  75                  80

Val Tyr Glu Ala Asp Asp Val Ile Leu His Thr Pro Gly Cys Val Pro
                85                  90                  95

Cys Val Gln Asp Gly Asn Thr Ser Ala Cys Trp Thr Pro Val Thr Pro
            100                 105                 110

Thr Val Ala Val Arg Tyr Val Gly Ala Thr Thr Ala Ser Ile Arg Arg
        115                 120                 125

His Val Asp Met Leu Val Gly Ala Ala Thr Met Cys Ser Ala Leu Tyr
    130                 135                 140

Val Gly Asp Met Cys Gly Ala Val Phe Leu Val Gly Gln Ala Phe Thr
145                 150                 155                 160

Phe Arg Pro Arg Arg His Gln Thr Val Gln Thr Cys Asn Cys Ser Leu
                165                 170                 175

Tyr Pro Gly His Leu Ser Gly His Arg Met Ala
            180                 185

<210> SEQ ID NO 208
<211> LENGTH: 187
<212> TYPE: PRT
<213> ORGANISM: hepatitis C virus

<400> SEQUENCE: 208

Leu Met Gly Tyr Ile Pro Leu Val Gly Ala Pro Val Gly Gly Val Ala
1               5                   10                  15

Arg Ala Leu Ala His Gly Val Arg Ala Leu Glu Asp Gly Ile Asn Phe
```

```
                   20                  25                  30

Ala Thr Gly Asn Leu Pro Gly Cys Ser Phe Ser Ile Phe Leu Leu Ala
            35                  40                  45

Leu Phe Ser Cys Leu Ile His Pro Ala Ala Gly Leu Glu Trp Arg Asn
 50                  55                  60

Thr Ser Gly Leu Tyr Val Leu Thr Asn Asp Cys Ser Asn Ser Ser Ile
 65                  70                  75                  80

Val Tyr Glu Ala Asp Asp Val Ile Leu His Ala Pro Gly Cys Val Pro
                85                  90                  95

Cys Val Gln Asp Gly Asn Thr Ser Thr Cys Trp Thr Pro Val Thr Pro
                100                 105                 110

Thr Val Ala Val Arg Tyr Val Gly Ala Thr Thr Ala Ser Ile Arg Ser
            115                 120                 125

His Val Asp Leu Leu Val Gly Ala Ala Thr Met Cys Ser Ala Leu Tyr
        130                 135                 140

Val Gly Asp Met Cys Gly Ala Val Phe Leu Val Gly Gln Ala Phe Thr
145                 150                 155                 160

Phe Arg Pro Arg Arg His Gln Thr Val Gln Thr Cys Asn Cys Ser Leu
                165                 170                 175

Tyr Pro Gly His Leu Ser Gly His Arg Met Ala
                180                 185

<210> SEQ ID NO 209
<211> LENGTH: 187
<212> TYPE: PRT
<213> ORGANISM: hepatitis C virus

<400> SEQUENCE: 209

Leu Met Gly Tyr Ile Pro Leu Val Gly Ala Pro Val Gly Gly Val Ala
 1               5                  10                  15

Arg Ala Leu Ala His Gly Val Arg Ala Leu Glu Asp Gly Ile Asn Phe
                20                  25                  30

Ala Thr Gly Asn Leu Pro Gly Cys Ser Phe Ser Ile Phe Leu Leu Ala
            35                  40                  45

Leu Phe Ser Cys Leu Ile His Pro Ala Ala Ser Leu Glu Trp Arg Asn
 50                  55                  60

Thr Ser Gly Leu Tyr Val Leu Thr Asn Asp Cys Ser Asn Ser Ser Ile
 65                  70                  75                  80

Val Tyr Glu Ala Asp Asp Val Ile Leu His Thr Pro Gly Ile Val Pro
                85                  90                  95

Cys Val Gln Asp Gly Asn Thr Ser Thr Cys Trp Thr Pro Val Thr Pro
                100                 105                 110

Thr Val Ala Val Lys Tyr Val Gly Ala Thr Thr Ala Ser Ile Arg Ser
            115                 120                 125

His Val Asp Leu Leu Val Gly Ala Ala Thr Met Cys Ser Ala Leu Tyr
        130                 135                 140

Val Gly Asp Met Cys Gly Ala Val Phe Leu Val Gly Gln Ala Phe Thr
145                 150                 155                 160

Phe Arg Pro Arg Arg His Gln Thr Val Gln Thr Cys Asn Cys Ser Leu
                165                 170                 175

Tyr Pro Gly His Leu Ser Gly His Arg Met Ala
                180                 185

<210> SEQ ID NO 210
<211> LENGTH: 193
```

-continued

```
<212> TYPE: PRT
<213> ORGANISM: hepatitis C virus

<400> SEQUENCE: 210

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Leu
            20                  25                  30

Glu Asp Gly Ile Asn Phe Ala Thr Gly Asn Leu Pro Gly Cys Ser Phe
        35                  40                  45

Ser Ile Phe Leu Leu Ala Leu Phe Ser Cys Leu Ile His Pro Ala Ala
    50                  55                  60

Ser Leu Glu Trp Arg Asn Thr Ser Gly Leu Tyr Val Leu Thr Asn Asp
65                  70                  75                  80

Cys Ser Asn Ser Ser Ile Val Tyr Glu Ala Asp Asp Val Ile Leu His
                85                  90                  95

Thr Pro Gly Cys Val Pro Cys Val Gln Asp Gly Asn Thr Ser Thr Cys
            100                 105                 110

Trp Thr Pro Val Thr Pro Thr Val Ala Val Arg Tyr Val Gly Ala Thr
        115                 120                 125

Thr Ala Ser Ile Arg Ser His Val Asp Leu Leu Val Gly Ala Ala Thr
    130                 135                 140

Met Cys Ser Ala Leu Tyr Val Gly Asp Met Cys Gly Ala Val Phe Leu
145                 150                 155                 160

Val Gly Gln Ala Phe Thr Phe Arg Pro Arg Arg His Gln Thr Val Gln
                165                 170                 175

Thr Cys Asn Cys Ser Leu Tyr Pro Gly His Leu Ser Gly His Arg Met
            180                 185                 190

Ala

<210> SEQ ID NO 211
<211> LENGTH: 319
<212> TYPE: PRT
<213> ORGANISM: hepatitis C virus

<400> SEQUENCE: 211

Met Ser Thr Leu Pro Lys Pro Gln Arg Gln Thr Lys Arg Asn Thr Leu
1               5                   10                  15

Arg Arg Pro Gln Asn Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Val Arg Lys Thr Ser Glu Arg Ser Gln Pro Arg Lys Gln Arg His Leu
    50                  55                  60

Ile Pro Lys Ala Arg Ser Arg Glu Gly Arg Ser Trp Ala Gln Pro Gly
65                  70                  75                  80

Tyr Pro Trp Pro Leu Tyr Gly Asn Lys Gly Cys Gly Leu Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Phe Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Gly Asp
```

```
                145                 150                 155                 160
Gly Val Asn Tyr Ala Thr Gly Asn Leu Pro Gly Cys Ser Phe Ser Ile
                    165                 170                 175

Phe Leu Leu Ala Leu Phe Ser Cys Leu Thr Cys Pro Ala Ser Gly Leu
                180                 185                 190

Glu Tyr Thr Asn Thr Ser Gly Leu Tyr Val Leu Thr Asn Asp Cys Ser
                    195                 200                 205

Asn Gly Ser Ile Val Tyr Glu Ala Glu Asp Val Ile Leu His Leu Pro
                210                 215                 220

Gly Cys Val Pro Cys Val Thr Thr Gly Asn Gln Ser Ser Cys Trp Thr
225                 230                 235                 240

Thr Val Ser Thr Thr Val Ala Val Arg Thr Leu Gly Val Thr Thr Ala
                    245                 250                 255

Ser Ile Arg Thr His Val Asp Met Leu Val Gly Ala Arg Gln Leu Cys
                260                 265                 270

Ser Ala Leu Tyr Val Gly Asp Ala Phe Gly Ala Val Phe Leu Val Gly
                275                 280                 285

Gln Ala Phe Thr Phe Arg Pro Arg Arg His Thr Thr Val Gln Thr Cys
    290                 295                 300

Asn Cys Ser Ile Tyr Pro Gly His Val Ser Gly His Arg Met Ala
305                 310                 315

<210> SEQ ID NO 212
<211> LENGTH: 193
<212> TYPE: PRT
<213> ORGANISM: hepatitis C virus

<400> SEQUENCE: 212

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
        50                  55                  60

Ala Glu His Tyr Arg Asn Ala Ser Gly Ile Tyr His Ile Thr Asn Asp
65                  70                  75                  80

Cys Pro Asn Ser Ser Val Val Tyr Glu Thr Asp His His Ile Leu His
                85                  90                  95

Leu Pro Gly Cys Val Pro Cys Val Arg Ala Gly Asn Val Ser Arg Cys
            100                 105                 110

Trp Thr Pro Val Thr Pro Thr Val Ala Val Ser Met Asp Ala Pro
        115                 120                 125

Leu Glu Ser Phe Arg Arg His Val Asp Leu Met Val Gly Ala Ala Thr
    130                 135                 140

Val Cys Ser Val Leu Tyr Val Gly Asp Leu Cys Gly Gly Ala Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
            180                 185                 190

Ala
```

-continued

```
<210> SEQ ID NO 213
<211> LENGTH: 193
<212> TYPE: PRT
<213> ORGANISM: hepatitis C virus

<400> SEQUENCE: 213

Thr Cys Gly Phe Ala Asp Leu Met Gly Tyr Ile Pro Leu Val Gly Ala
1               5                   10                  15

Pro Val Gly Gly Val Ala Arg Ala Leu Glu His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Ser Leu Leu Ala Leu Leu Ser Cys Leu Thr Val Pro Thr Ser
    50                  55                  60

Ala Val Asn Tyr Arg Asn Ala Ser Gly Val Tyr His Ile Thr Asn Asp
65                  70                  75                  80

Cys Pro Asn Ser Ser Ile Val Tyr Glu Ala Asp Tyr His Ile Leu His
                85                  90                  95

Leu Pro Gly Leu Val Pro Cys Val Arg Val Gly Asn Gln Ser Arg Cys
            100                 105                 110

Trp Val Ala Leu Thr Pro Thr Val Ala Pro Tyr Val Gly Ala Pro
        115                 120                 125

Leu Glu Ser Leu Arg Ser His Val Asp Leu Met Val Gly Ala Ala Thr
    130                 135                 140

Val Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
                165                 170                 175

Asp Cys Asn Cys Ser Ile Tyr Ala Gly His Val Thr Gly His Arg Met
            180                 185                 190

Ala

<210> SEQ ID NO 214
<211> LENGTH: 193
<212> TYPE: PRT
<213> ORGANISM: hepatitis C virus

<400> SEQUENCE: 214

Thr Cys Gly Phe Ala Asp Leu Met Gly Tyr Ile Pro Leu Val Gly Ala
1               5                   10                  15

Pro Val Gly Gly Val Ala Arg Ala Leu Glu His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Tyr Leu Leu Ala Leu Leu Ser Cys Leu Thr Val Pro Thr Ser
    50                  55                  60

Ala Ile His Tyr Arg Asn Ala Ser Gly Val Tyr His Val Thr Asn Asp
65                  70                  75                  80

Cys Pro Asn Ser Ser Ile Val Tyr Glu Ala Asp His His Ile Leu His
                85                  90                  95

Leu Pro Gly Leu Val Pro Cys Val Arg Val Gly Asn Gln Ser Arg Cys
            100                 105                 110

Trp Val Ala Leu Ser Pro Thr Val Ala Pro Tyr Ile Gly Ala Pro
        115                 120                 125

Val Glu Ser Phe Arg Arg His Val Asp Met Met Val Gly Ala Ala Thr
    130                 135                 140
```

-continued

Val Cys Ser Ala Leu Tyr Ile Gly Asp Leu Cys Gly Gly Val Phe Leu
145                 150                 155                 160

Val Gly Gln Met Phe Ser Phe Arg Pro Arg Arg His Trp Thr Thr Gln
                165                 170                 175

Asp Cys Asn Cys Ser Ile Tyr Ala Gly His Ile Thr Gly His Gly Met
            180                 185                 190

Ala

<210> SEQ ID NO 215
<211> LENGTH: 193
<212> TYPE: PRT
<213> ORGANISM: hepatitis C virus

<400> SEQUENCE: 215

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Thr Ser
        50                  55                  60

Ala Val Asn Tyr Arg Asn Ala Ser Gly Ile Tyr His Ile Thr Asn Asp
65                  70                  75                  80

Cys Pro Asn Ser Ser Ile Val Tyr Glu Thr Glu His His Ile Leu His
                85                  90                  95

Leu Pro Gly Leu Val Pro Cys Val Arg Val Gly Asn Gln Ser Arg Cys
                100                 105                 110

Trp Val Ala Leu Thr Pro Thr Val Ala Ala Pro Tyr Ile Gly Ala Pro
            115                 120                 125

Leu Glu Ser Leu Arg Ser His Val Asp Leu Met Val Gly Ala Ala Thr
        130                 135                 140

Ala Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
                165                 170                 175

Asp Cys Asn Cys Ser Ile Tyr Ala Gly His Val Thr Gly His Arg Met
            180                 185                 190

Ala

<210> SEQ ID NO 216
<211> LENGTH: 24
<212> TYPE: PRT
<213> ORGANISM: hepatitis C virus

<400> SEQUENCE: 216

Thr Cys Gly Phe Ala Asp Leu Met Gly Tyr Ile Pro Leu Val Gly Ala
1               5                   10                  15

Pro Val Gly Gly Val Ala Arg Ala
                20

<210> SEQ ID NO 217
<211> LENGTH: 319
<212> TYPE: PRT
<213> ORGANISM: hepatitis C virus

<400> SEQUENCE: 217

```
Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Leu Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Val Val Gly Ala Pro Val
        130                 135                 140

Gly Gly Val Ala Arg Ala Leu Ala His Gly Val Arg Leu Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Asn Tyr Arg Asn Ser Ser Gly Val Tyr His Val Thr Asn Asp Cys Pro
            195                 200                 205

Asn Ser Ser Ile Val Tyr Glu Thr Asp Tyr His Ile Leu His Leu Pro
210                 215                 220

Gly Cys Val Pro Cys Val Arg Glu Gly Asn Lys Ser Thr Cys Trp Val
225                 230                 235                 240

Ser Leu Thr Pro Thr Val Ala Ala Gln His Leu Asn Ala Pro Leu Glu
                245                 250                 255

Ser Leu Arg Arg His Val Asp Leu Met Val Gly Gly Ala Thr Leu Cys
            260                 265                 270

Ser Ala Leu Tyr Ile Gly Asp Val Cys Gly Val Phe Leu Val Gly
            275                 280                 285

Gln Leu Phe Thr Phe Gln Pro Arg Arg His Trp Thr Thr Gln Asp Cys
        290                 295                 300

Asn Cys Ser Ile Tyr Thr Gly His Ile Thr Gly His Arg Met Ala
305                 310                 315
```

<210> SEQ ID NO 218
<211> LENGTH: 319
<212> TYPE: PRT
<213> ORGANISM: hepatitis C virus
<220> FEATURE:
<221> NAME/KEY: MISC_FEATURE
<222> LOCATION: (102)..(102)
<223> OTHER INFORMATION: Xaa is any amino acid
<220> FEATURE:
<221> NAME/KEY: MISC_FEATURE
<222> LOCATION: (105)..(105)
<223> OTHER INFORMATION: Xaa is any amino acid
<220> FEATURE:
<221> NAME/KEY: MISC_FEATURE
<222> LOCATION: (114)..(114)
<223> OTHER INFORMATION: Xaa is any amino acid -continued

```
<400> SEQUENCE: 218

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Thr Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Xaa Ser Arg Xaa Ser Trp Gly Pro Asn Asp Pro
            100                 105                 110

Arg Xaa Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Val Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Thr Ser Ala Val
            180                 185                 190

Asn Tyr Arg Asn Ala Ser Gly Ile Tyr His Ile Thr Asn Asp Cys Pro
        195                 200                 205

Asn Ala Ser Ile Val Tyr Glu Thr Glu Asn His Ile Leu His Leu Pro
    210                 215                 220

Gly Cys Val Pro Cys Val Arg Thr Gly Asn Gln Ser Arg Cys Trp Val
225                 230                 235                 240

Ala Leu Thr Pro Thr Val Ala Ser Pro Tyr Ala Gly Ala Pro Leu Glu
                245                 250                 255

Pro Leu Arg Arg His Val Asp Leu Met Val Gly Ala Ala Thr Met Cys
            260                 265                 270

Ser Ala Leu Tyr Ile Gly Asp Leu Cys Gly Gly Leu Phe Leu Val Gly
        275                 280                 285

Gln Met Phe Thr Phe Gln Pro Arg Arg His Trp Thr Thr Gln Asp Cys
    290                 295                 300

Asn Cys Ser Ile Tyr Thr Gly His Ile Thr Gly His Arg Met Ala
305                 310                 315

<210> SEQ ID NO 219
<211> LENGTH: 319
<212> TYPE: PRT
<213> ORGANISM: hepatitis C virus

<400> SEQUENCE: 219

Met Ser Thr Asn Pro Lys Leu Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45
```

```
Thr Arg Lys Thr Ser Glu Arg Ser Gln Pro Arg Gly Arg Arg Gln Pro
     50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Val
            130                 135                 140

Gly Gly Val Ala Arg Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Gly Val
                180                 185                 190

Asn Tyr Arg Asn Ala Ser Gly Val Tyr His Ile Thr Asn Asp Cys Pro
            195                 200                 205

Asn Ala Ser Ile Val Tyr Glu Thr Asp Asn His Ile Leu His Leu Pro
210                 215                 220

Gly Cys Val Pro Cys Val Lys Thr Gly Asn Gln Ser Arg Cys Trp Val
225                 230                 235                 240

Ala Leu Thr Pro Thr Val Ala Ser Pro Tyr Val Gly Ala Pro Leu Glu
                245                 250                 255

Pro Leu Arg Arg His Val Asp Leu Met Val Gly Ala Ala Thr Val Cys
            260                 265                 270

Ser Ala Leu Tyr Val Gly Asp Leu Cys Gly Gly Leu Phe Leu Val Gly
            275                 280                 285

Gln Met Phe Thr Phe Gln Pro Arg Arg His Trp Thr Thr Gln Asp Cys
    290                 295                 300

Asn Cys Ser Ile Tyr Ala Gly His Ile Thr Gly His Arg Met Ala
305                 310                 315

<210> SEQ ID NO 220
<211> LENGTH: 193
<212> TYPE: PRT
<213> ORGANISM: hepatitis C virus

<400> SEQUENCE: 220

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Ala Ser
    50                  55                  60

Ala Val His Tyr His Asn Thr Ser Gly Ile Tyr His Leu Thr Asn Asp
65                  70                  75                  80

Cys Pro Asn Ser Ser Ile Val Phe Glu Ala Val His His Ile Leu His
                85                  90                  95

Leu Pro Gly Cys Val Pro Cys Val Arg Thr Gly Asn Gln Ser Arg Cys
                100                 105                 110
```

-continued

Trp Val Ala Leu Thr Pro Thr Leu Ala Ala Pro Tyr Leu Gly Ala Pro
            115                 120                 125

Leu Glu Ser Met Arg Arg His Val Asp Leu Met Val Gly Thr Ala Thr
130                 135                 140

Leu Cys Ser Ala Leu Tyr Val Gly Asp Leu Cys Gly Ile Phe Leu
145                 150                 155                 160

Ala Gly Gln Met Phe Thr Phe Arg Pro Arg Leu His Trp Thr Thr Gln
                165                 170                 175

Glu Cys Asn Cys Ser Thr Tyr Pro Gly His Ile Thr Gly His Arg Met
            180                 185                 190

Ala

<210> SEQ ID NO 221
<211> LENGTH: 193
<212> TYPE: PRT
<213> ORGANISM: hepatitis C virus

<400> SEQUENCE: 221

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Ala Ser
    50                  55                  60

Ala Gln His Tyr Arg Asn Ile Ser Gly Ile Tyr His Val Thr Asn Asp
65                  70                  75                  80

Cys Pro Asn Ser Ser Ile Val Tyr Glu Ala Asp His His Ile Met His
                85                  90                  95

Leu Pro Gly Cys Val Pro Cys Val Arg Thr Gly Asn Thr Ser Arg Cys
            100                 105                 110

Trp Val Pro Leu Thr Pro Thr Val Ala Ala Pro Tyr Val Gly Ala Pro
            115                 120                 125

Leu Glu Ser Met Arg Arg His Val Asp Leu Met Val Gly Ala Ala Thr
130                 135                 140

Val Cys Ser Ala Leu Tyr Ile Gly Asp Leu Cys Gly Gly Val Phe Leu
145                 150                 155                 160

Val Gly Gln Met Phe Thr Phe Arg Pro Arg Arg His Trp Thr Thr Gln
                165                 170                 175

Asp Cys Asn Cys Ser Ile Tyr Asp Gly His Ile Thr Gly His Arg Met
            180                 185                 190

Ala

<210> SEQ ID NO 222
<211> LENGTH: 193
<212> TYPE: PRT
<213> ORGANISM: hepatitis C virus

<400> SEQUENCE: 222

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe

```
                35                  40                  45
Ser Ile Phe Leu Leu Val Leu Leu Ser Arg Leu Thr Val Pro Ala Ser
         50                  55                  60

Ala Gln His Tyr Arg Asn Ala Ser Gly Ile Tyr His Val Thr Asn Asp
 65                  70                  75                  80

Cys Pro Asn Ser Ser Ile Val Tyr Glu Ala Asp His His Ile Met His
                 85                  90                  95

Leu Pro Gly Cys Val Pro Cys Val Arg Thr Gly Asn Val Ser Arg Cys
                100                 105                 110

Trp Ile Pro Leu Thr Pro Thr Val Ala Val Pro Tyr Leu Gly Ala Pro
            115                 120                 125

Leu Thr Ser Val Arg Gln His Val Asp Leu Met Val Gly Ala Ala Thr
        130                 135                 140

Leu Cys Ser Ala Leu Tyr Ile Gly Asp His Cys Gly Gly Val Phe Leu
145                 150                 155                 160

Ala Gly Gln Met Val Ser Phe Gln Pro Arg Arg His Trp Thr Thr Gln
                165                 170                 175

Asp Cys Asn Cys Ser Ile Tyr Val Gly His Ile Thr Gly His Arg Met
                180                 185                 190

Ala

<210> SEQ ID NO 223
<211> LENGTH: 193
<212> TYPE: PRT
<213> ORGANISM: hepatitis C virus
<220> FEATURE:
<221> NAME/KEY: MISC_FEATURE
<222> LOCATION: (24)..(24)
<223> OTHER INFORMATION: Xaa is any amino acid
<220> FEATURE:
<221> NAME/KEY: MISC_FEATURE
<222> LOCATION: (190)..(190)
<223> OTHER INFORMATION: Xaa is any amino acid
<220> FEATURE:
<221> NAME/KEY: MISC_FEATURE
<222> LOCATION: (191)..(193)
<223> OTHER INFORMATION: Xaa is any amino acid

<400> SEQUENCE: 223

Thr Cys Gly Phe Ala Asp Leu Met Gly Tyr Ile Pro Leu Val Gly Ala
 1               5                  10                  15

Pro Val Gly Gly Val Ala Arg Xaa Leu Ala His Gly Val Arg Ala Leu
                20                  25                  30

Glu Asp Gly Ile Asn Tyr Ala Thr Gly Asn Leu Pro Gly Cys Ser Phe
            35                  40                  45

Ser Ile Ser Leu Leu Glu Leu Leu Ser Cys Leu Thr Val Pro Ala Ser
         50                  55                  60

Ala Ile His Tyr Arg Asn Ala Ser Asp Gly Tyr Tyr Ile Thr Asn Asp
 65                  70                  75                  80

Cys Pro Asn Ser Ser Ile Val Tyr Glu Ala Glu Asn His Ile Leu His
                 85                  90                  95

Leu Pro Gly Ile Val Pro Cys Val Lys Thr Gly Asn Gln Ser Arg Cys
                100                 105                 110

Trp Val Ala Leu Thr Pro Thr Leu Ala Ala Pro His Leu Arg Ala Pro
            115                 120                 125

Leu Ser Ser Leu Arg Ala His Val Asp Leu Met Val Gly Ala Ala Thr
        130                 135                 140

Ala Cys Ser Ala Phe Tyr Ile Gly Asp Leu Cys Gly Gly Val Phe Leu
```

-continued

```
                145                 150                 155                 160
Ala Gly Gln Leu Phe Thr Ile Arg Pro Arg Ile His Glu Thr Thr Gln
                    165                 170                 175

Asp Cys Asn Cys Ser Ile Tyr Ser Gly His Ile Thr Gly Xaa Xaa Xaa
                180                 185                 190

Xaa

<210> SEQ ID NO 224
<211> LENGTH: 193
<212> TYPE: PRT
<213> ORGANISM: hepatitis C virus
<220> FEATURE:
<221> NAME/KEY: MISC_FEATURE
<222> LOCATION: (51)..(51)
<223> OTHER INFORMATION: Xaa is any amino acid

<400> SEQUENCE: 224

Ala Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Xaa Leu Leu Ala Leu Leu Ser Cys Leu Thr Val Pro Ala Ser
    50                  55                  60

Ala Gln His Tyr Arg Asn Val Ser Gly Ile Tyr His Val Thr Asn Asp
65                  70                  75                  80

Cys Pro Asn Ser Ser Ile Val Tyr Glu Ala Asp His His Ile Met His
                85                  90                  95

Leu Pro Gly Ile Val Pro Cys Val Arg Thr Gly Asn Val Ser Arg Cys
            100                 105                 110

Trp Val Ser Leu Thr Pro Thr Val Ala Ala Pro Tyr Leu Gly Ala Pro
        115                 120                 125

Leu Thr Ser Leu Arg Arg His Val Asp Leu Met Val Gly Ala Ala Thr
    130                 135                 140

Leu Cys Ser Ala Leu Tyr Val Gly Asp Leu Cys Gly Gly Val Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Val Gly His Ile Thr Gly His Arg Met
            180                 185                 190

Ala

<210> SEQ ID NO 225
<211> LENGTH: 117
<212> TYPE: PRT
<213> ORGANISM: hepatitis C virus
<220> FEATURE:
<221> NAME/KEY: MISC_FEATURE
<222> LOCATION: (95)..(95)
<223> OTHER INFORMATION: Xaa is any amino acid

<400> SEQUENCE: 225

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
```

```
                35                  40                  45
Thr Arg Lys Thr Ser Glu Arg Ser Gln Pro Arg Gly Arg Arg Gln Pro
             50                  55                  60
Ile Pro Lys Ala Arg Arg Ser Glu Gly Arg Ser Trp Ala Gln Pro Gly
 65                  70                  75                  80
Tyr Pro Trp Pro Leu Tyr Gly Asn Glu Gly Cys Gly Trp Ala Xaa Trp
                 85                  90                  95
Leu Leu Ser Pro Arg Gly Ser Arg Pro Ser Trp Gly Pro Asn Asp Pro
                100                 105                 110
Arg Arg Arg Ser Arg
                115

<210> SEQ ID NO 226
<211> LENGTH: 319
<212> TYPE: PRT
<213> ORGANISM: hepatitis C virus

<400> SEQUENCE: 226

Met Ser Thr Asn Pro Lys Pro Gln Arg Lys Thr Lys Arg Asn Thr Asn
  1               5                  10                  15
Arg Arg Pro Gln Asp Val Lys Phe Pro Gly Gly Gly Gln Ile Val Gly
                 20                  25                  30
Gly Val Tyr Leu Leu Pro Arg Arg Gly Pro Arg Met Gly Val Arg Ala
                 35                  40                  45
Thr Arg Lys Thr Ser Glu Arg Ser Gln Pro Arg Gly Arg Arg Gln Pro
             50                  55                  60
Ile Pro Lys Ala Arg Gln Pro Thr Gly Arg Ser Trp Gly Gln Pro Gly
 65                  70                  75                  80
Tyr Pro Trp Pro Leu Tyr Ala Asn Glu Gly Leu Gly Trp Ala Gly Trp
                 85                  90                  95
Leu Leu Ser Pro Arg Gly Ser Arg Pro Asn Trp Gly Pro Asn Asp Pro
                100                 105                 110
Arg Arg Lys Ser Arg Asn Leu Gly Lys Val Ile Asp Thr Leu Thr Cys
                115                 120                 125
Gly Phe Ala Asp Leu Met Gly Tyr Ile Pro Leu Val Gly Gly Pro Ile
                130                 135                 140
Gly Gly Val Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Ile Leu Ala Leu Leu Ser Cys Leu Thr Val Pro Ala Ser Ala Val
                180                 185                 190
Pro Tyr Arg Asn Ala Ser Gly Ile Tyr His Val Thr Asn Asp Cys Pro
                195                 200                 205
Asn Ser Ser Ile Val Tyr Glu Ala Asp Asn Leu Ile Leu His Ala Pro
                210                 215                 220
Gly Cys Val Pro Cys Val Met Thr Gly Asn Val Ser Arg Cys Trp Val
225                 230                 235                 240
Gln Ile Thr Pro Thr Leu Ser Ala Pro Ser Leu Gly Ala Val Thr Ala
                245                 250                 255
Pro Leu Arg Arg Ala Val Asp Tyr Leu Ala Gly Gly Ala Ala Leu Cys
                260                 265                 270
Ser Ala Leu Tyr Val Gly Asp Ala Cys Gly Ala Leu Phe Leu Val Gly
                275                 280                 285
```

```
Gln Met Phe Thr Tyr Arg Pro Arg Gln His Ala Thr Val Gln Asn Cys
    290                 295                 300

Asn Cys Ser Ile Tyr Ser Gly His Val Thr Gly His Arg Met Ala
305                 310                 315
```

<210> SEQ ID NO 227
<211> LENGTH: 193
<212> TYPE: PRT
<213> ORGANISM: hepatitis C virus

<400> SEQUENCE: 227

```
Thr Cys Gly Phe Ala Asp Leu Val Gly Tyr Ile Pro Leu Val Gly Gly
1               5                   10                  15

Pro Val Gly Gly Val Ala Arg Ala Leu Ala His Gly Val Arg Val Leu
                20                  25                  30

Glu Asp Gly Val Asn Tyr Ala Thr Gly Asn Leu Pro Gly Cys Ser Phe
            35                  40                  45

Ser Ile Phe Ile Leu Ala Leu Leu Ser Cys Leu Thr Val Pro Ala Ser
        50                  55                  60

Ala Val Pro Tyr Arg Asn Ala Ser Gly Ile Tyr His Val Thr Asn Asp
65                  70                  75                  80

Cys Pro Asn Ser Ser Ile Val Tyr Glu Ala Asp Asp Leu Ile Leu His
                85                  90                  95

Ala Pro Gly Cys Val Pro Cys Val Arg Lys Asp Asn Val Ser Arg Cys
            100                 105                 110

Trp Val Gln Ile Thr Pro Thr Leu Ser Ala Pro Ser Phe Gly Ala Val
        115                 120                 125

Thr Ala Pro Leu Arg Arg Ala Val Asp Tyr Leu Val Gly Gly Ala Ala
    130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asp Cys Asn Cys Ser Ile Tyr Ser Gly His Val Thr Gly His Gln Met
            180                 185                 190

Ala
```

<210> SEQ ID NO 228
<211> LENGTH: 319
<212> TYPE: PRT
<213> ORGANISM: hepatitis C virus

<400> SEQUENCE: 228

```
Met Ser Thr Leu Pro Lys Pro Gln Arg Lys Thr Lys Arg Asn Thr Asn
1               5                   10                  15

Arg Arg Pro Thr Asp Val Lys Phe Pro Gly Gly Gln Ile Val Gly Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Gln Gly Arg His Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro His Trp Gly Pro Asn Asp Pro
```

-continued

```
                    100                 105                 110
Arg Arg Arg Ser Arg Asn Leu Gly Lys Val Ile Asp Thr Leu Thr Cys
            115                 120                 125

Gly Phe Ala Asp Leu Met Gly Tyr Ile Pro Val Gly Ala Pro Leu
    130                 135                 140

Gly Gly Val Ala Ala Leu Ala His Gly Val Arg Ala Ile Glu Asp
145                 150                 155                 160

Gly Ile Asn Tyr Ala Thr Gly Asn Leu Pro Gly Cys Ser Phe Ser Ile
            165                 170                 175

Phe Leu Leu Ala Leu Leu Ser Cys Leu Thr Thr Pro Ala Ser Ala Leu
            180                 185                 190

Thr Tyr Gly Asn Ser Ser Gly Leu Tyr His Leu Thr Asn Asp Cys Pro
            195                 200                 205

Asn Ser Ser Ile Val Leu Glu Ala Asp Ala Met Ile Leu His Leu Pro
210                 215                 220

Gly Cys Leu Pro Cys Val Arg Val Asp Asp Arg Ser Thr Cys Trp His
225                 230                 235                 240

Ala Val Thr Pro Thr Leu Ala Ile Pro Asn Ala Ser Thr Pro Ala Thr
            245                 250                 255

Gly Phe Arg Arg His Val Asp Leu Leu Ala Gly Ala Ala Val Val Cys
            260                 265                 270

Ser Ser Leu Tyr Ile Gly Asp Leu Cys Gly Ser Leu Phe Leu Ala Gly
            275                 280                 285

Gln Leu Phe Thr Phe Gln Pro Arg Arg His Trp Thr Val Gln Asp Cys
            290                 295                 300

Asn Cys Ser Ile Tyr Thr Gly His Val Thr Gly His Arg Met Ala
305                 310                 315
```

```
<210> SEQ ID NO 229
<211> LENGTH: 319
<212> TYPE: PRT
<213> ORGANISM: hepatitis C virus
<220> FEATURE:
<221> NAME/KEY: MISC_FEATURE
<222> LOCATION: (128)..(129)
<223> OTHER INFORMATION: Xaa is any amino acid
<220> FEATURE:
<221> NAME/KEY: MISC_FEATURE
<222> LOCATION: (308)..(308)
<223> OTHER INFORMATION: Xaa is any amino acid
<220> FEATURE:
<221> NAME/KEY: MISC_FEATURE
<222> LOCATION: (310)..(310)
<223> OTHER INFORMATION: Xaa is any amino acid

<400> SEQUENCE: 229
```

```
Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Val Arg Gln Pro Thr Gly Arg Ser Trp Gly Gln Pro Gly
65                  70                  75                  80

Tyr Pro Trp Pro Leu Tyr Gly Asn Glu Gly Cys Gly Trp Ala Gly Trp
            85                  90                  95
```

-continued

```
Leu Leu Ser Pro Arg Gly Ser Arg Pro Asn Trp Gly Pro Asn Asp Pro
            100                 105                 110

Arg Arg Arg Ser Arg Asn Leu Gly Lys Val Ile Asp Thr Leu Thr Xaa
        115                 120                 125

Xaa Leu Ala Asp Leu Met Gly Tyr Ile Pro Val Leu Gly Gly Pro Leu
    130                 135                 140

Gly Gly Val Ala Ala Leu Ala His Gly Val Arg Ala Ile Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Ile
                180                 185                 190

Gln Val Lys Asn Ala Ser Gly Ile Tyr His Leu Thr Asn Asp Cys Ser
                195                 200                 205

Asn Asn Ser Ile Val Phe Glu Ala Glu Thr Met Ile Leu His Leu Pro
        210                 215                 220

Gly Cys Val Pro Cys Ile Lys Ala Gly Asn Glu Ser Arg Cys Trp Leu
225                 230                 235                 240

Pro Val Ser Pro Thr Leu Ala Val Pro Asn Ser Ser Val Pro Ile His
                245                 250                 255

Gly Phe Arg His Val Asp Leu Leu Val Gly Ala Ala Phe Cys
                260                 265                 270

Ser Ala Met Tyr Ile Gly Asp Leu Cys Gly Ser Ile Ile Leu Val Gly
            275                 280                 285

Gln Leu Phe Thr Phe Arg Pro Lys Tyr His Gln Val Thr Gln Asp Cys
        290                 295                 300

Asn Cys Ser Xaa Asn Xaa Gly His Val Thr Gly His Arg Met Ala
305                 310                 315

<210> SEQ ID NO 230
<211> LENGTH: 319
<212> TYPE: PRT
<213> ORGANISM: hepatitis C virus
<220> FEATURE:
<221> NAME/KEY: MISC_FEATURE
<222> LOCATION: (144)..(144)
<223> OTHER INFORMATION: Xaa is any amino acid
<220> FEATURE:
<221> NAME/KEY: MISC_FEATURE
<222> LOCATION: (149)..(149)
<223> OTHER INFORMATION: Xaa is any amino acid
<220> FEATURE:
<221> NAME/KEY: MISC_FEATURE
<222> LOCATION: (156)..(157)
<223> OTHER INFORMATION: Xaa is any amino acid
<220> FEATURE:
<221> NAME/KEY: MISC_FEATURE
<222> LOCATION: (161)..(161)
<223> OTHER INFORMATION: Xaa is any amino acid
<220> FEATURE:
<221> NAME/KEY: MISC_FEATURE
<222> LOCATION: (167)..(167)
<223> OTHER INFORMATION: Xaa is any amino acid
<220> FEATURE:
<221> NAME/KEY: MISC_FEATURE
<222> LOCATION: (171)..(172)
<223> OTHER INFORMATION: Xaa is any amino acid
<220> FEATURE:
<221> NAME/KEY: MISC_FEATURE
<222> LOCATION: (174)..(174)
<223> OTHER INFORMATION: Xaa is any amino acid
<220> FEATURE:
<221> NAME/KEY: MISC_FEATURE
<222> LOCATION: (177)..(177)
<223> OTHER INFORMATION: Xaa is any amino acid
```

```
<220> FEATURE:
<221> NAME/KEY: MISC_FEATURE
<222> LOCATION: (232)..(232)
<223> OTHER INFORMATION: Xaa is any amino acid
<220> FEATURE:
<221> NAME/KEY: MISC_FEATURE
<222> LOCATION: (233)..(233)
<223> OTHER INFORMATION: Xaa is any amino acid

<400> SEQUENCE: 230

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Val Arg His Gln Thr Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Xaa
130                 135                 140

Gly Gly Val Ala Xaa Ala Leu Ala His Gly Val Xaa Xaa Ile Glu Asp
145                 150                 155                 160

Xaa Val Asn Tyr Ala Thr Xaa Asn Leu Pro Xaa Xaa Ser Xaa Ser Ile
                165                 170                 175

Xaa Leu Leu Ala Leu Leu Ser Cys Leu Thr Pro Ala Ser Ala Ala
            180                 185                 190

His Tyr Thr Asn Lys Ser Gly Leu Tyr His Leu Thr Asn Asp Cys Pro
        195                 200                 205

Asn Ser Ser Ile Val Tyr Glu Ala Glu Thr Leu Ile Leu His Leu Pro
210                 215                 220

Gly Cys Val Pro Cys Val Lys Xaa Xaa Asn Gln Ser Arg Cys Trp Val
225                 230                 235                 240

Gln Ala Ser Pro Thr Leu Ala Val Pro Asn Ala Ser Thr Pro Val Thr
                245                 250                 255

Gly Phe Arg Lys His Val Asp Ile Met Val Gly Ala Ala Phe Cys
            260                 265                 270

Ser Ala Met Tyr Val Gly Asp Leu Cys Gly Gly Leu Phe Leu Val Gly
        275                 280                 285

Gln Leu Phe Thr Leu Arg Pro Arg Met His Gln Val Val Gln Glu Cys
290                 295                 300

Asn Cys Ser Ile Tyr Thr Gly His Ile Thr Gly His Arg Met Ala
305                 310                 315

<210> SEQ ID NO 231
<211> LENGTH: 319
<212> TYPE: PRT
<213> ORGANISM: hepatitis C virus
<220> FEATURE:
<221> NAME/KEY: MISC_FEATURE
<222> LOCATION: (108)..(108)
```

```
<223> OTHER INFORMATION: Xaa is any amino acid
<220> FEATURE:
<221> NAME/KEY: MISC_FEATURE
<222> LOCATION: (114)..(114)
<223> OTHER INFORMATION: Xaa is any amino acid
<220> FEATURE:
<221> NAME/KEY: MISC_FEATURE
<222> LOCATION: (152)..(152)
<223> OTHER INFORMATION: Xaa is any amino acid
<220> FEATURE:
<221> NAME/KEY: MISC_FEATURE
<222> LOCATION: (178)..(178)
<223> OTHER INFORMATION: Xaa is any amino acid

<400> SEQUENCE: 231

Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Ala Arg Gly Arg Arg Gln Pro
    50                  55                  60

Ile Pro Lys Val Arg Gln Asn Gln Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Asp Trp Xaa Pro Asn Asp Pro
            100                 105                 110

Arg Xaa Arg Ser Arg Asn Leu Gly Lys Val Ile Asp Thr Leu Thr Cys
        115                 120                 125

Gly Phe Ala Asp Leu Met Glu Tyr Ile Pro Val Val Gly Ala Pro Leu
    130                 135                 140

Gly Gly Val Ala Ala Glu Leu Xaa His Gly Val Arg Ala Ile Glu Asp
145                 150                 155                 160

Gly Ile Asn Tyr Ala Thr Gly Asn Leu Pro Gly Cys Ser Phe Ser Ile
                165                 170                 175

Phe Xaa Leu Ala Leu Leu Ser Cys Leu Thr Thr Pro Ala Ser Ala Leu
            180                 185                 190

Asn Tyr Ala Asn Lys Ser Gly Leu Tyr His Leu Thr Asn Asp Cys Pro
        195                 200                 205

Asn Ser Ser Ile Val Tyr Glu Ala Asn Gly Met Ile Leu His Leu Pro
    210                 215                 220

Gly Cys Val Pro Cys Val Lys Thr Gly Asn Leu Thr Lys Cys Trp Leu
225                 230                 235                 240

Ser Ala Ser Pro Thr Leu Ala Val Gln Asn Ala Ser Val Ser Ile Arg
                245                 250                 255

Gly Val Arg Glu His Val Asp Leu Leu Val Gly Ala Ala Phe Cys
            260                 265                 270

Ser Ala Met Tyr Val Gly Asp Leu Cys Gly Gly Leu Phe Leu Val Gly
        275                 280                 285

Gln Leu Phe Thr Phe Arg Pro Arg Met Tyr Glu Ile Ala Gln Asp Cys
    290                 295                 300

Asn Cys Ser Ile Tyr Ala Gly His Ile Thr Gly His Arg Met Ala
305                 310                 315

<210> SEQ ID NO 232
<211> LENGTH: 100
```

-continued

```
<212> TYPE: PRT
<213> ORGANISM: hepatitis C virus

<400> SEQUENCE: 232

Met Ser Thr Leu Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Val Arg His Gln Thr Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro
            100

<210> SEQ ID NO 233
<211> LENGTH: 100
<212> TYPE: PRT
<213> ORGANISM: hepatitis C virus
<220> FEATURE:
<221> NAME/KEY: MISC_FEATURE
<222> LOCATION: (17)..(17)
<223> OTHER INFORMATION: Xaa is any amino acid

<400> SEQUENCE: 233

Met Ser Thr Leu Pro Lys Pro Gln Arg Lys Thr Lys Arg Asn Thr Asn
1               5                   10                  15

Xaa Arg Pro Gln Asp Val Lys Phe Pro Gly Gly Gly Gln Ile Val Gly
            20                  25                  30

Gly Val Tyr Val Leu Pro Arg Arg Gly Pro Gln Leu Gly Val Arg Ala
        35                  40                  45

Val Arg Lys Thr Ser Glu Arg Ser Gln Pro Arg Ser Arg Arg Gln Pro
50                  55                  60

Ile Pro Arg Ala Arg Arg Thr Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro
            100

<210> SEQ ID NO 234
<211> LENGTH: 128
<212> TYPE: PRT
<213> ORGANISM: hepatitis C virus

<400> SEQUENCE: 234

Val Glu Val Lys Asp Thr Gly Asp Ser Tyr Met Pro Thr Asn Asp Cys
1               5                   10                  15

Ser Asn Ser Ser Ile Val Trp Gln Leu Glu Gly Ala Val Leu His Thr
            20                  25                  30

Pro Gly Cys Val Pro Cys Glu Arg Thr Ala Asn Val Ser Arg Cys Trp
        35                  40                  45

Val Pro Val Ala Pro Asn Leu Ala Ile Ser Gln Pro Gly Ala Leu Thr
50                  55                  60
```

```
Lys Gly Leu Arg Ala His Ile Asp Ile Ile Val Met Ser Ala Thr Val
 65                  70                  75                  80

Cys Ser Ala Leu Tyr Val Gly Asp Val Cys Gly Ala Leu Met Leu Ala
                 85                  90                  95

Ala Gln Val Val Val Ser Pro Gln His His Thr Phe Val Gln Glu
            100                 105                 110

Cys Asn Cys Ser Ile Tyr Pro Gly Arg Ile Thr Gly His Arg Met Ala
            115                 120                 125
```

<210> SEQ ID NO 235
<211> LENGTH: 149
<212> TYPE: PRT
<213> ORGANISM: hepatitis C virus

<400> SEQUENCE: 235

```
Asp Gly Val Asn Tyr Ala Thr Gly Asn Leu Pro Gly Cys Ser Phe Ser
  1               5                  10                  15

Ile Phe Leu Leu Ala Leu Leu Ser Cys Val Thr Val Pro Val Ser Ala
                 20                  25                  30

Val Gln Val Lys Asn Thr Ser Thr Met Tyr Met Ala Thr Asn Asp Cys
             35                  40                  45

Ser Asn Asn Ser Ile Ile Trp Gln Met Gln Gly Ala Val Leu His Val
         50                  55                  60

Pro Gly Cys Val Pro Cys Glu Leu Gln Gly Asn Lys Ser Arg Cys Trp
 65                  70                  75                  80

Ile Pro Val Thr Pro Asn Val Ala Val Asn Gln Pro Gly Ala Leu Thr
                 85                  90                  95

Arg Gly Leu Arg Thr His Ile Asp Thr Ile Val Met Val Ala Thr Leu
            100                 105                 110

Cys Ser Ala Leu Tyr Ile Gly Asp Val Cys Gly Ala Val Met Ile Ala
            115                 120                 125

Ala Gln Val Val Ile Val Ser Pro Gln His His Asn Phe Ser Gln Asp
        130                 135                 140

Cys Asn Cys Ser Ile
145
```

<210> SEQ ID NO 236
<211> LENGTH: 154
<212> TYPE: PRT
<213> ORGANISM: hepatitis C virus

<400> SEQUENCE: 236

```
Asp Gly Ile Asn Tyr Ala Thr Gly Asn Leu Pro Gly Cys Ser Phe Ser
  1               5                  10                  15

Ile Phe Leu Leu Ala Leu Leu Ser Cys Leu Thr Val Pro Ala Ser Ala
                 20                  25                  30

Val Gln Val Lys Asn Thr Ser His Ser Tyr Met Val Thr Asn Asp Cys
             35                  40                  45

Ser Asn Ser Ser Ile Val Trp Gln Leu Lys Asp Ala Val Leu His Val
         50                  55                  60

Pro Gly Cys Val Pro Cys Glu Arg His Gln Asn Gln Ser Arg Cys Trp
 65                  70                  75                  80

Ile Pro Val Thr Pro Asn Val Ala Val Ser Gln Pro Gly Ala Leu Thr
                 85                  90                  95

Arg Gly Leu Arg Thr His Ile Asp Thr Ile Val Ala Ser Ala Thr Val
            100                 105                 110
```

```
Cys Ser Ala Leu Tyr Val Gly Asp Phe Cys Gly Ala Val Met Leu Val
            115                 120                 125

Ser Gln Phe Phe Met Ile Ser Pro Gln His His Ile Phe Val Gln Asp
        130                 135                 140

Cys Asn Cys Ser Ile Tyr Pro Gly His Ile
145                 150

<210> SEQ ID NO 237
<211> LENGTH: 118
<212> TYPE: PRT
<213> ORGANISM: hepatitis C virus
<220> FEATURE:
<221> NAME/KEY: MISC_FEATURE
<222> LOCATION: (95)..(95)
<223> OTHER INFORMATION: Xaa is any amino acid

<400> SEQUENCE: 237

Asp Gly Ile Asn Tyr Ala Thr Gly Asn Leu Pro Gly Cys Ser Phe Ser
1               5                   10                  15

Ile Phe Leu Leu Ala Leu Leu Ser Cys Ile Thr Val Pro Val Ser Ala
            20                  25                  30

Val Gln Val Ala Asn Arg Ser Gly Ser Tyr Met Val Thr Asn Asp Cys
        35                  40                  45

Ser Asn Ser Ser Ile Val Trp Gln Leu Glu Glu Ala Val Leu His Val
    50                  55                  60

Pro Gly Cys Val Pro Cys Glu Trp Lys Asp Asn Thr Ser Arg Cys Trp
65                  70                  75                  80

Ile Pro Val Thr Pro Asn Ile Ala Val Ser Gln Pro Gly Ala Xaa Thr
                85                  90                  95

Lys Gly Leu Arg Thr His Ile Asp Ile Ile Val Ala Ser Ala Thr Phe
            100                 105                 110

Cys Ser Ala Leu Tyr Val
        115

<210> SEQ ID NO 238
<211> LENGTH: 128
<212> TYPE: PRT
<213> ORGANISM: hepatitis C virus

<400> SEQUENCE: 238

Glu His Tyr Arg Asn Ala Ser Gly Ile Tyr His Ile Thr Asn Asp Cys
1               5                   10                  15

Pro Asn Ser Ser Ile Val Tyr Glu Ala Asp His His Ile Leu His Leu
            20                  25                  30

Pro Gly Cys Val Pro Cys Val Met Thr Gly Asn Thr Ser Arg Cys Trp
        35                  40                  45

Thr Pro Val Thr Pro Thr Val Ala Val His Pro Gly Ala Pro Leu
    50                  55                  60

Glu Ser Phe Arg Arg His Val Asp Leu Met Val Gly Ala Ala Thr Leu
65                  70                  75                  80

Cys Ser Ala Leu Tyr Val Gly Asp Leu Cys Gly Gly Ala Phe Leu Met
                85                  90                  95

Gly Gln Met Ile Thr Phe Arg Pro Arg Arg His Trp Thr Thr Gln Glu
            100                 105                 110

Cys Asn Cys Ser Ile Tyr Thr Gly His Ile Thr Gly His Arg Met Ala
        115                 120                 125

<210> SEQ ID NO 239
```

```
<211> LENGTH: 128
<212> TYPE: PRT
<213> ORGANISM: hepatitis C virus

<400> SEQUENCE: 239

Val His Tyr Arg Asn Ala Ser Gly Val Tyr His Val Thr Asn Asp Cys
1               5                   10                  15

Pro Asn Thr Ser Ile Val Tyr Glu Thr Glu His His Ile Met His Leu
            20                  25                  30

Pro Gly Cys Val Pro Cys Val Arg Thr Glu Asn Thr Ser Arg Cys Trp
            35                  40                  45

Val Pro Leu Thr Pro Thr Val Ala Ala Pro Tyr Pro Asn Ala Pro Leu
        50                  55                  60

Glu Ser Met Arg Arg His Val Asp Leu Met Val Gly Ala Ala Thr Met
65                  70                  75                  80

Cys Ser Ala Phe Tyr Ile Gly Asp Leu Cys Gly Gly Val Phe Leu Val
                85                  90                  95

Gly Gln Leu Phe Asp Phe Arg Pro Arg Arg His Trp Thr Thr Gln Asp
            100                 105                 110

Cys Asn Cys Ser Ile Tyr Pro Gly His Val Ser Gly His Arg Met Ala
            115                 120                 125

<210> SEQ ID NO 240
<211> LENGTH: 128
<212> TYPE: PRT
<213> ORGANISM: hepatitis C virus

<400> SEQUENCE: 240

Val Asn Tyr Arg Asn Ala Ser Gly Val Tyr His Val Thr Asn Asp Cys
1               5                   10                  15

Pro Asn Ser Ser Ile Val Tyr Glu Ala Glu His Gln Ile Leu His Leu
            20                  25                  30

Pro Gly Leu Val Pro Cys Val Arg Val Gly Asn Gln Ser Arg Cys Trp
            35                  40                  45

Val Ala Leu Thr Pro Thr Val Ala Val Ser Tyr Ile Gly Ala Pro Leu
        50                  55                  60

Asp Ser Leu Arg Arg His Val Asp Leu Met Val Gly Ala Ala Thr Val
65                  70                  75                  80

Cys Ser Ala Leu Tyr Val Gly Asp Leu Cys Gly Gly Ala Phe Leu Val
                85                  90                  95

Gly Gln Met Phe Ser Phe Gln Pro Arg Arg His Trp Thr Thr Gln Asp
            100                 105                 110

Cys Asn Cys Ser Ile Tyr Ala Gly His Ile Thr Gly His Arg Met Ala
            115                 120                 125

<210> SEQ ID NO 241
<211> LENGTH: 128
<212> TYPE: PRT
<213> ORGANISM: hepatitis C virus

<400> SEQUENCE: 241

Val Asn Tyr His Asn Ala Ser Gly Val Tyr His Ile Thr Asn Asp Cys
1               5                   10                  15

Pro Asn Ser Ser Ile Met Tyr Glu Ala Glu His His Ile Leu His Leu
            20                  25                  30

Pro Gly Cys Val Pro Cys Val Arg Glu Gly Asn Gln Ser Arg Cys Trp
            35                  40                  45
```

```
Val Ala Leu Thr Pro Thr Val Ala Pro Tyr Ile Gly Ala Pro Leu
        50                   55                   60

Glu Ser Ile Arg Arg His Val Asp Leu Met Val Gly Ala Ala Thr Val
 65                      70                  75                  80

Cys Ser Ala Leu Tyr Ile Gly Asp Leu Cys Gly Val Phe Leu Val
                85                   90                   95

Gly Gln Met Phe Ser Phe Gln Pro Arg Arg His Trp Thr Thr Gln Asp
                100                     105                 110

Cys Asn Cys Ser Ile Tyr Ala Gly His Val Thr Gly His Arg Met Ala
                115                     120                 125

<210> SEQ ID NO 242
<211> LENGTH: 169
<212> TYPE: PRT
<213> ORGANISM: hepatitis C virus

<400> SEQUENCE: 242

Leu Ala His Gly Val Arg Ala Val Glu Asp Gly Ile Asn Tyr Ala Thr
 1                   5                  10                  15

Gly Asn Leu Pro Gly Cys Ser Phe Ser Ile Phe Leu Leu Ala Leu Leu
                20                   25                  30

Ser Cys Leu Thr Val Pro Ala Ser Ala Val His Tyr His Asn Thr Ser
            35                   40                  45

Gly Ile Tyr His Ile Thr Asn Asp Cys Pro Asn Ser Ser Ile Val Phe
        50                   55                   60

Glu Ala Glu His His Ile Leu His Leu Pro Gly Cys Val Pro Cys Val
 65                      70                  75                  80

Arg Thr Gly Asn Gln Ser Arg Cys Trp Ile Ala Leu Thr Pro Thr Leu
                85                   90                  95

Ala Ala Pro His Ile Gly Ala Pro Leu Glu Ser Met Arg Arg His Val
            100                      105                 110

Asp Leu Met Val Gly Thr Ala Thr Leu Cys Ser Ala Leu Tyr Ile Gly
                115                     120                 125

Asp Leu Cys Gly Gly Ile Phe Leu Val Gly Gln Met Phe Asn Phe Arg
            130                      135                 140

Pro Arg Leu His Trp Thr Thr Gln Glu Cys Asn Cys Ser Ile Tyr Pro
145                     150                     155                 160

Gly His Ile Thr Gly His Arg Met Ala
                165

<210> SEQ ID NO 243
<211> LENGTH: 149
<212> TYPE: PRT
<213> ORGANISM: hepatitis C virus

<400> SEQUENCE: 243

Asp Gly Ile Asn Tyr Ala Thr Gly Asn Leu Pro Gly Cys Ser Phe Ser
 1                   5                  10                  15

Ile Phe Leu Leu Ala Leu Leu Ser Cys Leu Thr Val Pro Ala Ser Ala
                20                   25                  30

Ile Asn Tyr Arg Asn Thr Ser Gly Ile Tyr His Val Thr Asn Asp Cys
            35                   40                  45

Pro Asn Ser Ser Ile Val Tyr Glu Ala Asp His His Ile Leu His Leu
         50                  55                  60

Pro Gly Cys Val Pro Cys Val Arg Thr Gly Asn Gln Ser Arg Cys Trp
 65                      70                  75                  80
```

```
Val Ala Leu Thr Pro Thr Val Ala Ala Pro Tyr Ile Gly Ala Pro Leu
                 85                  90                  95

Glu Ser Leu Arg Ser His Val Asp Leu Met Val Gly Ala Ala Thr Val
            100                 105                 110

Cys Ser Ala Leu Tyr Ile Gly Asp Leu Cys Gly Gly Leu Phe Leu Val
        115                 120                 125

Gly Gln Met Phe Ser Phe Arg Pro Arg His Trp Thr Ala Gln Asp
    130                 135                 140

Cys Asn Cys Ser Ile
145

<210> SEQ ID NO 244
<211> LENGTH: 149
<212> TYPE: PRT
<213> ORGANISM: hepatitis C virus

<400> SEQUENCE: 244

Asp Gly Ile Asn Tyr Ala Thr Gly Asn Leu Pro Gly Cys Ser Phe Ser
1               5                   10                  15

Ile Phe Leu Leu Ala Leu Leu Ser Cys Leu Thr Val Pro Ala Ser Ala
            20                  25                  30

Ile Asn Tyr His Asn Thr Ser Gly Ile Tyr His Ile Thr Asn Asp Cys
        35                  40                  45

Pro Asn Ser Ser Ile Val Tyr Glu Ala Asp His His Ile Leu His Leu
    50                  55                  60

Pro Gly Cys Val Pro Cys Val Arg Val Gly Asn Gln Ser Ser Cys Trp
65                  70                  75                  80

Val Ala Leu Thr Pro Thr Ile Ala Pro Tyr Ile Gly Ala Pro Leu
                85                  90                  95

Glu Ser Leu Arg Ser His Val Asp Leu Met Val Gly Ala Ala Thr Val
            100                 105                 110

Cys Ser Ala Leu Tyr Ile Gly Asp Leu Cys Gly Gly Ala Phe Leu Val
        115                 120                 125

Gly Gln Met Phe Ser Phe Arg Pro Arg His Trp Thr Thr Gln Asp
    130                 135                 140

Cys Asn Cys Ser Ile
145

<210> SEQ ID NO 245
<211> LENGTH: 149
<212> TYPE: PRT
<213> ORGANISM: hepatitis C virus
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (120)..(120)
<223> OTHER INFORMATION: Xaa is any amino acid
<220> FEATURE:
<221> NAME/KEY: MISC_FEATURE
<222> LOCATION: (134)..(134)
<223> OTHER INFORMATION: Xaa is any amino acid

<400> SEQUENCE: 245

Asp Gly Ile Asn Tyr Ala Thr Gly Asn Ile Pro Gly Cys Xaa Phe Ser
1               5                   10                  15
```

-continued

```
Ile Phe Leu Xaa Ala Leu Leu Ser Cys Leu Thr Val Pro Ala Ser Ala
            20                  25                  30

Thr Asn Tyr Arg Asn Val Ser Gly Ile Tyr His Val Thr Asn Asp Cys
        35                  40                  45

Pro Asn Ser Ser Ile Val Tyr Glu Ala Asp His His Ile Leu Ala Leu
    50                  55                  60

Pro Gly Cys Val Pro Cys Val Arg Val Gly Asn Gln Ser Arg Cys Trp
65                  70                  75                  80

Val Ala Leu Thr Pro Thr Val Ala Pro Tyr Thr Ala Ala Pro Leu
                85                  90                  95

Glu Ser Leu Arg Ser His Val Asp Leu Met Val Gly Ala Ala Thr Val
            100                 105                 110

Cys Ser Ala Leu Tyr Ile Gly Xaa Leu Cys Gly Gly Leu Phe Leu Val
            115                 120                 125

Gly Gln Met Phe Ser Xaa Gln Pro Arg Arg His Trp Thr Thr Gln Asp
        130                 135                 140

Cys Asn Cys Ser Ile
145

<210> SEQ ID NO 246
<211> LENGTH: 149
<212> TYPE: PRT
<213> ORGANISM: hepatitis C virus
<220> FEATURE:
<221> NAME/KEY: MISC_FEATURE
<222> LOCATION: (9)..(9)
<223> OTHER INFORMATION: Xaa is any amino acid

<400> SEQUENCE: 246

Asp Gly Ile Asn Tyr Ala Thr Gly Xaa Leu Pro Gly Cys Ser Phe Ser
1               5                   10                  15

Ile Phe Leu Leu Ala Leu Leu Ser Cys Leu Thr Val Pro Ala Ser Ala
            20                  25                  30

Thr Asn Tyr Arg Asn Val Ser Gly Ile Tyr His Val Thr Asn Asp Cys
        35                  40                  45

Pro Asn Ser Ser Ile Val Phe Glu Ala Asp His His Ile Leu His Leu
    50                  55                  60

Pro Gly Cys Val Pro Cys Val Lys Glu Gly Asn His Ser Arg Cys Trp
65                  70                  75                  80

Val Ala Leu Thr Pro Thr Val Ala Pro Tyr Ile Gly Ala Pro Leu
                85                  90                  95

Glu Ser Leu Arg Ser His Val Asp Val Met Val Gly Ala Ala Thr Val
            100                 105                 110

Cys Ser Ala Leu Tyr Ile Gly Asp Leu Cys Gly Gly Leu Phe Leu Val
            115                 120                 125

Gly Gln Met Phe Ser Phe Arg Pro Arg Arg His Trp Thr Thr Gln Glu
        130                 135                 140

Cys Asn Cys Ser Ile
145

<210> SEQ ID NO 247
<211> LENGTH: 149
<212> TYPE: PRT
<213> ORGANISM: hepatitis C virus

<400> SEQUENCE: 247

Asp Gly Ile Asn Tyr Ala Thr Gly Asn Leu Pro Gly Cys Ser Phe Ser
```

```
1               5                    10                   15
Ile Phe Ile Leu Ala Leu Leu Ser Cys Leu Thr Val Pro Ala Ser Ala
            20                  25                  30

Gln His Tyr Arg Asn Val Ser Gly Ile Tyr His Val Thr Asn Asp Cys
            35                  40                  45

Pro Asn Ser Ser Ile Val Tyr Glu Ser Asp His His Ile Leu His Leu
50                      55                  60

Pro Gly Cys Val Pro Cys Val Lys Thr Gly Asn Thr Ser Arg Cys Trp
65                  70                  75                  80

Val Ala Leu Thr Pro Thr Val Ala Ala Pro Ile Leu Ser Ala Pro Leu
                85                  90                  95

Met Ser Val Arg Arg His Val Asp Leu Met Val Gly Ala Ala Thr Leu
            100                 105                 110

Ser Ser Ala Leu Tyr Val Gly Asp Leu Cys Gly Gly Ala Phe Leu Val
            115                 120                 125

Gly Gln Met Phe Thr Phe Gln Pro Arg Arg His Trp Thr Val Gln Asp
            130                 135                 140

Cys Asn Cys Ser Ile
145

<210> SEQ ID NO 248
<211> LENGTH: 119
<212> TYPE: PRT
<213> ORGANISM: hepatitis C virus

<400> SEQUENCE: 248

Tyr His Ile Thr Asn Asp Cys Pro Asn Ser Ser Val Val Tyr Glu Thr
1               5                   10                  15

Asp His His Ile Leu His Leu Pro Gly Cys Val Pro Cys Val Arg Thr
            20                  25                  30

Gly Asn Val Ser Arg Cys Trp Thr Pro Val Thr Pro Thr Val Ala Ala
            35                  40                  45

Val Ser Val Asp Ala Pro Leu Glu Ser Phe Arg Arg His Val Asp Leu
50                  55                      60

Met Val Gly Ala Ala Thr Leu Cys Ser Val Leu Tyr Val Gly Asp Leu
65                  70                  75                  80

Cys Gly Gly Ala Phe Leu Val Gly Gln Met Phe Thr Phe Gln Pro Arg
                85                  90                  95

Arg His Trp Thr Thr Gln Asp Cys Asn Cys Ser Ile Tyr Thr Gly His
            100                 105                 110

Ile Thr Gly His Arg Met Ala
        115

<210> SEQ ID NO 249
<211> LENGTH: 128
<212> TYPE: PRT
<213> ORGANISM: hepatitis C virus

<400> SEQUENCE: 249

Val Pro Tyr Arg Asn Ala Ser Gly Val Tyr His Val Thr Asn Asp Cys
1               5                   10                  15

Pro Asn Ser Ser Ile Val Tyr Glu Ala Asp Asn Leu Ile Leu His Ala
            20                  25                  30

Pro Gly Cys Val Pro Cys Val Arg Gln Asp Asn Val Ser Lys Cys Trp
            35                  40                  45

Val Gln Ile Thr Pro Thr Leu Ser Ala Pro Asn Leu Gly Ala Val Thr
```

-continued

```
            50                  55                  60
Ala Pro Leu Arg Arg Ala Val Asp Tyr Leu Ala Gly Gly Ala Ala Leu
 65                  70                  75                  80

Cys Ser Ala Leu Tyr Val Gly Asp Ala Cys Gly Ala Val Phe Leu Val
                 85                  90                  95

Gly Gln Met Phe Thr Tyr Arg Pro Arg Gln His Thr Thr Val Gln Asp
            100                 105                 110

Cys Asn Cys Ser Ile Tyr Ser Gly His Ile Thr Gly His Arg Met Ala
        115                 120                 125

<210> SEQ ID NO 250
<211> LENGTH: 68
<212> TYPE: PRT
<213> ORGANISM: hepatitis C virus

<400> SEQUENCE: 250

Ile Gly Gly Ala Gly Asn Asn Thr Leu His Cys Pro Thr Asp Cys Phe
  1               5                  10                  15

Arg Lys His Pro Asp Ala Thr Tyr Ser Arg Cys Gly Ser Gly Pro Trp
                 20                  25                  30

Ile Thr Pro Arg Cys Leu Val Asp Tyr Pro Tyr Arg Leu Trp His Tyr
             35                  40                  45

Pro Cys Thr Ile Asn Tyr Thr Ile Phe Lys Ile Arg Met Tyr Val Gly
         50                  55                  60

Gly Val Glu His
 65

<210> SEQ ID NO 251
<211> LENGTH: 68
<212> TYPE: PRT
<213> ORGANISM: hepatitis C virus

<400> SEQUENCE: 251

Ile Gly Gly Val Gly Asn Asn Thr Leu Leu Cys Pro Thr Asp Cys Phe
  1               5                  10                  15

Arg Lys Tyr Pro Glu Ala Thr Tyr Ser Arg Cys Gly Ser Gly Pro Arg
                 20                  25                  30

Ile Thr Pro Arg Cys Met Val Asp Tyr Pro Tyr Arg Leu Trp His Tyr
             35                  40                  45

Pro Cys Thr Ile Asn Tyr Thr Ile Phe Lys Val Arg Met Tyr Val Gly
         50                  55                  60

Gly Val Glu His
 65

<210> SEQ ID NO 252
<211> LENGTH: 68
<212> TYPE: PRT
<213> ORGANISM: hepatitis C virus

<400> SEQUENCE: 252

Ile Gly Gly Gly Gly Asn Asn Thr Leu His Cys Pro Thr Asp Cys Phe
  1               5                  10                  15

Arg Lys His Pro Glu Ala Thr Tyr Ser Arg Cys Gly Ser Gly Pro Trp
                 20                  25                  30

Ile Thr Pro Arg Cys Leu Val Asp Tyr Pro Tyr Arg Leu Trp His Tyr
             35                  40                  45

Pro Cys Thr Ile Asn Tyr Thr Ile Phe Lys Val Arg Met Tyr Val Gly
         50                  55                  60
```

Gly Val Glu His
65

<210> SEQ ID NO 253
<211> LENGTH: 68
<212> TYPE: PRT
<213> ORGANISM: hepatitis C virus

<400> SEQUENCE: 253

Ile Gly Gly Val Gly Asn Asn Thr Leu Val Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Met Val Asp Tyr Pro Tyr Arg Leu Trp His Tyr
        35                  40                  45

Pro Cys Thr Val Asn Phe Thr Val Phe Lys Val Arg Met Tyr Val Gly
    50                  55                  60

Gly Val Glu His
65

<210> SEQ ID NO 254
<211> LENGTH: 68
<212> TYPE: PRT
<213> ORGANISM: hepatitis C virus

<400> SEQUENCE: 254

Ile Gly Gly Val Gly Asn His Thr Leu Thr Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Leu Val Asp Tyr Pro Tyr Arg Leu Trp His Tyr
        35                  40                  45

Pro Cys Thr Phe Asn Phe Ser Ile Phe Lys Val Arg Met Tyr Val Gly
    50                  55                  60

Gly Val Glu His
65

<210> SEQ ID NO 255
<211> LENGTH: 68
<212> TYPE: PRT
<213> ORGANISM: hepatitis C virus

<400> SEQUENCE: 255

Ile Gly Gly Val Gly Asn Arg Thr Leu Ile Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Leu Val Asp Tyr Pro Tyr Arg Leu Trp His Tyr
        35                  40                  45

Pro Cys Thr Leu Asn Phe Ser Ile Phe Lys Val Arg Met Tyr Val Gly
    50                  55                  60

Gly Val Glu His
65

<210> SEQ ID NO 256
<211> LENGTH: 68
<212> TYPE: PRT
<213> ORGANISM: hepatitis C virus -continued

```
<400> SEQUENCE: 256

Ile Gly Gly Val Gly Asn Asn Thr Leu Thr Cys Pro Thr Asp Cys Phe
1               5                   10                  15

Arg Lys His Pro Glu Ala Thr Tyr Thr Arg Cys Gly Ser Gly Pro Trp
            20                  25                  30

Leu Thr Pro Arg Cys Leu Val Asp Tyr Pro Tyr Arg Leu Trp His Tyr
        35                  40                  45

Pro Cys Thr Val Asn Phe Ala Ile Phe Lys Val Arg Met Tyr Val Gly
    50                  55                  60

Gly Val Glu His
65

<210> SEQ ID NO 257
<211> LENGTH: 68
<212> TYPE: PRT
<213> ORGANISM: hepatitis C virus

<400> SEQUENCE: 257

Ile Gly Gly Val Gly Asn Leu Thr Leu Thr Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Ile Val Asp Tyr Pro Tyr Arg Leu Trp His Tyr
        35                  40                  45

Pro Cys Thr Val Asn Phe Thr Ile Phe Lys Val Arg Met Tyr Val Gly
    50                  55                  60

Gly Val Glu His
65

<210> SEQ ID NO 258
<211> LENGTH: 68
<212> TYPE: PRT
<213> ORGANISM: hepatitis C virus

<400> SEQUENCE: 258

Ile Gly Gly Val Gly Asn Leu Thr Leu Thr Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Ile Val Asp Tyr Pro Tyr Arg Leu Trp His Tyr
        35                  40                  45

Pro Cys Thr Val Asn Phe Thr Ile Phe Lys Val Arg Met Tyr Val Gly
    50                  55                  60

Gly Val Glu His
65

<210> SEQ ID NO 259
<211> LENGTH: 68
<212> TYPE: PRT
<213> ORGANISM: hepatitis C virus

<400> SEQUENCE: 259

Ile Gly Gly Val Gly Asn Asn Thr Leu Thr Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Met Val Asp Tyr Pro Tyr Arg Leu Trp His Tyr
        35                  40                  45
```

```
Pro Cys Thr Val Asn Phe Thr Ile Phe Lys Val Arg Met Tyr Val Gly
        50                  55                  60

Gly Val Glu His
65

<210> SEQ ID NO 260
<211> LENGTH: 68
<212> TYPE: PRT
<213> ORGANISM: hepatitis C virus

<400> SEQUENCE: 260

Ile Gly Gly Ala Gly Asn Asn Thr Leu Thr Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Met Val Asp Tyr Pro Tyr Arg Leu Trp His Tyr
        35                  40                  45

Pro Cys Thr Phe Asn Phe Thr Ile Phe Lys Ile Arg Met Tyr Val Gly
        50                  55                  60

Gly Val Glu His
65

<210> SEQ ID NO 261
<211> LENGTH: 68
<212> TYPE: PRT
<213> ORGANISM: hepatitis C virus

<400> SEQUENCE: 261

Ile Gly Gly Gly Gly Asn Asn Thr Leu Val Cys Pro Thr Asp Cys Phe
1               5                   10                  15

Arg Lys His Pro Glu Ala Thr Tyr Thr Lys Cys Gly Ser Gly Pro Trp
            20                  25                  30

Leu Thr Pro Arg Cys Met Val Asp Tyr Pro Tyr Arg Leu Trp His Tyr
        35                  40                  45

Pro Cys Thr Val Asn Phe Thr Ile Phe Lys Val Arg Met Tyr Val Gly
        50                  55                  60

Gly Val Glu His
65

<210> SEQ ID NO 262
<211> LENGTH: 68
<212> TYPE: PRT
<213> ORGANISM: hepatitis C virus

<400> SEQUENCE: 262

Ile Gly Gly Ser Gly Asn Asn Thr Leu Leu Cys Pro Thr Asp Cys Phe
1               5                   10                  15

Arg Lys His Pro Asp Ala Thr Tyr Ser Arg Cys Gly Ser Gly Pro Trp
            20                  25                  30

Leu Thr Pro Arg Cys Leu Val Asp Tyr Pro Tyr Arg Leu Trp His Tyr
        35                  40                  45

Pro Cys Thr Val Asn Tyr Thr Ile Phe Lys Ile Arg Met Phe Val Gly
        50                  55                  60

Gly Val Glu His
65

<210> SEQ ID NO 263
<211> LENGTH: 70
```

-continued

```
<212> TYPE: PRT
<213> ORGANISM: hepatitis C virus

<400> SEQUENCE: 263

Ile Arg Ala Asp Phe Asn Ala Ser Met Asp Leu Leu Cys Pro Thr Asp
1               5                   10                  15

Cys Phe Arg Lys His Pro Asp Thr Thr Tyr Ile Lys Cys Gly Ser Gly
            20                  25                  30

Pro Trp Leu Thr Pro Arg Cys Leu Ile Asp Tyr Pro Tyr Arg Leu Trp
        35                  40                  45

His Tyr Pro Cys Thr Val Asn Tyr Thr Ile Phe Lys Ile Arg Met Tyr
    50                  55                  60

Val Gly Gly Val Glu His
65                  70

<210> SEQ ID NO 264
<211> LENGTH: 70
<212> TYPE: PRT
<213> ORGANISM: hepatitis C virus

<400> SEQUENCE: 264

Ile Arg Lys Asp Tyr Asn Ser Thr Ile Asp Leu Leu Cys Pro Thr Asp
1               5                   10                  15

Cys Phe Arg Lys His Pro Asp Ala Thr Tyr Leu Lys Cys Gly Ala Gly
            20                  25                  30

Pro Trp Leu Thr Pro Arg Cys Leu Val Asp Tyr Pro Tyr Arg Leu Trp
        35                  40                  45

His Tyr Pro Cys Thr Val Asn Phe Thr Ile Phe Lys Ala Arg Met Tyr
    50                  55                  60

Val Gly Gly Val Glu His
65                  70

<210> SEQ ID NO 265
<211> LENGTH: 278
<212> TYPE: PRT
<213> ORGANISM: hepatitis C virus

<400> SEQUENCE: 265

Gly Val Ala Lys Ala Val Asp Phe Ile Pro Val Glu Asn Leu Glu Thr
1               5                   10                  15

Thr Met Arg Ser Pro Val Phe Thr Asp Asn Ser Ser Pro Pro Val Val
            20                  25                  30

Pro Gln Ser Phe Gln Val Ala His Leu His Ala Pro Thr Gly Ser Gly
        35                  40                  45

Lys Ser Thr Lys Val Pro Ala Ala Tyr Ala Ala Gln Gly Tyr Lys Val
    50                  55                  60

Leu Val Leu Asn Pro Ser Val Ala Ala Thr Leu Gly Phe Gly Ala Tyr
65                  70                  75                  80

Met Ser Lys Ala His Gly Ile Asp Pro Asn Ile Arg Thr Gly Val Arg
            85                  90                  95

Thr Ile Thr Thr Gly Ser Pro Ile Thr Tyr Ser Thr Tyr Gly Lys Phe
        100                 105                 110

Leu Ala Asp Gly Gly Cys Ser Gly Gly Ala Tyr Asp Ile Ile Ile Cys
    115                 120                 125

Asp Glu Cys His Ser Thr Asp Ala Thr Ser Ile Leu Gly Ile Gly Thr
    130                 135                 140

Val Leu Asp Gln Ala Glu Thr Ala Gly Ala Arg Leu Val Val Leu Ala
```

-continued

```
145                 150                 155                 160
Thr Ala Thr Pro Pro Gly Ser Val Thr Val Pro His Pro Asn Ile Glu
                165                 170                 175

Glu Val Ala Leu Ser Thr Thr Gly Glu Ile Pro Phe Tyr Gly Lys Ala
            180                 185                 190

Ile Pro Leu Glu Val Ile Lys Gly Gly Arg His Leu Ile Phe Cys His
        195                 200                 205

Ser Lys Lys Lys Cys Asp Glu Leu Ala Ala Lys Leu Val Ala Leu Gly
    210                 215                 220

Ile Asn Ala Val Ala Tyr Tyr Arg Gly Leu Asp Val Ser Val Ile Pro
225                 230                 235                 240

Thr Ser Gly Asp Val Val Val Ala Thr Asp Ala Leu Met Thr Gly
                245                 250                 255

Tyr Thr Gly Asp Phe Asp Ser Val Ile Asp Cys Asn Thr Cys Val Thr
                260                 265                 270

Gln Thr Val Asp Phe Ser
        275

<210> SEQ ID NO 266
<211> LENGTH: 278
<212> TYPE: PRT
<213> ORGANISM: hepatitis C virus

<400> SEQUENCE: 266

Gly Val Ala Lys Ala Val Asp Phe Ile Pro Val Glu Asn Leu Glu Thr
1               5                   10                  15

Thr Met Arg Ser Pro Val Phe Thr Asp Asn Ser Ser Pro Pro Ala Val
            20                  25                  30

Pro Gln Ser Phe Gln Val Ala His Leu His Ala Pro Thr Gly Ser Gly
        35                  40                  45

Lys Ser Thr Lys Val Pro Ala Ala Tyr Ala Ala Lys Gly Tyr Lys Val
    50                  55                  60

Leu Val Leu Asn Pro Ser Val Ala Ala Thr Leu Gly Phe Gly Ala Tyr
65                  70                  75                  80

Met Ser Lys Ala His Gly Val Asp Pro Asn Ile Arg Thr Gly Val Arg
                85                  90                  95

Thr Ile Thr Thr Gly Ser Pro Ile Thr Tyr Ser Thr Tyr Gly Lys Phe
            100                 105                 110

Leu Ala Asp Ala Gly Cys Ser Gly Gly Ala Tyr Asp Ile Ile Ile Cys
        115                 120                 125

Asp Glu Cys His Ser Thr Asp Ala Thr Ser Ile Ser Gly Ile Gly Thr
    130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Ser His Pro Asn Ile Glu
                165                 170                 175

Glu Val Ala Leu Ser Thr Thr Gly Glu Ile Pro Phe Tyr Gly Lys Ala
            180                 185                 190

Ile Pro Leu Glu Val Ile Lys Gly Gly Arg His Leu Ile Phe Cys His
        195                 200                 205

Ser Lys Lys Lys Cys Asp Glu Leu Ala Ala Lys Leu Val Ala Leu Gly
    210                 215                 220

Ile Asn Ala Val Ala Tyr Tyr Arg Gly Leu Asp Val Ser Val Ile Pro
225                 230                 235                 240
```

```
Thr Ser Gly Asp Val Val Val Ser Thr Asp Ala Leu Met Thr Gly
                245                 250                 255

Phe Thr Gly Asp Phe Asp Ser Val Ile Asp Cys Asn Thr Cys Val Thr
                260                 265                 270

Gln Thr Val Asp Phe Ser
        275

<210> SEQ ID NO 267
<211> LENGTH: 278
<212> TYPE: PRT
<213> ORGANISM: hepatitis C virus

<400> SEQUENCE: 267

Gly Val Ala Lys Ala Val Asp Phe Ile Pro Val Glu Ser Leu Glu Thr
1               5                   10                  15

Thr Met Arg Ser Pro Val Phe Thr Asp Asn Ser Ser Pro Pro Ala Val
                20                  25                  30

Pro Gln Ser Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
50                  55                  60

Leu Val Leu Asn Pro Ser Val Ala Ala Thr Leu Gly Phe Gly Ala Tyr
65                  70                  75                  80

Met Ser Lys Ala His Gly Ile Asp Pro Asn Ile Arg Thr Gly Val Arg
                85                  90                  95

Thr Ile Thr Thr Gly Ser Pro Ile Thr Tyr Ser Thr Tyr Gly Lys Phe
            100                 105                 110

Leu Ala Asp Gly Gly Cys Ser Gly Gly Ala Tyr Asp Ile Ile Ile Cys
        115                 120                 125

Asp Glu Cys His Ser Thr Asp Ala Thr Ser Val Leu Gly Ile Gly Thr
130                 135                 140

Val Leu Asp Gln Ala Glu Thr Ala Gly Ala Arg Leu Val Val Leu Ala
145                 150                 155                 160

Thr Ala Thr Pro Pro Gly Ser Ile Thr Val Pro His Ala Asn Ile Glu
                165                 170                 175

Glu Val Ala Leu Ser Thr Thr Gly Glu Ile Pro Phe Tyr Gly Lys Ala
            180                 185                 190

Ile Pro Leu Glu Ala Ile Lys Gly Gly Arg His Leu Ile Phe Cys His
        195                 200                 205

Ser Lys Lys Lys Cys Asp Glu Leu Ala Ala Lys Leu Val Ala Leu Gly
210                 215                 220

Val Asn Ala Val Ala Tyr Tyr Arg Gly Leu Asp Val Ser Val Ile Pro
225                 230                 235                 240

Thr Ser Gly Asp Val Val Val Ala Thr Asp Ala Leu Met Thr Gly
                245                 250                 255

Tyr Thr Gly Asp Phe Asp Ser Val Ile Asp Cys Asn Thr Cys Val Thr
                260                 265                 270

Gln Thr Val Asp Phe Ser
        275

<210> SEQ ID NO 268
<211> LENGTH: 278
<212> TYPE: PRT
<213> ORGANISM: hepatitis C virus

<400> SEQUENCE: 268
```

Gly Val Ala Lys Ala Val Asp Phe Ile Pro Val Glu Ser Met Glu Thr
1               5                   10                  15

Thr Met Arg Ser Pro Val Phe Thr Asp Asn Ser Ser Pro Pro Ala Val
                20                  25                  30

Pro Gln Thr Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
        50                  55                  60

Leu Val Leu Asn Pro Ser Val Ala Ala Thr Leu Gly Phe Gly Ala Tyr
65                  70                  75                  80

Met Ser Lys Ala His Gly Ile Glu Pro Asn Ile Arg Thr Gly Val Arg
                85                  90                  95

Thr Ile Thr Thr Gly Gly Pro Ile Thr Tyr Ser Thr Tyr Cys Lys Phe
            100                 105                 110

Leu Ala Asp Gly Gly Cys Ser Gly Gly Ala Tyr Asp Ile Ile Ile Cys
            115                 120                 125

Asp Glu Cys His Ser Thr Asp Ser Thr Thr Ile Leu Gly Ile Gly Thr
            130                 135                 140

Val Leu Asp Gln Ala Glu Thr Ala Gly Ala Arg Leu Val Val Leu Ala
145                 150                 155                 160

Thr Ala Thr Pro Pro Gly Ser Ile Thr Val Pro His Pro Asn Ile Glu
                165                 170                 175

Glu Val Ala Leu Ser Asn Thr Gly Glu Ile Pro Phe Tyr Gly Lys Ala
                180                 185                 190

Ile Pro Ile Glu Ala Ile Lys Gly Gly Arg His Leu Ile Phe Cys His
            195                 200                 205

Ser Lys Lys Lys Cys Asp Glu Leu Ala Ala Lys Leu Thr Gly Leu Gly
            210                 215                 220

Leu Asn Ala Val Ala Tyr Tyr Arg Gly Leu Asp Val Ser Val Ile Pro
225                 230                 235                 240

Thr Ser Gly Asp Val Val Val Ala Thr Asp Ala Leu Met Thr Gly
                245                 250                 255

Phe Thr Gly Asp Phe Asp Ser Val Ile Asp Cys Asn Thr Cys Val Thr
                260                 265                 270

Gln Thr Val Asp Phe Ser
                275

<210> SEQ ID NO 269
<211> LENGTH: 278
<212> TYPE: PRT
<213> ORGANISM: hepatitis C virus

<400> SEQUENCE: 269

Gly Val Ala Lys Ala Val Asp Phe Ile Pro Val Glu Ser Met Glu Thr
1               5                   10                  15

Thr Met Arg Ser Pro Val Phe Thr Asp Asn Ser Ser Pro Pro Ala Val
                20                  25                  30

Pro Gln Thr Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
        50                  55                  60

Leu Val Leu Asn Pro Ser Val Ala Ala Thr Leu Gly Phe Gly Ala Tyr
65                  70                  75                  80

Met Pro Lys Ala His Gly Ile Asp Pro Asn Ile Arg Thr Gly Val Arg
                85                  90                  95

-continued

```
Thr Ile Thr Thr Gly Gly Pro Ile Thr Tyr Ser Thr Tyr Gly Lys Phe
            100                 105                 110

Leu Ala Asp Gly Gly Cys Ser Gly Gly Ala Tyr Asp Ile Ile Ile Cys
            115                 120                 125

Asp Glu Cys His Ser Thr Asp Ser Thr Thr Ile Leu Gly Ile Gly Thr
            130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Ile Gly Leu Ser Asn Asn Gly Glu Ile Pro Phe Tyr Gly Lys Ala
            180                 185                 190

Ile Pro Ile Glu Ala Ile Lys Gly Gly Arg His Leu Ile Phe Cys His
            195                 200                 205

Ser Lys Lys Lys Cys Asp Glu Leu Ala Ala Lys Leu Thr Gly Leu Gly
            210                 215                 220

Leu Asn Ala Val Ala Tyr Tyr Arg Gly Leu Asp Val Ser Val Ile Pro
225                 230                 235                 240

Pro Ile Gly Asp Val Ala Val Ala Thr Asp Ala Leu Met Thr Gly
                245                 250                 255

Phe Thr Gly Asp Phe Asp Ser Val Ile Asp Cys Asn Thr Cys Val Thr
                260                 265                 270

Gln Thr Val Asp Phe Ser
            275

<210> SEQ ID NO 270
<211> LENGTH: 278
<212> TYPE: PRT
<213> ORGANISM: hepatitis C virus

<400> SEQUENCE: 270

Gly Val Ala Lys Ala Val Asp Phe Ile Pro Val Glu Ser Met Glu Thr
1               5                   10                  15

Thr Met Arg Ser Pro Val Phe Thr Asp Asn Ser Ser Pro Pro Ala Val
            20                  25                  30

Pro Gln Thr Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
            50                  55                  60

Leu Val Leu Asn Pro Ser Val Ala Ala Thr Leu Gly Phe Gly Ala Tyr
65                  70                  75                  80

Met Ser Lys Ala His Gly Ile Asp Pro Asn Ile Arg Thr Gly Val Arg
            85                  90                  95

Thr Ile Thr Thr Gly Gly Ser Ile Thr Tyr Ser Thr Tyr Gly Lys Phe
            100                 105                 110

Leu Ala Asp Gly Gly Cys Ser Gly Gly Ala Tyr Asp Ile Ile Ile Cys
            115                 120                 125

Asp Glu Cys His Ser Thr Asp Ser Thr Thr Ile Leu Gly Ile Gly Thr
            130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Ile Gly Leu Ser Asn Asn Gly Glu Ile Pro Phe Tyr Gly Lys Ala
```

-continued

```
                180                 185                 190
Ile Pro Ile Glu Ala Ile Lys Gly Gly Arg His Leu Ile Phe Cys His
            195                 200                 205

Ser Lys Lys Cys Asp Glu Leu Ala Ala Lys Leu Thr Gly Leu Gly
    210                 215                 220

Leu Asn Ala Val Ala Tyr Tyr Arg Gly Leu Asp Val Ser Val Ile Pro
225                 230                 235                 240

Pro Ile Gly Asp Val Val Val Ala Thr Asp Ala Leu Met Thr Gly
            245                 250                 255

Phe Thr Gly Asp Phe Asp Ser Val Ile Asp Cys Asn Thr Cys Val Thr
            260                 265                 270

Gln Thr Val Asp Phe Ser
            275

<210> SEQ ID NO 271
<211> LENGTH: 278
<212> TYPE: PRT
<213> ORGANISM: hepatitis C virus

<400> SEQUENCE: 271

Gly Val Ala Lys Ala Val Asp Phe Ile Pro Val Glu Thr Met Glu Thr
1               5                   10                  15

Thr Met Arg Ser Pro Val Phe Thr Asp Asn Ser Ser Pro Pro Ala Val
                20                  25                  30

Pro Gln Thr Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
    50                  55                  60

Leu Val Leu Asn Pro Ser Val Ala Ala Thr Leu Gly Phe Gly Ala Tyr
65                  70                  75                  80

Met Ser Lys Ala His Gly Val Asp Pro Asn Ile Arg Thr Gly Val Arg
                85                  90                  95

Thr Ile Thr Thr Gly Ala Pro Ile Thr Tyr Ser Thr Tyr Gly Lys Phe
            100                 105                 110

Leu Ala Asp Gly Gly Cys Ser Gly Gly Ala Tyr Asp Ile Ile Ile Cys
    115                 120                 125

Asp Glu Cys His Ser Thr Asp Ser Thr Thr Ile Leu Gly Ile Gly Thr
130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Val Ala Leu Ser Asn Thr Gly Glu Ile Pro Phe Tyr Gly Lys Ala
            180                 185                 190

Ile Pro Ile Glu Ala Ile Arg Gly Gly Arg His Leu Ile Phe Cys His
            195                 200                 205

Ser Lys Lys Cys Asp Glu Leu Ala Ala Lys Leu Ser Ser Leu Gly
    210                 215                 220

Leu Asn Ala Val Ala Tyr Tyr Arg Gly Leu Asp Val Ser Val Ile Pro
225                 230                 235                 240

Ser Ser Gly Asp Val Val Val Ala Thr Asp Ala Leu Met Thr Gly
            245                 250                 255

Phe Thr Gly Asp Phe Asp Ser Val Ile Asp Cys Asn Thr Cys Val Thr
            260                 265                 270
```

-continued

```
Gln Thr Val Asp Phe Ser
        275

<210> SEQ ID NO 272
<211> LENGTH: 278
<212> TYPE: PRT
<213> ORGANISM: hepatitis C virus

<400> SEQUENCE: 272

Gly Val Ala Lys Ala Val Asp Phe Ile Pro Val Glu Ser Met Glu Thr
1               5                   10                  15

Thr Met Arg Ser Pro Val Phe Thr Asp Asn Ser Ser Pro Pro Ala Val
            20                  25                  30

Pro Gln Thr Phe Gln Val Ala His Leu His Ala Pro Thr Gly Ser Gly
        35                  40                  45

Lys Ser Thr Lys Val Pro Ala Ala Tyr Ala Ala Gln Gly Tyr Lys Val
    50                  55                  60

Leu Val Leu Asn Pro Ser Val Ala Ala Thr Leu Gly Phe Gly Ala Tyr
65                  70                  75                  80

Met Ser Lys Ala His Gly Thr Asp Pro Asn Ile Arg Thr Gly Val Arg
                85                  90                  95

Thr Ile Thr Thr Gly Ala Pro Ile Thr Tyr Ser Thr Tyr Gly Lys Phe
            100                 105                 110

Leu Ala Asp Gly Gly Cys Ser Gly Gly Ala Tyr Asp Ile Ile Ile Cys
        115                 120                 125

Asp Glu Cys His Ser Thr Asp Ser Thr Thr Ile Leu Gly Ile Gly Thr
    130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Val Ala Leu Ser Asn Thr Gly Glu Ile Pro Phe Tyr Gly Lys Ala
            180                 185                 190

Ile Pro Leu Glu Ala Ile Lys Gly Gly Arg His Leu Ile Phe Cys His
        195                 200                 205

Ser Lys Lys Lys Cys Asp Glu Leu Ala Ala Lys Leu Ser Gly Leu Gly
    210                 215                 220

Ile Asn Ala Val Ala Tyr Tyr Arg Gly Leu Asp Val Ser Val Ile Pro
225                 230                 235                 240

Thr Ser Gly Asp Val Val Ile Val Ala Thr Asp Ala Leu Met Thr Gly
                245                 250                 255

Tyr Thr Gly Asp Phe Asp Ser Val Ile Asp Cys Asn Thr Cys Val Thr
            260                 265                 270

Gln Thr Val Asp Phe Ser
        275

<210> SEQ ID NO 273
<211> LENGTH: 278
<212> TYPE: PRT
<213> ORGANISM: hepatitis C virus
<220> FEATURE:
<221> NAME/KEY: MISC_FEATURE
<222> LOCATION: (60)..(60)
<223> OTHER INFORMATION: Xaa is any amino acid

<400> SEQUENCE: 273

Gly Val Ala Lys Ala Val Asp Phe Ile Pro Val Glu Ser Met Glu Thr
1               5                   10                  15
```

```
Thr Met Arg Ser Pro Val Phe Thr Asp Asn Ser Ser Pro Pro Ala Val
                20                  25                  30

Pro Gln Thr Phe Gln Val Ala His Leu His Ala Pro Thr Gly Ser Gly
            35                  40                  45

Lys Ser Thr Lys Val Pro Ala Ala Tyr Ala Ala Xaa Gly Tyr Lys Val
 50                  55                  60

Leu Val Leu Asn Pro Ser Val Ala Ala Thr Leu Gly Phe Gly Ala Tyr
 65                  70                  75                  80

Met Ser Lys Ala His Gly Thr Asp Pro Asn Ile Arg Thr Gly Val Arg
                85                  90                  95

Thr Ile Thr Thr Gly Gly Pro Ile Thr Tyr Ser Thr Tyr Gly Lys Phe
               100                 105                 110

Leu Ala Asp Gly Gly Cys Ser Gly Gly Ala Tyr Asp Ile Ile Ile Cys
               115                 120                 125

Asp Glu Cys His Ser Thr Asp Ser Thr Thr Ile Leu Gly Ile Gly Thr
           130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Val Ala Leu Ser Asn Thr Gly Glu Ile Pro Phe Tyr Gly Lys Ala
                180                 185                 190

Ile Pro Ile Glu Val Ile Lys Gly Gly Arg His Leu Ile Phe Cys His
                195                 200                 205

Ser Lys Lys Lys Cys Asp Glu Leu Ala Ala Lys Leu Ser Gly Leu Gly
            210                 215                 220

Ile Asn Ala Val Ala Tyr Tyr Arg Gly Leu Asp Val Ser Val Ile Pro
225                 230                 235                 240

Thr Ser Gly Asp Val Val Val Ala Thr Asp Ala Leu Met Thr Gly
                245                 250                 255

Tyr Thr Gly Asp Phe Asp Ser Val Ile Asp Cys Asn Thr Cys Val Thr
                260                 265                 270

Gln Thr Val Asp Phe Ser
            275

<210> SEQ ID NO 274
<211> LENGTH: 278
<212> TYPE: PRT
<213> ORGANISM: hepatitis C virus

<400> SEQUENCE: 274

Gly Val Ala Lys Ala Val Asp Phe Val Pro Val Glu Ser Met Glu Thr
 1               5                  10                  15

Thr Met Arg Ser Pro Val Phe Thr Asp Asn Ser Ser Pro Pro Ala Val
                20                  25                  30

Pro Gln Ser Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
 50                  55                  60

Leu Val Leu Asn Pro Ser Val Ala Ala Thr Leu Gly Phe Gly Ala Tyr
 65                  70                  75                  80

Met Ser Lys Ala His Gly Ile Asp Pro Asn Ile Arg Thr Gly Val Arg
                85                  90                  95

Thr Ile Thr Thr Gly Ala Pro Val Thr Tyr Ser Thr Tyr Gly Lys Phe
```

-continued

```
                100                 105                 110
Leu Ala Asp Gly Gly Cys Ser Gly Gly Ala Tyr Asp Ile Ile Ile Cys
            115                 120                 125

Asp Glu Cys His Ser Thr Asp Ser Thr Thr Ile Leu Gly Ile Gly Thr
        130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Val Ala Leu Ser Asn Thr Gly Glu Ile Pro Phe Tyr Gly Lys Ala
            180                 185                 190

Ile Pro Ile Glu Ala Ile Arg Gly Gly Arg His Leu Ile Phe Cys His
            195                 200                 205

Ser Lys Lys Lys Cys Asp Glu Leu Ala Ala Lys Leu Ser Gly Leu Gly
        210                 215                 220

Ile Asn Ala Val Ala Tyr Tyr Arg Gly Leu Asp Val Ser Val Ile Pro
225                 230                 235                 240

Thr Ile Gly Asp Val Val Val Ala Thr Asp Ala Leu Met Thr Gly
                245                 250                 255

Tyr Thr Gly Asp Phe Asp Ser Val Ile Asp Cys Asn Thr Cys Val Thr
                260                 265                 270

Gln Thr Val Asp Phe Ser
        275

<210> SEQ ID NO 275
<211> LENGTH: 278
<212> TYPE: PRT
<213> ORGANISM: hepatitis C virus

<400> SEQUENCE: 275

Gly Val Ala Lys Ala Val Asp Phe Ile Pro Val Glu Ser Met Glu Thr
1               5                   10                  15

Thr Met Arg Ser Pro Val Phe Thr Asp Asn Ser Ser Pro Pro Ala Val
            20                  25                  30

Pro Gln Thr Phe Gln Val Ala His Leu His Ala Pro Thr Gly Ser Gly
        35                  40                  45

Lys Ser Thr Lys Val Pro Ala Ala Tyr Ala Ala Gln Gly Tyr Lys Val
    50                  55                  60

Leu Val Leu Asn Pro Ser Val Ala Ala Thr Leu Gly Phe Gly Ala Tyr
65                  70                  75                  80

Met Ser Lys Ala His Gly Val Asp Pro Asn Ile Ser Thr Gly Val Arg
                85                  90                  95

Thr Ile Thr Thr Gly Ala Pro Ile Thr Tyr Ser Thr Tyr Gly Lys Phe
            100                 105                 110

Leu Ala Asp Gly Gly Cys Ser Gly Gly Ala Tyr Asp Ile Ile Ile Cys
        115                 120                 125

Asp Glu Cys His Ser Thr Asp Ser Thr Ser Ile Leu Gly Ile Gly Thr
    130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Val Ala Leu Pro Asn Thr Gly Glu Ile Pro Phe Tyr Gly Lys Ala
            180                 185                 190
```

```
Ile Pro Leu Glu Thr Ile Lys Gly Gly Arg His Leu Ile Phe Cys His
        195                 200                 205

Ser Lys Lys Lys Cys Asp Glu Leu Ala Ala Lys Leu Ser Ala Leu Gly
    210                 215                 220

Val Asn Ala Val Ala Tyr Tyr Arg Gly Leu Asp Val Ser Val Ile Pro
225                 230                 235                 240

Thr Ser Gly Asp Val Val Val Ala Thr Asp Ala Leu Met Thr Gly
                245                 250                 255

Tyr Thr Gly Asp Phe Asp Ser Val Ile Asp Cys Asn Thr Cys Val Thr
                260                 265                 270

Gln Thr Val Asp Phe Ser
            275

<210> SEQ ID NO 276
<211> LENGTH: 278
<212> TYPE: PRT
<213> ORGANISM: hepatitis C virus

<400> SEQUENCE: 276

Gly Val Ala Lys Ala Val Asp Phe Val Pro Val Glu Ser Met Glu Thr
1               5                   10                  15

Thr Met Arg Ser Pro Val Phe Thr Asp Asn Ser Ser Pro Pro Ala Val
            20                  25                  30

Pro Gln Ala Phe Gln Val Ala His Leu His Ala Pro Thr Gly Ser Gly
        35                  40                  45

Lys Ser Thr Lys Val Pro Ala Ala Tyr Ala Ala Gln Gly Tyr Lys Val
    50                  55                  60

Leu Val Leu Asn Pro Ser Val Ala Thr Leu Gly Phe Gly Ala Tyr
65                  70                  75                  80

Met Ser Lys Ala His Gly Val Asp Pro Asn Ile Arg Thr Gly Val Arg
                85                  90                  95

Thr Ile Thr Thr Gly Ala Pro Ile Thr Tyr Ser Thr Tyr Gly Lys Phe
            100                 105                 110

Leu Ala Asp Gly Gly Cys Ser Gly Gly Ala Tyr Asp Ile Ile Met Cys
        115                 120                 125

Asp Glu Cys His Ser Thr Asp Ser Thr Thr Ile Leu Gly Ile Gly Thr
130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
                165                 170                 175

Glu Ile Ala Leu Ser Asn Thr Gly Glu Ile Pro Phe Tyr Gly Lys Ala
            180                 185                 190

Ile Pro Ile Glu Thr Ile Lys Gly Gly Arg His Leu Ile Phe Cys His
        195                 200                 205

Ser Lys Lys Lys Cys Asp Glu Leu Ala Ala Lys Leu Ser Ala Leu Gly
    210                 215                 220

Ile His Ala Val Ala Tyr Tyr Arg Gly Leu Asp Val Ser Val Ile Pro
225                 230                 235                 240

Ala Ser Gly Asn Val Val Val Ala Thr Asp Ala Leu Met Thr Gly
                245                 250                 255

Phe Thr Gly Asp Phe Asp Ser Val Ile Asp Cys Asn Thr Cys Val Thr
                260                 265                 270

Gln Thr Val Asp Phe Ser
            275
```

```
<210> SEQ ID NO 277
<211> LENGTH: 277
<212> TYPE: PRT
<213> ORGANISM: hepatitis C virus

<400> SEQUENCE: 277

Gly Val Ala Lys Ser Ile Asp Phe Ile Pro Val Glu Thr Leu Asp Ile
1               5                   10                  15

Val Thr Arg Ser Pro Thr Phe Ser Asp Asn Ser Thr Pro Pro Ala Val
            20                  25                  30

Pro Gln Thr Tyr Gln Val Gly Tyr Leu His Ala Pro Thr Gly Ser Gly
        35                  40                  45

Lys Ser Thr Lys Val Pro Val Ala Tyr Ala Ala Gln Gly Tyr Lys Val
    50                  55                  60

Leu Val Leu Asn Pro Ser Val Ala Ala Thr Leu Gly Phe Gly Ala Tyr
65                  70                  75                  80

Leu Ser Lys Ala His Gly Ile Pro Asn Ile Arg Thr Gly Val Arg Thr
                85                  90                  95

Val Thr Thr Gly Ala Pro Ile Thr Tyr Ser Thr Tyr Gly Lys Phe Leu
            100                 105                 110

Ala Asp Gly Gly Cys Ala Gly Gly Ala Tyr Asp Ile Ile Ile Cys Asp
        115                 120                 125

Glu Cys His Ala Val Asp Ser Thr Thr Ile Leu Gly Ile Gly Thr Val
    130                 135                 140

Leu Asp Gln Ala Glu Thr Ala Gly Val Arg Leu Thr Val Leu Ala Thr
145                 150                 155                 160

Ala Thr Pro Pro Gly Ser Val Thr Thr Pro His Pro Asn Ile Glu Glu
                165                 170                 175

Val Ala Leu Gly Gln Glu Gly Glu Ile Pro Phe Tyr Gly Arg Ala Ile
            180                 185                 190

Pro Leu Ser Tyr Ile Lys Gly Gly Arg His Leu Ile Phe Cys His Ser
        195                 200                 205

Lys Lys Lys Cys Asp Glu Leu Ala Ala Ala Leu Arg Gly Met Gly Leu
    210                 215                 220

Asn Ala Val Ala Tyr Tyr Arg Gly Leu Asp Val Ser Val Ile Pro Thr
225                 230                 235                 240

Gln Gly Asp Val Val Val Ala Thr Asp Ala Leu Met Thr Gly Phe
                245                 250                 255

Thr Gly Asp Phe Asp Ser Val Ile Asp Cys Asn Val Ala Val Thr Gln
            260                 265                 270

Val Val Asp Phe Ser
        275

<210> SEQ ID NO 278
<211> LENGTH: 277
<212> TYPE: PRT
<213> ORGANISM: hepatitis C virus

<400> SEQUENCE: 278

Gly Val Ala Lys Ser Ile Asp Phe Ile Pro Val Glu Ser Leu Asp Val
1               5                   10                  15

Ala Thr Arg Thr Pro Ser Phe Ser Asp Asn Ser Thr Pro Pro Ala Val
            20                  25                  30

Pro Gln Ser Tyr Gln Val Gly Tyr Leu His Ala Pro Thr Gly Ser Gly
        35                  40                  45
```

```
Lys Ser Thr Lys Val Pro Ala Ala Tyr Ala Ser Gln Gly Tyr Lys Val
    50                  55                  60
Leu Val Leu Asn Pro Ser Val Ala Ala Thr Leu Gly Phe Gly Ala Tyr
65                  70                  75                  80
Met Ser Lys Ala His Gly Ile Pro Asn Ile Arg Thr Gly Val Arg Thr
                85                  90                  95
Val Thr Thr Gly Asp Ser Ile Thr Tyr Ser Thr Tyr Gly Lys Phe Ile
                100                 105                 110
Ala Asp Gly Gly Cys Ala Ala Gly Ala Tyr Asp Ile Ile Ile Cys Asp
            115                 120                 125
Glu Cys His Ser Val Asp Ala Thr Thr Ile Leu Gly Ile Gly Thr Val
    130                 135                 140
Leu Asp Gln Ala Glu Thr Ala Gly Val Arg Leu Val Val Leu Ala Thr
145                 150                 155                 160
Ala Thr Pro Pro Gly Thr Val Thr Thr Pro His Ser Asn Ile Glu Glu
                165                 170                 175
Val Ala Leu Gly His Glu Gly Glu Ile Pro Phe Tyr Gly Lys Ala Ile
                180                 185                 190
Pro Leu Ala Phe Ile Lys Gly Gly Arg His Leu Ile Phe Cys His Ser
            195                 200                 205
Lys Lys Lys Cys Asp Glu Leu Ala Ala Ala Leu Arg Gly Met Gly Val
    210                 215                 220
Asn Ala Val Ala Tyr Tyr Arg Gly Leu Asp Val Ser Val Ile Pro Thr
225                 230                 235                 240
Gln Gly Asp Val Val Val Val Ala Thr Asp Ala Leu Met Thr Gly Tyr
                245                 250                 255
Thr Gly Asp Phe Asp Ser Val Ile Asp Cys Asn Val Ala Val Ser Gln
                260                 265                 270
Ile Val Asp Phe Ser
            275

<210> SEQ ID NO 279
<211> LENGTH: 149
<212> TYPE: PRT
<213> ORGANISM: hepatitis C virus
<220> FEATURE:
<221> NAME/KEY: MISC_FEATURE
<222> LOCATION: (30)..(30)
<223> OTHER INFORMATION: Xaa is any amino acid
<220> FEATURE:
<221> NAME/KEY: MISC_FEATURE
<222> LOCATION: (91)..(91)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is any amino acid
<220> FEATURE:
<221> NAME/KEY: MISC_FEATURE
<222> LOCATION: (109)..(109)
<223> OTHER INFORMATION: Xaa is any amino acid
<220> FEATURE:
<221> NAME/KEY: MISC_FEATURE
<222> LOCATION: (110)..(110)
<223> OTHER INFORMATION: Xaa is any amino acid
<220> FEATURE:
<221> NAME/KEY: MISC_FEATURE
<222> LOCATION: (119)..(119)
<223> OTHER INFORMATION: Xaa is any amino acid

<400> SEQUENCE: 279

Asp Gly Val Asn Tyr Ala Thr Gly Asn Leu Pro Gly Cys Ser Phe Ser
```

```
                1               5                   10                  15
            Ile Phe Leu Leu Ala Leu Leu Ser Cys Leu Thr Val Pro Xaa Thr Ala
                            20                  25                  30

His Glu Val Arg Asn Ala Ser Gly Val Tyr His Val Thr Asn Asp Cys
                        35                  40                  45

Ser Asn Ser Ser Ile Ile Tyr Glu Met Asp Gly Met Ile Met His Tyr
                    50                  55                  60

Pro Gly Cys Val Pro Cys Val Arg Glu Asp Asn His Leu Arg Cys Trp
            65                  70                  75                  80

Met Ala Leu Thr Pro Thr Leu Ala Val Lys Xaa Ala Ser Val Pro Thr
                            85                  90                  95

Xaa Ala Ile Arg Arg His Val Asp Leu Leu Val Gly Xaa Xaa Thr Phe
                        100                 105                 110

Cys Ser Ala Met Tyr Val Xaa Asp Leu Cys Gly Ser Val Phe Leu Ala
                    115                 120                 125

Gly Gln Leu Phe Thr Phe Ser Pro Arg Met His His Thr Thr Gln Glu
                130                 135                 140

Cys Asn Cys Ser Ile
            145

<210> SEQ ID NO 280
            <211> LENGTH: 149
            <212> TYPE: PRT
            <213> ORGANISM: hepatitis C virus
            <220> FEATURE:
            <221> NAME/KEY: MISC_FEATURE
            <222> LOCATION: (82)..(82)
            <223> OTHER INFORMATION: Xaa is any amino acid

<400> SEQUENCE: 280

Asp Gly Val Asn Tyr Ala Thr Gly Asn Leu Pro Gly Cys Ser Phe Ser
            1               5                   10                  15

Ile Phe Leu Leu Ala Phe Leu Ser Cys Leu Thr Val Pro Thr Thr Ala
                            20                  25                  30

His Glu Val Arg Asn Ala Ser Gly Val Tyr His Leu Thr Asn Asp Cys
                        35                  40                  45

Ser Asn Ser Ser Ile Ile Tyr Glu Met Ser Gly Met Ile Leu His Ala
                    50                  55                  60

Pro Gly Cys Val Pro Cys Val Arg Glu Asn Asn Ser Ser Arg Cys Trp
            65                  70                  75                  80

Met Xaa Leu Thr Pro Thr Leu Ala Val Lys Asp Ala Asn Val Pro Thr
                            85                  90                  95

Ala Ala Ile Arg Arg His Val Asp Leu Leu Val Gly Thr Ala Ala Phe
                        100                 105                 110

Arg Ser Ala Met Tyr Val Gly Asp Leu Cys Gly Ser Val Phe Leu Val
                    115                 120                 125

Gly Gln Leu Phe Thr Phe Ser Pro Arg Leu Tyr His Thr Thr Gln Glu
                130                 135                 140

Cys Asn Cys Ser Ile
            145

<210> SEQ ID NO 281
            <211> LENGTH: 37
            <212> TYPE: PRT
            <213> ORGANISM: hepatitis C virus
            <220> FEATURE:
            <221> NAME/KEY: MISC_FEATURE
            <222> LOCATION: (1)..(1)
```

```
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (28)..(29)
<223> OTHER INFORMATION: Xaa is any amino acid

<400> SEQUENCE: 281

Xaa Arg Ser Arg Asn Asn Gly Lys Val Asn Asp Thr Leu Xaa Cys Gly
 1               5                  10                  15

Phe Ala Asp Leu Met Gly Tyr Ile Pro Leu Val Xaa Xaa Pro Leu Gly
            20                  25                  30

Gly Ile Glu Arg Ala
        35

<210> SEQ ID NO 282
<211> LENGTH: 15
<212> TYPE: PRT
<213> ORGANISM: hepatitis C virus

<400> SEQUENCE: 282

Tyr Ile Pro Leu Val Gly Ala Pro Leu Asn Gly Ala Ala Arg Ala
 1               5                  10                  15

<210> SEQ ID NO 283
<211> LENGTH: 149
<212> TYPE: PRT
<213> ORGANISM: hepatitis C virus
<220> FEATURE:
<221> NAME/KEY: MISC_FEATURE
<222> LOCATION: (121)..(121)
<223> OTHER INFORMATION: Xaa is any amino acid
<220> FEATURE:
<221> NAME/KEY: MISC_FEATURE
<222> LOCATION: (123)..(123)
<223> OTHER INFORMATION: Xaa is any amino acid

<400> SEQUENCE: 283

Asp Gly Ile Asn Phe Ala Thr Gly Asn Leu Pro Gly Cys Ser Phe Ser
 1               5                  10                  15

Ile Phe Leu Leu Ala Leu Leu Ser Cys Leu Thr Val Pro Ala Ser Ala
            20                  25                  30

Ile Asn Tyr Arg Asn Val Ser Gly Ile Tyr Tyr Val Thr Asn Asp Cys
        35                  40                  45

Pro Asn Ser Ser Ile Val Tyr Glu Ala Asp His His Ile Leu His Leu
    50                  55                  60

Pro Gly Cys Val Pro Cys Val Arg Glu Gly Asn Gln Ser Arg Cys Trp
65                  70                  75                  80

Val Ala Leu Thr Pro Thr Val Ala Pro Tyr Ile Gly Ala Pro Leu
                85                  90                  95

Glu Ser Leu Arg Ser His Val Asp Leu Met Val Gly Ala Ala Thr Val
            100                 105                 110

Cys Ser Ala Leu Tyr Ile Gly Asp Xaa Cys Xaa Gly Leu Phe Leu Val
        115                 120                 125

Gly Gln Met Phe Ser Phe Arg Pro Arg Arg His Trp Thr Thr Gln Asp
    130                 135                 140

Cys Asn Cys Ser Ile
145
```

-continued

```
<210> SEQ ID NO 284
<211> LENGTH: 149
<212> TYPE: PRT
<213> ORGANISM: hepatitis C virus
<220> FEATURE:
<221> NAME/KEY: MISC_FEATURE
<222> LOCATION: (85)..(85)
<223> OTHER INFORMATION: Xaa is any amino acid
<220> FEATURE:
<221> NAME/KEY: MISC_FEATURE
<222> LOCATION: (108)..(108)
<223> OTHER INFORMATION: Xaa is any amino acid
<220> FEATURE:
<221> NAME/KEY: MISC_FEATURE
<222> LOCATION: (128)..(128)
<223> OTHER INFORMATION: Xaa is any amino acid

<400> SEQUENCE: 284

Asp Gly Ile Asn Phe Ala Thr Gly Asn Leu Pro Gly Cys Ser Phe Ser
1               5                   10                  15

Ile Phe Leu Leu Ala Leu Phe Ser Cys Leu Leu Thr Pro Thr Ala Gly
            20                  25                  30

Leu Glu Tyr Arg Asn Ala Ser Gly Leu Tyr Met Val Thr Asn Asp Cys
        35                  40                  45

Ser Asn Gly Ser Ile Val Tyr Glu Ala Gly Asp Ile Ile Leu His Leu
    50                  55                  60

Pro Gly Cys Val Pro Cys Val Arg Ser Gly Asn Thr Ser Arg Cys Trp
65                  70                  75                  80

Ile Pro Val Ser Xaa Thr Val Ala Val Lys Ser Pro Cys Ala Ala Thr
                85                  90                  95

Ala Ser Leu Arg Thr His Val Asp Met Met Val Xaa Ala Ala Thr Leu
            100                 105                 110

Cys Ser Ala Leu Tyr Val Gly Asp Leu Cys Gly Ala Leu Phe Leu Xaa
        115                 120                 125

Gly Gln Gly Phe Ser Trp Arg His Arg Gln His Trp Thr Val Gln Asp
    130                 135                 140

Cys Asn Cys Ser Ile
145

<210> SEQ ID NO 285
<211> LENGTH: 24
<212> TYPE: PRT
<213> ORGANISM: hepatitis C virus
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid

<400> SEQUENCE: 285

Thr Cys Xaa Xaa Ala Asp Leu Met Gly Tyr Xaa Pro Val Val Gly Ala
1               5                   10                  15

Pro Val Gly Gly Xaa Ala Arg Ala
            20

<210> SEQ ID NO 286
<211> LENGTH: 19
<212> TYPE: PRT
```

```
<213> ORGANISM: hepatitis C virus

<400> SEQUENCE: 286

Val Gln Asp Cys Asn Cys Ser Ile Tyr Pro Gly His Ile Thr Gly His
1               5                   10                  15

Arg Met Ala
```